US009415099B2

(12) United States Patent
Pavlakis et al.

(10) Patent No.: US 9,415,099 B2
(45) Date of Patent: Aug. 16, 2016

(54) METHOD OF ALTERING THE IMMUNDOMINANCE HIERARCHY OF HIV GAG BY DNA VACCINE EXPRESSING CONSERVED REGIONS

(71) Applicants: THE UNITED STATES OF AMERICA, AS REPRESENTED BY THE SECRETARY OF THE DEPARTMENT OF HEALTH AND HUMAN SERVICES, Washington, DC (US); UNIVERSITY OF WASHINGTON THROUGH ITS CENTER FOR COMMERCIALIZATION, Seattle, WA (US)

(72) Inventors: George Pavlakis, Rockville, MD (US); Barbara Felber, Rockville, MD (US); James Mullins, Seattle, WA (US)

(73) Assignees: The United States of America as Represented by the Secretary of the Department of Health and Human Services, Washington, DC (US); University of Washington through its Center for Commercialization, Seattle, WA (US)

( * ) Notice: Subject to any disclaimer, the term of this patent is extended or adjusted under 35 U.S.C. 154(b) by 0 days.

(21) Appl. No.: 14/382,281

(22) PCT Filed: Mar. 4, 2013

(86) PCT No.: PCT/US2013/028932

§ 371 (c)(1),
(2) Date: Aug. 29, 2014

(87) PCT Pub. No.: WO2013/131099

PCT Pub. Date: Sep. 6, 2013

(65) Prior Publication Data

US 2015/0056237 A1 Feb. 26, 2015

Related U.S. Application Data

(60) Provisional application No. 61/606,265, filed on Mar. 2, 2012.

(51) Int. Cl.
*A61K 39/21* (2006.01)
*A61K 39/12* (2006.01)
(Continued)

(52) U.S. Cl.
CPC ................ *A61K 39/21* (2013.01); *A61K 39/12* (2013.01); *A61N 1/327* (2013.01); *C07K 14/005* (2013.01);
(Continued)

(58) Field of Classification Search
None
See application file for complete search history.

(56) References Cited

U.S. PATENT DOCUMENTS

| | | | |
|---|---|---|---|
| 7,981,430 B2 | 7/2011 | Hanke et al. |
| 8,071,107 B2 | 12/2011 | Hayes et al. |
| 2011/0269937 A1 | 11/2011 | Mullins et al. |

FOREIGN PATENT DOCUMENTS

| | | |
|---|---|---|
| WO | 02/36806 A2 | 5/2002 |
| WO | 2007/136585 A2 | 11/2007 |
| WO | 2008/089144 A2 | 7/2008 |

OTHER PUBLICATIONS

Rolland et al. HIV-1 Group M Conserved Elements Vaccine, PLoS Pathog. 2007; 3(11): 1551-1555.*

(Continued)

*Primary Examiner* — Daniel E Kolker
*Assistant Examiner* — Stuart W Snyder
(74) *Attorney, Agent, or Firm* — Kilpatrick Townsend & Stockton LLP

(57) ABSTRACT

The invention provides methods and compositions for eliciting broad immune responses. The methods employ nucleic acid vaccines that encodes highly conserved elements from a virus.

19 Claims, 34 Drawing Sheets

(51) Int. Cl.
*C07K 14/005* (2006.01)
*A61N 1/32* (2006.01)
*C12N 7/00* (2006.01)
*A61K 39/00* (2006.01)

(52) U.S. Cl.
CPC .............. *C12N 7/00* (2013.01); *A61K 2039/53* (2013.01); *A61K 2039/545* (2013.01); *C12N 2740/16222* (2013.01); *C12N 2740/16234* (2013.01); *C12N 2740/16271* (2013.01)

(56) References Cited

OTHER PUBLICATIONS

Koup et al. Priming Immunization with DNA Augments Immunogenicity of Recombinant Adenoviral Vectors for Both HIV-1 Specific Antibody and T-Cell Responses. PLoS One, 2010; 5(2): 1-15.*

International Search Report and Written Opinion dated Jul. 8, 2013 of International Patent Application No. PCT/US2013/028932, 16 pages.

Chikhlikar et al., "Inverted Terminal Repeat Sequences of Adeno-Associated Virus Enhance the Antibody and CD8+Responses to a HIV-1 p55Gag/LAMP DNA Vaccine Chimera", Virology, vol. 323, No. 2, pp. 220-232 (2004).

Ferrari et al., "Identification of Highly Conserved and Broadly Cross-Reactive HIV Type 1 Cytotoxic T Lymphocyte Epitopes as Candidate for Immunogens for Inclusion in *Mycobacterium bovis* BCG-Vectored HIV Vaccines", *AIDS Research and Human Retroviruses*, vol. 16, No. 14, pp. 4133-1443 (2000).

Kulkarni et al., "Comparison of Immune Responses Generated by Optimized DNA Vaccination Against SIV antigens in Mice and Macaques", *Vaccine*, vol. 29, No. 39, pp. 6742-6754 (2011).

Kulkarni et al., "HIV-1 p24(gag) Derived Conserved Element DNA Vaccine Increases the Breadth of Immune Response in Mice", *Plos One*, vol. 8, No. 3, (2013).

Letoumeau et al., "Design and Pre-Clinical Evaluation of a Universal HIV-1 Vaccine", *PlosOne*, vol. 2, No. 10, e984, 11 pages (2007).

Mothe et al., "CTL Responses of High Functional Avidity and Broad Variant Cross-Reactivity Are Associated with HIV Control", *Plos One*, vol. 7, No. 1, pp. e29717 (2012).

Mullins et al., "A Global AIDS Vaccine Based on Conserved Elements of the Viral Proteome", *AIDS Research and Human Retroviruses*, vol. 26, No. 10, pp. A2 (2010). XP002701145, XP002701146, XP002701147, 22 pages.

Niu et al., "Preclinical Evaluation of HIV-1 Therapeutic ex vivo Dendritic Cell Vaccines Expressing Consensus Gag Antigens and Conserved Gag Epitopes", *Vaccine*, vol. 29, No. 11, pp. 2110-2119 (2011).

Pavlakis et al., "Conserved Elements (CE) Vaccine", *AIDS Research and Human Retroviruses*, vol. 27, No. 10, pp. A110 (2011), XP-002701142, XP-002701143 & XP-002701144, 3 pages.

Palvakis et al., "DNA Vaccines Expressing Conserved Elements Provide Potent and Broad Immune Responses", *Retrovirology*, vol. 9, No. Supplementary 2, pp. 67 (2012).

Rolland et al., "HIV-1 Group M Conserved Elements Vaccine", *Plos Pathogens*, vol. 3, No. 11, e157, pp. 1551-1555 (2007).

Shiver, "A Non-Replicating Adenoviral Vector as a Potential HIV Vaccine", *The Body Pro* (2003), 3 pages. http://www.thebodypro.com/content/art34193.html?ts+pf.

Wilson et al., "Development of a DNA Vaccine Designed to Induce Cytotoxic T Lymphocyte Responses to Multiple Conserved Epitopes in HIV-1", *The Journal of Immunology*, vol. 171, No. 10, pp. 5611-5623 (2003).

Yang, "Candidate Vaccine Sequences to Represent Intra- and Inter-Clade HIV-1 Variation", *PloS One*, vol. 4, No. 10, e7388, 14 pages (2009).

* cited by examiner

Figure 8
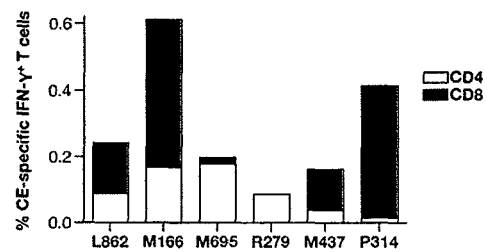
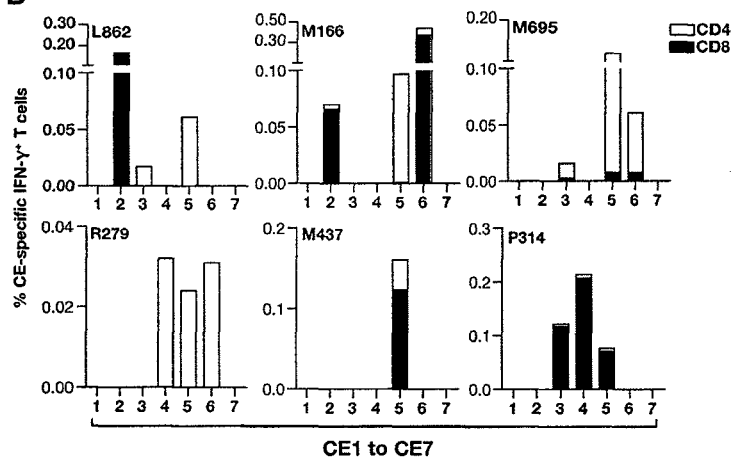
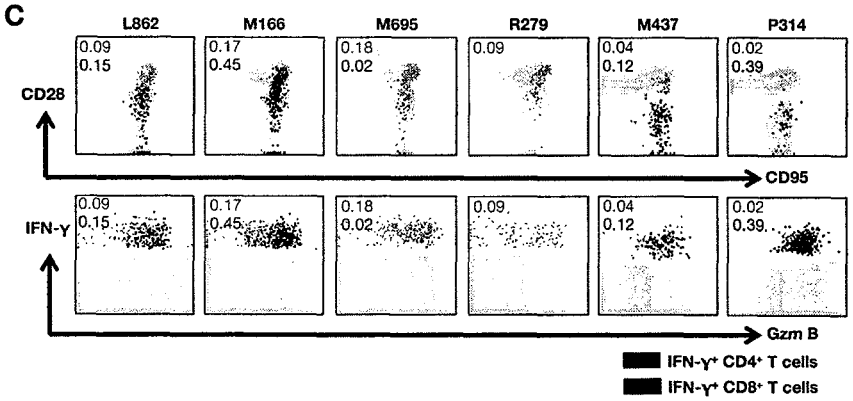

Figure 13 p24CEc

```
configuration p24CEc:  CE8-9-3-4-5-6
           CE8                       CE9                            CE3
P24CE1c    QGQMVHQAISPRTLNAWVKVLAKEEKAFSPEVIPMFSALSEGATPQDLNAAKVGGHQAAMQMLKETINEEAAEWDRAAAE
P24CE2c    QGQMVHQALSPRTLNAWVKVLAKEEKGFNPEVIPMFTALSEGATPQDLNAAKVGGHQAAMQMLKDTINEEAAEWDRAAAE
           CE4                      CE5                    CE6
p24CE1c    PRGSDIAGTTSTLQEQIGWAAAKRWIILGLNKIVRMYSPTSIAAKYVDRFYKTLRAEQA
p24CE2c    PRGSDIAGTTSTLQEQIAWAAAKRWIILGLNKIVRMYSPVSIAAKYVDRFFKTLRAEQA
``` p24CE1c
QGQMVHQAISPRTLNAWVKVLAKEEKAFSPEVIPMFSALSEGATPQDLNAAKVGGHQAAMQMLKETINEEAAEWDRAAAE
PRGSDIAGTTSTLQEQIGWAAAKRWIILGLNKIVRMYSPTSIAAKYVDRFYKTLRAEQA p24CE2c
QGQMVHQALSPRTLNAWVKVLAKEEKGFNPEVIPMFTALSEGATPQDLNAAKVGGHQAAMQMLKDTINEEAAEWDRAAAE
PRGSDIAGTTSTLQEQIAWAAAKRWIILGLNKIVRMYSPVSIAAKYVDRFFKTLRAEQA p24CEd

```
configuration p24CEd:  CE9-3-4-5-6-8
           CE9                          CE3                          CE4
p24CE1d    EEKAFSPEVIPMFSALSEGATPQDLNAAKVGGHQAAMQMLKETINEEAAEWDRAAAEPRGSDIAGTTSTLQEQIGWAAA
P24CE2d    EEKGFNPEVIPMFTALSEGATPQDLNAAKVGGHQAAMQMLKDTINEEAAEWDRAAAEPRGSDIAGTTSTLQEQIAWAAA CE5                    CE6              CE8
p24CE1d    KRWIILGLNKIVRMYSPTSIAAKYVDRFYKTLRAEQAALQGQMVHQAISPRTLNAWVKV
p24CE2d    KRWIILGLNKIVRMYSPVSIAAKYVDRFFKTLRAEQAALQGQMVHQALSPRTLNAWVKV
``` p24CE1d
EEKAFSPEVIPMFSALSEGATPQDLNAAKVGGHQAAMQMLKETINEEAAEWDRAAAEPRGSDIAGTTSTLQEQIGWAAA
KRWIILGLNKIVRMYSPTSIAAKYVDRFYKTLRAEQAALQGQMVHQAISPRTLNAWVKV p24CE2d
EEKGFNPEVIPMFTALSEGATPQDLNAAKVGGHQAAMQMLKDTINEEAAEWDRAAAEPRGSDIAGTTSTLQEQIAWAAA
KRWIILGLNKIVRMYSPVSIAAKYVDRFFKTLRAEQAALQGQMVHQALSPRTLNAWVKV

Figure 14b

```
   1 CCTGGCCATTGCATACGTTGTATCCATATCATAATATGTACATTTATATTGGCTCATGTCCAACATTACCGCCATGTTGACATTGATTATTGACTAGTTATTAATAGTAA
 111 TCAATTACGGGGTCATTAGTTCATAGCCCATATATGGAGTTCCGCGTTACATAACTTACGGTAAATGGCCCGCCTGGCTGACCGCCCAACGACCCCCGCCCATTGACGTC
 221 AATAATGACGTATGTTCCCATAGTAACGCCAATAGGGACTTTCCATTGACGTCAATGGGTGGAGTATTTACGGTAAACTGCCCACTTGGCAGTACATCAAGTGTATCATA
 331 TGCCAAGTACGCCCCCTATTGACGTCAATGATGGTAAATGGCCCGCCTGGCATTATGCCCAGTACATGACCTTATGGGACTTTCCTACTTGGCAGTACATCTACGTATTA
 441 GTCATCGCTATTACCATGGTGATGCGGTTTTGGCAGTACATCAATGGGCGTGGATAGCGGTTTGACTCACGGGGATTTCCAAGTCTCCACCCCATTGACGTCAATGGGAG
 551 TTTGTTTTGGCACCAAAATCAACGGGACTTTCCAAAATGTCGTAACAACTCCGCCCCATTGACGCAAATGGGCGGTAGGCGTGTACGGTGGGAGGTCTATATAAGCAGAG
 661 CTCGTTTAGTGAACCGTCAGATCGCCTGGAGACGCCATCCACGCTGTTTTGACCTCCATAGAAGACACCGGGACCGATCCAGCCTCCGCGGGCGCGCGTCGACAAGAA
                                                                                                              ▶
 769 ATG TGG CTC CAG AGC CTG CTA CTC CTG GGG ACG GTG GCC TGC AGC ATC TCG GTC ATC CCG ATG TTC TCG GCG CTC AGC GAG
   1▶ M   W   L   Q   S   L   L   L   L   G   T   V   A   C   S   I   S
   1▶ M   W   L   Q   S   L   L   L   L   G   T   V   A   C   S   I   S   V   I   P   M   F   S   A   L   S   E
                                                                         1▶V   I   P   M   F   S   A   L   S   E
 850 GGA GCG ACG CCG CAG GAC CTG AAC GCG GCC GTC GGA GGT CAC CAG GCA GCG ATG CAG ATG CTG AAG GAC ACG ATC AAC GAG
  28▶ G   A   T   P   Q   D   L   N   A   A   V   G   G   H   Q   A   A   M   Q   M   L   K   D   T   I   N   E
  11▶ G   A   T   P   Q   D   L   N   A   A   V   G   G   H   Q   A   A   M   Q   M   L   K   D   T   I   N   E
 931 GAG GCG GCC GAG TGG GAC CGG GCG GCA GCC GAG CCA CGC GGT TCC GAC ATC GCG GGC ACC ACC TCG ACG CTC CAG GAG CAG
  55▶ E   A   A   E   W   D   R   A   A   A   E   P   R   G   S   D   I   A   G   T   T   S   T   L   Q   E   Q
  38▶ E   A   A   E   W   D   R   A   A   A   E   P   R   G   S   D   I   A   G   T   T   S   T   L   Q   E   Q
1012 ATC GGG TGG GCC GCA GCT AAG CGC TGG ATC ATC CTC GGG CTG AAC AAG ATC GTC CGG ATG TAC AGC CCG ACG TCG ATC GCT
  82▶ I   G   W   A   A   A   K   R   W   I   I   L   G   L   N   K   I   V   R   M   Y   S   P   T   S   I   A
  65▶ I   G   W   A   A   A   K   R   W   I   I   L   G   L   N   K   I   V   R   M   Y   S   P   T   S   I   A
1093 GCT AAG TAC GTT GAC CGG TTC TAC AAG ACC CTG AGG GCC GAG CAG GCG GCC GGA CTG GAG GAG ATG ATG ACC GCG TGC CAG
 109▶ A   K   Y   V   D   R   F   Y   K   T   L   R   A   E   Q   A   A   G   L   E   E   M   M   T   A   C   Q
  92▶ A   K   Y   V   D   R   F   Y   K   T   L   R   A   E   Q   A   A   G   L   E   E   M   M   T   A   C   Q
1174 GGG GTC GGT GGA CCA GGG CAC AAG GCC GCG ATC TCG CCG CGC ACG CTG AAC GCG TGG GTG AAG GTC TGA TAA Gaattcgctagcgg
 136▶ G   V   G   P   G   H   K   A   A   I   S   P   R   T   L   N   A   W   V   K   V   •   •
 119▶ G   V   G   P   G   H   K   A   A   I   S   P   R   T   L   N   A   W   V   K   V   •   •
1260 cgcgccagatctgatatcggatctGCTGTGCCTTCTAGTTGCCAGCCATCTGTTGTTTGCCCCTCCCCCGTGCCTTCCTTGACCCTGGAAGGTGCCACTCCCACTGTCCT
1370 TTCCTAATAAAATGAGGAAATTGCATCGCATTGTCTGAGTAGGTGTCATTCTATTCTGGGGGGTGGGGTGGGGCAGGACAGCAAGGGGGAGGATTGGGAAGACAATAGCA
1480 GGCATGCTGGGGATGCGGTGGGCTCTATGGGTACCCAGGTGCTGAAGAATTGACCCGGTTCCTCCTGGGCCAGAAAGAAGCAGGCACATCCCCTTCTCTGTGACACACCC
1590 TGTCCACGCCCCTGGTTCTTAGTTCCAGCCCCACTCATAGGACACTCATAGCTCAGGAGGGCTCCGCCTTCAATCCCACCCGCTAAAGTACTTGGAGCGGTCTCTCCCTC
1700 CCTCATCAGCCCACCAAACCAAACCTAGCCTCCAAGAGTGGGAAGAAATTAAAGCAAGATAGGCTATTAAGTGCAGAGGGAGAGAAAATGCCTCCAACATGTGAGGAAGT
1810 AATGAGAGAAATCATAGAATTTCTTCCGCTTCCTCGCTCACTGACTCGCTGCGCTCGGTCGTTCGGCTGCGGCGAGCGGTATCAGCTCACTCAAAGGCGGTAATACGGTT
                                                                         ▶
1920 ATCCACAGAATCAGGGGATAACGCAGGAAAGAACATGTGAGCAAAAGGCCAGCAAAAGGCCAGGAACCGTAAAAAGGCCGCGTTGCTGGCGTTTTTCCATAGGCTCCGCC
2030 CCCCTGACGAGCATCACAAAAATCGACGCTCAAGTCAGAGGTGGCGAAACCCGACAGGACTATAAAGATACCAGGCGTTTCCCCCTGGAAGCTCCCTCGTGCGCTCTCCT
2140 GTTCCGACCCTGCCGCTTACCGGATACCTGTCCGCCTTTCTCCCTTCGGGAAGCGTGGCGCTTTCTCATAGCTCACGCTGTAGGTATCTCAGTTCGGTGTAGGTCGTTCG
2250 CTCCAAGCTGGGCTGTGTGCACGAACCCCCCGTTCAGCCCGACCGCTGCGCCTTATCCGGTAACTATCGTCTTGAGTCCAACCCGGTAAGACACGACTTATCGCCACTGG
2360 CAGCAGCCACTGGTAACAGGATTAGCAGAGCGAGGTATGTAGGCGGTGCTACAGAGTTCTTGAAGTGGTGGCCTAACTACGGCTACACTAGAAGAACAGTATTTGGTATC
2470 TGCGCTCTGCTGAAGCCAGTTACCTTCGGAAAAAGAGTTGGTAGCTCTTGATCCGGCAAACAAACCACCGCTGGTAGCGGTGGTTTTTTTGTTTGCAAGCAGCAGATTAC
2580 GCGCAGAAAAAAAGGATCTCAAGAAGATCCTTTGATCTTTTCTACGGGGTCTGACGCTCAGTGGAACGAAAACTCACGTTAAGGGATTTTGGTCATGAGATTATCAAAA
2690 GGATCTTCACCTAGATCCTTTTAAATTAAAAATGAAGTTTTAAATCAATCTAAAGTATATATGAGTAAACTTGGTCTGACAGTTACCAATGCTTAATCAGTGAGGCACCT
2800 ATCTCAGCGATCTGTCTATTTCGTTCATCCATAGTTGCCTGACTCGGGGGGGGGGCGCTGAGGTCTGCCTCGTGAAGAAGGTGTTGCTGACTCATACCAGGCCTGAAT
2910 CGCCCCATCATCCAGCCAGAAGTGAGGGAGCCACGGTTGATGAGAGCTTTGTTGTAGGTGGACCAGTTGGTGATTTTGAACTTTTGCTTTGCCACGGAACGGTCTGCGT
3020 TGTCGGGAAGATGCGTGATCTGATCCTTCAACTCAGCAAAAGTTCGATTTATTCAACAAAGCCGCCGTCCCGTCAAGTCAGCGTAATGCTCTGCCAGTGTTACAACCAAT
3130 TAACCAATTCTGATTAGAAAAACTCATCGAGCATCAAATGAAACTGCAATTTATTCATATCAGGATTATCAATACCATATTTTTGAAAAAGCCGTTTCTGTAATGAAGGA
     271◀ F   F   E   D   L   M   L   H   F   Q   L   K   N   M   D   P   N   D   I   G   Y   K   Q   F   L   R   K   Q   L   S   P
3240 GAAAACTCACCGAGGCAGTTCCATAGGATGGCAAGATCCTGGTATCGGTCTGCGATTCCGACTCGTCCAACATCAATACAACCTATTAATTTCCCCTCGTCAAAAATAAG
     239◀ S   F   E   G   L   C   N   W   L   I   A   L   D   Q   Y   R   D   A   I   G   V   R   G   V   D   I   C   G   I   L   K   G   E   D   F   I   L
3350 GTTATCAAGTGAGAAATCACCATGAGTGACGACTGAATCCGGTGAGAATGGCAAAAGCTTATGCATTTCTTTCCAGACTTGTTCAACAGGCCAGCCATTACGCTCGTCAT
     203◀ N   D   L   S   F   D   G   H   T   V   V   S   D   P   S   F   P   L   L   K   H   M   E   K   W   V   Q   E   V   P   W   G   N   R   E   D   D
3460 CAAAATCACTCGCATCAACCAAACCGTTATTCATTCGTGATTGCGCCTGAGCGAGACGAAATACGCGATCGCTGTTAAAAGGACAATTACAAACAGGAATCGAATGCAAC
     166◀ F   D   S   A   D   V   L   G   N   N   M   R   S   Q   A   A   Q   A   L   R   F   V   R   D   S   N   F   P   C   N   C   V   P   I   S   H   L
3570 CGGCGCAGGAACACTGCCAGCGCATCAACAATATTTTCACCTGAATCAGGATATTCTTCTAATACCTGGAATGCTGTTTTCCCGGGGATCGCAGTGGTGAGTAACCATGC
     129◀ R   R   L   F   V   A   L   A   D   V   I   N   E   G   S   D   P   Y   E   E   L   V   Q   F   A   T   K   G   P   I   A   T   T   L   L   W   A
3680 ATCATCAGGAGTACGGATAAAATGCTTGATGGTCGGAAGAGGCATAAATTCCGTCAGCCAGTTTAGTCTGACCATCTCATCTGTAACATCATTGGCAACGCTACCTTTGC
      93◀ D   D   P   T   R   I   F   H   K   I   T   P   L   P   M   F   E   T   L   W   N   L   R   V   M   E   D   T   V   D   N   A   V   S   G   K   G
3790 CATGTTTCAGAAACAACTCTGGCGCATCGGGCTTCCCATACAATCGATAGATTGTCGCACCTGATTGCCCGACATTATCGCGAGCCCATTTATACCCATATAAATCAGCA
      56◀ H   K   L   F   L   E   P   A   D   P   K   G   Y   L   R   Y   I   T   A   G   S   Q   G   V   N   D   R   A   W   K   Y   G   Y   L   D   A
3900 TCCATGTTGGAATTTAATCGCGGCCTCGAGCAAGACGTTTCCCGTTGAATATGGCTCATAACACCCCTTGTATTACTGTTTATGTAAGCAGACAGTTTTATTGTTCATGA
      19◀ D   M   N   S   N   L   R   P   R   S   C   S   T   E   R   Q   I   H   S   M
4010 TGATATATTTTTATCTTGTGCAATGTAACATCAGAGATTTTGAGACACAACGTGGATCATCCAGACATGATAAGATACATTGATGAGTTTGGACAAACCACAACTAGAAT
                                                                                                 ◀
4120 GCAGTGAAAAAAATGCTTTATTTGTGAAATTTGTGATGCTATTGCTTTATTTGTAACCATTATAAGCTGCAATAAACAAGTTAACAACAACAATTGCATTCATTTTATGT
4230 TTCAGGTTCAGGGGGAGGTGTGGGAGGTTTTTTAAAGCAAGTAAAACCTCTACAAATGTGGTATGGCTGATTATGATCgtcgaggatccggcg TTA TCA GAC CTT
                                                                                              142◀ •   •   V   K
                                                                                              159◀ •   •   V   K
```

Figure 14b (con.)

```
4335 CAC CCA GGC GTT GAG GGT GCG AGG CGA GAG GGC CGC CTT GTG CGA CGG TCC TCC GAC TCC CTG GCA GGC TGT CAT CAT CTC
138◁ V   W   A   N   L   T   R   P   S   L   A   A   K   H   S   P   G   G   V   G   Q   C   A   T   M   M   E
155◁ V   W   A   N   L   T   R   P   S   L   A   A   K   H   S   P   G   G   V   G   Q   C   A   T   M   M   E
4416 CTC GAG ACC CGC GGC CTG CTC TGC CCT CAG CGT CTT GAA GAA GCG GTC TAC GTA TTT GGC CGC GAT GCT GAC TGG GCT GTA
111◁ E   L   G   A   A   Q   E   A   R   L   T   K   F   F   R   D   V   Y   K   A   A   I   S   V   P   S   Y
128◁ E   L   G   A   A   Q   E   A   R   L   T   K   F   F   R   D   V   Y   K   A   A   I   S   V   P   S   Y
4497 CAT CCT GAC GAT CTT GTT GAG GCC CAG GAT GAT CCA GCG CTT GGC TGC AGC CCA GGC GAT CTG CTC CTG GAG GGT GCT GGT
84◁  M   R   V   I   K   N   L   G   L   I   I   W   R   K   A   A   A   W   A   I   Q   E   Q   L   T   S   T
101◁ M   R   V   I   K   N   L   G   L   I   I   W   R   K   A   A   A   W   A   I   Q   E   Q   L   T   S   T
4578 CGT GCC TGC GAT GTC GCT ACC CCT TGG CTC AGC TGC TGC CCT GTC CCA CTC GGC TGC CTC CTC GTT GAT GGT CTC CTT GAG
57◁  T   G   A   I   D   S   G   R   P   E   A   A   A   R   D   W   E   A   A   E   E   N   I   T   E   K   L
74◁  T   G   A   I   D   S   G   R   P   E   A   A   A   R   D   W   E   A   A   E   E   N   I   T   E   K   L
4659 CAT CTG CAT TGC CGC CTG GTG TCC ACC GAC CGC GGC GTT GAG GTC CTG CGG TGT CGC ACC CTC ACT GAG TGC GGT GAA CAT
30◁  M   Q   M   A   A   Q   H   G   G   V   A   A   N   L   D   Q   P   T   A   G   E   S   L   A   T   F   M
47◁  M   Q   M   A   A   Q   H   G   G   V   A   A   N   L   D   Q   P   T   A   G   E   S   L   A   T   F   M
4740 GGG GAT GAC CGA GAT CGA GCA CGC CAC GGT CCC GAG TAG CAG GAG CGA CTG CAG CCA CAT ttcttccgtttaaacgtcgacagatccaa
3◁   P   I   V◁  S   I   S   C   A   V   T   G   L   L   L   L   S   Q   L   W   M
20◁  P   I   V   S   I   S   C   A   V   T   G   L   L   L   L   S   Q   L   W   M
4829 acGCTCCTCCGACGTCCCCAGGCAGAATGGCGGTTCCCTAAACGAGCATTGCTTATATAGACCTCCCATTAGGCACGCCTACCGCCCATTTACGTCAATGGAACGCCCAT
     ◀─────────────────────────────────────────────────────────────────────────────────────────────────────────
4939 TTGCGTCATTGCCCCTCCCCATTGACGTCAATGGGGATGTACTTGGCAGCCATCGCGGGCCATTTACCGCCATTGACGTCAATGGGAGTACTGCCAATGTACCCTGGCGT 5049 ACTTCCAATAGTAATGTACTTGCCAAGTTACTATTAATAGATATTGATGTACTGCCAAGTGGGCCATTTACCGTCATTGACGTCAATAGGGGGCGTGAGAACGGATATGA 5159 ATGGGCAATGAGCCATCCCATTGACGTCAATGGTGGGTGGTCCTATTGACGTCAATGGGCATTGAGCCAGGCGGGCCATTTACCGTAATTGACGTCAATGGGGAGGCGC 5269 CATATACGTCAATAGGACCGCCCATATGACGTCAATAGGTAAGACCATGAGGCCCTTTCGTCTCGCGCGTTTCGGTGATGACGGTGAAAACCTCTGACACATGCAGCTCC 5379 CGGAGACGGTCACAGCTTGTCTGTAAGCGGATGCCGGGAGCAGACAAGCCCGTCAGGGCGCGTCAGCGGGTGTTGGCGGGTGTCGGGGCTGGCTTAACTATGCGGCATCA
5489 GAGCAGATTGTACTGAGAGTGCACCATATGCGGTGTGAAATACCGCACAGATGCGTAAGGAGAAAATACCGCATCAGATTGGCTATTGGCATTATGCC
```

Figure 15b

```
   1 CCTGGCCATTGCATACGTTGTATCCATATCATAATATGTACATTTATATTGGCTCATGTCCAACATTACCGCCATGTTGACATTGATTATTGACTAGTTATTAATAGTAA

111 TCAATTACGGGGTCATTAGTTCATAGCCCATATATGGAGTTCCGCGTTACATAACTTACGGTAAATGGCCCGCCTGGCTGACCGCCCAACGACCCCCGCCCATTGACGTC

221 AATAATGACGTATGTTCCCATAGTAACGCCAATAGGGACTTTCCATTGACGTCAATGGGTGGAGTATTTACGGTAAACTGCCCACTTGGCAGTACATCAAGTGTATCATA

331 TGCCAAGTACGCCCCCTATTGACGTCAATGATGGTAAATGGCCCGCCTGGCATTATGCCCAGTACATGACCTTATGGGACTTTCCTACTTGGCAGTACATCTACGTATTA

441 GTCATCGCTATTACCATGGTGATGCGGTTTTGGCAGTACATCAATGGGCGTGGATAGCGGTTTGACTCACGGGGATTTCCAAGTCTCCACCCCATTGACGTCAATGGGAG

551 TTTGTTTTGGCACCAAAATCAACGGGACTTTCCAAAATGTCGTAACAACTCCGCCCCATTGACGCAAATGGGCGGTAGGCGTGTACGGTGGGAGGTCTATATAAGCAGAG

661 CTCGTTTAGTGAACCGTCAGATCGCCTGGAGACGCCATCCACGCTGTTTTGACCTCCATAGAAGACACCGGGACCGATCCAGCCTCGcgggcgcgcgtcgactagc 768 ATG GCG CCC CGC AGC GCC CGG CGA CCC CTG CTG CTG CTA CTG CTG TTG CTG CTG CTC GGC CTC ATG CAT TGT GCG TCA GCA
   1▸ M   A   P   R   S   A   R   R   P   L   L   L   L   L   L   L   L   L   L   G   L   M   H   C   A   S   A
   1▸ M   A   P   R   S   A   R   R   P   L   L   L   L   L   L   L   L   L   L   G   L   M   H   C   A   S   A
 849 GCA ATG TTT ATG GTG AAA AAT GGC AAC GGG ACC GCG TGC ATA ATG GCC AAC TTC TCT GCT GCC TTC TCA GTG AAC TAC GAC
  28▸ A   M   F   M   V   K   N   G   N   G   T   A   C   I   M   A   N   F   S   A   A   F   S   V   N   Y   D
  28▸ A   M   F   M   V   K   N   G   N   G   T   A   C   I   M   A   N   F   S   A   A   F   S   V   N   Y   D
 930 ACC AAG AGT GGC CCT AAG AAC ATG ACC CTT GAC CTG CCA TCA GAT GCC ACA GTG GTG CTC AAC CGC AGC TCC TGT GGA AAA
  55▸ T   K   S   G   P   K   N   M   T   L   D   L   P   S   D   A   T   V   V   L   N   R   S   S   C   G   K
  55▸ T   K   S   G   P   K   N   M   T   L   D   L   P   S   D   A   T   V   V   L   N   R   S   S   C   G   K
1011 GAG AAC ACT TCT GAC CCC AGT CTC GTG ATT GCT TTT GGA AGA CAT ACA CTC ACT CTC AAT TTC ACG AGA AAT GCA ACA
  82▸ E   N   T   S   D   P   S   L   V   I   A   F   G   R   H   T   L   T   L   N   F   T   R   N   A   T
  82▸ E   N   T   S   D   P   S   L   V   I   A   F   G   R   G   H   T   L   T   L   N   F   T   R   N   A   T
1092 CGT TAC AGC GTT CAG CTC ATG AGT TTT GTT TAT AAC TTG TCA GAC ACA CAC CTT TTC CCC AAT GCG AGC TCC AAA GAA ATC
 109▸ R   Y   S   V   Q   L   M   S   F   V   Y   N   L   S   D   T   H   L   F   P   N   A   S   S   K   E   I
 109▸ R   Y   S   V   Q   L   M   S   F   V   Y   N   L   S   D   T   H   L   F   P   N   A   S   S   K   E   I
1173 AAG ACT GTG GAA TCT ATA ACT GAC ATC AGG GCA GAT ATA GAT AAA AAA TAC AGA TGT GTT AGT GGC ACC CAG GTC CAC ATG
 136▸ K   T   V   E   S   I   T   D   I   R   A   D   I   D   K   K   Y   R   C   V   S   G   T   Q   V   H   M
 136▸ K   T   V   E   S   I   T   D   I   R   A   D   I   D   K   K   Y   R   C   V   S   G   T   Q   V   H   M
1254 AAC AAC GTG ACC GTA ACG CTC CAT GAT GCC ACC ATC CAG GCG TAC CTT TCC AAC AGC AGC TTC AGC AGG GGA GAG ACA CGC
 163▸ N   N   V   T   V   T   L   H   D   A   T   I   Q   A   Y   L   S   N   S   S   F   S   R   G   E   T   R
 163▸ N   N   V   T   V   T   L   H   D   A   T   I   Q   A   Y   L   S   N   S   S   F   S   R   G   E   T   R
1335 TGT GAA CAA GAC AGG CCT TCC CCA ACC ACA GCG CCC CCT GCG CCA CCC AGC CCC TCG CCC TCA CCC GTG CCC AAG AGC CCC
 190▸ C   E   Q   D   R   P   S   P   T   T   A   P   P   A   P   P   S   P   S   P   S   P   V   P   K   S   P
 190▸ C   E   Q   D   R   P   S   P   T   T   A   P   P   A   P   P   S   P   S   P   S   P   V   P   K   S   P
1416 TCT GTG GAC AAG TAC AAC GTG AGC GGC ACC AAC GGG ACC TGC CTG CTG GCC AGC ATG GGG CTG CAG CTG AAC CTC ACC TAT
 217▸ S   V   D   K   Y   N   V   S   G   T   N   G   T   C   L   L   A   S   M   G   L   Q   L   N   L   T   Y
 217▸ S   V   D   K   Y   N   V   S   G   T   N   G   T   C   L   L   A   S   M   G   L   Q   L   N   L   T   Y
1497 GAG AGG AAG GAC AAC ACG ACG GTG ACA AGG CTT CTC AAC ATC AAC CCC AAC AAG ACC TCG GCC AGC GGG AGC TGC GGC GCC
 244▸ E   R   K   D   N   T   T   V   T   R   L   L   N   I   N   P   N   K   T   S   A   S   G   S   C   G   A
 244▸ E   R   K   D   N   T   T   V   T   R   L   L   N   I   N   P   N   K   T   S   A   S   G   S   C   G   A
1578 CAC CTG GTG ACT CTG GAG CTG CAC AGC GAG GGC ACC ACC GTC CTG CTC TTC CAG TTC GGG ATG AAT GCA AGT TCT AGC CGG
 271▸ H   L   V   T   L   E   L   H   S   E   G   T   T   V   L   L   F   Q   F   G   M   N   A   S   S   S   R
 271▸ H   L   V   T   L   E   L   H   S   E   G   T   T   V   L   L   F   Q   F   G   M   N   A   S   S   S   R
1659 TTT TTC CTA CAA GGA ATC CAG TTG AAT ACA ATT CTT CCT GAC GCC AGA GAC CCT GCC TTT AAA GCT GCC AAC GGC TCC CTG
 298▸ F   F   L   Q   G   I   Q   L   N   T   I   L   P   D   A   R   D   P   A   F   K   A   A   N   G   S   L
 298▸ F   F   L   Q   G   I   Q   L   N   T   I   L   P   D   A   R   D   P   A   F   K   A   A   N   G   S   L
1740 CGA GCG CTG CAG GCC ACA GTC GGC AAT TCC TAC AAG TGC AAC GAG GAG CAC GTC CGT GTC ACG AAG GCG TTT TCA GTC
 325▸ R   A   L   Q   A   T   V   G   N   S   Y   K   C   N   A   E   E   H   V   R   V   T   K   A   F   S   V
 325▸ R   A   L   Q   A   T   V   G   N   S   Y   K   C   N   A   E   E   H   V   R   V   T   K   A   F   S   V
1821 AAT ATA TTC AAA GTG TGG GTC CAG GCT TTC AAG GTG GAA GGT GGC CAG TTT GGC TCT GTG GAG GAG TGT CTG CTG GAC GAG
 352▸ N   I   F   K   V   W   V   Q   A   F   K   V   E   G   G   Q   F   G   S   V   E   E   C   L   L   D   E
 352▸ N   I   F   K   V   W   V   Q   A   F   K   V   E   G   G   Q   F   G   S   V   E   E   C   L   L   D   E
1902 AAC AGC CTC GAG GAT ATC GTC ATC CCG ATG TTC ACG GCG CTC AGC GAG GGA GCG ACG CCG CAG GAC CTG AAC GCG GCC GTC
 379▸ N   S               1▸ V   I   P   M   F   T   A   L   S   E   G   A   T   P   Q   D   L   N   A   A   V
 379▸ N   S   L   E   D   I   V   I   P   M   F   T   A   L   S   E   G   A   T   P   Q   D   L   N   A   A   V
1983 GGA GGT CAC CAG GCA GCG ATG CAG ATG CTG AAG GAG ACG ATC AAC GAG GAG GCG GCC GAG TGG GAC CGG GCG GCA GCC GAG
  22▸ G   G   H   Q   A   A   M   Q   M   L   K   E   T   I   N   E   E   A   A   E   W   D   R   A   A   A   E
 406▸ G   G   H   Q   A   A   M   Q   M   L   K   E   T   I   N   E   E   A   A   E   W   D   R   A   A   A   E
2064 CCA CGC GGT TCC GAC ATC GCG GGC ACC ACC TCG ACG GCG GAG ATC GCG TGG GCC GCA GCT AAG CGC TGG ATC ATC
  49▸ P   R   G   S   D   I   A   G   T   T   S   T   L   Q   E   Q   I   A   W   A   A   A   K   R   W   I   I
 433▸ P   R   G   S   D   I   A   G   T   T   S   T   L   Q   E   Q   I   A   W   A   A   A   K   R   W   I   I
2145 CTC GGG CTG AAC AAG ATC GTC CGG ATG TAC AGC CCG GTC TCG ATC GCT GCT AAG TAC GTT GAC CGG TTC TTC AAG ACC CTG
  76▸ L   G   L   N   K   I   V   R   M   Y   S   P   V   S   I   A   A   K   Y   V   D   R   F   F   K   T   L
 460▸ L   G   L   N   K   I   V   R   M   Y   S   P   V   S   I   A   A   K   Y   V   D   R   F   F   K   T   L
2226 AGG GCC GAG CAG GCG GCC GGA CTG GAG GAG ATG ATG ACC GCG TGC CAG GGG GTC GGT GGA CCA TCG CAC AAG GCC GCG CTC
 103▸ R   A   E   Q   A   A   G   L   E   E   M   M   T   A   C   Q   G   V   G   G   P   S   H   K   A   A   L
 487▸ R   A   E   Q   A   A   G   L   E   E   M   M   T   A   C   Q   G   V   G   G   P   S   H   K   A   A   L
2307 TCG CCG CGC ACG CTG AAC GCG TGG GTG AAG GTC GGA TCC GAA TTC ACG CTG ATC CCC ATC GCT GTG GGT GGT GCC CTG GCG
 130▸ S   P   R   T   L   N   A   W   V   K   V                   1▸ T   L   I   P   I   A   V   G   G   A   L   A
 514▸ S   P   R   T   L   N   A   W   V   K   V   G   S   E   F   T   L   I   P   I   A   V   G   G   A   L   A
2388 GGG CTG GTC CTC ATC GTC CTC ATC GCC TAC CTC GTC GGC AGG AAG AGG AGT CAC GCA GGC TAC CAG ACT ATC TAG ggtacctcta
  13▸ G   L   V   L   I   V   L   I   A   Y   L   V   G   R   K   R   S   H   A   G   Y   Q   T   I   •
 541▸ G   L   V   L   I   V   L   I   A   Y   L   V   G   R   K   R   S   H   A   G   Y   Q   T   I   •
2473 gGATCTGCTGTGCCTTCTAGTTGCCAGCCATCTGTTGTTTGCCCCTCCCCCGTGCCTTCCTTGACCCTGGAAGGTGCCACTCCCACTGTCCTTTCCTAATAAATGAGGA 2583 AATTGCATCGCATTGTCTGAGTAGGTGTCATTCTATTCTGGGGGGTGGGTGGGGCAGGACAGCAAGGGGGAGGATTGGGAAGACAATAGCAGGCATGCTGGGGATGCGG 2693 TGGGCTCTATGGGTACCCAGGTGCTGAAGAATTGACCCGGTTCCTCCTGGGCCAGAAAGAAGCAGGCACATCCCCTTCTCTGTGACACACCCTGTCCACGCCCCTGGTTC
```

Figure 15b (con.)

```
2803 TTAGTTCCAGCCCCACTCATAGGACACTCATAGCTCAGGAGGGCTCCGCCTTCAATCCCACCCGCTAAAGTACTTGGAGCGGTCTCTCCCTCCCTCATCAGCCCACCAAA

2913 CCAAACCTAGCCTCCAAGAGTGGGAAGAAATTAAAGCAAGATAGGCTATTAAGTGCAGAGGGAGAGAAAATGCCTCCAACATGTGAGGAAGTAATGAGAGAAATCATAGA
                                                                                                              →
3023 ATTTCTTCCGCTTCCTCGCTCACTGACTCGCTGCGCTCGGTCGTTCGGCTGCGGCGAGCGGTATCAGCTCACTCAAAGGCGGTAATACGGTTATCCACAGAATCAGGGGA
3133 TAACGCAGGAAAGAACATGTGAGCAAAAGGCCAGCAAAAGGCCAGGAACCGTAAAAAGGCCGCGTTGCTGGCGTTTTTCCATAGGCTCCGCCCCCCTGACGAGCATCACA
3243 AAAATCGACGCTCAAGTCAGAGGTGGCGAAACCCGACAGGACTATAAAGATACCAGGCGTTTCCCCCTGGAAGCTCCCTCGTGCGCTCTCCTGTTCCGACCCTGCCGCTT
3353 ACCGGATACCTGTCCGCCTTTCTCCCTTCGGGAAGCGTGGCGCTTTCTCAATGCTCACGCTGTAGGTATCTCAGTTCGGTGTAGGTCGTTCGCTCCAAGCTGGGCTGTGT
3463 GCACGAACCCCCCGTTCAGCCCGACCGCTGCGCCTTATCCGGTAACTATCGTCTTGAGTCCAACCCGGTAAGACACGACTTATCGCCACTGGCAGCAGCCACTGGTAACA
3573 GGATTAGCAGAGCGAGGTATGTAGGCGGTGCTACAGAGTTCTTGAAGTGGTGGCCTAACTACGGCTACACTAGAAGAACAGTATTTGGTATCTGCGCTCTGCTGAAGCCA
3683 GTTACCTTCGGAAAAAGAGTTGGTAGCTCTTGATCCGGCAAACAAACCACCGCTGGTAGCGGTGGTTTTTTTGTTTGCAAGCAGCAGATTACGCGCAGAAAAAAAGGATC
3793 TCAAGAAGATCCTTTGATCTTTTCTACGGGGTCTGACGCTCAGTGGAACGAAAACTCACGTTAAGGGATTTTGGTCATGAGATTATCAAAAAGGATCTTCACCTAGATCC
3903 TTTTAAATTAAAAATGAAGTTTTAAATCAATCTAAAGTATATATGAGTAAACTTGGTCTGACAGTTACCAATGCTTAATCAGTGAGGCACCTATCTCAGCGATCTGTCTA
4013 TTTCGTTCATCCATAGTTGCCTGACTCGGGGGGGGGGGGGCGCTGAGGTCTGCCTCGTGAAGAAGGTGTTGCTGACTCATACCAGGCCTGAATCGCCCCATCATCCAGCC
4123 AGAAAGTGAGGGAGCCACGGTTGATGAGAGCTTTGTTGTAGGTGGACCAGTTGGTGATTTTGAACTTTTGCTTTGCCACGGAACGGTCTGCGTTGTCGGGAAGATGCGTG
4233 ATCTGATCCTTCAACTCAGCAAAAGTTCGATTTATTCAACAAAGCCGCCGTCCCGTCAAGTCAGCGTAATGCTCTGCCAGTGTTACAACCAATTAACCAATTCTGATTA
4342 GAA AAA CTC ATC GAG CAT CAA ATG AAA CTG CAA TTT ATT CAT ATC AGG ATT ATC AAT ACC ATA TTT TTG AAA AAG CCG TTT
271◀  F   F   E   D   L   M   L   H   F   Q   L   K   N   M   D   P   N   D   I   G   Y   K   Q   F   L   R   K
4423 CTG TAA TGA AGG AGA AAA CTC ACC GAG GCA GTT CCA TAG GAT GGC AAG ATC CTG GTA TCG GTC TGC GAT TCC GAC TCG TCC
244◀  Q   L   S   P   S   F   E   G   L   C   N   W   L   I   A   L   D   Q   Y   R   D   A   I   G   V   R   G
4504 AAC ATC AAT ACA ACC TAT TAA TTT CCC CTC GTC AAA AAT AAG GTT ATC AAG TGA GAA ATC ACC ATG AGT GAC GAC TGA ATC
217◀  V   D   I   C   G   I   L   K   G   E   D   F   I   L   N   D   L   S   F   D   G   H   T   V   V   S   D
4585 CGG TGA GAA TGG CAA AAG CTT ATG CAT TTC TTT CCA GAC TTG TTC AAC AGG CCA GCC ATT ACG CTC GTC ATC AAA ATC ACT
190◀  P   S   F   P   L   L   K   H   M   E   K   W   V   Q   E   V   P   W   G   N   R   E   D   D   F   D   S
4666 CGC ATC AAC CAA ACC GTT ATT CAT TCG TGA TTG CGC CTG AGC GAG GCG AAA TAC GCG ATC GCT GTT AAA AGG ACA ATT ACA
163◀  A   D   V   L   G   N   N   M   R   S   Q   A   Q   A   L   R   F   V   R   D   S   N   F   P   C   N   C
4747 AAC AGG AAT CGA ATG CAA CCG GCG CAG GAA CAC TGC CAG CGC ATC AAC AAT ATT TTC ACC TGA ATC AGG ATA TTC TTC TAA
136◀  V   P   I   S   H   L   R   R   L   F   V   A   L   A   D   V   I   N   E   G   S   D   P   Y   E   E   L
4828 TAC CTG GAA TGC TGT TTT CCC GGG GAT CGC AGT GGT GAG TAA CCA TGC ATC ATC AGG AGT ACG GAT AAA ATG CTT GAT GGT
109◀  V   Q   F   A   T   K   G   P   I   A   T   T   L   L   W   A   D   P   T   R   I   F   H   K   I   T
4909 CGG AAG AGG CAT AAA TTC CGT CAG CCA GTT TAG TCT GAC CAT CTC ATC TGT AAC ATC ATT GGC AAC GCT ACC TTT GCC ATG
 82◀  P   L   P   M   F   E   T   L   W   N   L   R   V   M   E   D   T   V   D   N   A   V   S   G   K   G   H
4990 TTT CAG AAA CAA CTC TGG CGC ATC GGG CTT CCC ATA CAA TCG ATA GAT TGT CGC ACC TGA TTG CCC GAC ATT ATC GCG AGC
 55◀  K   L   F   L   E   P   A   D   P   K   G   Y   L   R   Y   I   T   A   G   S   Q   G   V   N   D   R   A
5071 CCA TTT ATA CCC ATA TAA ATC AGC ATC CAT GTT GGA ATT TAA TCG CGG CCT GGA GCA AGA CGT TTC CCG TTG AAT ATG GCT
 28◀  W   K   Y   G   Y   L   D   A   D   M   N   S   N   L   R   P   R   S   C   S   T   E   R   Q   I   H   S
5152 CAT AACACCCCTTGTATTACTGTTTATGTAAGCAGACAGTTTTATTGTTCATGATGATATATTTTTATCTTGTGCAATGTAACATCAGAGATTTTGAGACACAACGTGG
  1◀  M
5261 CTTTCCCCCCCCCCCCCATTATTGAAGCATTTATCAGGGTTATTGTCTCATGAGCGGATACATATTTGAATGTATTTAGAAAAATAAACAAATAGGGGTTCCGCGCACATT
5371 TCCCCGAAAAGTGCCACCTGACGTCTAAGAAACCATTATTATCATGACATTAACCTATAAAAATAGGCGTATCACGAGGCCCTTTCGTCTCGCGCGTTTCGGTGATGACG
5481 GTGAAAACCTCTGACACATGCAGCTCCCGGAGACGGTCACAGCTTGTCTGTAAGCGGATGCCGGGAGCAGACAAGCCCGTCAGGGCGCGTCAGCGGGTGTTGGCGGGTGT
5591 CGGGGCTGGCTTAACTATGCGGCATCAGAGCAGATTGTACTGAGAGTGCACCATATGCGGTGTGAAATACCGCACAGATGCGTAAGGAGAAAATACCGCATCAGATTGGC
5701 TATTGG
```

Figure 16b

```
   1 CCTGGCCATTGCATACGTTGTATCCATATCATAATATGTACATTTATATTGGCTCATGTCCAACATTACCGCCATGTTGACATTGATTATTGACTAGTTATTAATAGTAA
 111 TCAATTACGGGGTCATTAGTTCATAGCCCATATATGGAGTTCCGCGTTACATAACTTACGGTAAATGGCCCGCCTGGCTGACCGCCCAACGACCCCCGCCCATTGACGTC
 221 AATAATGACGTATGTTCCCATAGTAACGCCAATAGGGACTTTCCATTGACGTCAATGGGTGGAGTATTTACGGTAAACTGCCCACTTGGCAGTACATCAAGTGTATCATA
 331 TGCCAAGTACGCCCCCTATTGACGTCAATGATGGTAAATGGCCCGCCTGGCATTATGCCCAGTACATGACCTTATGGGACTTTCCTACTTGGCAGTACATCTACGTATTA
 441 GTCATCGCTATTACCATGGTGATGCGGTTTTGGCAGTACATCAATGGGCGTGGATAGCGGTTTGACTCACGGGGATTTCCAAGTCTCCACCCCATTGACGTCAATGGGAG
 551 TTTGTTTTGGCACCAAAATCAACGGGACTTTCCAAAATGTCGTAACAACTCCGCCCCATTGACGCAAATGGGCGGTAGGCGTGTACGGTGGGAGGTCTATATAAGCAGAG
 661 CTCGTTTAGTGAACCGTCAGATCGCCTGGAGACGCCATCCACGCTGTTTTGACCTCCATAGAAGACACCGGGACCGATCCAGCCTCCGcgggcgcgcgtcgactagc
```

```
 768 ATG GCG CCC CGC AGC GCC CGG CGA CCC CTG CTG CTG CTA CTG CTG TTG CTG CTG CTC GGC CTC ATG CAT TGT GCG TCA GCA
   1▸ M   A   P   R   S   A   R   R   P   L   L   L   L   L   L   L   L   L   L   G   L   M   H   C   A   S   A
   1▸ M   A   P   R   S   A   R   R   P   L   L   L   L   L   L   L   L   L   L   G   L   M   H   C   A   S   A
 849 GCA ATG TTT ATG GTG AAA AAT GGC AAC GGG ACC GCG TGC ATA ATG GCC AAC TTC TCT GCT GCC TTC TCA GTG AAC TAC GAC
  28▸ A   M   F   M   V   K   N   G   N   G   T   A   C   I   M   A   N   F   S   A   A   F   S   V   N   Y   D
  28▸ A   M   F   M   V   K   N   G   N   G   T   A   C   I   M   A   N   F   S   A   A   F   S   V   N   Y   D
 930 ACC AAG AGT GGC CCT AAG AAC ATG ACC CTT GAC CTG CCA TCA GAT GCC ACA GTG GTG CTC AAC CGC AGC TCC TGT GGA AAA
  55▸ T   K   S   G   P   K   N   M   T   L   D   L   P   S   D   A   T   V   V   L   N   R   S   S   C   G   K
  55▸ T   K   S   G   P   K   N   M   T   L   D   L   P   S   D   A   T   V   V   L   N   R   S   S   C   G   K
1011 GAG AAC ACT TCT GAC CCC AGT CTC GTG ATT GCT TTT GGA AGA GGA CAT ACA CTC ACT CTC AAT TTC ACG AGA AAT GCA ACA
  82▸ E   N   T   S   D   P   S   L   V   I   A   F   G   R   G   H   T   L   T   L   N   F   T   R   N   A   T
  82▸ E   N   T   S   D   P   S   L   V   I   A   F   G   R   G   H   T   L   T   L   N   F   T   R   N   A   T
1092 CGT TAC AGC GTT CAG CTC ATG AGT TTT GTT TAT AAC TTG TCA GAC ACA CAC CTT TTC CCC AAT GCG AGC TCC AAA GAA ATC
 109▸ R   Y   S   V   Q   L   M   S   F   V   Y   N   L   S   D   T   H   L   F   P   N   A   S   S   K   E   I
 109▸ R   Y   S   V   Q   L   M   S   F   V   Y   N   L   S   D   T   H   L   F   P   N   A   S   S   K   E   I
1173 AAG ACT GTG GAA TCT ATA ACT GAC ATC AGG GCA GAT ATA GAT AAA AAA TAC AGA TGT GTT AGT GGC ACC CAG GTC CAC ATG
 136▸ K   T   V   E   S   I   T   D   I   R   A   D   I   D   K   K   Y   R   C   V   S   G   T   Q   V   H   M
 136▸ K   T   V   E   S   I   T   D   I   R   A   D   I   D   K   K   Y   R   C   V   S   G   T   Q   V   H   M
1254 AAC AAC GTG ACC GTA ACG CTC CAT GAT GCC ACC ATC CAG GCG TAC CTT TCC AAC AGC AGC TTC AGC AGG GGA GGA ACA CGC
 163▸ N   N   V   T   V   T   L   H   D   A   T   I   Q   A   Y   L   S   N   S   S   F   S   R   G   E   T   R
 163▸ N   N   V   T   V   T   L   H   D   A   T   I   Q   A   Y   L   S   N   S   S   F   S   R   G   E   T   R
1335 TGT GAA CAA GAC AGG CCT TCC CCA ACC ACA GCG CCC CCT GCG CCA CCC AGC CCC TCG CCC TCA CCC GTG CCC AAG AGC CCC
 190▸ C   E   Q   D   R   P   S   P   T   T   A   P   P   A   P   P   S   P   S   P   S   P   V   P   K   S   P
 190▸ C   E   Q   D   R   P   S   P   T   T   A   P   P   A   P   P   S   P   S   P   S   P   V   P   K   S   P
1416 TCT GTG GAC AAG TAC AAC GTG AGC GGC ACC AAC GGG ACC TGC CTG CTG GCC AGC ATG GGG CTG CAG CTG AAC CTC ACC TAT
 217▸ S   V   D   K   Y   N   V   S   G   T   N   G   T   C   L   L   A   S   M   G   L   Q   L   N   L   T   Y
 217▸ S   V   D   K   Y   N   V   S   G   T   N   G   T   C   L   L   A   S   M   G   L   Q   L   N   L   T   Y
1497 GAG AGG AAG GAC AAC ACG ACG GTG ACA AGG CTT CTC AAC ATC AAC CCC AAC AAG ACC TCG GCC AGC GGG AGC TGC GGC GCC
 244▸ E   R   K   D   N   T   T   V   T   R   L   L   N   I   N   P   N   K   T   S   A   S   G   S   C   G   A
 244▸ E   R   K   D   N   T   T   V   T   R   L   L   N   I   N   P   N   K   T   S   A   S   G   S   C   G   A
1578 CAC CTG GTG ACT CTG GAG CTG CAC AGC GAG GGC ACC ACC GTC CTC CTC CAG TTC GGG ATG AAT GCA AGT TCT AGC CGG
 271▸ H   L   V   T   L   E   L   H   S   E   G   T   T   V   L   L   F   Q   F   G   M   N   A   S   S   S   R
 271▸ H   L   V   T   L   E   L   H   S   E   G   T   T   V   L   L   F   Q   F   G   M   N   A   S   S   S   R
1659 TTT TTC CTA CAA GGA ATC CAG TTG AAT ACA ATT CTT CCT GAC GCC AGA GAC CCT GCC TTT AAA GCT GCC AAC GGC TCC CTG
 298▸ F   F   L   Q   G   I   Q   L   N   T   I   L   P   D   A   R   D   P   A   F   K   A   A   N   G   S   L
 298▸ F   F   L   Q   G   I   Q   L   N   T   I   L   P   D   A   R   D   P   A   F   K   A   A   N   G   S   L
1740 CGA GCG CTG CAG GCC ACA GTC GGC AAT TCC TAC AAG TGC AAC GCG GAG GAG CAC GTC CGT GTC ACG GCG TTT TCA GTC
 325▸ R   A   L   Q   A   T   V   G   N   S   Y   K   C   N   A   E   E   H   V   R   V   T   K   A   F   S   V
 325▸ R   A   L   Q   A   T   V   G   N   S   Y   K   C   N   A   E   E   H   V   R   V   T   K   A   F   S   V
1821 AAT ATA TTC AAA GTG TGG GTC CAG GCT TTC AAG GTG GAA GGT GGC CAG TTT GGC TCT GTG GAG GAG TGT CTG CTG GAC GAG
 352▸ N   I   F   K   V   W   V   Q   A   F   K   V   E   G   G   Q   F   G   S   V   E   E   C   L   L   D   E
 352▸ N   I   F   K   V   W   V   Q   A   F   K   V   E   G   G   Q   F   G   S   V   E   E   C   L   L   D   E
1902 AAC AGC CTC GAG GAT ATC GTC ATC CCG ATG TTC TCG GCG CTC AGC GAG GGA GCG ACG CCG CAG GAC CTG AAC GCG GCC GTC
 379▸ N   S                 1▸  I   V   I   P   M   F   S   A   L   S   E   G   A   T   P   Q   D   L   N   A   A   V
 379▸ N   S   L   E   D   I   V   I   P   M   F   S   A   L   S   E   G   A   T   P   Q   D   L   N   A   A   V
1983 GGA GGT CAC CAG GCA GCG ATG CAG ATG CTG AAG GAC ACG ATC AAG GAG GCG GCC GAG TGG GAC CGG GCG GCA GCC GAG
  22▸ G   G   H   Q   A   A   M   Q   M   L   K   D   T   I   N   E   E   A   A   E   W   D   R   A   A   A   E
 406▸ G   G   H   Q   A   A   M   Q   M   L   K   D   T   I   N   E   E   A   A   E   W   D   R   A   A   A   E
2064 CCA CGC GGT TCC GAC ATC GCG GGC ACC ACC TCG ACG CTC CAG GAG CAG ATC GGG TGG GCC GCA GCT AAG CGC TGG ATC ATC
  49▸ P   R   G   S   D   I   A   G   T   T   S   T   L   Q   E   Q   I   G   W   A   A   A   K   R   W   I   I
 433▸ P   R   G   S   D   I   A   G   T   T   S   T   L   Q   E   Q   I   G   W   A   A   A   K   R   W   I   I
2145 CTC GGG CTG AAC AAG ATC GTC CGG ATG TAC AGC CCG ACG TCG ATC GCT GCT AAG TAC GTT GAC CGG TTC TAC AAG ACC CTG
  76▸ L   G   L   N   K   I   V   R   M   Y   S   P   T   S   I   A   A   K   Y   V   D   R   F   Y   K   T   L
 460▸ L   G   L   N   K   I   V   R   M   Y   S   P   T   S   I   A   A   K   Y   V   D   R   F   Y   K   T   L
2226 AGG GCC GAG CAG GCG GCC GGA CTG GAG GAG ATG ATG ACC GCG TGC CAG GGG GTC GGT GGA CCA GGG CAC AAG GCC GCG ATC
 103▸ R   A   E   Q   A   A   G   L   E   E   M   M   T   A   C   Q   G   V   G   G   P   G   H   K   A   A   I
 487▸ R   A   E   Q   A   A   G   L   E   E   M   M   T   A   C   Q   G   V   G   G   P   G   H   K   A   A   I
2307 TCG CCG CGC ACG CTG AAC GCG TGG GTG AAG GTC GGA TCC GAA TTC ACG CTG ATC CCC ATC GCT GTG GGT GCC CTG GCG
 130▸ S   P   R   T   L   N   A   W   V   K   V              1▸ T   L   I   P   I   A   V   G   G   A   L   A
 514▸ S   P   R   T   L   N   A   W   V   K   V   G   S   E   F   T   L   I   I   A   V   G   G   A   L   A
2388 GGG CTG GTC CTC ATC GTC CTC ATC GCC TAC CTC GTC GGC AGG AAG AGT CAC GCA GGC TAC CAG ACT ATC TAG ggtacctcta
  13▸ G   L   V   L   I   V   L   I   A   Y   L   V   G   R   K   R   S   H   A   G   Y   Q   T   I   *
 541▸ G   L   V   L   I   V   L   I   A   Y   L   V   G   R   K   R   S   H   A   G   Y   Q   T   I   *
```

```
2473 gGATCTGCTGTGCCTTCTAGTTGCCAGCCATCTGTTGTTTGCCCCTCCCCGTGCCTTCCTTGACCCTGGAAGGTGCCACTCCCACTGTCCTTTCCTAATAAAATGAGGA
2583 AATTGCATCGCATTGTCTGAGTAGGTGTCATTCTATTCTGGGGGGTGGGGTGGGGCAGGACAGCAAGGGGGAGGATTGGGAAGACAATAGCAGGCATGCTGGGGATGCGG
2693 TGGGCTCTATGGGTACCCAGGTGCTGAAGAATTGACCCGGTTCCTCCTGGGCCAGAAAGAAGCAGGCACATCCCCTTCTCTGTGACACACCCTGTCCACGCCCCTGGTTC
```

Figure 16b (con.)

```
2803 TTAGTTCCAGCCCCACTCATAGGACACTCATAGCTCAGGAGGGCTCCGCCTTCAATCCCACCCGCTAAAGTACTTGGAGCGGTCTCTCCCTCCCTCATCAGCCCACCAAA
2913 CCAAACCTAGCCTCCAAGAGTGGGAAGAAATTAAAGCAAGATAGGCTATTAAGTGCAGAGGGAGAGAAAATGCCTCCAACATGTGAGGAAGTAATGAGAGAAATCATAGA
3023 ATTTCTTCCGCTTCCTCGCTCACTGACTCGCTGCGCTCGGTCGTTCGGCTGCGGCGAGCGGTATCAGCTCACTCAAAGGCGGTAATACCGGTTATCCACAGAATCAGGGGA
3133 TAACGCAGGAAAGAACATGTGAGCAAAAGGCCAGCAAAAGGCCAGGAACCGTAAAAAGGCCGCGTTGCTGGCGTTTTTCCATAGGCTCCGCCCCCCTGACGAGCATCACA
3243 AAAATCGACGCTCAAGTCAGAGGTGGCGAAACCCGACAGGACTATAAAGATACCAGGCGTTTCCCCCTGGAAGCTCCCTCGTGCGCTCTCCTGTTCCGACCCTGCCGCTT
3353 ACCGGATACCTGTCCGCCTTTCTCCCTTCGGGAAGCGTGGCGCTTTCTCAATGCTCACGCTGTAGGTATCTCAGTTCGGTGTAGGTCGTTCGCTCCAAGCTGGGCTGTGT
3463 GCACGAACCCCCCGTTCAGCCCGACCGCTGCGCCTTATCCGGTAACTATCGTCTTGAGTCCAACCCGGTAAGACACGACTTATCGCCACTGGCAGCAGCCACTGGTAACA
3573 GGATTAGCAGAGCGAGGTATGTAGGCGGTGCTACAGAGTTCTTGAAGTGGTGGCCTAACTACGGCTACACTAGAAGAACAGTATTTGGTATCTGCGCTCTGCTGAAGCCA
3683 GTTACCTTCGGAAAAAGAGTTGGTAGCTCTTGATCCGGCAAACAAACCACCGCTGGTAGCGGTGGTTTTTTTGTTTGCAAGCAGCAGATTACGCGCAGAAAAAAAGGATC
3793 TCAAGAAGATCCTTTGATCTTTTCTACGGGGTCTGACGCTCAGTGGAACGAAAACTCACGTTAAGGGATTTTGGTCATGAGATTATCAAAAAGGATCTTCACCTAGATCC
3903 TTTTAAATTAAAAATGAAGTTTTAAATCAATCTAAAGTATATATGAGTAAACTTGGTCTGACAGTTACCAATGCTTAATCAGTGAGGCACCTATCTCAGCGATCTGTCTA
4013 TTTCGTTCATCCATAGTTGCCTGACTCGGGGGGGGGGGGGCGCTGAGGTCTGCCTCGTGAAGAAGGTGTTGCTGACTCATACCAGGCCTGAATCGCCCCATCATCCAGCC
4123 AGAAAGTGAGGGAGCCACGGTTGATGAGAGCTTTGTTGTAGGTGGACCAGTTGGTGATTTTGAACTTTTGCTTTGCCACGGAACGGTCTGCGTTGTCGGGAAGATGCGTG
4233 ATCTGATCCTTCAACTCAGCAAAAGTTCGATTTATTCAACAAAGCCGCCGTCCCGTCAAGTCAGCGTAATGCTCTGCCAGTGTTACAACCAATTAACCAATTCTGATTA
4342 GAA AAA CTC ATC GAG CAT CAA ATG AAA CTG CAA TTT ATT CAT ATC AGG ATT ATC AAT ACC ATA TTT TTG AAA AAG CCG TTT
271◀ F   F   E   D   L   M   L   H   F   Q   L   K   N   M   D   P   N   D   I   G   Y   K   Q   F   L   R   K
4423 CTG TAA TGA AGG AGA AAA CTC ACC GAG GCA GTT CCA TAG GAT GGC AAG ATC CTG GTA TCG GTC TGC GAT TCC GAC TCG TCC
244◀ Q   L   S   P   S   F   E   G   L   C   N   W   L   I   A   L   D   Q   Y   R   D   A   I   G   V   R   G
4504 AAC ATC AAT ACA ACC TAT TAA TTT CCC CTC GTC AAA AAT AAG GTT ATC AAG TGA GAA ATC ACC ATG AGT GAC GAC TGA ATC
217◀ V   D   I   C   G   I   L   K   G   E   D   F   I   L   N   D   L   S   F   D   G   H   T   V   V   S   D
4585 CGG TGA GAA TGG CAA AAG CTT ATG CAT TTC TTT CCA GAC TTG TTC AAC AGG CCA GCC ATT ACG CTC GTC ATC AAA ATC ACT
190◀ P   S   F   P   L   L   K   H   M   E   K   W   V   Q   E   V   P   W   G   N   R   E   D   D   F   D   S
4666 CGC ATC AAC CAA ACC GTT ATT CAT TCG TGA TTG CGC CTG AGC GAG ACG AAA TAC GCG ATC GCT GTT AAA AGG ACA ATT ACA
163◀ A   D   V   L   G   N   N   M   R   S   Q   A   Q   A   L   R   F   V   R   D   S   N   F   P   C   N   C
4747 AAC AGG AAT CGA ATG CAA CCG GCG CAG GAA CAC TGC CAG CGC ATC AAC AAT ATT TTC ACC TGA ATC AGG ATA TTC TTC TAA
136◀ V   P   I   S   H   L   R   R   L   F   V   A   L   A   D   V   I   N   E   G   S   D   P   Y   E   E   L
4828 TAC CTG GAA TGC TGT TTT CCC GGG GAT CGC AGT GGT GAG TAA CCA TGC ATC ATC AGG AGT ACG GAT AAA ATG CTT GAT GGT
109◀ V   Q   F   A   T   K   G   P   I   A   T   T   L   L   W   A   D   D   P   T   R   I   F   H   K   I   T
4909 CGG AAG AGG CAT AAA TTC CGT CAG CCA GTT TAG TCT GAC GAT CTC ATC TGT AAC ATC ATT GGC AAC GCT ACC TTT GCC ATG
82◀  P   L   P   M   F   E   T   L   W   N   L   R   V   M   E   D   T   V   D   N   A   V   S   G   K   G   H
4990 TTT CAG AAA CAA CTC TGG CGC ATC GGG CTT CCC ATA CAA TCG ATA GAT TGT CGC ACC TGA TTG CCC GAC ATT ATC GCG AGC
55◀  K   L   F   L   E   P   A   D   P   K   G   Y   L   R   Y   I   T   A   G   S   Q   G   V   N   D   R   A
5071 CCA TTT ATA CCC ATA TAA ATC CAT GTT GGA ATT TAA TCG CGG CCT GGA GCA AGA CGT TTC CCG TTG AAT ATG GCT
28◀  W   K   Y   G   Y   L   D   A   D   M   N   S   N   L   R   P   R   S   C   S   T   E   R   Q   I   H   S
5152 CAT AACACCCCTTGTATTACTGTTTATGTAAGCAGACAGTTTTATTGTTCATGATGATATATTTTTATCTTGTGCAATGTAACATCAGAGATTTTGAGACACAACGTGG
1◀   M
5261 CTTTCCCCCCCCCCCCATTATTGAAGCATTTATCAGGGTTATTGTCTCATGAGCGGATACATATTTGAATGTATTTAGAAAAATAAACAAATAGGGGTTCCGCGCACATT
5371 TCCCCGAAAAGTGCCACCTGACGTCTAAGAAACCATTATTATCGACATTAACCTATAAAAATAGGCGTATCACGAGGCCCTTCGTCTCGCGCGTTTCGGTGATGACG
5481 GTGAAAACCTCTGACACATGCAGCTCCCGGAGACGGTCACAGCTTGTCTGTAAGCGGATGCCGGGAGCAGACAAGCCCGTCAGGGCGCGTCAGCGGGTGTTGGCGGGTGT
5591 CGGGGCTGGCTTAACTATGCGGCATCAGAGCAGATTGTACTGAGAGTGCACCATATGCGGTGTGAAATACCGCACAGATGCGTAAGGAGAAAATACCGCATCAGATTGGC
5701 TATTGG
```

Figure 17b

```
   1 CCTGGCCATTGCATACGTTGTATCCATATCATAATATGTACATTTATATTGGCTCATGTCCAACATTACCGCCATGTTGACATTGATTATTGACTAGTTATTAATAGTAA
 111 TCAATTACGGGGTCATTAGTTCATAGCCCATATATGGAGTTCCGCGTTACATAACTTACGGTAAATGGCCCGCCTGGCTGACCGCCCAACGACCCCCGCCCATTGACGTC
 221 AATAATGACGTATGTTCCCATAGTAACGCCAATAGGGACTTTCCATTGACGTCAATGGGTGGAGTATTTACGGTAAACTGCCCACTTGGCAGTACATCAAGTGTATCATA
 331 TGCCAAGTACGCCCCCTATTGACGTCAATGATGGTAAATGGCCCGCCTGGCATTATGCCCAGTACATGACCTTATGGGACTTTCCTACTTGGCAGTACATCTACGTATTA
 441 GTCATCGCTATTACCATGGTGATGCGGTTTTGGCAGTACATCAATGGGCGTGGATAGCGGTTTGACTCACGGGGATTTCCAAGTCTCCACCCCATTGACGTCAATGGGAG
 551 TTTGTTTTGGCACCAAAATCAACGGGACTTTCCAAAATGTCGTAACAACTCCGCCCCATTGACGCAAATGGGCGGTAGGCGTGTACGGTGGGAGGTCTATATAAGCAGAG
 661 CTCGTTTAGTGAACCGTCAGATCGCCTGGAGACGCCATCCACGCTGTTTTGACCTCCATAGAAGACACCGGGACCGATCCAGCCTCCGCGGGcgcgcgtcgacaagaa
 769 ATG TGG AAG CCG ATG CCC TCG CCA AGC AAC ATG AAG GCG TCC GCC GCG CTC CTG TGC CTG CTC CTC ACG GCC GCG GCT TTC
  1▶ M   W   K   P   M   P   S   P   S   N   M   K   A   S   A   A   L   L   C   L   L   L   T   A   A   A   F
  1▶ M   W   K   P   M   P   S   P   S   N   M   K   A   S   A   A   L   L   C   L   L   L   T   A   A   A   F
 850 AGC CCC CAG GGG CTC GCG CAG CCG GTC GGG ATC AAC ACG AGC ACG ACC TGC TGC TAC CGG TTC ATC AAC AAG AAG ATC CCG
 28▶ S   P   Q   G   L   A   Q   P   V   G   I   N   T   S   T   T   C   C   Y   R   F   I   N   K   K   I   P
 28▶ S   P   Q   G   L   A   Q   P   V   G   I   N   T   S   T   T   C   C   Y   R   F   I   N   K   K   I   P
 931 AAG CAG CGT CTG GAG AGC TAC CGC CGG ACC ACG TCG AGC CAC TGC CCG GAG GCG GTC ATC TTC AAG ACG AAG CTG GAC
 55▶ K   Q   R   L   E   S   Y   R   R   T   T   S   S   H   C   P   R   E   A   V   I   F   K   T   K   L   D
 55▶ K   Q   R   L   E   S   Y   R   R   T   T   S   S   H   C   P   R   E   A   V   I   F   K   T   K   L   D
1012 AAG GAG ATC TGC GCC GAC CCG ACG CAG AAG TGG GTT CAG GAC TTC ATG AAG CAC CTG GAC AAG AAG ACG CAG ACG CCG AAG
 82▶ K   E   I   C   A   D   P   T   Q   K   W   V   Q   D   F   M   K   H   L   D   K   K   T   Q   T   P   K
 82▶ K   E   I   C   A   D   P   T   Q   K   W   V   Q   D   F   M   K   H   L   D   K   K   T   Q   T   P   K
1093 CTG GTC ATC CCG ATG TTC TCG GCG CTC AGC GAG GGA GCG ACG CCG CAG GAC CTG AAC GCG GCC GTC GGA GGT CAC CAG GCA
109▶ L
  1▶ V   I   P   M   F   S   A   L   S   E   G   A   T   P   Q   D   L   N   A   A   V   G   G   H   Q   A
109▶ L   V   I   P   M   F   S   A   L   S   E   G   A   T   P   Q   D   L   N   A   A   V   G   G   H   Q   A
1174 GCG ATG CAG ATG CTG AAG GAC ACG ATC AAC GAG GAG GCG GCC GAG TGG GAC CGG GCG GCA GCC GAG CCA CGC GGT TCC GAC
 27▶ A   M   Q   M   L   K   D   T   I   N   E   E   A   A   E   W   D   R   A   A   A   E   P   R   G   S   D
136▶ A   M   Q   M   L   K   D   T   I   N   E   E   A   A   E   W   D   R   A   A   A   E   P   R   G   S   D
1255 ATC GCG GGC ACC ACC TCG ACG CTC CAG GAG CAG ATC GGG TGG GCC GCA GCT AAG CGC TGG ATC ATC CTC GGG CTG AAC AAG
 54▶ I   A   G   T   T   S   T   L   Q   E   Q   I   G   W   A   A   A   K   R   W   I   I   L   G   L   N   K
163▶ I   A   G   T   T   S   T   L   Q   E   Q   I   G   W   A   A   A   K   R   W   I   I   L   G   L   N   K
1336 ATC GTC CGG ATG TAC AGC CCG ACG TCG ATC GCT GCT AAG TAC GTT GAC CGG TTC TAC AAG ACC CTG AGG GCC AGC CAG GCG
 81▶ I   V   R   M   Y   S   P   T   S   I   A   A   K   Y   V   D   R   F   Y   K   T   L   R   A   E   Q   A
190▶ I   V   R   M   Y   S   P   T   S   I   A   A   K   Y   V   D   R   F   Y   K   T   L   R   A   E   Q   A
1417 GCC GGA CTG GAG GAG ATG ATG ACC GCG TGC CAG GGG GTC GGT GGA CCA GGG CAC AAG GCC GCG ATC TCG CCG CGC ACG CTG
108▶ A   G   L   E   E   M   M   T   A   C   Q   G   V   G   G   P   G   H   K   A   A   I   S   P   R   T   L
217▶ A   G   L   E   E   M   M   T   A   C   Q   G   V   G   G   P   G   H   K   A   A   I   S   P   R   T   L
1498 AAC GCG TGG GTG AAG GTC TGA TAA gaattcgcggatatcggttaacggatccaGATCTGCTGTGCCTTCTAGTTGCCAGCCATCTGTTGTTTGCCCCTCCCC
135▶ N   A   W   V   K   V   •   •
244▶ N   A   W   V   K   V   •   •
1600 CGTGCCTTCCTTGACCCTGGAAGGTGCCACTCCCACTGTCCTTTCCTAATAAAATGAGGAAATTGCATCGCATTGTCTGAGTAGGTGTCATTCTATTCTGGGGGGTGGGG
1710 TGGGGCAGGACAGCAAGGGGGAGGATTGGGAAGACAATAGCAGGCATGCTGGGGATGCGGTGGGCTCTATGGGTACCCAGGTGCTGAAGAATTGACCCGCTTCCTCCTGG
1820 GCCAGAAAGAAGCAGGCACATCCCCTTCTCTGTGACACACCCTGTCCACGCCCCTGGTTCTTAGTTCCAGCCCCACTCATAGGACACTCATAGCTCAGGAGGGCTCCGCC
1930 TTCAATCCCACCCGCTAAAGTACTTGGAGCGGTCTCTCCCTCCCTCATCAGCCCACCAAACCAAACCTAGCCTCCAAGAGTGGGAAGAAATTAAAGCAAGATAGGCTATT
2040 AAGTGCAGAGGGAGAGAAAATGCCTCCAACATGTGAGGAAGTAATGAGAGAAATCATAGAATTTCTTCCGCTTCCTCGCTCACTGACTCGCTGCGCTCGGTCGTTCGGCT
2150 GCGGCGAGCGGTATCAGCTCACTCAAAGGCGGTAATACGGTTATCCACAGAATCAGGGGATAACGCAGGAAAGAACATGTGAGCAAAAGGCCAGCAAAAGGCCAGGAACC
2260 GTAAAAAGGCCGCGTTGCTGGCGTTTTTCCATAGGCTCCGCCCCCCTGACGAGCATCACAAAAATCGACGCTCAAGTCAGAGGTGGCGAAACCCGACAGGACTATAAAGA
2370 TACCAGGCGTTTCCCCCTGGAAGCTCCCTCGTGCGCTCTCCTGTTCCGACCCTGCCGCTTACCGGATACCTGTCCGCCTTTCTCCCTTCGGGAAGCGTGGCGCTTTCTCA
2480 TAGCTCACGCTGTAGGTATCTCAGTTCGGTGTAGGTCGTTCGCTCCAAGCTGGGCTGTGTGCACGAACCCCCCGTTCAGCCCGACCGCTGCGCCTTATCCGGTAACTATC
2590 GTCTTGAGTCCAACCCGGTAAGACACGACTTATCGCCACTGGCAGCAGCCACTGGTAACAGGATTAGCAGAGCGAGGTATGTAGGCGGTGCTACAGAGTTCTTGAAGTGG
2700 TGGCCTAACTACGGCTACACTAGAAGAACAGTATTTGGTATCTGCGCTCTGCTGAAGCCAGTTACCTTCGGAAAAAGAGTTGGTAGCTCTTGATCCGGCAAACAAACCAC
2810 CGCTGGTAGCGGTGGTTTTTTTGTTTGCAAGCAGCAGATTACGCGCAGAAAAAAAGGATCTCAAGAAGATCCTTTGATCTTTTCTACGGGGTCTGACGCTCAGTGGAACG
2920 AAAACTCACGTTAAGGGATTTTGGTCATGAGATTATCAAAAAGGATCTTCACCTAGATCCTTTTAAATTAAAAATGAAGTTTTAAATCAATCTAAAGTATATATGAGTAA
3030 ACTTGGTCTGACAGTTACCAATGCTTAATCAGTGAGGCACCTATCTCAGCGATCTGTCTATTTCGTTCATCCATAGTTGCCTGACTCGGGGGGGGGGGCGCTGAGGTCT
3140 GCCTCGTGAAGAAGGTGTTGCTGACTCATACCAGGCCTGAATCGCCCCATCATCCAGCCAGAAAGTGAGGGAGCCACGGTTGATGAGAGCTTTGTTGTAGGTGGACCAGT
3250 TGGTGATTTTGAACTTTTGCTTTGCCACGGAACGGTCTGCGTTGTCGGGAAGATGCGTGATCTGATCCTTCAACTCAGCAAAAGTTCGATTTATTCAACAAAGCCGCCGT
3360 CCCGTCAAGTCAGCGTAATGCTCTGCCAGTGTTACAACCAATTAACCAATTCTGATTAGAAAAACTCATCGAGCATCAAATGAAACTGCAATTTATTCATATCAGGATTA
271◀ F   F   E   D   L   M   L   H   F   Q   L   K   N   M   D   P   N
3470 TCAATACCCATATTTTTGAAAAAGCCGTTTCTGTAATGAAGGAGAAAACTCACCGAGGCAGTTCCATAGGATGGCAAGATCCTGGTATCGGTCTGCGATTCCGACTCGTCC
253◀ D   I   G   Y   K   Q   F   L   R   K   Q   L   S   P   S   F   E   G   L   C   N   W   L   I   A   L   D   Q   Y   R   D   A   I   G   V   R   G
3580 AACATCAATACAACCTATTAATTTCCCCTCGTCAAAAATAAGGTTATCAAGTGAGAAATCACCATGAGTGACGACTGAATCCGGTGAGAATGGCAAAAGCTTATGCATTT
217◀ V   D   I   C   G   I   L   K   G   E   D   F   I   L   N   D   L   S   F   D   G   H   T   V   V   S   D   P   S   F   P   L   L   K   H   M   E
3690 CTTTCCAGACTTGTTCAACAGGCCAGCCATTACGCTCGTCATCAAAATCACTCGCATCAACCAAACCGTTATTCATTCGTGATTGCGCCTGAGCGAGACGAAATACGCGA
180◀ K   W   V   Q   E   V   P   W   G   N   R   E   D   D   F   D   S   A   D   V   L   G   N   N   M   R   S   Q   A   Q   A   L   R   F   V   R
```

Figure 17b (con.)

```
3800 TCGCTGTTAAAAGGACAATTACAAACAGGAATCGAATGCAACCGGCGCAGGAACACTGCCAGCGCATCAACAATATTTTCACCTGAATCAGGATATTCTTCTAATACCTG
1434 D  S  N  F  P  C  N  C  V  P  I  S  H  L  R  R  L  F  V  A  L  A  D  V  I  N  E  G  S  D  P  Y  E  E  L  V  Q
3910 GAATGCTGTTTTCCCGGGGATCGCAGTGGTGAGTAACCATGCATCATCAGGAGTACGGATAAAATGCTTGATGGTCGGAAGAGGCATAAATTCCGTCAGCCAGTTTAGTC
1074 F  A  T  K  G  P  I  A  T  T  L  L  W  A  D  D  P  T  R  I  F  H  K  I  T  P  L  P  M  F  E  T  L  W  N  L  R
4020 TGACCATCTCATCTGTAACATCATTGGCAACGCTACCTTTGCCATGTTTCAGAAACAACTCTGGCGCATCGGGCTTCCCATACAATCGATAGATTGTCGCACCTGATTGC
704  V  M  E  D  T  V  D  N  A  V  S  G  K  G  H  K  L  F  L  E  P  A  D  P  K  G  Y  L  R  Y  I  T  A  G  S  Q
4130 CCGACATTATCGCGAGCCCATTTATACCCATATAAATCAGCATCCATGTTGGAATTTAATCGCGGCCTCGAGCAAGACGTTTCCCGTTGAATATGGCTCATAACACCCCT
334  G  V  N  D  R  A  W  K  Y  G  Y  L  D  A  D  M  N  S  N  L  R  P  R  S  C  S  T  E  R  Q  I  H  S  M
4240 TGTATTACTGTTTATGTAAGCAGACAGTTTTATTGTTCATGATGATATATTTTTATCTTGTGCAATGTAACATCAGAGATTTTGAGACACAACGTGGCTTTCCCCCCCCC
4350 CCCATTATTGAAGCATTTATCAGGGTTATTGTCTCATGAGCGGATACATATTTGAATGTATTTAGAAAAATAAACAAATAGGGGTTCCGCGCACATTTCCCCGAAAAGTG
4460 CCACCTGACGTCTAAGAAACCATTATTATCATGACATTAACCTATAAAAATAGGCGTATCACGAGGCCCTTTCGTCTCGCGCGTTTCGGTGATGACGGTGAAAACCTCTG
4570 ACACATGCAGCTCCCGGAGACGGTCACAGCTTGTCTGTAAGCGGATGCCGGGAGCAGACAAGCCCGTCAGGGCGCGTCAGCGGGTGTTGGCGGGTGTCGGGGCTGGCTTA
4680 ACTATGCGGCATCAGAGCAGATTGTACTGAGAGTGCACCATATGCGGTGTGAAATACCGCACAGATGCGTAAGGAGAAAATACCGCATCAGATTGGCTATTGG
```

Figure 18b

```
   1 CCTGGCCATTGCATACGTTGTATCCATATCATAATATGTACATTTATATTGGCTCATGTCCAACATTACCGCCATGTTGACATTGATTATTGACTAGTTA
 101 TTAATAGTAATCAATTACGGGGTCATTAGTTCATAGCCCATATATGGAGTTCCGCGTTACATAACTTACGGTAAATGGCCCGCCTGGCTGACCGCCCAAC
 201 GACCCCCGCCCATTGACGTCAATAATGACGTATGTTCCCATAGTAACGCCAATAGGGACTTTCCATTGACGTCAATGGGTGGAGTATTTACGGTAAACTG
 301 CCCACTTGGCAGTACATCAAGTGTATCATATGCCAAGTACGCCCCCTATTGACGTCAATGATGGTAAATGGCCCGCCTGGCATTATGCCCAGTACATGAC
 401 CTTATGGGACTTTCCTACTTGGCAGTACATCTACGTATTAGTCATCGCTATTACCATGGTGATGCGGTTTTGGCAGTACATCAATGGGCGTGGATAGCGG
 501 TTTGACTCACGGGGATTTCCAAGTCTCCACCCCATTGACGTCAATGGGAGTTTGTTTTGGCACCAAAATCAACGGGACTTTCCAAAATGTCGTAACAACT
 601 CCGCCCCATTGACGCAAATGGGCGGTAGGCGTGTACGGTGGGAGGTCTATATAAGCAGAGCTCGTTTAGTGAACCGTCAGATCGCCTGGAGACGCCATCC
 701 ACGCTGTTTTGACCTCCATAGAAGACACCGGGACCGATCCAGCCTCCGCGGGcgcgcgtcgacaagaa ATG TGG AAG CCG ATG CCC TCG CCA
                                                              ─────────────────────▶
                                                                1▶ M   W   K   P   M   P   S   P
                                                                1▶ M   W   K   P   M   P   S   P
 793 AGC AAC ATG AAG GCG TCC GCC GCG CTC CTG TGC CTG CTC ACG GCC GCG GCT TTC AGC CCC CAG GGG CTC GCG
   9▶ S   N   M   K   A   S   A   A   A   L   L   C   L   L   L   T   A   A   A   F   S   P   Q   G   L   A
   9▶ S   N   M   K   A   S   A   A   A   L   L   C   L   L   L   T   A   A   A   F   S   P   Q   G   L   A
 868 CAG CCG GTC GGG ATC AAC ACG AGC ACG ACC TGC TGC TAC CGG TTC ATC AAC AAG AAG ATC CCG AAG CAG CGT CTG
  34▶ Q   P   V   G   I   N   T   S   T   T   C   C   Y   R   F   I   N   K   K   I   P   K   Q   R   L
  34▶ Q   P   V   G   I   N   T   S   T   T   C   C   Y   R   F   I   N   K   K   I   P   K   Q   R   L
 943 GAG AGC TAC CGC GAC ACG ACG TCG AGC CAC TGC CCG CGG GAG GCG GTC ATC TTC AAG ACG AAG CTG GAC AAG GAG
  59▶ E   S   Y   R   R   T   T   S   S   H   C   P   R   E   A   V   I   F   K   T   K   L   D   K   E
  59▶ E   S   Y   R   R   T   T   S   S   H   C   P   R   E   A   V   I   F   K   T   K   L   D   K   E
1018 ATC TGC GCC GAC CCG ACG CAG AAG TGG GTT CAG GAC TTC ATG AAG CAC CTG GAC AAG AAG ACG CAG ACG CCG AAG
  84▶ I   C   A   D   P   T   Q   K   W   V   Q   D   F   M   K   H   L   D   K   K   T   Q   T   P   K
  84▶ I   C   A   D   P   T   Q   K   W   V   Q   D   F   M   K   H   L   D   K   K   T   Q   T   P   K
1093 CTG GTC ATC CCG ATG TTC ACG GCG CTC AGC GAG GGA GCG ACG CCG CAG GAC CTG AAC GCG GCC GTC GGA GGT CAC
 109▶ L   V   I   P   M   F   T   A   L   S   E   G   A   T   P   Q   D   L   N   A   A   V   G   G   H
 109▶ L   V   I   P   M   F   T   A   L   S   E   G   A   T   P   Q   D   L   N   A   A   V   G   G   H
1168 CAG GCA GCG ATG CAG ATG CTG AAG GAG ACG ATC AAC GAG GAG GCG GCC GAG TGG GAC CGG GCG GCA GCC GAG CCA
  25▶ Q   A   A   M   Q   M   L   K   E   T   I   N   E   E   A   A   E   W   D   R   A   A   A   E   P
 134▶ Q   A   A   M   Q   M   L   K   E   T   I   N   E   E   A   A   E   W   D   R   A   A   A   E   P
1243 CGC GGT TCC GAC ATC GCG GGC ACC ACC TCG ACG CTC CAG GAG CAG ATC GCG TGG GCC GCA GCT AAG CGC TGG ATC
  50▶ R   G   S   D   I   A   G   T   T   S   T   L   Q   E   Q   I   A   W   A   A   A   K   R   W   I
 159▶ R   G   S   D   I   A   G   T   T   S   T   L   Q   E   Q   I   A   W   A   A   A   K   R   W   I
1318 ATC CTC GGG CTG AAC AAG ATC GTC CGG ATG TAC AGC CCG GTC TCG ATC GCT GCT AAG TAC GTT GAC CGG TTC TTC
  75▶ I   L   G   L   N   K   I   V   R   M   Y   S   P   V   S   I   A   A   K   Y   V   D   R   F   F
 184▶ I   L   G   L   N   K   I   V   R   M   Y   S   P   V   S   I   A   A   K   Y   V   D   R   F   F
1393 AAG ACC CTG AGG GCC GAG CAG GCG GCC GGA CTG GAG GAG ATG ATG ACC GCG TGC CAG GGG GTC GGT GGA CCA TCG
 100▶ K   T   L   R   A   E   Q   A   A   G   L   E   E   M   M   T   A   C   Q   G   V   G   G   P   S
 209▶ K   T   L   R   A   E   Q   A   A   G   L   E   E   M   M   T   A   C   Q   G   V   G   G   P   S
1468 CAC AAG GCC GCG CTC TCG CCG CGC ACG CTG AAC GCG TGG GTG AAG GTC TGA TAA gaattcgcggatatcggttaacggatcc
 125▶ H   K   A   A   L   S   P   R   T   L   N   A   W   V   K   V   •   •
 234▶ H   K   A   A   L   S   P   R   T   L   N   A   W   V   K   V   •   •
1550 aGATCTGCTGTGCCTTCTAGTTGCCAGCCATCTGTTGTTTGCCCCTCCCCCGTGCCTTCCTTGACCCTGGAAGGTGCCACTCCCACTGTCCTTTCCTAAT
1650 AAAATGAGGAAATTGCATCGCATTGTCTGAGTAGGTGTCATTCTATTCTGGGGGGTGGGTGGGGCAGGACAGCAAGGGGCAGGATTGGGAAGACAATAG
1750 CAGGCATGCTGGGGATGCGGTGGGCTCTATGGGTACCCAGGTGCTGAAGAATTGACCCGGTTCCTCCTGGGCCAGAAAGAAGCAGGCACATCCCCTTCTC
1850 TGTGACACACCCTGTCCACGCCCCTGGTTCTTAGTTCCAGCCCCACTCATAGGACACTCATAGCTCAGGAGGGCTCCGCCTTCAATCCCACCCGCTAAAG
1950 TACTTGGAGCGGTCTCTCCCTCCCTCATCAGCCCACCAAACCAAACCTAGCCTCCAAGAGTGGGAAGAAATTAAAGCAAGATAGGCTATTAAGTGCAGAG
2050 GGAGAGAAAATGCCTCCAACATGTGAGGAAGTAATGAGAGAAATCATAGAATTTCTTCCGCTTCCTCGCTCACTGACTCGCTGCGCTCGGTCGTTCGGCT
                                                                                    ───────────────────▶
2150 GCGGCGAGCGGTATCAGCTCACTCAAAGGCGGTAATACGGTTATCCACAGAATCAGGGGATAACGCAGGAAAGAACATGTGAGCAAAAGGCCAGCAAAAG
2250 GCCAGGAACCGTAAAAAGGCCGCGTTGCTGGCGTTTTTCCATAGGCTCCGCCCCCTGACGAGCATCACAAAAATCGACGCTCAAGTCAGAGGTGGCGAA
2350 ACCCGACAGGACTATAAAGATACCAGGCGTTTCCCCCTGGAAGCTCCCTCGTGCGCTCTCCTGTTCCGACCCTGCCGCTTACCGGATACCTGTCCGCCTT
2450 TCTCCCTTCGGGAAGCGTGGCGCTTTCTCATAGCTCACGCTGTAGGTATCTCAGTTCGGTGTAGGTCGTTCGCTCCAAGCTGGGCTGTGTGCACGAACCC
2550 CCCGTTCAGCCCGACCGCTGCGCCTTATCCGGTAACTATCGTCTTGAGTCCAACCCGGTAAGACACGACTTATCGCCACTGGCAGCAGCCACTGGTAACA
2650 GGATTAGCAGAGCGAGGTATGTAGGCGGTGCTACAGAGTTCTTGAAGTGGTGGCCTAACTACGGCTACACTAGAAGAACAGTATTTGGTATCTGCGCTCT
2750 GCTGAAGCCAGTTACCTTCGGAAAAAGAGTTGGTAGCTCTTGATCCGGCAAACAAACCACCGCTGGTAGCGGTGGTTTTTTTGTTTGCAAGCAGCAGATT
2850 ACGCGCAGAAAAAAAGGATCTCAAGAAGATCCTTTGATCTTTTCTACGGGGTCTGACGCTCAGTGGAACGAAAACTCACGTTAAGGGATTTTGGTCATGA
2950 GATTATCAAAAAGGATCTTCACCTAGATCCTTTTAAATTAAAAATGAAGTTTTAAATCAATCTAAAGTATATATGAGTAAACTTGGTCTGACAGTTACCA
3050 ATGCTTAATCAGTGAGGCACCTATCTCAGCGATCTGTCTATTTCGTTCATCCATAGTTGCCTGACTCGGGGGGGGGGGCGCTGAGGTCTGCCTCGTGAA
3150 GAAGGTGTTGCTGACTCATACCAGGCCTGAATCGCCCCATCATCCAGCCAGAAAGTGAGGGAGCCACGGTTGATGAGAGCTTTGTTGTAGGTGGACCAGT
3250 TGGTGATTTTGAACTTTTGCTTTGCCACGGAACGGTCTGCGTTGTCGGGAAGATGCGTGATCTGATCCTTCAACTCAGCAAAAGTTCGATTTATTCAACA
3350 AAGCCGCCGTCCCGTCAAGTCAGCGTAATGCTCTGCCAGTGTTACAACCAATTAACCAATTCTGATTAGAAAAACTCATCGAGCATCAAATGAAACTGCA
                                                                                   2711◀ F   F   E   D   L   M   L   H   F   Q   L
3450 ATTTATTCATATCAGGATTATCAATACCATATTTTTGAAAAAGCCGTTTCTGTAATGAAGGAGAAAACTCACCGAGGCAGTTCCATAGGATGGCAAGATC
 260◀ K   N   M   D   P   N   D   I   G   Y   K   Q   F   L   R   K   Q   L   S   P   S   F   E   G   L   C   N   W   L   I   A   L   D
3550 CTGGTATCGGTCTGCGATTCCGACTCGTCCAACATCAATACAACCTATTAATTTCCCCTCGTCAAAATAAGGTTATCAAGTGAGAAATCACCATGAGTG
 227◀ Q   Y   R   D   A   I   G   V   R   G   V   D   I   C   G   I   L   K   G   E   D   F   I   L   N   D   L   S   F   D   G   H   T
3650 ACGACTGAATCCGGTGAGAATGGCAAAAGCTTATGCATTTCTTTCCAGACTTGTTCAACAGGCCAGCCATTACGCTCGTCATCAAAATCACTCGCATCAA
 193◀ V   V   S   D   P   S   F   P   L   L   K   H   M   E   K   W   V   Q   E   V   P   W   G   N   R   E   D   D   F   D   S   A   D   V
3750 CCAAACCGTTATTCATTCGTGATTGCGCCTGAGCGAGACGAAATACGCGATCGCTGTTAAAAGGACAATTACAAACAGGAATCGAATGCAACCGGCGCAG
 160◀ L   G   N   N   M   R   S   Q   A   A   Q   A   L   R   F   V   R   D   S   N   F   P   C   N   C   V   P   I   S   H   L   R   R   L
3850 GAACACTGCCAGCGCATCAACAATATTTTCACCTGAATCAGGATATTCTTCTAATACCTGGAATGCTGTTTTCCCGGGGATCGCAGTGGTGAGTAACCAT
 127◀ F   V   A   L   A   D   V   I   N   E   G   S   D   P   Y   E   E   L   V   Q   F   A   T   K   G   P   I   A   T   T   L   L   W
```

Figure 18b (con.)

```
3950 GCATCATCAGGAGTACGGATAAAATGCTTGATGGTCGGAAGAGGCATAAATTCCGTCAGCCAGTTTAGTCTGACCATCTCATCTGTAACATCATTGGCAA
 934 A  D  D  P  T  R  I  F  H  K  I  T  P  L  P  M  F  E  T  L  W  N  L  R  V  M  E  D  T  V  D  N  A  V
4050 CGCTACCTTTGCCATGTTTCAGAAACAACTCTGGCGCATCGGGCTTCCCATACAATCGATAGATTGTCGCACCTGATTGCCCGACATTATCGCGAGCCCA
 604 S  G  K  G  H  K  L  F  L  E  P  A  D  P  K  G  Y  L  R  Y  I  T  A  G  S  Q  G  V  N  D  R  A  W
4150 TTTATACCCATATAAATCAGCATCCATGTTGGAATTTAATCGCGGCCTCGAGCAAGACGTTTCCCGTTGAATATGGCTCATAACACCCCTTGTATTACTG
 274 K  Y  G  Y  L  D  A  D  M  N  S  N  L  R  P  R  S  C  S  T  E  R  Q  I  H  S  M
4250 TTTATGTAAGCAGACAGTTTTATTGTTCATGATGATATATTTTTATCTTGTGCAATGTAACATCAGAGATTTTGAGACACAACGTGGCTTTCCCCCCCCC
4350 CCCATTATTGAAGCATTTATCAGGGTTATTGTCTCATGAGCGGATACATATTTGAATGTATTTAGAAAAATAAACAAATAGGGGTTCCGCGCACATTTCC
4450 CCGAAAAGTGCCACCTGACGTCTAAGAAACCATTATTATCATGACATTAACCTATAAAAATAGGCGTATCACGAGGCCCTTTCGTCTCGCGCGTTTCGGT
4550 GATGACGGTGAAAACCTCTGACACATGCAGCTCCCGGAGACGGTCACAGCTTGTCTGTAAGCGGATGCCGGGAGCAGACAAGCCCGTCAGGGCGCGTCAG
4650 CGGGTGTTGGCGGGTGTCGGGGCTGGCTTAACTATGCGGCATCAGAGCAGATTGTACTGAGAGTGCACCATATGCGGTGTGAAATACCGCACAGATGCGT
4750 AAGGAGAAAATACCGCATCAGATTGGCTATTGG
```

Figure 19b

METHOD OF ALTERING THE IMMUNDOMINANCE HIERARCHY OF HIV GAG BY DNA VACCINE EXPRESSING CONSERVED REGIONS

CROSS-REFERENCE TO RELATED APPLICATIONS

This application is a National Stage of International Application No. PCT/US2013/028932, filed Mar. 4, 2013, and which claims the benefit of U.S. provisional application No. 61/606,265 filed Mar. 2, 2012, which is herein incorporated by reference for all purposes.

BACKGROUND OF THE INVENTION

HIV-1 strains are highly variable and this diversity provides a major challenge for vaccine design. A candidate vaccine should provide protection against most clades of HIV. To address this problem, approaches to maximizing immunological strength and breadth are being explored, including strategies that use consensus, center-of-tree or ancestral sequences, multiple strains or mosaic immunogens, immunogens consisting of known epitopes from the database, and chimeric, molecules expressing a selection of the most conserved epitopes from different clades of HIV [1-17, 56, 96 ].

REFERENCE TO SEQUENCE LISTING

This application includes a Sequence Listing as a text file named "77867-913960-606100US-SEQLIST.txt" created Jul. 30, 2014, and containing 104,770 bytes. The material contained in this text file is incorporated by reference in its entirety for all purposes.

In addition to sequence diversity, the presence of potential immunodominant epitopes provides another hurdle in the development of effective HIV vaccines. Accumulating evidence indicates that immunodominant epitopes exist, and that they may constitute an impediment for the production of effective universal HIV vaccines [18-31], as subdominant epitopes within HIV proteins have generally been associated with virologic control [19,22]. The use of any gene encompassing a complete protein as immunogen contains variable as well as conserved regions. Since variable sequences can mutate to escape immune responses while retaining function, and can contain immunodominant T cell epitopes, we argue that variable segments should be excluded from the design [32]. Our vaccine approach thus focuses on the induction of immune responses to nearly invariable proteome segments, many of which should be essential for the function of the virus, and the prevention of responses against variable segments and potentially immunodominant "decoy" epitopes [32-34].

The conserved element approach is supported by the following observations: (i) Viral proteins recover ancestral amino acid (AA) states when transmitted to a new host [35], and in the absence of the specific immune responses found in the previous host, they can recover a more fit state [36-38]; (ii) changes in conserved AA of viral proteins can destroy or significantly weaken HIV, indicating a critical role in virus biology [39-42]; (iii) CTL responses against specific viral proteins (e.g., Gag) are associated with relative control of viremia [43-50], and in the case of controllers and long-term non-progressors, high avidity CTLs targeting conserved regions have been identified [34,51]; (iv) immunodominance of some epitopes can obscure or prevent reactivity against other, potentially protective epitopes [52]; (v) some AA segments in viral proteins are conserved throughout a given HIV-1 subtype, the entire group M, and, in some instances, in HIV-2 and SIV [32,53]. Together, these considerations predicted that an HIV vaccine that does not contain variable epitopes, and thus lacks potentially immunodominant decoy epitopes, but instead consists of strictly, conserved proteome elements is better fit to induce immune responses able to prevent virus acquisition or virus propagation [32,53]. The conserved elements used in our work differ from those used by others [11,12,16,17,54-56] that were selected using different criteria, as we have focused on both conservation and associations of particular sequences with immune control.

Previous work has been performed using Gag as a prototype vaccine, because Gag-specific T cell responses were found to correlate with control of viremia in clade B and C infected individuals [43,48-50]. Seven highly conserved elements (CE) were identified in HIV-1 $p24^{gag}$ [32,34] (see also FIG. 1A). Indeed, a cross-sectional ex vivo study showed broad recognition of several CE in the context of wide HLA diversity and identified T cell responses of high functional avidity and broad variant reactivity [34], predominantly in controller individuals, suggesting an association between these T-cell responses and HIV control.

The present invention address the need for an improved protocol for inducing an immune response by providing a strategy based on employing DNA constructs encoding conserve elements in conjunction with constructs encoding the substantially full-length protein from which the conserved element vaccine is derived.

BRIEF SUMMARY OF THE INVENTION

The immunogenic regimens of the present invention focus on immune responses to proteome segments important to the function of a protein, e.g., a viral protein such as a lentiviral gag protein, and preclude responses against segments that absorb much of the host immune response, but which can mutate to escape immune responses while retaining function (often referred to in the art as "immunodominant decoys") (32). A conserved element vaccine (CEvac) administered in accordance with the invention has properties of a universal vaccine against a virus, such as a lentivirus, e.g., HIV, and is able to induce immune responses to most or all circulating strains. In one embodiment, the invention provides a method of generating an immune response where the method comprises administering a $p24^{gag}$ DNA vaccine that expresses conserved elements, e.g., from 3 to 7 conserved elements (CE), of HIV-1 $p24^{gag}$ and excludes potential immunodominant Of variable regions acting as potential decoy epitopes (32); followed by administration of a DNA vaccine encoding a full-length gag, e.g., $p55^{gag}$.

In some embodiments, the invention provides a method of inducing broad immune response including those direct to the highly conserved elements, the method comprising vaccinating with CEvac DNA and gag DNA either sequentially or by co-immunization where responses are not produced upon vaccination with full-length p55gag immunogen. This vaccination approach overcomes the problem of diversity by generating cross-clade gag-specific immune responses and broadens the p55gag induced T cell and humoral immunity. In some embodiments, the vaccines are delivered as DNA vaccines, e.g., plasmid DNA vaccines. In some embodiments, the vaccines are delivered as adenovirus vaccines or vaccinia virus vaccine, or using another virus vector-based vaccination strategy.

In some embodiments, the invention provides vaccine compositions comprising a nucleic acid encoding six or seven highly conserved elements from p24gag. In some embodiments, the elements encoded by the nucleic acid are arranged collinearly. In some embodiments, the seven elements are separated by alanine linkers for efficient proteolytic cleavage. In some embodiments, DNA vectors are engineered to express the Core proteins (conserved element polypeptides comprising multiple conserved elements) only, to express secreted Core proteins having the N-terminal GM-CSF signal peptide (SPCore) or to express as a core fusion to the monocyte chemoattractant protein 3 (MCP3) chemokine to stabilize the protein expression and enhance secretion of the proteins, or to the lysosomal associated membrane protein 1 (LAMP-1) to direct the proteins to the lysosomal compartment including access to the MHC class II pathway.

In some embodiments, a method of the invention comprises administering a nucleic acid encoding a conserved element from a protein, e.g., a viral protein such as Gag, and a nucleic acid encoding a naturally occurring variant of the conserved element, where the variant differs from the conserved element by 1 amino acid, e.g., where the conserved element is 8 amino acids in length; or has at least 50%, typically at least 90% or greater sequence identity to the conserved element. In some embodiments, the variant may different from the conserved element by 1, 2, or 3 amino acids. The nucleic acids encoding the conserved element and variant conserved element may be present on the same vector or encoded by different vectors. In some embodiments, the conserved element is from HIV gag. In some embodiments where a nucleic acid encoding a conserved element and a nucleic acid encoding at least one variant conserved element are administered, the conserved element and variant conserved element sequences together account for at least 80%, or at least 90%, typically at least 91%, 92%, 93%, 94%, 95%, 96%, 97%, 98%, or 99% of naturally occurring variants of the protein. In some embodiments, conserved elements immunogens are constructed based on "regional focus", which will account for >80% of clade C HIV-1 or clade B HIV-1. Such an approach, for example, provides more specific vaccines.

The invention thus provides a methods of generating a broad immune response, the method comprising administering a nucleic acid encoding at least three conserved elements, typically at least 4, 5, or 6, or more conserved elements, from a protein of interest, to an individual and administering a nucleic acid encoding the full-length protein to the individual. In some embodiments the conserved element is from a highly diverse viral proteins, e.g., an HIV protein such as HIV gag or env.

In one aspect, the invention provides a method of inducing an immune response in a subject, the method comprising administering a first Gag conserved element nucleic acid that encodes a first Gag conserved element polypeptide ("CE1 polypeptide") that comprises six conserved elements from Gag to the subject, wherein the conserved elements are from different regions of Gag, and further, wherein each conserved element is at least 12 amino acids in length, but less than 30 amino acids in length and the conserved elements are not contiguous; and administering a nucleic acid encoding a full-length Gag protein. In some embodiments, the conserved elements are from HIV-1 p24gag. In some embodiments, the first conserved element polypeptide comprises at least one conserved element that has an amino acid sequence set forth in SEQ ID NOS:1-7, 32, or 33. In some embodiments, the first conserved element polypeptide comprises at least two, three, four five, or six conserved elements that have an amino acid sequence set forth in SEQ ID NOS:1-7, 32, or 33. In one embodiment, the first conserved element polypeptide comprises conserved elements that each have a sequence set forth in SEQ ID NOS:1-7; or the first conserved element polypeptide comprises conserved elements that each have a sequence set forth in SEQ ID NOS:3-6, 32, and 33.

In some embodiments, the methods of the invention further comprise administering a second Gag conserved element nucleic acid that encodes a second Gag conserved element polypeptide ("CE2 polypeptide") that comprises at least one variant of a conserved element contained in the first Gag conserved element polypeptide, wherein the variant in the 2nd polypeptide differs from the variant in the first polypeptide by 1, 2, or 3 amino acids. Typically, the variant conserved element differs from the conserved element by only 1 amino acid. In some embodiment, the conserved element and variant conserved element each have a sequence set forth in FIG. 1; or FIG. 13. In one embodiment, the first conserved element polypeptide comprises the sequence of SEQ ID NO:15 and the second Gag conserved element polypeptide comprises the sequence of SEQ ID NO:16. In some embodiments the first conserved element polypeptide comprises the sequence of p24CE1c and the second conserved element comprises the sequence of p24CE2c as shown in FIG. 13. In some embodiments the first conserved element polypeptide comprises the sequence of p24CE1d and the second conserved element comprises the sequence of p24CE2d as shown in FIG. 13. The first and second Gag conserved element nucleic acids can be administered sequentially or concurrently. In some embodiments, one or more of the conserved element polypeptides comprise a signal peptide, such as GM-CSF or MCP-3. In some embodiments, one or More, of the conserved element polypeptides comprise a sequence that targets the protein for degradation, e.g., a LAMP sequence. In some embodiments, the first and second nucleic acid Gag conserved element polypeptides are encoded by the same vector. In some embodiments, the first and second nucleic acid Gag conserved element polypeptides are encoded by different vectors. The nucleic acids encoding the first and second conserved element polypeptides may be administered multiple times. In some embodiments, the nucleic acid encoding the full-length Gag protein is administered after a nucleic acid encoding a conserved element polypeptide, e.g, at least 2 weeks or 4 weeks, or longer after a nucleic acid encoding a conserved element polypeptide.

In a further aspect, the invention provides a method of inducing an immune response to an HIV gag protein, the method comprising
(a) administering:
(i) a nucleic acid encoding a polypeptide comprising SEQ ID NO:15 and a nucleic acid encoding a polypeptide comprising SEQ ID NO:16 to a subject; or
(ii) a nucleic acid encoding a polypeptide comprising p24CE1d as shown in FIG. 13 and a nucleic acid encoding a polypeptide comprising p24CE2d as shown in FIG. 13 to the subject; or
(iii) a nucleic acid encoding a polypeptide comprising p24CE1d as shown in FIG. 13 and a nucleic acid encoding a polypeptide comprising p24CE2d as shown in FIG. 13 to the subject; and
(b) administering a nucleic acid encoding p55gag.

In some embodiments, the nucleic acid pairs set forth in (i), (ii), or (iii) of step (a) are encoded by the same vector. In some embodiments, the polypeptides are fused to a GM-CSF signal peptide. In some embodiments, the nucleic acid encoding p55 gag is administered at least two weeks after step (a).

In a further aspect, the invention provides a method of inducing an immune response to an HIV gag protein, the method comprising administering at least one nucleic acid encoding a conserved element polypeptide comprising a sequence set forth in SEQ ID NO:18, SEQ ID NO:19, SEQ ID NO:21, SE ID NO:23, SEQ ID NO:25, SEQ ID NO:27, SE ID NO:29, SEQ ID NO:31, SEQ ID NO:35, SEQ ID NO:37, ear SEQ ID NO:39 to the patient; and administering a nucleic acid encoding a full-length gag protein. In some embodiments, the full-length gag protein is administered at least 2 weeks after administering the nucleic acid encoding the conserved element polypeptide.

In a further aspect, the invention provides a method of inducing an immune response to a protein of interest, the method comprising administering a nucleic acid encoding a conserved element polypeptide, wherein the conserved elements are from the protein of interest and the polypeptide comprises at least three conserved elements, each of less than 30 amino acids in length where the conserved elements are joined by linkers; followed by administering a nucleic acid encoding the full-length protein, wherein the nucleic acid encoding the full-length protein is administered at least two weeks after the nucleic acid encoding the conserved element polypeptide.

In some embodiments the nucleic acid constructs encoding the conserved element polypeptides and full-length Gag polypeptide are administered intramuscularly by in vivo electroporation.

BRIEF DESCRIPTION OF THE DRAWINGS

FIG. 8: CE-specific cellular immune responses upon vaccination of macaques with p24CE DNAs. (A) Macaques were vaccinated with p24CE DNA and the frequency of CE-specific T cells was measured 2 weeks after the 2$^{nd}$ vaccination (EP2wk2). IFN-γ$^+$ CD4$^+$ (open bars) and CD8$^+$ (filled bars) T cells are shown. (B) Mapping of individual CE-specific responses in the 6 immunized macaques from panel A. The frequency of IFN-γ$^+$ CD4$^+$ (open bars) and CD8$^+$ (filled bars) T cells specific for each CE is shown. (C) Phenotypic characterization of the CE-specific CD4$^+$ (red) and CD8$^+$ (black) T cells with CD28$^+$CD95$^+$ (central memory) or CD28$^-$CD95$^+$ (effector memory phenotype) is shown in the top panel; IFN-γ$^+$ and granzyme B expression is shown in the bottom panel.

FIG. 13: Sequences and configurations of p24CEc polypeptides and p24CEd polypeptides.

DETAILED DESCRIPTION OF THE INVENTION

Definitions

Figure 1:
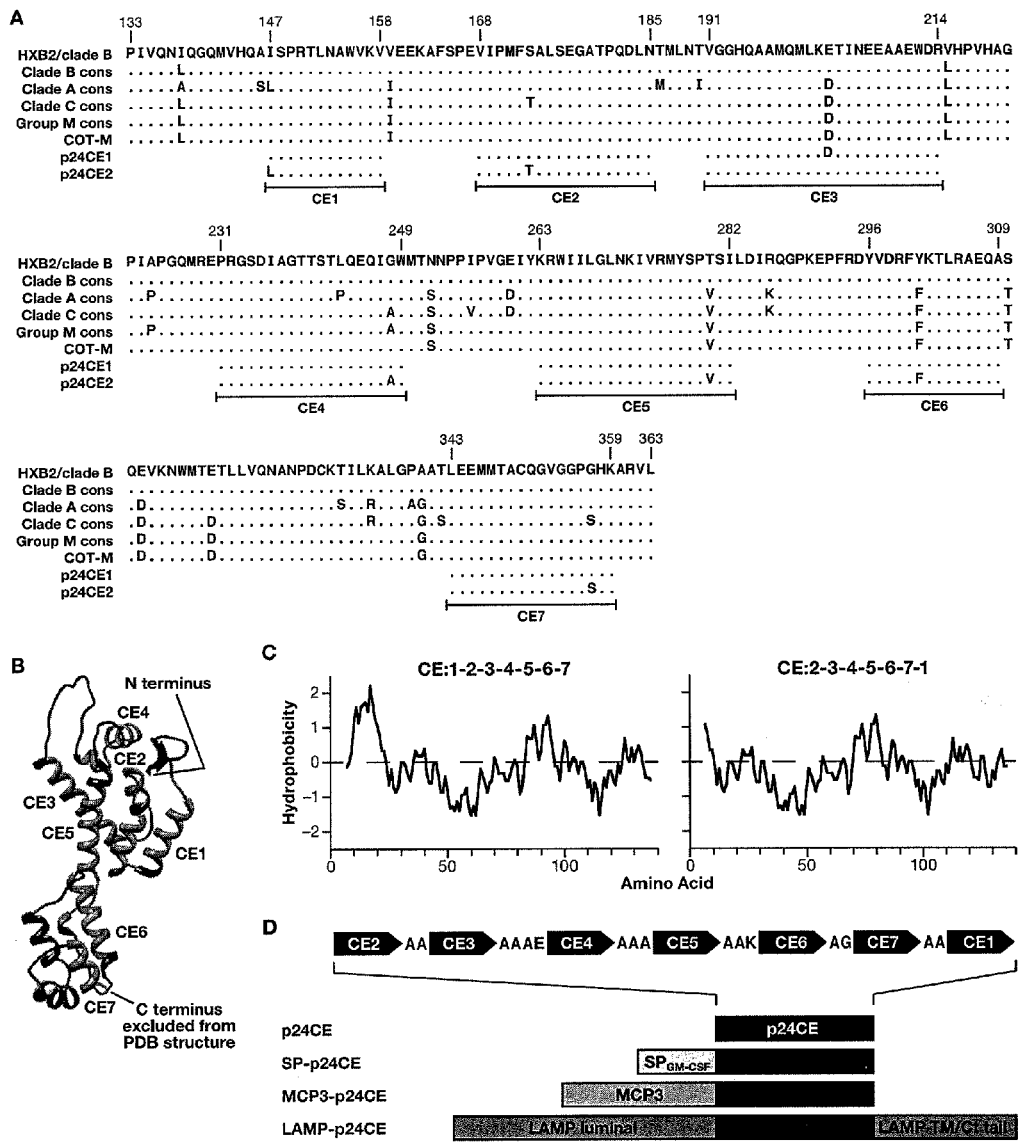
FIG. 1: Design of the p24CE DNA vaccine. (A) Alignment of the HXB2 p24$^{gag}$ protein sequences with the consensus clades A, B and C and the Group M consensus, the Group M Center-of-Tree (COT-M) and the 7 CE included in p24CE1 and p24CE2. The 'toggle' amino acid differences between the CE1 and CE2 sequences are indicated. (B) Localization of CE within the hexameric p24$^{gag}$ structure. The p24$^{gag}$ structure is modified from Pornillos et al. [97] and shows the location of CE1-CE7 (red), the toggle AA (blue) and the AA not included in the CE (black). The crystal structure of the hexamer was obtained from the www http address ebi.ac.uk/pdbsum (C) Kyte-Dolittle hydrophobicity plots for two different collinear arrangements of the (D) The p24CE (p24CE1 and p24CE2) proteins are composed of 7 CE arranged collinearly and linked via amino acid linkers. The secreted SP-p24CE contains the GM-CSF signal peptide. MCP3-p24CE is a fusion protein with the Monocyte chemoattractant protein 3 (MCP-3) chemokine. LAMP-p24CE is a fusion with the lysosomal associated membrane protein 1 (LAMP-1)

A "conserved element" as used herein refers to a protein sequence that is conserved across a protein that has high sequence diversity in nature, e.g., a viral protein such as an gag. The conserved element need not have 100% sequence identity across the diversity of naturally occurring sequence of the protein, but the sequence variability in the naturally occurring sequences is low, e.g., less than 20%. In some embodiments, the sequence variability is less than 10%. A conserved element is usually eight amino acids, or greater, e.g., 9, 10, 11, 12, 13, 14, 15, 16, 17, 18, 19, or 20 amino acids in length. Typically a conserved element is less than 50 amino acids in length and often is less than 40 or less than 30 amino acids. In some embodiments, a conserved element is less than 25 amino acids in length.

A "nucleic acid vaccine" as used herein includes both naked DNA vaccines, e.g., plasmid vaccine, and viral vector-based nucleic acids vaccines that are comprised by a viral vector and/or delivered as viral particles.

Unless otherwise indicated, a particular nucleic acid sequence also implicitly encompasses conservatively modified variants thereof (e.g. degenerate codon substitutions) and complementary sequences, as well as the sequence explicitly indicated. Degenerate codon substitutions can be achieved by generating sequences in which the third position of one or more selected (or all) codons is substituted with mixed-base and/or deoxyinosine residues (Balzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term "nucleic acid" is used interchangeably with gene, cDNA, oligonucleotide, and polynucleotide. A "nucleic acid" encompasses RNA as well as DNA.

The terms "identical" or percent "identity," in the context of two or more nucleic acids or polypeptide sequences, refer to two or more sequences or subsequences that are the same or have a specified percentage of amino acid residues or nucleotides that are the same (e.g., about 80%, 85%, 90%, 91%, 92%, 93%, 94%, 95%, 96%, 97%, 98%, 99%, or higher identity over a specified region is polypeptide sequence comprising conserved elements), when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or can be applied to, the compliment of a test sequence. The definition also includes sequences that have deletions and/or additions, as well as those that have substitutions. As described below, the preferred algorithms can account for gaps and the like. Preferably, identity exists over a region that is at least about 25, 50, 75, 100, 150, 200 amino acids or nucleotides in length, and oftentimes over a region that is 225, 250, 300, 350, 400, 450, 500 amino acids or nucleotides in length or over the full-length of an amino acid or nucleic acid sequences.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A preferred example of algorithm that is suitable for determining percent sequence identity and sequence similarity are the BLAST algorithms, which are described in Altschul et al., *Nuc. Acids Res.* 25:3389-3402 (1977) and Altschul et al., *J. Mol. Biol.* 215:403-410 (1990), respectively. BLAST software is publicly available through the National Center for Biotechnology Information on the worldwide web at ncbi.nlm.nih.gov/. Both default parameters or other non-default parameters can be used. The BLASTN program (for nucleotide sequences) uses as defaults a wordlength (W) of 11, an expectation (E) of 10, M=5, N=-4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=-4, and a comparison of both strands.

The term "operably linked" refers to a functional linkage between a first nucleic acid sequence and a second nucleic acid sequence, such that the first and second nucleic acid sequences are transcribed into a single nucleic acid sequence. Operably linked nucleic acid sequences need not be physically adjacent to each other. The term "operably linked" also refers to a functional linkage between a nucleic acid expression control sequence (such as a promoter, or array of transcription factor binding sites) and a transcribable nucleic acid sequence, wherein the expression control sequence directs transcription of the nucleic acid corresponding to the transcribable sequence.

Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

"Conservatively modified variants" as used herein applies to amino acid sequences. One of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins (1984)).

The terms "mammal" or "mammalian" refer to any animal within the taxonomic classification mammalia. A mammal can refer to a human or a non-human primate. A mammal can refer to a domestic animal, including for example, canine, feline, rodentia, including lagomorpha, murine, rattus, Cricetinae (hamsters), etc. A mammal can refer to an agricultural animal, including for example, bovine, ovine, porcine, equine, etc.

The terms "enhanced immune response" or "increased immune response" as used herein refers to an immune response to the conserved element nucleic acid and full-length, or substantially full length protein that are administered, where the immune response is increased in comparison to when only the conserved element vaccine or full-length protein is administered. An "enhanced immune response" may include increases in the level of immune cell activation and/or an increase in the duration of the response and/or immunological memory as well as an improvement in the kinetics of the immune response. The increase can be demonstrated by either a numerical increase, e.g., an increased in levels of antibody in a particular time frame, as assessed in an assay to measure the response assay or by prolonged longevity of the response.

The terms "treating" and "treatment" refer to delaying the onset of, retarding or reversing the progress of, or alleviating or preventing either the disease or condition to which the term applies, or one or more symptoms of such disease or condition.

An "antigen" refers to a molecule, typically a protein molecule in the current invention, containing one or more epitopes (either linear, conformational or both) that will stimulate a host's immune system to make a Immoral and/or cellular antigen-specific response. The term is used interchangeably with the term "immunogen." Normally, an epitope will comprise between about 7 and 15 amino acids, such as, 9, 10, 12 or 15 amino acids. The term "antigen" includes both subunit antigens, (i.e., antigens which are separate and discrete from a whole organism with which the antigen is associated in nature), as well as inactivated organisms, such as viruses.

Introduction

The invention is based in part, on the discovery that administration of one or more nucleic acids encoding a polypeptide comprising conserved elements from a protein to a subject in conjunction with administration of a nucleic acid encoding the full-length protein, or substantially full-length protein, enhances the immune response to the conserved element sequences. The protein can be any protein, but is typically a viral protein that exhibits sequence diversity in naturally occurring variants. In some embodiments, the viral protein is a retrovirus protein, such as a lentiviral protein. In some embodiments, the viral protein is a retroviral gag or env protein.

In some embodiments, administration of the nucleic acid encoding the full-length protein, or substantially full-length protein, follows administration of a conserved element nucleic acid construct. Thus, the invention further provides methods of inducing an immune response comprising sequential administration of at least one conserved element nucleic acid construct followed by administration of a nucleic acid construct comprising substantially a full length protein from which the conserved elements are derived.

Conserved Element Nucleic Acid Constructs

Conserved elements of a protein sequence can be determined using known methods. For examples U.S. Patent Application Publication No. 20110269937, which is incorporated by reference, describes methods of evaluating protein sequences that exhibit natural variability to identify regions that are conserved using computational methods.

A conserved element nucleic acid construct is typically generated by linking nucleic acid sequences that encode multiple conserved elements that target conserved sequence that are present within all or a high percentage, e.g., at least 80%, at least 90%, or at least 95%, or greater, of the naturally occurring variants of the protein in a population. In typical embodiments, a conserved element is from a region of a protein that when mutated, has deleterious effects on the function of the protein. In typical embodiments, a conserved element does not comprise an amino acid sequence that does not occur in a naturally occurring variant, i.e., the conserved element does not contain amino acid substitutions that would result in a sequence that has not been identified in a naturally occurring variant.

In some embodiments a immunogenic compositions employed in the invention relates to a viral protein, e.g., a retrovirus protein such as Gag. Conserved elements of Gag have been identified (see, e.g., U.S. Patent Application Publication No. 20110269937; Rolland et al., *PLoS Pathog* 3: e157, 2007; Motile et al., *PLoS One* 7: e29717, 2012).

In some embodiments, the nucleic acid construct encoding the conserved element polypeptide encodes a polypeptide that comprises at least one, two, three, four, five, six, or seven conserved elements set forth in FIG. 1. In some embodiments, the nucleic acid construct encodes a polypeptide that comprises at least 8, typically, at least 9, 10, 11, 12, 14, 15, 16, 17, 18, 19, 20, or more consecutive amino acids from the conserved elements set forth in FIG. 1; or in SEQ ID NOS:1-14, 32, 33. 40 and 41.

In typical embodiments, more than one nucleic acid construct encoding the conserved elements is used where one construct encodes a first set of conserved elements and the second construct encodes a second set of conserved elements where one or more elements, often each of the conserved elements, of the second set of conserved elements differs from the first set by 3 or fewer amino acids. The residues where the sequences differ, however, are at sites of naturally occurring variation, so that each of the conserved elements in the first and second sets corresponds to a naturally occurring protein sequence. In some embodiments, each element of the second set is at least 80% or at least 90% identical to the corresponding element in the first set of conserved sequences. The nucleic acid construct encoding the first set of conserved elements and the nucleic acid construct encoding the second set of conserved elements may be present in the same vector or different vectors.

Each conserved element useful for an immunogenic nucleic acid administered in accordance with the methods of the invention is typically less than 30 amino acids in length. In some embodiments, the conserved element is less than 25, 24, 23, 22, 21, 20, or 15 amino acids in length. In some embodiments, the conserved element is 8, 9, 10, 11, 12, 13, 14, 15, 16, 17, 18, 19, 20, 21, 22, 23, 24, or 25 amino acids in length.

In the present invention, the conserved elements contained within the conserved elements are not contiguous in the native protein sequence. The individual conserved elements are typically joined to one another in the nucleic acid construct by a peptide such as an alanine linker. Linker sequences are well known in the art. Typical peptide linker sequences contain Gly, Ser, Ala and Thr residues. Useful linkers include glycine-serine polymers; glycine-alanine polymers; alanine-serine polymers. In some embodiments, the linker is AA, AAAE, AAAA, AAK, AG, AA, LAK, AAK, AAAAL, and the like.

The conserved elements may be present in any order in the construct, they need not occur in the order of the naturally occurring sequence. For example, a conserved element that occurs toward the N-terminus of a protein may be encoded at region of the construct encoding the C-terminal end.

In some embodiments, a nucleic acid encoding a conserved element polypeptide for use in the invention encodes a polypeptide that comprises the conserved elements set forth in SEQ ID NOS:1-7. In some embodiments, such a nucleic acid construct encodes a polypeptide comprising the amino acid sequence of SEQ ID NO:15 ("Core1"). In some embodiments, a nucleic acid encoding a conserved element encodes a polypeptide comprising the conserved elements set forth in SEQ ID NOS:8-14. In some embodiments, such a nucleic acid construct encodes a polypeptide that comprises the amino acid sequence of SEQ ID NO:16 ("Core2"). In some embodiments, a nucleic acid construct encoding a polypeptide comprising SEQ ID NO:15 is administered with a nucleic acid construct encoding a polypeptide comprising SEQ ID NO:16.

In some embodiments, a nucleic acid encoding a conserved element encodes a conserved elements set forth in SEQ ID NOS: 3, 4, 5, 6, 32, 33, 40 or 41, or a variant thereof that differs by 1 amino acid. In some embodiments, a variant of SEQ ID NO:33 may differ at 1, 2, or 3 amino acids. In some embodiments, the conserved element polypeptide comprises a sequence set forth in FIG. 13.

In the present invention, a conserved element nucleic acid construct is administered in conjunction with the full-length protein, or substantially full-length protein, from which the conserved elements are obtained. In the context of the present invention, "substantially full-length" refers to the region of the protein that includes all of the conserved elements, i.e., a sufficient length of the naturally occurring protein is provided that includes of the conserved elements that are used in the conserved element construct.

The nucleic acid encoding the full-length protein may be administered concurrently with the conserved element vaccine. In some embodiments, a full-length protein may be administered as the priming vaccine prior to administration of one or more conserved element constructs, which are administered as a boost. In preferred embodiments, one or more nucleic acids encoding conserved elements are administered as the prime and the nucleic acid encoding the full-length protein is administered as a boost. The boost is typically administered anywhere from two weeks to one, two, three, or four months, or longer, following, administration of the initial vaccine.

Often, the nucleic acid constructs encoding the conserved elements and/or full-length protein are one or more purified nucleic acid molecules, for example, one or more plasmid-based vectors ("naked" DNA).

In some embodiments, the nucleic acid component may comprise vectors that encode the antigen of interest where the vector is contained within a virus. Viral delivery systems include adenovirus vectors, adeno-associated viral (AAV) vectors, herpes viral vectors, retroviral vectors, poxviral vectors, or lentiviral vectors. Methods of constructing and using such vectors are well known in the art.

Recombinant viruses in the pox family of viruses can be used for delivering the nucleic acid molecules encoding the antigens of interest. These include vaccinia viruses and avian poxviruses, such as the fowlpox and canarypox viruses. Methods for producing recombinant pox viruses are known in the art and employ genetic recombination. See, e.g., WO 91/12882; WO 89/03429; and WO 92/03545. A detailed review of this technology is found in U.S. Pat. No. 5,863,542. Representative examples of recombinant pox viruses include ALVAC, TRW/AC, and NYVAC.

A number of adenovirus vectors have also been described that can be used to deliver one or more of the nucleic acid components of the vaccine. (Haj-Ahmad and Graham, J. Virol. (1986) 57:267-274; Bett et al., J. Virol. (1993) 67:5911-5921; Mittereder et al., Human Gene Therapy (1994) 5:717-729; Seth et al., J. Virol. (1994) 68:933-940; Barr et al., Gene Therapy (1994) 1:51-58; Berkner, K. L. BioTechniques (1988) 6:616-629; and Rich et al., Human Gene Therapy (1993) 4:461-476). Additionally, various adeno-associated virus (AAV) vector systems have been developed for gene delivery. AAV vectors can be readily constructed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al., Molec. Cell. Biol. (1988) 8:3988-3996; Vincent et al., Vaccines 90 (1990) (Cold Spring Harbor Laboratory Press); Carter, B. J. Current Opinion in Biotechnology (1992) 3:533-539; Muzyczka, N. Current Topics in Microbiol. and Immunol. (1992) 158:97-129; Kotin, R. M. Human Gene Therapy (1994) 5:793-801; Shelling and Smith, Gene Therapy (1994) 1:165-169; and Zhou et al., J. Exp. Med. (1994) 179:1867-1875.

Retroviruses also provide a platform for gene delivery systems. A number of retroviral systems have been described (U.S. Pat. No. 5,219,740: Miller and Rosman, BioTechniques (1989) 7:980-990; Miller, A. D., Human Gene Therapy (1990) 1:5-14; Scarpa et al., Virology (1991) 180:849-852; Burns et al., Proc. Natl. Acad. Sci, USA (1993) 90:8033-8037; and Boris-Lawrie and Temin, Cur. Opin. Genet. Develop. (1993) 3:102-109.

Molecular conjugate vectors, such as the adenovirus chimeric vectors described in Michael et al., J. Biol. Chem. (1993) 268:6866-6869 and Wagner et al., Proc. Natl. Acad. Sci, USA (1992) 89:6099-6103, can also be used for gene delivery.

Members of the Alphavirus genus, such as, but not limited to, vectors derived from the Sindbis, Semliki Forest, and Venezuelan Equine Encephalitis viruses, can also be used as viral vectors to deliver one or more nucleic acid components of the nucleic acid/protein combination vaccines of the invention. For a description of Sindbis-virus derived vectors useful for the practice of the instant methods, see, Dubensky et al., J. Virol, (1996) 70:508-519; and International Publication Nos. WO 95/07995 and WO 96/17072; as well as, Dubensky, Jr., T. W., et al., U.S. Pat. No. 5,843,723, issued Dec. 1, 1998, and Dubensky, Jr., T. W., U.S. Pat. No. 5,789,245, issued Aug. 4, 1998).

Expression Constructs Encoding Fusion Polypeptides Comprising a Degradation Signal or Signal Peptide Sequence In some embodiments, a nucleic acids encoding a conserved element vaccine encodes a form in which the conserved element is fused to a sequence to enhance the immune response, such as a signal peptide sequence or a sequence that targets the protein for lysosomal degradation. Such embodiments typically results in enhanced immune responses in comparison to embodiments where the conserved element vaccine is not fused to a signal peptide or degradation signal.

Lysosomal Targeting Sequence

In other embodiments, signals that target proteins to the lysosome may also be employed. For example, the lysosome associated membrane proteins1 and 2 (LAMP-1 and LAMP-2) include a region that targets proteins to the lysosome. Examples of lysosome targeting sequences are provided, e.g., in U.S. Pat. Nos. 5,633,234; 6,248,565; and 6,294,378.

Destabilizing sequences present in particular proteins are well known in the art. Exemplary destabilization sequences include c-myc aa 2-120; cyclin A aa 13-91; Cyclin B aa 13-91; IkBα aa 20-45: β-Catenin aa 19-44; β-Catenin aa 18-47, c-Jun aa1-67; and c-Mos aa1-35; and fragments and variants, of those segments that mediate destabilization. Such fragments can be identified using methodology well known in the art. For example, polypeptide half-life can be determined by a pulse-chase assay that detects the amount of polypeptide that is present over a time course using an antibody to the polypeptide, or to a tag linked to the polypeptide. Exemplary assays are described, e.g., in WO02/36806, which is incorporated by reference.

Variants of such sequences, e.g., that have at least 90% identity, usually at least 91%, 92%, 93%, 94%, 95%, 96%, 97%, 98%, 99%, or greater, identity to the sequences noted above, e.g., a LAMP degradation sequence, can be employed in this invention, e.g., for fusion to an gag conserved element polypeptide.

Additional degradation signals that can be used to modify retroviral antigens, e.g. HIV antigens in accordance with the invention include the F-box degradation signal, such as the F-BOX signal 47aa (182-228) from protein beta-TrCP (Liu, et al., *Biochem Biophys Res Comm.* 313:1023-1029, 2004). Accordingly, in some embodiments, an expression vector for use in the invention may encode a fusion protein where an F-box degradation signal is attached to an HIV antigen, e.g., gag.

Targeting to the Proteasome and Other Degradation Signals

Many polypeptide sequences that target a protein for degradation are known in the art. One example of destabilizing sequences are so-called PEST sequences, which are abundant in the amino acids Pro, Asp, Glu, Ser, Thr (they need not be in a particular order), and can occur in internal positions in a protein sequence. A number of proteins reported to have PEST sequence elements are rapidly targeted to the 26S proteasome. A PEST sequence typically correlates with a) predicted surface exposed loops or turns and b) serine phosphorylation sites, e.g. the motif S/TP is the target site for cyclin dependent kinases.

Additional destabilization sequences relate to sequences present in the N-terminal region. In particular the rate of ubiquitination, which targets proteins for degradation by the 26S proteasome can be influenced by the identity of the N-terminal residue of the protein. Thus, destabilization sequences can also comprise such N-terminal residues, "N-end rule" targeting (see, e.g., Tobery et al., *J. Exp. Med.* 185:909-920).

Other targeting signals include the destruction box sequence that is present, e.g., in cyclins. Such a destruction box has a motif of 9 amino acids, R1(A/T)2(A)3L4(G)5X6 (I/V)7(G/T)8(N)9, in which the only invariable residues are R and L in positions 1 and 4, respectively. The residues shown in brackets occur in most destruction sequences. (see, e.g., Hershko & Ciechanover, Annu. Rev. Biochem. 67:425-79, 1998). In other instances, destabilization sequences lead to phosphorylation of a protein at a serine residue (e.g., Iκbα).

In some embodiments, a conserved element polypeptide of the invention is fused to a LAMP degradation sequence. For example, the methods of the invention may employ a polypeptide in which SEQ ID NO:15 or SEQ ID NO:16 is fused to a LAMP degradation sequence.

Expression Constructs that Encode Secreted Fusion Proteins

A secretory polypeptide in the context of this invention is a polypeptide signal sequence that results in secretion of the protein to which it is attached. In some embodiments, the secretory polypeptide is a chemokine, cytokine, or lymphokine, or a fragment of the chemokine, cytokine, or lymphokine that retains immunostimulatory activity. Examples of chemokines secretory polypeptides include MCP-3 and IP-10. In other embodiments, the secretory polypeptide is a polypeptide signal sequence from a secreted protein such as tissue plasminogen activator (tPA) protein, growth hormone, GM-CSF, a cytokine, or an immunoglobulin protein. Constructs encoding secretory fusion proteins are disclosed, e.g., in WO02/36806.

In some embodiments, the signal peptide is a GM-CSF sequence, e.g., a mammalian GM-CSF sequence such as a human GM-CSF signal peptide sequence.

In some embodiments, a secretory signal for use in the invention is MCP-3 amino acids 33-109, e.g., linked to IP-10 secretory peptide.

In some embodiments, a conserved element polypeptide is joined to a GM-CSF signal peptide sequence. For example, in some embodiments, the methods of the invention may employ a polypeptide comprising SEQ ID NO:15 fused to a GM-CSF signal peptide and/or a polypeptide comprising SEQ ID NO:16 fused to a GM-CSF signal peptide.

Similarly, an expression construct encoding a full-length polypeptide, e.g., a construct that encodes p55 gag, may also be modified with a degradation sequence and/or a secretory sequence. Moreover, more than one construct encoding the full-length polypeptide, e.g, p55gag may be administered. For example a construct in which p55 gag is fused to a signal polypeptide such as GM-CSF may be used in conjunction with a construct in which p55gag is fused to a degradation sequence, such as LAMP.

Additional Properties of Expression Constructs

Within each expression cassette, sequences encoding an antigen for use in the nucleic acid vaccines of the invention will be operably linked to expression regulating sequences. "Operably linked" sequences include both expression control sequences that are contiguous with the nucleic acid of interest and expression control sequences that act in trans or at a distance to control the gene of interest. Expression control sequences include appropriate transcription initiation, termination, promoter and enhancer sequences; efficient RNA processing signals such as splicing and polyadenylation signals; sequences that stabilize cytoplasmic mRNA; sequences that promote RNA export (e.g., a constitutive transport element (CTE), a RNA transport element (RTE), or combinations thereof; sequences that enhance translation efficiency (e.g., Kozak consensus sequence); sequences that enhance protein stability; and when desired, sequences that enhance protein secretion.

Any of the conventional vectors used for expression in eukaryotic cells may be used for directly introducing nucleic acids into tissue. Expression vectors containing regulatory elements from eukaryotic viruses are often used in eukaryotic expression vectors. Such regulatory elements include, e.g., human CMV, simian CMV, viral LTRs, and the like. Typical vectors may comprise, e.g. those with a human CMV promoter, bovine growth hormone polyA site and an antibiotic resistance gene for selective growth in bacteria.

Other expression vector components are well known in the art, including, but not limited to, the following: transcription enhancer elements, transcription termination signals, polyadenylation sequences, splice sites, sequences for optimization of initiation of translation, and translation termination sequences.

In some embodiments, the nucleic acid component may comprises one or more RNA molecules, such as viral RNA molecules or mRNA molecules that encode the antigen of interest.

In typical embodiments, the nucleic acid constructs are codon-optimized for expression.

In the present invention, a "nucleic acid" molecule can include cDNA, and genomic DNA sequences, RNA, and synthetic nucleic acid sequences. Thus, "nucleic acid" also encompasses embodiments in which analogs of DNA and RNA are employed.

An immunogenic composition of the invention can be administered as one or more constructs. For example, where two sets of conserved elements are employed, e.g., conserved element polypeptides Core1 and Core2, or conserved element polypeptides p2CE1c and p24CE2c or conserved element polypeptides p2CE1d and p24CE2d, a nucleic acid construct can encode both sets, or each set may be encoded by a separate expression vector. Thus, the expression constructs administered in accordance with the invention may be administered as multiple expression vectors, or as one or more expression vectors encoding multiple expression units, e.g., a discistronic, or otherwise multicistronic, expression vectors. For example, an expression vector may be employed that encodes both SEQ ID NO:15 and SEQ ID NO:16 or multiple expression vectors may be employed where SEQ ID NO:15 is encoded by one vector and SEQ ID NO:16 is encoded by another vector.

Preparation of Immunogenic Compositions

In the methods of the invention, the nucleic acid component is often directly introduced into the cells of the individual receiving the immunogenic composition. This approach is described, for instance, in Wolff et. al., *Science* 247:1465 (1990) as well as U.S. Pat. Nos. 5,580,859; 5,589,466; 5,804,566; 5,739,118; 5,736,524; 5,679,647; and WO 98/04720. Examples of DNA-based delivery technologies include, "naked DNA", facilitated (bupivicaine, polymers, peptide-mediated) delivery, and cationic lipid complexes or liposomes. The nucleic acids can be administered using ballistic delivery as described, for instance, in U.S. Pat. No. 5,204,253 or pressure (see, e.g., U.S. Pat. No. 5,922,687). Using this technique, particles comprised solely of DNA are administered, or in an alternative embodiment, the DNA can be adhered to particles, such as gold particles, for administration.

In some embodiments, e.g, where a nucleic acid component of the invention is encoded by a viral vector, the nucleic acid component can be delivered by infecting the cells with the virus containing the vector. This can be performed using any delivery technology, e.g., as described in the previous paragraph.

In some embodiments, the immunogenic compositions of the invention are administered by injection or electroporation, or a combination of injection and electroporation, Assessment of Immunogenic Response To assess a patient's immune system during and after treatment and to further evaluate the treatment regimen, various parameters can be measured. Measurements to evaluate vaccine response include: antibody measurements in the plasma, serum, or other body fluids; and analysis of in vitro cell proliferation in response to a specific antigen, indicating the function of CD4+ cells. Such assays are well known in the art. For example, for measuring CD4+ T cells, many laboratories measure absolute CD4+ T-cell levels in whole blood by a multi-platform, three-stage process. The CD4+ T-cell number is the product of three laboratory techniques: the white blood cell (WBC) count; the percentage of WBCs that are lymphocytes (differential); and the percentage of lymphocytes that are CD4+ T-cells. The last stage in the process of measuring the percentage of CD4+ T-lymphocytes in the whole-blood sample is referred to as "immunophenotyping by flow cytometry. Systems for measuring CD4+ cells are commercially available. For example Becton Dickenson's FACSCount System automatically measure absolutes CD4+, CD8+, and CD3+ T lymphocytes.

Other measurements of immune response include assessing CD8+ responses. These techniques are well known. CD8+ T-cell responses can be measured, for example, by using tenamer staining of fresh or cultured PBMC (see, e.g., Altman, et al., *Proc. Natl. Acad. Sci. USA* 90:10330, 1993; Altman, et al., *Science* 274:94, 1996), or γ-interferon release assays such as ELISPOT assays (see, e.g., Lalvani, et al., *J. Exp. Med.* 186:859, 1997; Dunbar, et al., *Curr. Biol.* 8:413, 1998; Murali-Krishna, et al., *Immunity* 8:177, 1998), or by using functional cytotoxicity assays.

Viral Titer

Viremia is measured by assessing viral titer in a patient. There are a variety of methods of perform this. For example, plasma HIV RNA concentrations can be quantified by either target amplification methods (e.g., quantitative RT polymerase chain reaction [RT-PCR], Amplicor HIV Monitor assay, Roche Molecular Systems; or nucleic acid sequence-based amplification, [NASBA®], NucliSensTM HIV-1 OT assay, Organon Teknika) or signal amplification methods (e.g., branched DNA [bDNA], QuantiplexTM HIV RNA bDNA assay, Chiron Diagnostics). The bDNA signal amplification method amplifies the signal obtained from a captured HIV RNA target by using sequential oligonucleotide hybridization steps, whereas the RT-PCR and NASBA® assays use enzymatic methods to amplify the target HIV RNA into measurable amounts of nucleic acid product. Target HIV RNA sequences are quantitated by comparison with internal or external reference standards, depending upon the assay used.

Administration of DNA Constructs

The DNA vectors are formulated for pharmaceutical administration. While any suitable carrier known to those of ordinary skill in the art may be employed in the pharmaceutical compositions of this invention, the type of carrier will vary depending on the mode of administration. For parenteral administration, including intranasal, intradermal, subcutaneous or intramuscular injection or electroporation, the carrier preferably comprises water, saline, and optionally an alcohol, a fat, a polymer, a wax, one or more stabilizing amino acids or a buffer. General formulation technologies are known to those of skill in the art (see, for example, Remington: The Science and Practice of Pharmacy (20th edition), Gennaro, ed., 2000, Lippincott Williams & Wilkins; Injectable Dispersed Systems: Formulation, Processing And Performance, Burgess, ed., 2005, CRC Press; and Pharmaceutical Formulation Development of Peptides and Proteins, Frkjr et al., eds., 2000, Taylor & Francis).

Naked DNA can be administered in solution (e.g., a phosphate-buffered saline solution) by injection, usually by an intra-arterial, intravenous, subcutaneous or intramuscular route. In general, the dose of a naked nucleic acid composition is from about 10 µg, to 10 mg for a typical 70 kilogram patient. Subcutaneous or intramuscular doses for naked nucleic acid (typically DNA encoding a fusion protein) will range from 0.1 mg to 50 mg for a 70 kg patient in generally good health.

DNA immunogenic compositions can be administered once or multiple limes. DNA vaccination is performed More than once, for example, 2, 3, 4, 5, 6, 7, 8, 10, 15, 20 or more times as needed to induce the desired response (e.g., specific antigenic response or proliferation of immune cells). Multiple administrations can be administered, for example, bi-weekly, weekly, bi-monthly, monthly, or more or less often, as needed, for a time period sufficient to achieve the desired response.

The nucleic acid constructs in accordance with the invention are administered to a mammalian host. The mammalian host usually is a human or a primate. In some embodiments, the mammalian host can be a domestic animal, for example, canine, feline, lagomorpha, rodentia, rattus, hamster, murine. In other embodiment, the mammalian host is an agricultural animal, for example, bovine, ovine, porcine, equine, etc.

Immunogenic compositions containing the DNA expression constructs can be formulated in accordance with standard techniques well known to those skilled in the pharmaceutical art. Such compositions can be administered in dosages and by techniques well known to those skilled in the medical arts taking into consideration such factors as the age, sex, weight, and condition of the particular patient, and the route of administration.

Iii therapeutic applications, the vaccines are administered to a patient in an amount sufficient to elicit a therapeutic effect, e.g., a $CD8^+$, $CD4^+$, and/or antibody response to the HIV-1 antigens encoded by the vaccines that at least partially arrests or slows symptoms and/or complications of HIV infection. An amount adequate to accomplish this is defined as "therapeutically effective dose." Amounts effective for this use will depend on, e.g., the particular composition of the vaccine regimen administered, the manner of administration, the stage and severity of the disease, the general state of health of the patient, and the judgment of the prescribing physician.

Suitable quantities of DNA, e.g., plasmid or naked DNA can be about 1 µg to about 100 mg, preferably 0.1 to 10 mg, but lower levels such as 1-10 µg can be employed. For example, an HIV DNA vaccine, e.g., naked DNA or polynucleotide in an aqueous carrier, can be injected into tissue, e.g., intramuscularly or intradermally, in amounts of from 10 µl per site to about 1 nil per site. The concentration of polynucleotide in the formulation is usually from about 0.1 µg/ml to about 4 mg/mi.

The vaccine may be delivered in a physiologically compatible solution such as sterile PBS in a volume of, e.g., one ml. The vaccines may also be lyophilized prior to delivery. As well known to those in the art, the dose may be proportional to weight.

The compositions included in the regimen descried herein for inducing an immune response can be administered alone, or can be co-administered or sequentially administered with other immunological, antigenic, vaccine, or therapeutic compositions.

Compositions that may also be administered with the vaccines include other agents to potentiate or broaden the immune response, e.g., IL-15, IL-12, IL-2 or CD40 ligand, which can be administered at specified intervals of time, or continuously administered.

The vaccines can additionally be complexed with other components such as peptides, polypeptides and carbohydrates for delivery. For example, expression vectors, nucleic acid vectors that are not contained within a viral particle, can be complexed to particles or beads that can be administered to an individual, for example, using a vaccine gun.

Nucleic acid vaccines are administered by methods well known in the art as described in Donnelly et al. (*Ann. Rep. Immunol.* 15:617-648 (1997)); Feigner et al. (U.S. Pat. No. 5,580,859, issued Dec. 3, 1996); Feigner (U.S. Pat. No. 5,703, 055, issued Dec. 30, 1997); and Carson et al. (U.S. Pat. No. 5,679,647, issued Oct. 21, 1997), each of which is incorporated herein by reference. One skilled in the art would know that the choice of a pharmaceutically acceptable carrier, including a physiologically acceptable compound, depends, for example, on the route of administration of the expression vector.

As noted above, immunogenic DNA compositions can be delivered via a variety of routes. Typical delivery routes include parenteral administration, intradermal, intramuscular or subcutaneous routes. Administration of expression vectors of the invention to muscle and by electroporation can be a particularly effective method of administration, including intradermal and subcutaneous injections and transdermal administration. Transdermal administration, such as by iontophoresis, is also an effective method to deliver expression vectors of the invention to muscle. Epidermal administration of expression vectors of the invention can also be employed. Epidermal administration involves mechanically or chemically irritating the outermost layer of epidermis to stimulate an immune response to the irritant (Carson et al., U.S. Pat. No. 5,679,647).

The immunogenic compositions can also be formulated for administration via the nasal passages. Formulations suitable for nasal administration, wherein the carrier is a solid, include a coarse powder having a particle size, for example, in the range of about 10 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the active ingredient. For further discussions of nasal administration of AIDS-related vaccines, references are made to the following patents, U.S. Pat. Nos. 5,846,978, 5,663,169, 5,578,597, 5,502,060, 5,476, 874, 5,413,999, 5,308,854, 5,192,668, and 5,187,074.

The vaccines can be incorporated, if desired, into liposomes, microspheres or other polymer matrices (see, e.g., Feigner et al., U.S. Pat. No. 5,703,055; Gregoriadis, *Liposome Technology*, Vols. I to III (2nd ed. 1993). Liposomes, for example, which consist of phospholipids or other lipids, are nontoxic, physiologically acceptable and metabolizable carriers that are relatively simple to make and administer. Liposomes include emulsions, foams, micelles, insoluble monolayers, liquid crystals, phospholipid dispersions, lamellar layers and the like.

EXAMPLES ILLUSTRATING THE INVENTION

Example 1

Core DNA Vaccination Induces Cross-Clade Specific Cellular Immune Responses in Mice Results
Conserved Element DNA Vaccines A set of conserved elements (CE) was identified in $p24^{gag}$ composed of amino acids (AA) highly conserved across the entire HIV-1 group M, as determined by using the Los Alamos HIV database (www site is hiv.lanl.gov/) [32]. A refined list of 7 CE was selected based on several criteria (FIG. 1A, see Materials and Methods): a minimum length of 8 AA; inclusion of specific epitopes that have been correlated with viral control (low viral loads) in vivo; and exclusion of epitopes associated with high viral loads. The selected CE span 12-24 amino acids each, and together a total of 124 AA, thus representing 54% of $p24^{gag}$ sequence. The CE are highlighted on the $p24^{gag}$ capsid ribbon structure [97], revealing that they encompass most of the extended coiled regions of the $p24^{gag}$ protein (FIG. 1B).

We generated multiple DNA-based vaccines in which the 7 CE were collinearly arranged (FIG. 1C), and connected via short linker sequences (FIG. 1D), designed for efficient proteolytic cleavage [91, 92]. Proteolytic processing of CE peptides in vitro revealed production of optimal epitopes or slightly extended optimal epitopes from 6 of the 7 CE segments (S. Le Gall, in preparation). Therefore, the CE immunogen is predicted to be able to present a significant number of native T cell epitopes after expression. For optimal arrangement of the different segments within the p24CE immunogens, the hydrophobicity of individual CE was taken into consideration (FIG. 1C). To avoid the strongly hydrophobic N-terminus in the arrangement CE1-2-3-4-5-6-7 (left panel), which could impact the intracellular trafficking of the protein, the CE1 peptide was placed at the C-terminus (right panel).

The majority of the AA included in the p24CE immunogens are essentially invariant since they are found in >98% of HIV isolates. The length of p24CE was expanded by including some less well-conserved AA ('toggle' sites), thus expressing additional potentially immunogenic regions. This allowed the extension of the 7 CE to the length of 12-24 AA, as mentioned above, and led to two p24CE sequences differing by 7 AA, one in each CE (FIG. 1A), named p24CE1 and p24CE2. These two sequences cover >99% of all known HIV-1 group M sequences. The p24CE1 and p24CE2 sequences were RNA/codon optimized [73-75] to maximize mRNA processing, transport, stability and translation (see Material and Methods). The p24CE coding regions were cloned into the pCMVkan vaccine vector (p24CE; FIG. 1D). Additional expression plasmids were generated in order to alter the intracellular trafficking and processing of the p24CE proteins. Plasmids SP-p24CE1 and SP-p24CE2 contain the CM-CSF signal peptide at the N-terminus of p24CE to promote secretion of the p24CE proteins. Plasmids MCP3-p24CE1 and MCP3-p24CE2 express fusion proteins with the monocyte chemoattractant protein 3 (MCP-3) chemokine, previously shown to stabilize the encoded protein and to enhance trafficking to antigen presenting cells [80,81]. Plasmids LAMP-p24CE1 and LAMP-p24CE2 express fusion proteins with the human lysosomal associated membrane protein 1 (LAMP-1). Fusion of Gag to LAMP was previously shown to direct it to the lysosomal compartment and to facilitate access to the MHC class II pathway as well as to the extracellular compartment [98-102].

Expression of the p24CE Proteins in Human Cells

Figure 2:
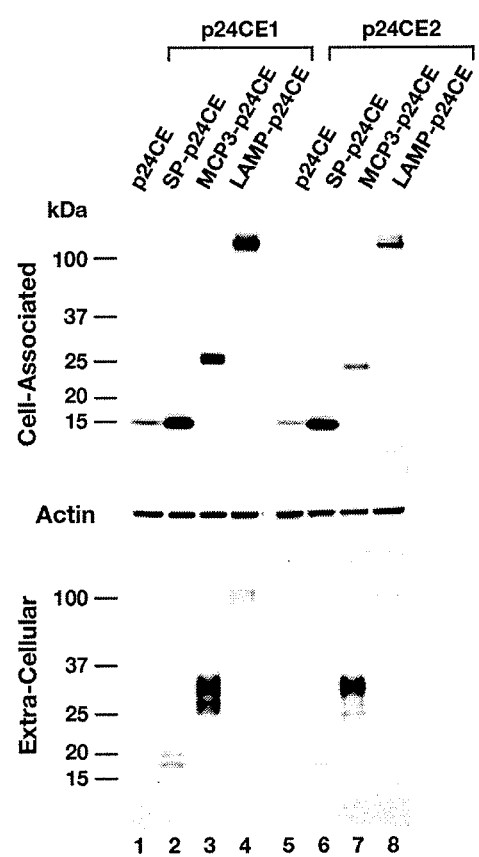
FIG. 2: Expression of the p24CE plasmids upon transient transfection in cultured cells. Plasmid DNA (1 µg) expressing different variants of either p24CE1 (left panel) or p24CE2 (right panel) proteins were transfected in HEK293 cells. The cultures were harvested 24 hrs later and proteins from equal amounts (1/250) from the cell-associated (top panel) and extracellular (bottom panel) fractions were resolved on a 12% NuPAGE Bis-Tris gel and analyzed by Western immunoblot using a goat anti-p24$^{gag}$ antiserum and visualized using enhanced ECL. The membrane containing the cell-associated fractions was also probed with anti-human pan actin antibody to control for equal loading of the samples.

The expression of the p24CE vectors shown in FIG. 1D was evaluated by Western immunoblots using cell extracts and supernatants from transiently transfected HEK293 cells (FIG. 2). To control for equal loading, the membrane containing the cell-associated samples were probed with an antibody against human beta actin as internal control (middle panel) demonstrating that similar amounts of proteins were loaded into each lane which validates our conclusions regarding the stability and different distribution of the proteins encoded by the different transfected plasmids (see below). Very low levels of the p24CE1 and p24CE2 proteins were detected in the cell-associated fractions (lanes 1 and 5, respectively), and no proteins were found in the extracellular compartment, indicating that the p24CE proteins were unstable. We also noted that p24CE2, differing only by 7 of the 124 AA from p24CE1, produced an even less stable antigen. The presence of the GM-CSF signal peptide (SP) greatly increased the levels of both p24CE proteins (lanes 2 and 6) in both the cell-associated and the extracellular fractions. These data indicate that the signal peptide altered the trafficking of the p24CE proteins, and promoted increase in stability and secretion. We noted the presence of additional bands of the secreted p24CE proteins, likely due to posttranslational modifications related to the altered cellular trafficking (compare lane 2 and lane 1; lane 6 to lane 5). The MCP3-p24CE (lanes 3 and 7) and LAMP-p24CE fusion proteins (lanes 4 and 8) were also readily detectable, and thus these fusions greatly stabilized the p24CE proteins. MCPS-p24CE localization in the extracellular fraction (lanes 3 and 7) as several bands, was similar to our previous report on a MCPS-Gag fusion protein [81]. The LAMP-p24CE proteins accumulated primarily in the cell-associated fraction (lanes 4 and 8), although some protein could also be found in the extracellular fraction, as we previously observed for the LAMP-p55$^{gag}$ protein [101]. These data shoved that altering the trafficking of the p24CE proteins, by adding the GM-CSF signal peptide or upon fusion to the MCP3 or LAMP molecules, enhanced the stability and modulated the trafficking of p24CE proteins.

Vaccination with p24CE Induces GE-Specific Cellular Immune Responses in C57BL/6 Mice We next evaluated the immunogenicity of different p24CE proteins after DNA vaccination of C57BL/6 mice. Groups of mice (N=5) were vaccinated twice (0 and 4 weeks) with the indicated p24CE plasmids or sham plasmid DNA, as negative control, by intramuscular injection followed by in vivo electroporation (EP). Two weeks after the last vaccination (week 6), the mice were sacrificed and the presence of CE-specific cellular responses was determined by polychromatic flow cytometry. Splenocytes from the individual animals from each of the vaccine groups and the sham DNA inoculated negative control group were stimulated with a Group M consensus Gag peptide pool (15-mer peptides overlapping by 11 AA) (FIG. 3A) or with a COT-M peptide pool (10-mer overlapping by 9 AA) consisting of both p24CE1 and p24CE2 sequences (FIG. 3B). The use of the 15-mer peptide pool allowed for the detection of both CD4$^+$ and CD8$^+$ T cell responses, whereas the 10-mer peptide pool favors mainly CD8$^+$ T cell responses. Vaccination with plasmids expressing p24CE or the secreted p24CE (SP-p24CE) proteins induced both CE-specific CD4$^+$ and CD8$^+$ T cell immune responses (FIG. 3A) contrast, vaccination with the p24CE fusion proteins, MCP3-p24CE or LAMP-p24CE, elicited CE-specific responses that were almost exclusively mediated by CD4$^+$ T cells. In agreement with these results, splenocyte stimulation with 10-mer peptide pools, which are mainly associated with MHC class I antigens, induced very low responses in MCP3-p24CE DNA vaccinated mice and no responses in the LAMP-p24CE immunized mice, which verified the previous conclusions (FIG. 3B). We hypothesize that altered intracellular trafficking of the p24CE fusion antigens could be responsible for the distinct preference for CD4$^+$ or CD8$^+$ T cell responses. Responses elicited by p24CE1 proteins were in general higher than those induced by p24CE2 (FIGS. 3A and 3B, note the different scales for p24CE1 and p24CE2), likely reflecting the higher expression of p24CE as indicated by the transient transfection experiments (see FIG. 2). As expected, no cellular responses were found in splenocytes from sham DNA vaccinated mice.

The cross-reactivity of the induced responses was analyzed using peptide pools representing different HIV-1 chides (A, B, and C; see also FIG. 1A). SP-p24CE1 DNA vaccination induced cross-clade reactive CD4$^+$ and CD8$^+$ cellular responses, which were similar in magnitude to those obtained with the Group M peptide pool (FIG. 3C). Cross-Clade reactivity was also obtained upon vaccination with the other p24CE plasmids (data not shown). In contrast, splenocytes from mice immunized with sham DNA failed to recognize peptides from any of the three glade-specific peptide pools.

Fine Specificity of CE-Specific T Cell Responses from Vaccinated C57BL/6 mice

Figure 4:
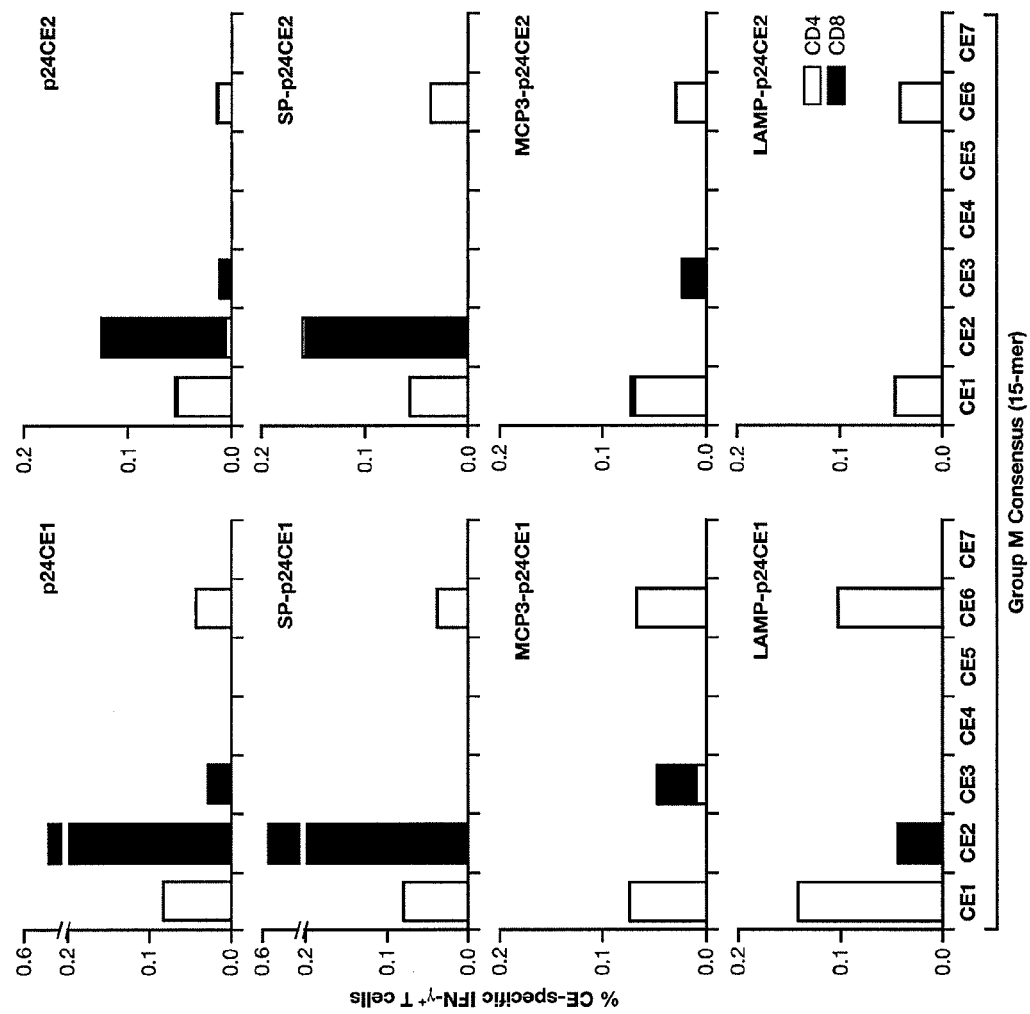
FIG. 4: Mapping of the p24CE-induced cellular immune responses. Pooled splenocytes from C57BL/6 mice (N=5) vaccinated with the indicated p24CE1 (left panels) or p24CE2 (right panels) DNAs were stimulated with the Group M Consensus peptide pools (15-mers overlapping by 11 AA) spanning the individual CEs. The frequency of CE-specific IFN-γ producing T cells was measured. CD4$^+$ (open bars) and CD8$^+$ (filled bars) Gag-specific T cells are shown.

Next, we assessed the distribution of the p24CE-induced cellular responses among the different CE (FIG. 4). Pooled splenocytes from the DNA vaccinated C57BL/6 mice (N=5/group) were stimulated with Group M consensus peptide pools (15-mer) encompassing the 7 individual CE. Polychromatic flow cytometry was used to determine the frequency of the CE-specific IFN-γ producing T cells and to discriminate between CD4$^+$ and CD8$^+$ T cell responses. Immunization with the different p24CE1 (left panels) and p24CE2 (right panels) plasmid DNAs induced cellular responses to CE1 and CE6, which were mediated almost exclusively by CD4$^+$ T cells. Interestingly, mice immunized with plasmids encoding the native p24CE: protein (p24CE and SP-p24CE) developed also high CD8$^+$ mediated cellular responses to CE2. These data are in agreement with the cellular localization of the encoded proteins: the native p24CE protein remains mainly intracellular, while the SP-p24CE and MCP3-p24CE fusion are actively secreted and the LAMP-p24CE associates with the MHC class TI compartment. Low levels of CD8$^+$ T cell responses to CE3 were also identified upon immunization with the p24CE and the MCP3-p24CE plasmids. In conclusion, the p24CE proteins induced responses to 4 of the 7 CE (CE1, CE2, CE3, CE6) in mice, although these responses were generally lower in animals immunized with the p24CE2 plasmids, demonstrating that vaccination induced broad CD4$^+$ and CD8$^+$ T cell responses.

p24CE Induces Broader Immune Responses than the Full-Length p55$^{gag}$

We compared the immune responses to the individual CE upon vaccination with a p55$^{gag}$ plasmid DNA or with a mixture of SP-p24CE1 and SP-p24CE2 DNAs. The mice (N=0.5 group) received 3 vaccinations (week 0, 3 and 6) and were sacrificed at week 8 (FIG. 5A). Vaccine-induced T cell responses were analyzed from pooled splenocytes (FIG. 5B) stimulated with 15-mer peptide pools specific for p24$^{gag}$ of clade A, B, or C (left panel) and the group M consensus (right panel). The overall responses induced by the p55$^{gag}$ immunogen were lower than those obtained by the p24CE immunogen, and remarkably, lacked CD8$^+$-specific T cells. Using peptide pools spanning the individual CE (FIG. 5C) showed that p55$^{gag}$ DNA elicited low responses to CE1 and CE6 only (right panel), mediated exclusively by CD4$^+$ T cells. In contrast, vaccination with SP-p24CE DNA mixture elicited higher responses towards several CE (CE1, CE2 CE3 and CE6), as also expected from the data shown in FIG. 4.

Figure 5:
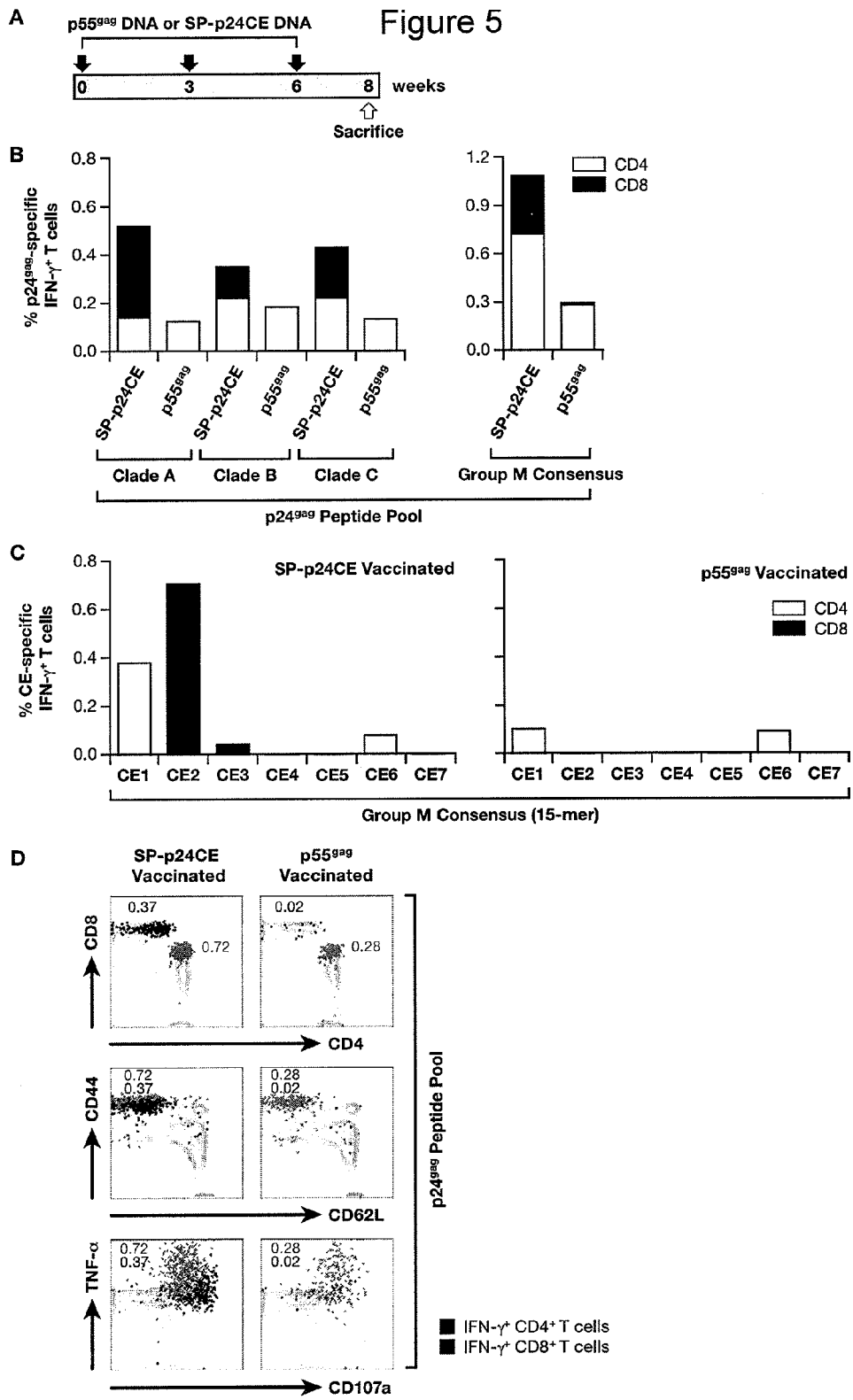
FIG. 5: Phenotypic and functional analysis of T cell responses generated by p55$^{gag}$ and p24CE DNA vaccination. (A) Mice (N=5/group) were vaccinated 3 times (week 0, 3 and 6) with 20 µg of a plasmid expressing HXB2 p55$^{gag}$ (clade B) or 20 µg of a mixture of plasmids expressing SP-p24CE1 and SP-p24CE2. The mice were sacrificed 2 weeks after the last immunization. Three independent experiments were performed and a representative experiment is shown. (B) Pooled splenocytes were stimulated with Clade A, B or C peptide pools (15-mers) spanning the p24$^{gag}$ region (left panel) and the Group M consensus peptide pool (right panel). The frequency of the CD4$^+$ (open bars) and CD8$^+$ (filled bars) p24$^{gag}$-specific IFN-γ producing T cells was determined (C) The splenocytes from the SP-24CE (left panel) and p55$^{gag}$ (right panel) DNA vaccinated mice were stimulated with peptide pools specific for the individual CEs. The frequency of the CD4$^+$ (open bars) and CD8$^+$ (filled bars) CE-specific IFN-γ producing T cells was determined. (D) Plot overlays show the phenotypic and functional characterization of the antigen-specific T cells induced by SP-p24CE (left panels) and p55$^{gag}$ (right panels) DNA vaccines upon stimulation with p24$^{gag}$-specific peptide pool. Total T cells recovered from the spleen are shown as grey contours, and the antigen-specific IFN-γ$^+$ T cells are overlaid as red (CD4$^+$ T cells) or black (CD8$^+$ T cells) dots. The plots show the CD4/CD8 distribution (top panel), memory phenotype as determined by CD44/CD62L staining (middle panel) and TNFα/CD107a expression (bottom panel) among the T cells from vaccinated mice. The frequency of CD4 (red) and CD8 (black) IFN-γ T lymphocytes is shown.
Figure 6:
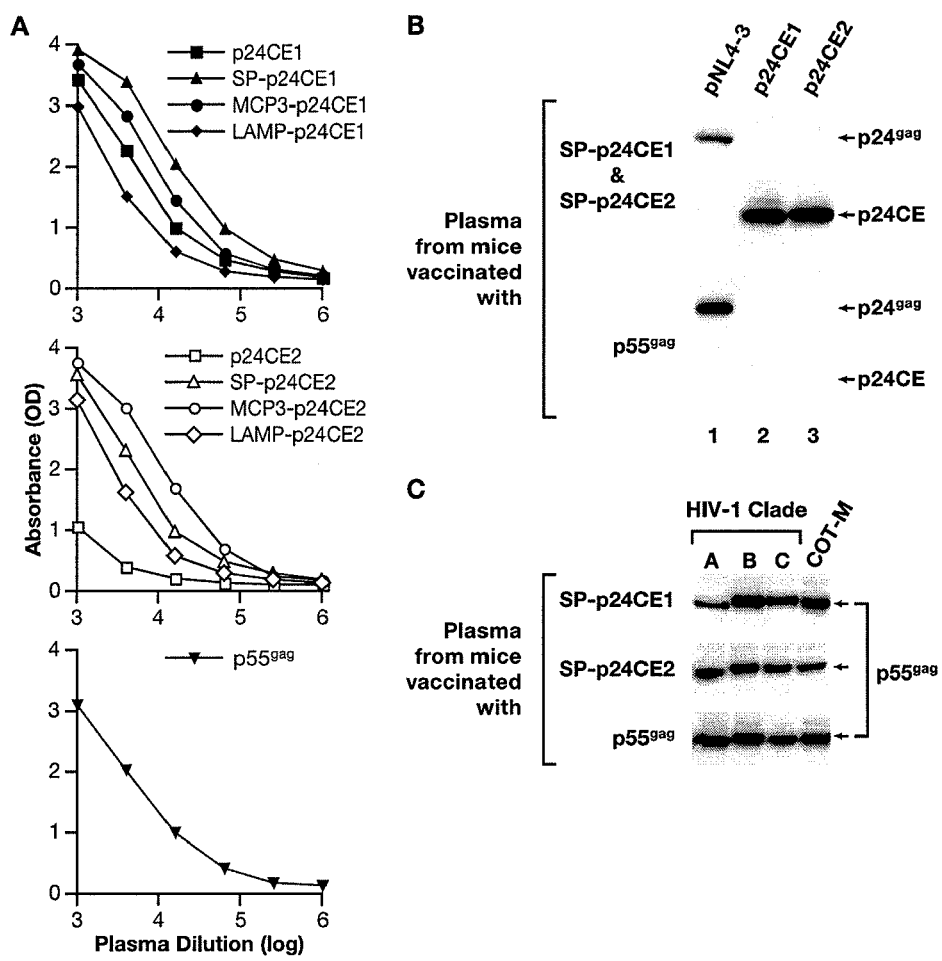
FIG. 6: Humoral immune responses in p24CE DNA vaccinated mice. (A) Anti-HIV-1 p24$^{gag}$ antibodies were measured in plasma from p24CE and p55$^{gag}$ DNA vaccinated C57BL/6 mice by a standard chide B p24$^{gag}$ ELISA. The graphs show absorbance (optical density, OD) and pooled plasma samples dilutions from mice vaccinated with the different p24CE1 plasmids (top panel), p24CE2 plasmids (middle panel), or p55$^{gag}$ DNA (bottom panel). (B) Humoral responses induced upon SP-p24CE or p55$^{gag}$ DNA vaccination in mice were analyzed by Western immunoblot assays. The membranes contain p24$^{gag}$ protein collected from supernatants of HEK293 cells transfected with 5 µg of the infectious molecular clone pNL4-3 (lane 1) or the p24CE proteins collected from the cell-associated fractions of cells transfected with SP-p24CE1 and SP-p24CE2 plasmids (lanes 2 and 3, respectively). The membranes were probed with plasma (1:5000 dilution) from mice vaccinated with a mixture of SP-p24CE1&2 DNAs (top panel) or p55$^{gag}$ DNA (bottom panel) followed by anti-mouse IgG-HRP labeled antibody and visualized by ECL. (C) Detection of humoral responses to full-length p55$^{gag}$ in mice vaccinated with p24CE or p55$^{gag}$ DNA by Western immunoblot assay. The p55$^{gag}$ proteins were obtained from HEK293 cells transfected with 0.5 µg of RNA/codon optimized plasmids expressing unprocessed p55$^{gag}$ from clades A, B and C or COT-M, respectively. The proteins were resolved on 10% NuPAGE Bis-Tris gels, and the membranes were probed with plasma (dilution 1:200) from mice immunized with DNAs expressing the secreted p24CE proteins SP-p24CE1 (top panel), SP-p24CE2 (middle panel) and p55$^{gag}$ (bottom panel).

We also evaluated the quality of the cellular immune responses elicited by the different immunogens (FIG. 5D) using the p24$^{gag}$ peptide pool followed by intracellular cytokine staining and polychromatic flow cytometry. Vaccination with p55$^{gag}$ DNA induced primarily CD4$^+$ (red) T cell responses, while p24CE vaccination induced both CD4$^+$ (red) (CE1 and CE6) and CD8$^+$ (black) (CE2 and CE3) T cell responses (FIGS. 5B and 5C, top panel). Both immunogens induced effector memory T cells (CD44$^{hi}$ an and CD62L$^{neg}$) (FIG. 5C, middle panel), which were mainly CD4$^+$ (0.28% of total T cells) in mice vaccinated with p55$^{gag}$ DNA, and both CD4$^+$ (0.72% of total T cells) and CD8$^+$ (0.37% of total T cells) in the mice vaccinated with the SP-p24CE DNA. Further analyses revealed that antigen-specific IFN-γ$^+$ T cells produced TNF-α and expressed CD107a on the surface upon stimulation with antigen, indicating induction of cytotoxic T cells (FIG. 5D, bottom panel). We also noted that the CD8$^+$ T cells (black), induced only by SP-p24CE DNA vaccination, expressed higher levels of CD107a and lower levels of TNFα than the CD4$^+$ T cells (red), a phenotype consistent with the degranulation associated with CTL activity. Collectively our results show that the p24CE vaccine increased breadth and magnitude of cellular responses to p24$^{gag}$ region in DNA vaccinated mice, by inducing robust responses to several of the highly conserved elements, and that the responses are multifunctional, a desired feature for an effective HIV vaccine, Vaccination with p24CE Induces Cross-Clade Reactive Humoral Immune Responses We next examined the induction of humoral immune responses using pooled plasma samples from p24CE DNA vaccinated mice (N=5/group) by an ELISA measuring clade B p24$^{gag}$ responses (FIG. 6A). The different p24CE antigens readily induced high levels of humoral responses with titers similar or greater than those achieved in p55$^{gag}$ DNA vaccinated mice (except p24CE2, middle panel). Vaccination with p24CE DNA induced antibodies to both the p24CE proteins (FIG. 6B, top panel, lanes 2 and 3) as well as to the processed p24$^{gag}$ protein (lane 1). In contrast, the antibodies induced by p55$^{gag}$ DNA vaccination readily detected p24$^{gag}$ (FIG. 6B, bottom panel, lane 1), but failed to recognize the p24CE proteins (lanes 2 and 3). Thus, similar to the cellular immune responses (see FIG. 5), the antibodies elicited upon vaccination with full-length p55$^{gag}$ DNA were unable to recognize the conserved elements.

We also examined the cross-clade reactivity of these responses by Western immunoblot analysis (FIG. 6C). Membranes containing p55$^{gag}$ proteins from consensus clades A and C, clade B (HXB2) and COT-M, obtained from transiently transfected were probed with pooled plasma samples from mice vaccinated with plasmids expressing SP-p24CE1, SP-p24CE2 or p55$^{gag}$. The Western immunoblot assays showed that the antibodies induced by the p24CE and p55$^{gag}$ DNA vaccinated mice detect the different p55$^{gag}$ proteins. These data suggest that similar to p55$^{gag}$, p24 CE vaccinated mice induce cross-clade reactive antibodies.

Together, these data show that p24CE DNA vaccination induced strong Immoral (FIG. 6) and cellular (FIG. 4) immune responses to the highly conserved elements in p24$^{gag}$, and that CE segments are not or only poorly immunogenic when expressed as part of the complete p55$^{gag}$ in DNA vaccinated C57BL/6 mice.

Discussion

The experiments performed in mice demonstrated that a DNA vaccine expressing 7 selected highly Conserved Elements within HIV-1 p24$^{gag}$ can be produced and that this DNA vaccine is immunogenic in comparison to DNA-encoded full-length native p55$^{gag}$. We have previously demonstrated that individuals chronically infected with HIV-1 develop cellular immune responses specific for the peptides encoded by the 7 conserved elements described in this work [34]. Furthermore, we found that the breadth, magnitude and avidity of these cellular responses to some CE were significantly higher among patients able to control HIV-1 infection, which suggests that responses against these conserved regions are clinically relevant [34].

Starting from our understanding of the rules for robust gene expression, and to avoid the escape potential of HIV, we constructed optimized DNA vectors that express maximal levels of new artificial immunogens based on highly conserved elements of the p24$^{gag}$ region. This vaccine design is based on two principles, (i) the immunogen must include critical and highly conserved elements of the virus that cannot mutate without a severe loss in viability, and (ii) the immunogen must exclude HIV epitopes that are capable of mutating without significantly affecting viral fitness. The former may induce responses against a large number of HIV isolates, and the latter avoids immunodominant competition from variable regions, which may render ineffective the vaccine-induced immune response. Not only expression, but also the stability and presentation of the artificial antigens encoded by the DNA vectors were optimized To this end, different fusion constructs were designed. We previously noted that either addition of a signal peptide or fusion to either MCP3 or LAMP were beneficial for protein expression [81,80,94], and found that these modifications also stabilize the p24CE proteins.

To maximize stimulation of CD4$^+$ cells in addition to CD8$^+$ T cells, we designed S secreted immunogens. The p24CE antigen linked to the signal peptide of GM-CSF was expressed at high levels and also produced both CD4$^+$ and CD8$^+$ antigen-specific T cells as well as good antibody titers. In contrast, p24CE proteins fused to MCP-3 or LAMP directed the development of mostly CD4$^+$ T cell responses. These studies show that it is possible to manipulate many properties of an antigen, altering the immune response in predictable ways. Although CD8$^+$ T cell responses have been linked to control of viremia, we have also reported that cytotoxic CD4$^+$ T cell responses contribute to viral control [103].

Figure 3:
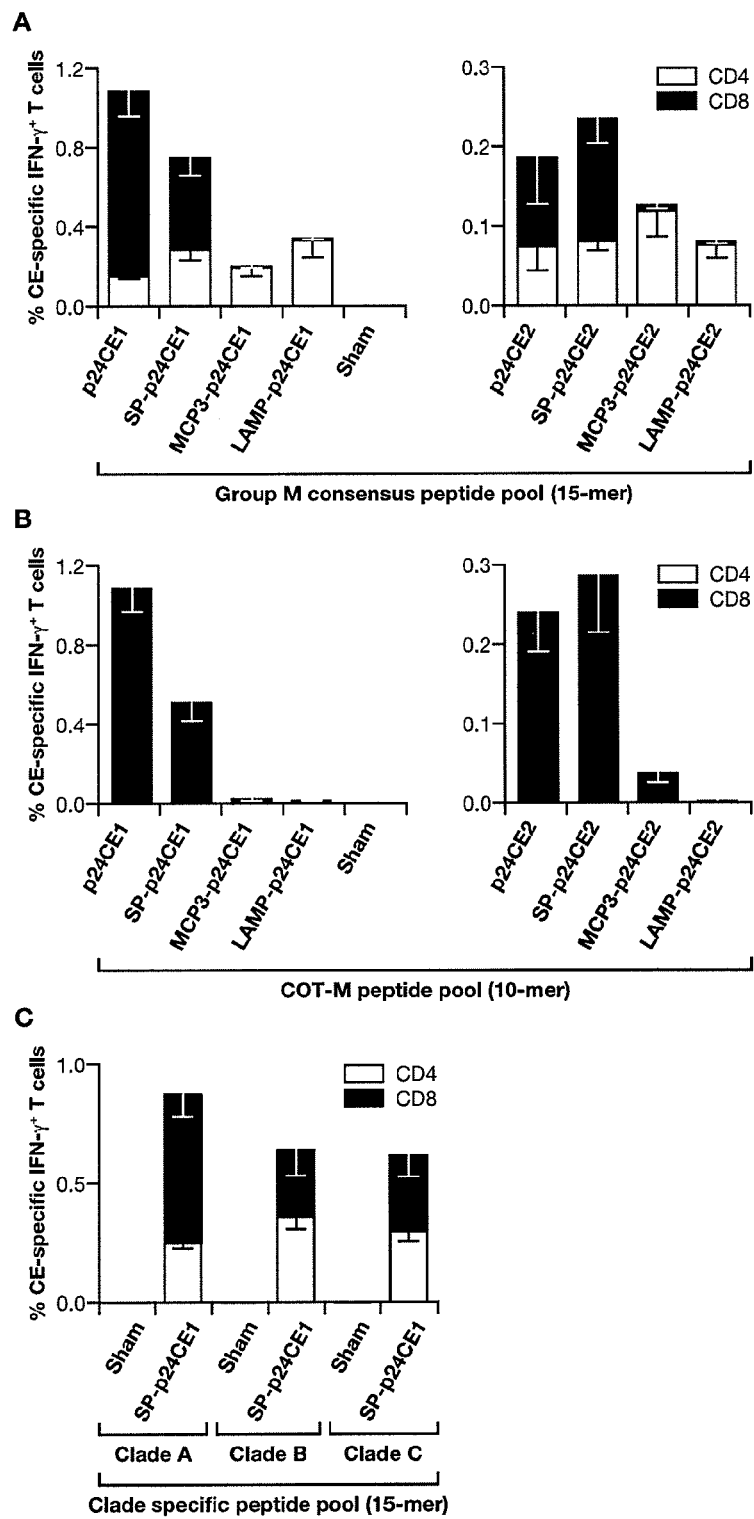
FIG. 3: Cellular responses in p24CE DNA vaccinated C57BL/6 mice. Mice were vaccinated using in vivo EP with 20 µg of the indicated p24CE1 (left panel) Of p24CE2 (right panel) DNA plasmids (A, B) or with SP-p24CE1 DNA (C). Splenocytes from individual animals were stimulated (A) with the Group M Consensus peptide pool (15-mer peptides overlapping by 11 AA), (B) with the COT-M peptide pool (10-mea overlapping by 9 AA) consisting of the matching peptides of p24CE1 and p24CE2 proteins, and (C) with peptide pools representing the clade A, B, and C p55$^{gag}$ sequences (15-mer peptides overlapping by 11 AA), as described in Materials and Methods. The frequency of CE-specific IFN-γ producing CD4$^+$ (open bars) and CD8$^+$ (filled bars) T cells was determined by polychromatic flow cytometry. The mean and SEM are shown. Three experiments were performed and data from a representative experiment are shown.

The p24CE vaccine induced both CD4+ (CE1 and CE6) as well as CD8+ (CE2 and CE3) specific T cell responses in the C57BL/6 mice; these CD8+ T cells had the functional phenotype of mature CTLs and were absent in mice immunized with the DNA encoding p55$^{gag}$. The molecules generated allow the selection of the most optimal combinations to achieve the best protective response for HIV prophylaxis. We have found that p24CE proteins are more immunogenic than the full-length Gag protein, expanding the quality of cellular responses to recruit CD8+ T cells with the functional properties of canonical CTLs in C57BL/6 mice. These findings suggest that the peptides containing the CE regions produced from the full-length p55$^{gag}$ antigen were not recognized efficiently by the T cells. This could be due to poor antigen processing or presentation, or alternatively due to interference by immunodominant peptides from other regions within p55$^{gag}$, which are able to divert or inhibit immune response. In addition, as shown in FIGS. 3 and 4, the trafficking of the protein greatly affected its immunogenicity, with the p24CE and SP-p24CE eliciting the highest and most balanced CD4 and CD8 responses. Selection of the most optimal p24CE protein induced higher and broader immunogenicity than p55$^{gag}$. We have recently also shown that dendritic cells in vitro loaded with RNA encoding the p24CE described in this work are able to stimulate T cell responses when mixed with autologous PBMC from HIV patients or to induce de novo T cell responses in PBMC from healthy donors. The responses elicited by p24CE were usually as high as those by full-length Gag [33].

All the immunogenicity studies described in the present work were performed in C57BL/6 mice. In our experience, p55$^{gag}$ DNA immunization using the Balb/c mouse mode induces higher T cell responses, but those responses are almost exclusively directed towards a single immunodominant epitope, AMQMLKETI, which is present in our p24CE construct. Therefore, to avoid the restrictions imposed by this limited repertoire, we chose the C57BL/6 mouse model for the work described herein. We found very low primary immune responses to the CE regions after DNA vaccination using full-length p55$^{gag}$. It will be of interest to further examine whether other vaccine modalities, i.e. recombinant viral vectors, expressing p55$^{gag}$ are able to induce higher immune responses to the CE. To our knowledge, this study is the first comparative evaluation of immunity induced by a full-length immunogen and that induced by highly conserved elements from within the same protein. Our analysis points to the negative effect of regions outside of the defined conserved elements, which, it is important to note, are present in the full-length wild type as well as in the consensus and mosaic molecules as well as in the reported epitope immunogens. Thus, the use of the highly Conserved. Element platform offers the advantage of focusing the immune responses to the invariable epitopes present in the viral proteome. Similar to the work described here, Letourneau et al. [11] previously demonstrated that a chimeric protein containing a string of several invariable regions from the HIV-1 proteome was immunogenic, but a direct comparison with the same sequences expressed within the natural proteins was not performed. In our study, we applied more stringent criteria to define conserved elements resulting in shorter peptide sequences (12-24 AA) that exclude adjacent more variable segments. In addition, our analysis of the immune responses was performed using peptide pools strictly confined to the conserved segments defined as immunogens and, therefore, the contribution to the T cell responses of putative artificial new epitopes created by the boundaries was completely excluded. In conclusion, we showed that the p24CE DNA vaccine induced broad cross-clade reactive cellular and humoral responses in vaccinated mice. We detected robust immune responses, including CD8+ T cells, to several CE upon p24CE DNA vaccination in mice, whereas only very poor (CD4+ only) or no responses to the CE were obtained by DNA vaccination with vectors expressing full-length p55$^{gag}$. Thus, the inclusion of DNA vectors expressing the conserved elements is a promising vaccine strategy to induce broader immunity compared to vaccination with the p55$^{gag}$ DNA alone. These results suggest further evaluation of the p24CE antigens in macaques.

Materials and Methods p24$^{gag}$ Conserved Elements Selection

Using all HIV-1 M group p24$^{gag}$ coding sequences available in the 2009 Los Alamos database, we identified sequences of at least 8 AA in length, in which all AA were conserved in at least 98% of all sequences. This requirement was then relaxed in two ways: First, using available data that correlated epitope recognition with clinical viral load, we sought to include complete epitopes that were associated with loin viral load and exclude epitopes that were associated with high viral load. Secondly, we allowed 1 toggle (variable) site/CE segment if the 2 most common AA at that site are together found in >99% of all known sequences [32]. To accommodate this variation, we created two plasmids, each with 7 CE segments from 12-24 AA in length, separated by 2-4 AA spacers (typically Ala-Ala-X) and differing only by the single toggle AA. The length and sequence of the spacers was set based on the existing knowledge of cleavage specificities and peptide availability [104], as well as to avoid fortuitous junctional homologies to HIV and the human proteome, the latter determined by searching against the HIV and human protein sequence databases.

DNA Plasmids

The p24CE and gag gene coding sequences were designed by RNA/codon optimization for efficient expression in mammalian cells [73-75] and chemically synthesized (GeneArt, Life Technologies, Grand Island, N.Y.). The genes were cloned into the pCMVkan vector [81] optimized for high gene expression. pCMVkan contains the human cytomegalovirus promoter, and the expressed transcripts contain a optimal surrounding for the AUG initiator codon from HIV-1 tat that prevents initiation of translation from internal AUGs [105], the bovine growth hormone (BGH) polyadenylation site, and the kanamycin resistance gene. This vector does not contain any splice sites or introns. The p24CE1 and p24CE2 proteins were produced from independent vectors (plasmids 164H and 182H, respectively). The secreted forms SP-p24CE1 and SP-p24CE2 contain the GM-CSF signal peptide (AA 1-17; Genbank accession Nr. NP_000749) at the N terminus (plasmids 234H and 235H). The MCP3-p24CE1 and MCP3-p24CE2 (plasmids 167H and 201H) are fusion proteins with the monocyte chemoattractant protein 3 (MCP-3) [80-81]. The LAMP-p24CE1 and LAMP-p24CE2 (plasmids 191H and 202H) are fusion proteins with the lysosomal associated membrane protein 1 (LAMP-1) [98-101]. Full-length p55$^{gag}$ proteins were produced from RNA/codon optimized genes cloned into the pCMVkan plasmid, expressing Gag from clade A (plasmid 187H, Genbank accession number AAQ98129), clade B (plasmid 114H, HXB2, Genbank accession number AAB50258), clade C (plasmid 160H, Genbank accession number AAD12096) and the center-of-tree COT-M (222H) [106]. For immunizations HXB2 p55$^{gag}$ was used. Endotoxin-free DNAs were prepared using Qiagen kit according to the manufacturer's protocol (Qiagen, Valencia, Calif.)

Transfection and Protein Analysis

DNA plasmids were transfected into 1×10⁶ HEK-293 cells using the calcium phosphate co-precipitation technique. Culture supernatants and cells were harvested 24 or 48 hours later, and protein expression was visualized by Western immunoblot analysis. The proteins were resolved on 10% or 12% NuPAGE Bis-Tris gels (Invitrogen, Carlsbad, Calif.), transferred onto nitrocellulose membranes (Invitrogen), which were probed with a goat anti-p24$^{gag}$ antibody (dilution 1:3000, provided by L. Arthur, SAIC, NCI, Frederick) followed by anti-goat IgG-HRP labeled antibody (dilution 1:10,000; Calbiochem, EMD chemicals, Gibbstown, N.J.) or with plasma (1:200 dilution) from DNA vaccinated mice followed by anti-mouse IgG-HRP labeled (1:10,000 dilution, GE Healthcare, Piscataway, N.J.). As control, the membranes were probed with anti-human pan-actin antibody (clone C4, EMD Millipore, Billerica, Mass.) at a dilution of 1:10,000. The bands were visualized using the enhanced chemiluminescence (ECL) plus Western blotting detection system (GE HealthCare, Piscataway, N.J.).

Mouse DATA Vaccination Studies

Female C57BL/6N (6 to 8 weeks old) were obtained from Charles River Laboratories, Inc. (Frederick, Md.) and were housed at the National Cancer institute, Frederick, Md., in a temperature-controlled, light-cycled facility. The mice were immunized with 20 μg of the vaccine DNAs by intramuscular injection followed by in vivo electroporation by ELGEN® constant current electroporation device (Inovio Pharmaceuticals, Inc, Blue Bell, Pa.). As negative controls, a group of mice received equal amount of sham DNA following the same immunization protocol. The animals were vaccinated two (0 and 4 weeks) or three times (0, 3, and 6 weeks), and were sacrificed 2 weeks after the last vaccination when spleens and blood were collected for the analysis of cellular and humoral responses.

Intracellular Cytokine Staining

The frequency of antigen specific cytokine⁺ T cells was measured using polychromatic flow cytometry, as previously described [80]. The following set of 15-mer Gag peptide pools, overlapping by 11 AA, were used to stimulate the vaccine-induced cellular responses: HINT-1 consensus clade A (Cat#8116), consensus clade C (Cat#8118), and Group M Consensus (Cat#11057), obtained from the AIDS Research and Reference Reagent Program (Germantown, Md.); Gag 15-mer from HXB2/Clade B (Infinity Biotech Research & Resource, Inc, Aston, Pa.). Peptide pools spanning p55$^{gag}$, p24$^{gag}$ or only CE were generated. In addition, we used pools of 10-mer peptides overlapping by 9 AA from COT-M spanning the individual CE1-CE7, not including linker sequences, of p24CE1 and p24CE2 (peptide synthesis facility of the Massachusetts General Hospital, Boston). Splenocytes were cultured at 37° C. and 5% CO$_2$ at a density of 2×10⁶ cells/ad in complete RPM1-1640 medium containing Gag peptide pools at a final concentration of 1 μg/nil of each peptide. In all experiments, splenocytes cultured in medium without peptide pools or stimulated with phorbol myristate acetate (PMA) and calcium ionophore (Sigma, St. Louis, Mo.) were used as negative and positive control respectively. Protein secretion was blocked by the addition of monensin (GolgiStop, BD Biosciences) 1 hour after stimulation. After 12 hours incubation, the cells were harvested and cell surface staining was performed using the following antibody cocktail: CD3-APCCy7, CD4-PerCP, and CD8-Pacific Blue (BD Pharmingen, San Diego, Calif.). Splenocytes were washed twice, fixed, permeabilized with Cytofix/Cytoperm (BD Pharmingen) and staining for intracellular cytokine detection was performed using IFN-γ-FITC (BD Pharmingen). In another set of experiments, the antibody cocktail for surface staining included: CD3-AF700, CD4-PerCP, CD8-Pacific Blue, CD44-V500, CD62L-PE CD107a-PE Cy7 (BD Pharmingen). The anti-CD 107a antibody was added during the culturing of splenocytes with peptides. IFN-γ-APC and TNF-α-APC Cy7 (BD Pharmingen) were used for intracellular cytokine staining. After intracellular staining, the cells were washed twice and the samples were analyzed on an LSR II flow cytometer (BD Pharmingen). Data analysis was performed using the FlowJo platform (Tree Star, Inc., Ashland, Oreg.). All antigen specific responses are reported after subtracting values obtained from the samples without peptide stimulation. Only splenocytes giving a response more than two fold higher than the value of the sample without peptides (medium alone) were considered positive.

Antibody Assays

Serial dilutions of plasma samples were analyzed by standard HIV-1 clade B p24$^{gag}$ ELISA (Advanced Bioscience Lab, Rockville, Md.), measuring optical absorbance at 450 nm.

Example 2

Figure 7:
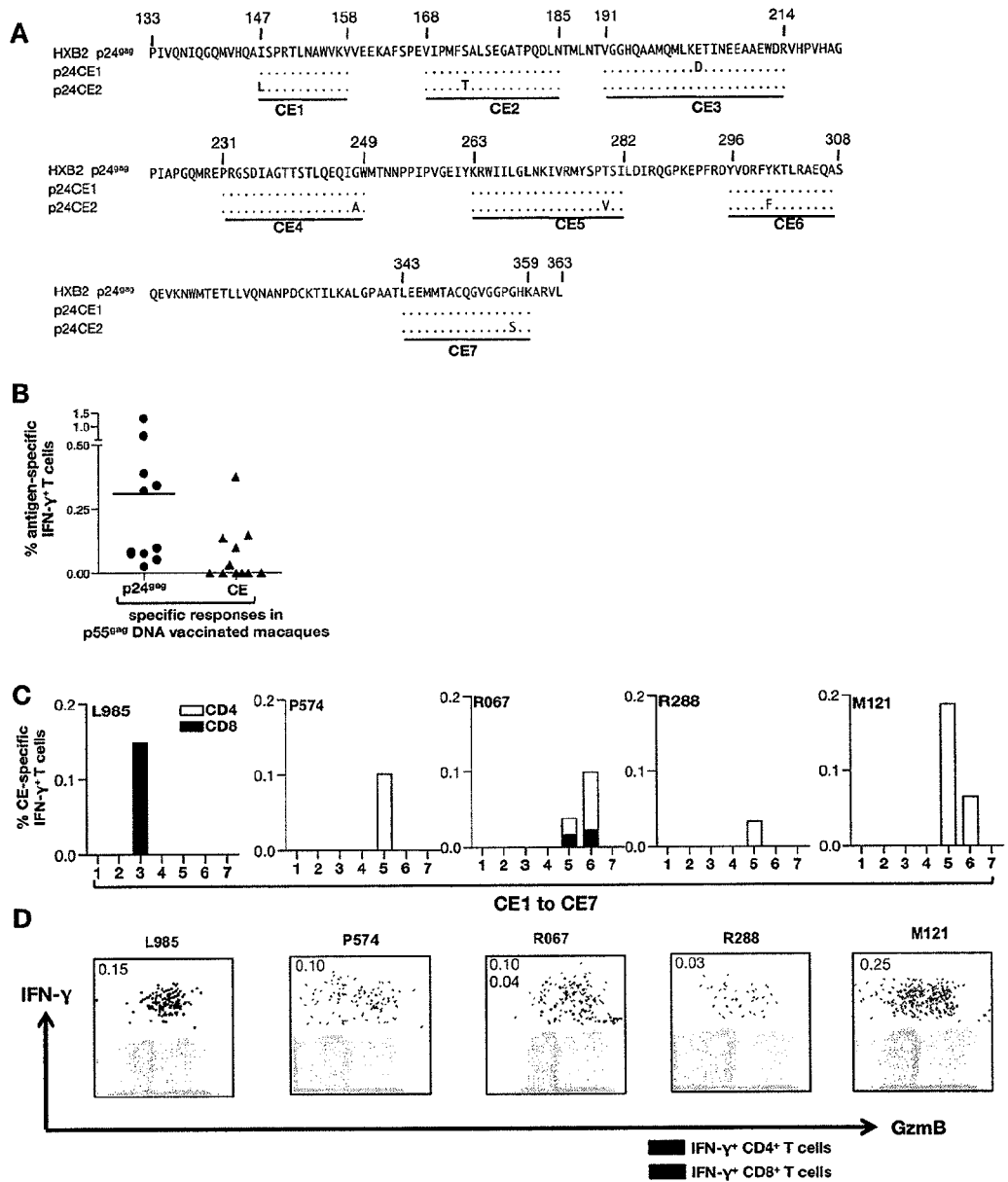
FIG. 7: p55$^{gag}$ DNA vaccination of macaques induces poor CE-specific cellular immune responses. (A) Alignment of the amino acid (AA) sequence of the 7 CE represented in the p24CE1 and p27CE2 proteins with HXB2 p24$^{gag}$ protein. The toggled AA in each CE is shown. The numbering of the AA in HXB2 p24$^{gag}$ protein is according to the HIV data base at the www site hiv.lanl.gov/. (B) Both p24$^{gag}$... specific and CE-specific T cell responses were measured at 2 weeks after the last vaccination from 11 macaques, which were immunized with plasmid DNA encoding HIV Gag. (C) Mapping of the individual CE-specific responses in 5 (of 11) macaques that had responses to CE (panel B). The frequency of IFN-γ$^+$ T cells specific for each of the 7 CE is shown. Open bars: CD4$^+$ T cells; filled bars: CD8$^+$ T cells. (D). Dot plots showing the IFN-γ$^+$ and granzyme B (GzmB) production of the CE-specific CD4$^+$ (red) and CD8$^+$ (black) T cells from the 5 macaques shown in panel C.

Core DNA Vaccination Induces Cross-Clade Specific Cellular Immune Responses in Macaques Results Vaccination with Gag DNA Induces Poor p24$^{gag}$ Conserved Element (CE)-Specific Cellular Immune Responses in Macaques We first investigated whether vaccination of macaques with a plasmid expressing p55$^{gag}$ was able to elicit immune responses to the 7 CE [32,34] identified within the p24$^{gag}$ sequence (FIG. 7). Four animals were vaccinated twice (0, 2 month) with COT-M p55$^{gag}$ DNA by IM injection followed by in vivo electroporation (EP). Seven animals previously vaccinated with a plasmid expressing the full-length p55$^{gag}$ delivered intramuscularly (N=4) [82] or with a plasmid expressing the p37$^{gag}$ protein delivered via IM/EP (N=3) [67] were included in the analysis. Induction of Gag-specific responses was evaluated upon stimulation of PBMC with a p24$^{gag}$ specific peptide pool as well as with a CE-specific peptide pool (see Material and Methods). All 11 macaques developed readily detectable responses to the p24$^{gag}$ region, however only 5 of the 11 macaques (45%) developed responses to CE (FIG. 7B). Next, we analyzed the specificity of the responses towards the individual conserved elements in the 5 macaques that showed CE recognition (FIG. 7C). We found that 3 macaques (L985, P574, R288) recognized only 1 CE (CE3 or CE5), whereas 2 macaques (R067 and M121) developed responses to 2 CE (CE4, CE5 and CE5, CE6, respectively). Moreover, only animal L985 developed significant CD8⁺ T cell responses against the CE, while the other 4 animals showed almost exclusively CD4⁺ T cell mediated responses. These CE-specific T cell responses included CD4⁺ and CD8⁺ T cells with cytotoxic potential, as judged by the presence of antigen-specific Granzyme B⁺ T cells in all 5 animals (FIG. 7D).

The lack of CE recognition in most of the vaccinated animals raised the concern drat the immunogenicity of the CE epitopes within the Gag protein may be impaired due to either suboptimal processing and presentation of the CE-containing peptides, or immunodominance exerted by variable regions within Gag directing the CTL responses away from CE.

Vaccination with p24CE DNA Induces Cellular Immune Responses in Macaques

Figure 9:
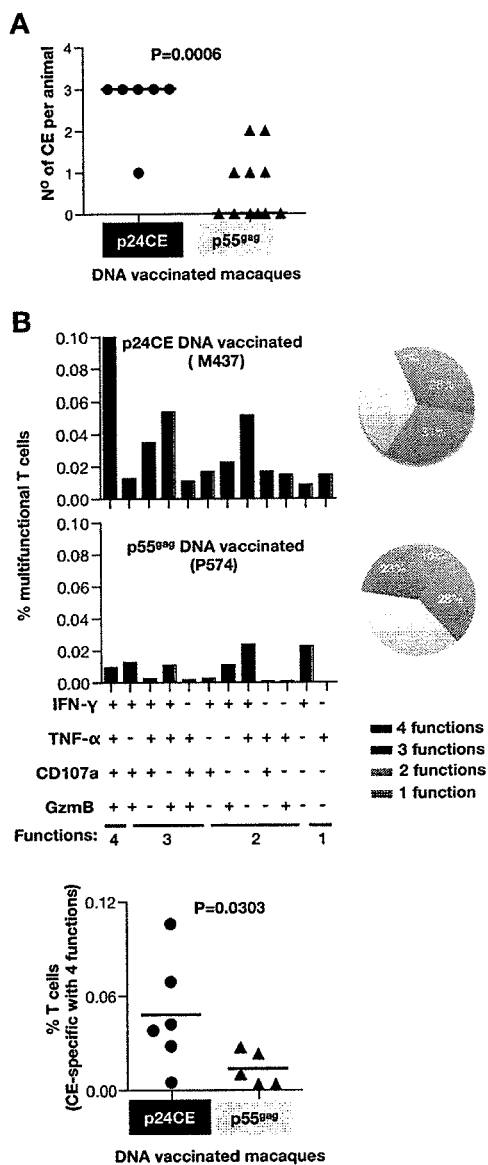
FIG. 9: induction of broad and polyfunctional T cell responses in p24CE vaccinated macaques. (A) The number of CE recognized per animal in macaques vaccinated with p24CE DNA and p55$^{gag}$ DNA are shown. (B) Frequency of CE-specific polyfunctional T cells was evaluated by their ability to produce IFN-γ, TNF-α, CD107a and granzyme B (GzmB). The data from one representative macaque from each group is shown: M437 (top panel) vaccinated with p24CE DNA; P574 (middle panel) vaccinated with p55$^{gag}$ DNA. The pie charts (right) show the proportion of polyfunctional responses in these macaques. Frequency of IFN-γ$^+$, TNF-α$^+$, CD107a$^+$ and GzmB$^+$ polyfunctional CE-specific T cells (4 functions) as % of total T cells in macaques vaccinated with p24CE DNA and p55$^{gag}$ DNA, respectively, are shown (bottom panel). Median values are indicated.

To test whether broader immune responses to the CE could be elicited in macaques, we vaccinated animals with a mixture of the two p24CE DNA vectors which were engineered to express the 7 CE collinearly arranged. (See Example 1). The two proteins differed by 1 AA ('toggle') per CE, (SP-p24CE1 and SP-p24CE2) (FIG. 7A). Four animals were vaccinated twice (0, 2 month) with p24CE DNA using IM/EP delivery. Cellular immune responses were measured in blood samples collected 2 weeks after the $2^{nd}$ vaccination (EP2wk2). Two additional macaques (M437, P314), previously immunized with p24CE plasmids, were also included in this analysis. All 6 macaques developed CE-specific cellular responses (FIG. 8A), as measured by the production of IFN-γ with a frequency ranging from 0.1% to 0.6% of total T cells. The overall levels of responses were non-significantly lower compared to those of the $p55^{gag}$ DNA vaccinated animals data not shown). These responses included both CD4$^+$ and CD8$^+$ T cells, although the CD8$^+$ T cell responses were dominant in 4 of the 6 vaccinated animals (FIG. 8A). These results are in contrast to those obtained upon $p55^{gag}$ DNA vaccination, where only 5 out 11 immunized animals developed CE responses, mediated mainly by CD4$^+$ T cells (FIG. 7). Mapping of the CE-specific responses (Figure BB) revealed recognition of all CE except CE1 and CE7, using out-bred animals with different MHC class I haplotypes. Comparison of animals vaccinated with p24CE or Gag DNA shows that there was no apparent correlation between haplotype and ability to develop responses to CE, hence the differences could be attributed to the immunogen. Five of the 6 CE vaccinated macaques developed responses to 3 CE and only one animal (M437) showed responses to 1 CE. Phenotypic analysis of the antigen-specific T cells revealed both central (CD28$^+$CD95$^+$) and effector memory (CD28$^-$CD95$^+$) (FIG. 8C, top panels). A subset of the CE-specific IFN-γ$^+$ T cells also expressed granzyme B, indicating a cytotoxic phenotype (Figure BC, bottom panels), thus eliciting cytotoxic. CE-specific responses. These results indicate that, similar to our observation from vaccinated mice (Example 1), the CE DNA vectors are immunogenic in all 6 macaques and that most (5 of 7) of the CE were immunogenic. These data also demonstrate that CE-containing peptides are processed and presented properly and suggest that the failure to induce CE-specific responses from $p55^{gag}$ or $p37^{gag}$ is likely the result of immunodominance exerted by epitopes located in the variable regions,

Vaccination with p24CE DNA Induces Broader and Higher Levels of Polyfunctional CE-Specific T Cell Response than Vaccination with $p55^{gag}$ DNA We further dissected CE immunogenicity by comparing the cellular responses induced by p24CE and $p55^{gag}$ DNA vaccination. First, we compared the number of CE recognized in the macaques vaccinated with DNA expressing the p24CE (N=6) Of full-length $p55^{gag}$ or $p37^{gag}$ (N=11) (FIG. 9A), immunization with p24CE induced responses to significantly more CE (p=0.0006; range 1-3 CE, median 3) than Gag DNA vaccination (range 0-2 CE) (FIG. 9A). These data demonstrate that p24CE DNA induced responses to more CE, indicating increased breadth of responses compared to $p55^{gag}$ DNA vaccination.

We also compared polyfunctionality (production of IFN-γ, TNF-α, CD107a and granzyme B) of the T cell responses upon stimulation with CE-specific peptides. FIG. 9B shows the distribution of CE-specific polyfunctional T cells from representative macaques that received either p24CE DNA (top panel) or $p55^{gag}$ DNA (middle panel). The proportion of polyfunctional T cells (1- to 4-function) is also shown as pie charts (right panels). These results demonstrate that p24CE DNA vaccination elicited higher CE-specific cytotoxic T cell levels than $p55^{gag}$ DNA vaccination. The frequency of CE-specific T cells secreting two cytokines, expressing granzyme B and able to degranulate upon antigen recognition (4-function) was also significantly higher (p=0.03) in macaques immunized with p24CE DNA (bottom panel). Together, these data show that the p24CE immunogen elicited significantly higher responses, including to more CE, and that these responses are multifunctional and have cytotoxic properties.

$P55^{gag}$ DNA Vaccination Boosts Pre-Existing CE-Specific T Cell Responses

Figure 10:
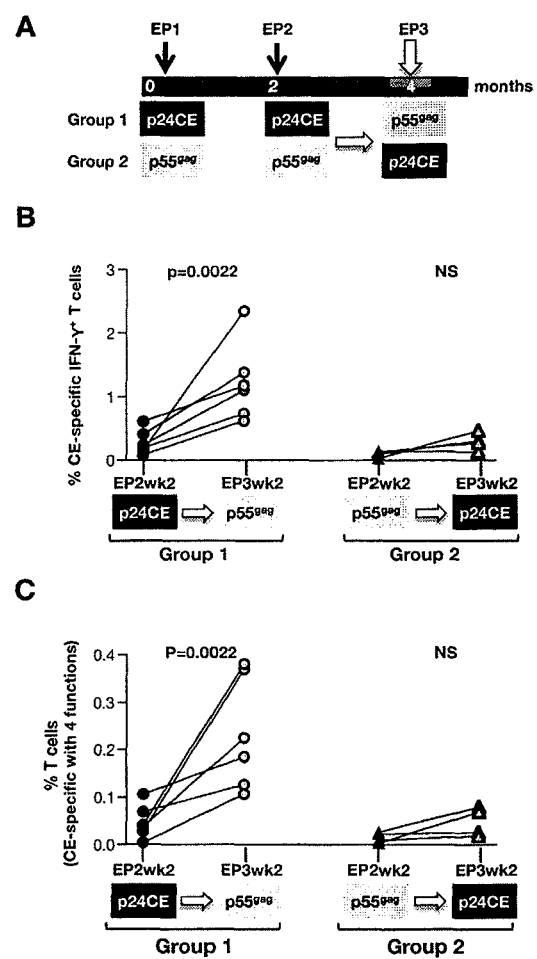
FIG. 10: Boosting of p24CE DNA primed macaques with p55$^{gag}$ DNA increases CE-specific cellular responses. (A) Vaccination schedule of group 1 with p24CE plasmid DNAs (EP1, EP2) followed by the heterologous p55$^{gag}$ DNA boost (EP3) and group 2 with p55$^{gag}$ DNA (EP1, EP2) followed by the heterologous p24CE DNA boost (EP3). (B) Frequency of the CE-specific IFN-γ$^+$ T cells in both groups before (EP2wk2) and after the heterologous boost (EP3wk2). (C) Frequency of IFN-γ$^+$ TNF-α$^+$CD107a$^+$GzmB$^+$ polyfunctional CE-specific T cells (4-function) in groups 1 and 2 before and after the heterologous boost.
Figure 11:
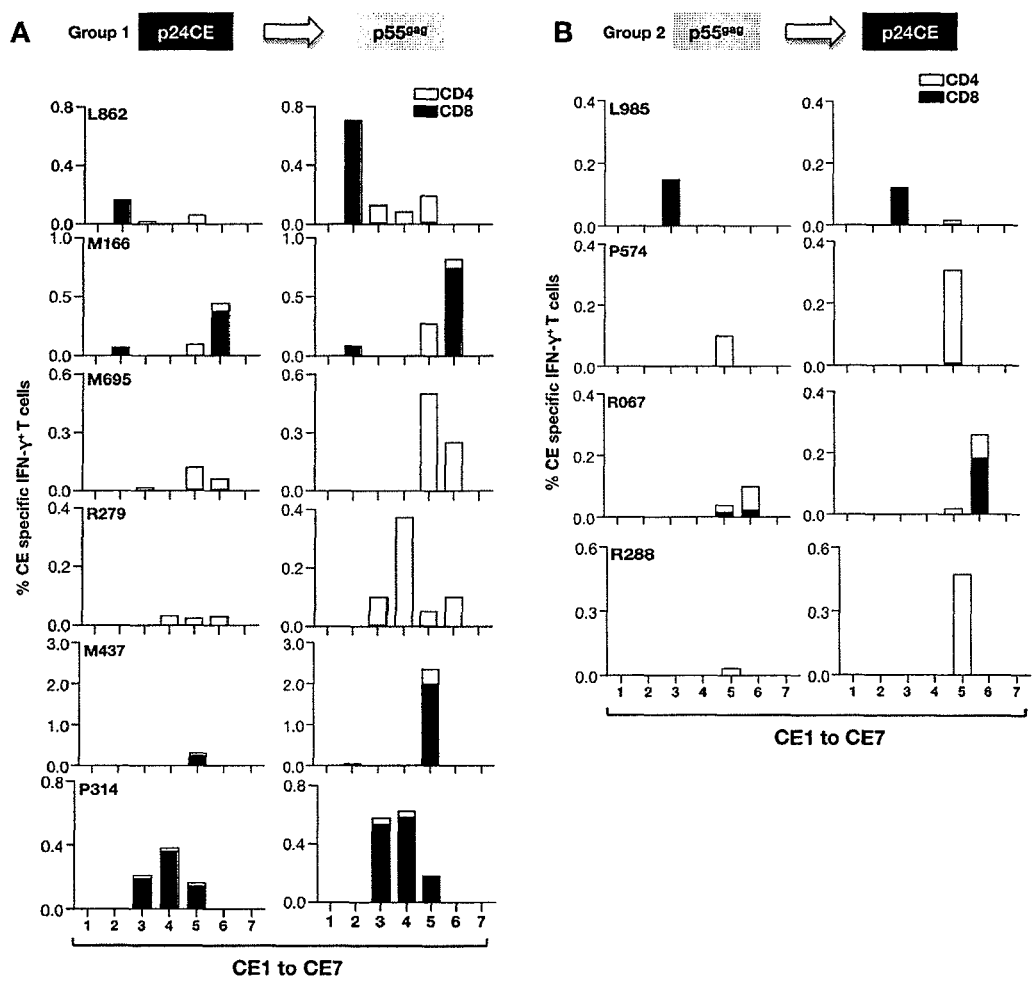
FIG. 11: Mapping of CE-specific T cell responses before and after heterologous boost. The CE-specific responses were mapped as described for FIG. 2B. The plots show comparisons of the responses upon p24CE DNA vaccination followed by p55$^{gag}$ DNA boost (group 1, A) and upon p55$^{gag}$ DNA vaccination followed by p24CE boost (group 2, B). The percentage of IFN-γ$^+$ CD4$^+$ (open bars) and CD8$^+$ (filled bars) T cells specific for each CE is shown.

Given that repeated vaccination with $p55^{gag}$ DNA failed or only poorly induced de nova CE-specific T cell responses (FIG. 7), we investigated whether full-length gag DNA vaccination could boost and/or broaden pre-existing CE-specific immunity. The p24CE-vaccinated macaques received an additional vaccination with a plasmid expressing COT-M $p55^{gag}$ DNA (FIG. 10A; group 1). This led to a significant increase (p=0.002) in CE-specific responses, reaching in some animals more than 1-2% of the total T cell population (FIG. 10B). Analysis of the polyfunctionality of these responses showed that the frequency of CE-specific T cells with 4 functions was also significantly boosted (p=0.002; FIG. 10C). Boosting with $p55^{gag}$ DNA also induced de novo responses to $p17^{gag}$ and C-terminal regions of Gag, thereby increasing the total Gag responses to levels similar to those obtained with the gag/p24CE DNA vaccine. Additionally, virtually the complete set of pre-existing responses to individual CE was boosted in 6 macaques (FIG. 11A, left panel). The number of the CE found to be immunogenic upon p24CE vaccination (1-3 CE/animal) increased to 2-4 CE/animal upon Gag DNA boost. These findings confirmed that the suboptimal responses induced by priming with full-length Gag were not related to the absence of processing or presentation of CE-containing peptides, but rather to their inability to induce de novo responses in the presence of other, likely more dominant, Gag epitopes outside of CE. Thus, the immunodominance exerted by Gag epitopes outside of CE was lost in the presence of pre-existing CE-specific responses.

We also investigated whether p24CE DNA vaccination could alter the CE-specific immunity in macaques previously vaccinated with $p55^{gag}$ DNA (FIG. 10A; group 2). Vaccination with p24CE DNA minimally increased the pre-existing CE-specific responses in 3 out of 4 macaques, (FIG. 10B, group 2) and modestly increased the polyfunctional CE responses in two of the vaccinated animals (FIG. 10C, group 2), although this increase was not statistically significant. Analysis of the individual CE (FIG. 11B) showed no new CE responses upon p24CE boost. The heterologous p24CE DNA boost did not alter the pre-existing CD4$^+$ or CD8$^+$ T cell distribution. Thus, the immunodominance exerted by epitopes outside of CE could not be overcome by p24CE vaccination, as this vaccine regimen did not alter the magnitude or breadth of Gag responses.

P24CE DNA Vaccination Induces Humoral Immune Responses that Recognize $p24^{gag}$ The development of Gag-specific humoral immune responses was also monitored over the course of study (FIG. 12A) using a $p24^{gag}$ ELISA. Upon vaccination with p24CE DNAs (group 1) antibodies recognizing $p24^{gag}$ were readily delectable and peaked 2 weeks after EP2 (mean reciprocal end-point dilution titer 5.2 log). Similarly, the $p24^{gag}$ antibody titers upon COT-M $p55^{gag}$ DNA vaccination also peaked 2 weeks post EP2 (mean reciprocal end-point dilution titer 5.3 log). Thus, both vaccines elicited similar $p24^{gag}$ antibody titers.

Figure 12:
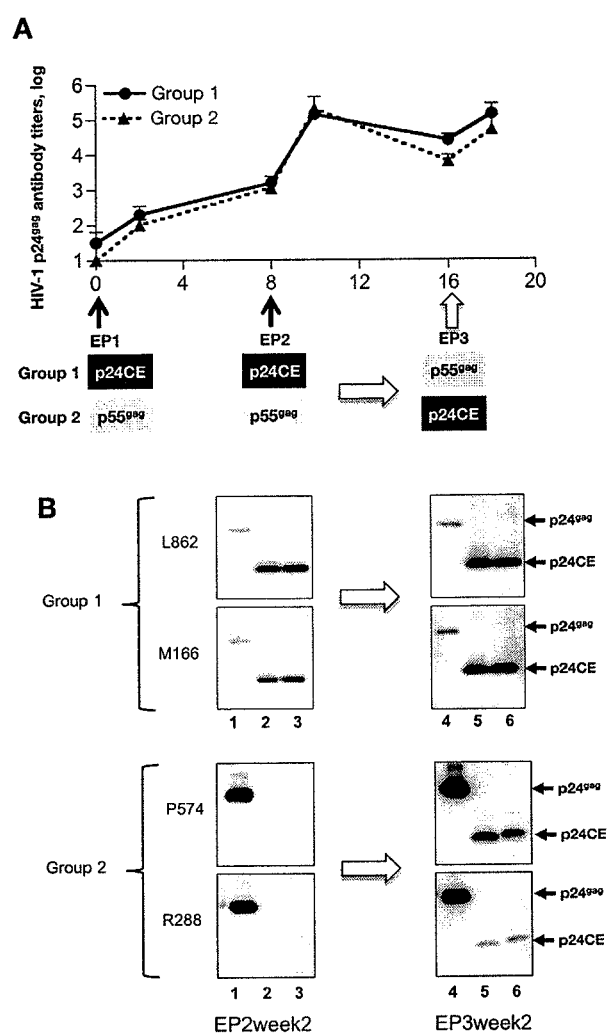
FIG. 12: Humoral immune responses upon p24CE DNA vaccination are boosted by p55$^{gag}$ DNA vaccination. (A) Reciprocal p24$^{gag}$ binding antibody endpoint titers (log) measured in plasma by ELISA at the indicated time points for macaques in group 1 and group 2 before and after the heterologous boosts. (B) Western immunoblot analysis was used to test the reactivity of the vaccine-induced antibodies from macaques in group 1 and 2 to p24$^{gag}$ and the p24CE proteins. The membranes contain either p24$^{gag}$ protein (lanes 1 and 4), p24CE1 (lanes 2 and 5) or p24CE2 (lanes 3 and 6) and were probed with plasma from macaques from group 1 (dilution 1:2000) and group 2 (dilution 1:500) collected before (EP2wk2; lanes 1-3) and after (EP3wk2, lanes 4-6) the heterologous boost.
Figure 14A:
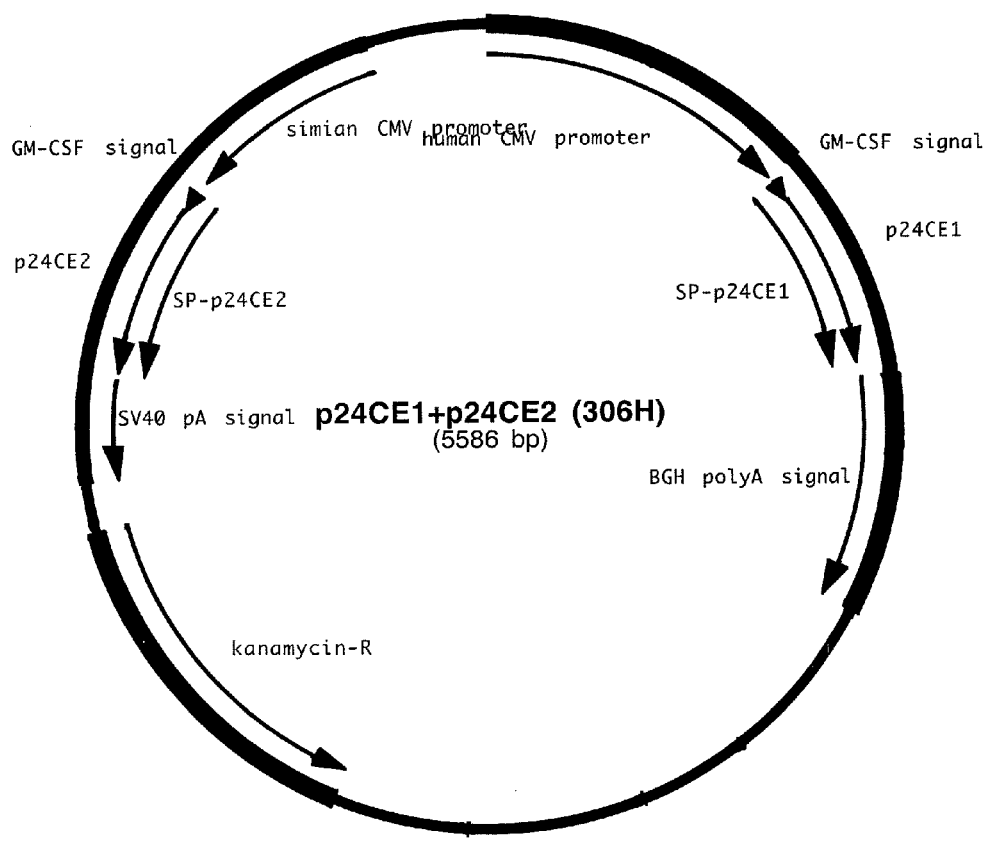
FIG. 14: Plasmid map (A) and sequence (B) of plasmid 306H that encodes p24 CE1+p24 CE2.
Figure 15A:
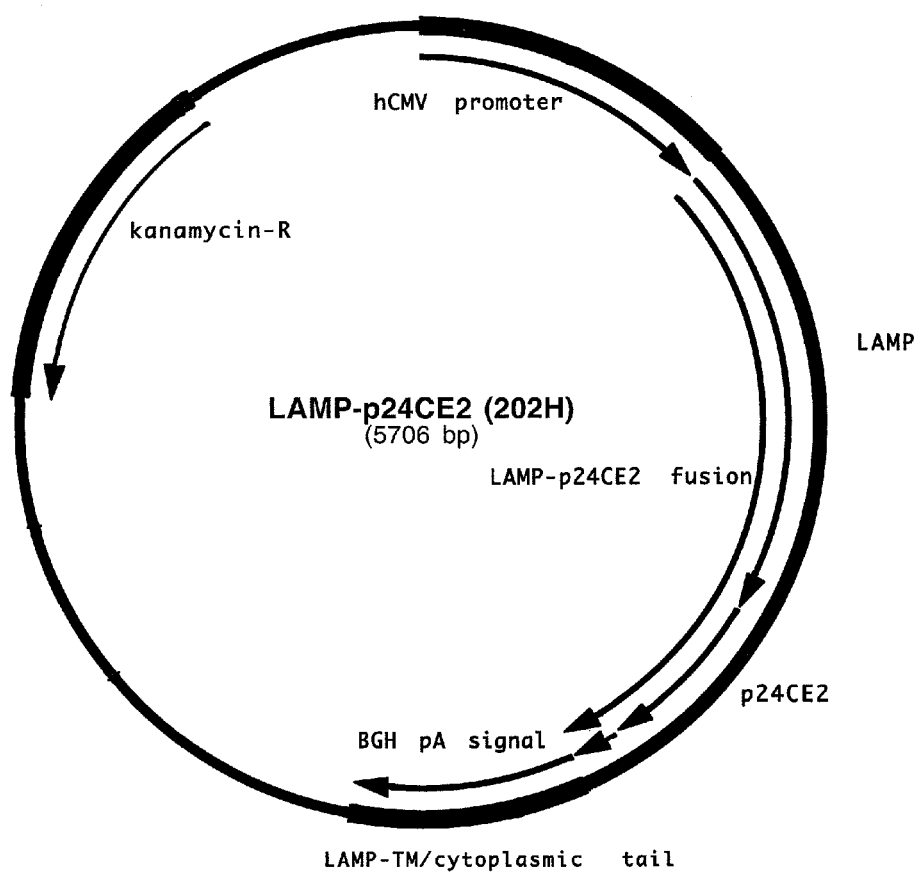
FIG. 15: Plasmid map (A) and sequence (B) of plasmid 202H that encodes LAMP-p24CE2.
Figure 16:
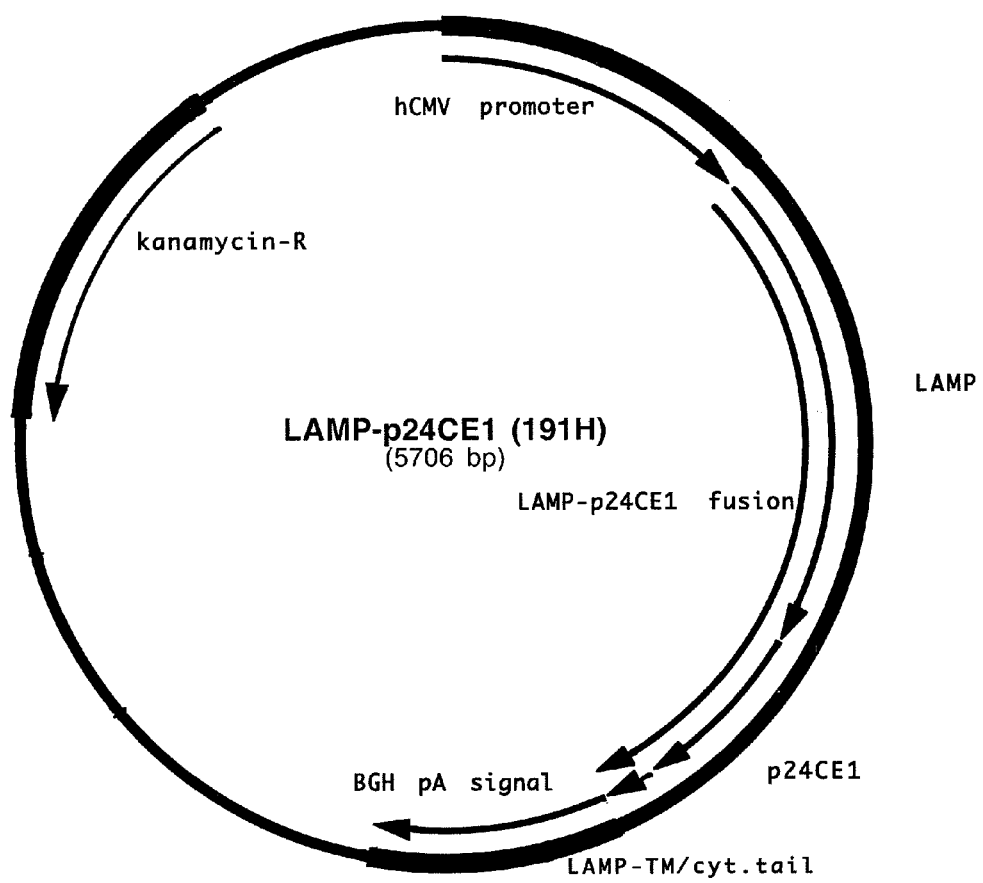
FIG. 16: Plasmid map (A) and sequence (B) of plasmid 191H that encodes LAMP-p24CE1.
Figure 17A:
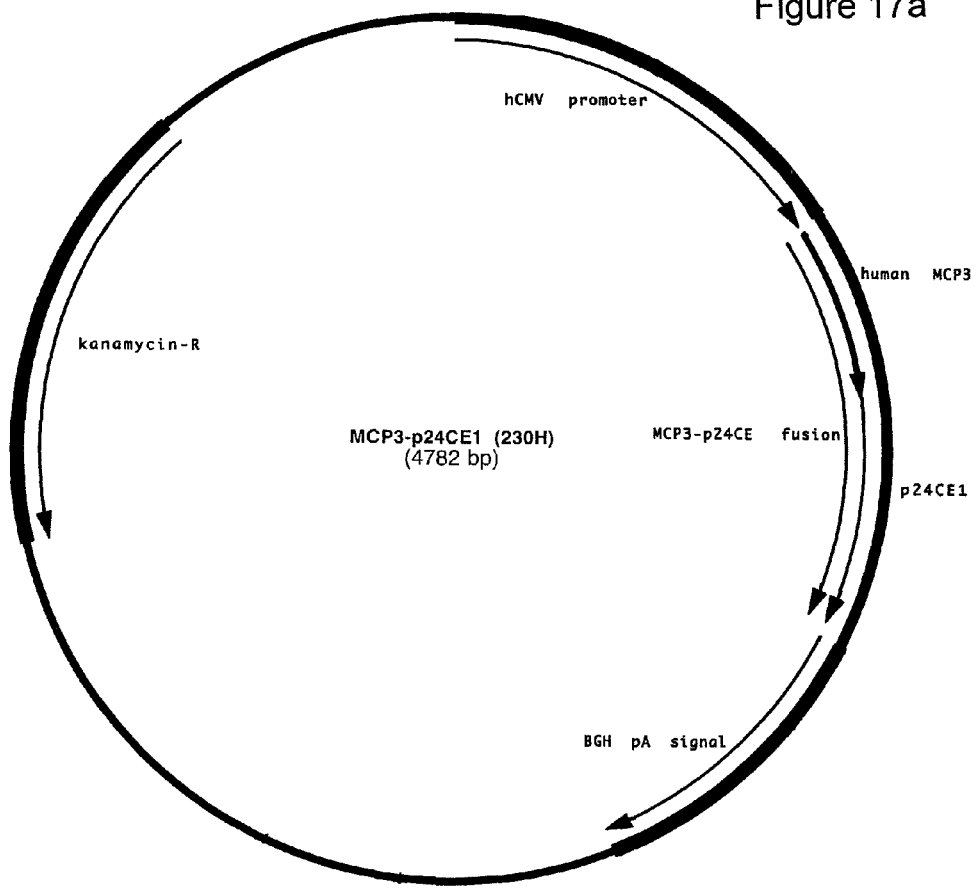
FIG. 17: Plasmid map (A) and sequence (B) of plasmid 230H that encodes MCP3-p24CE1.
Figure 18A:
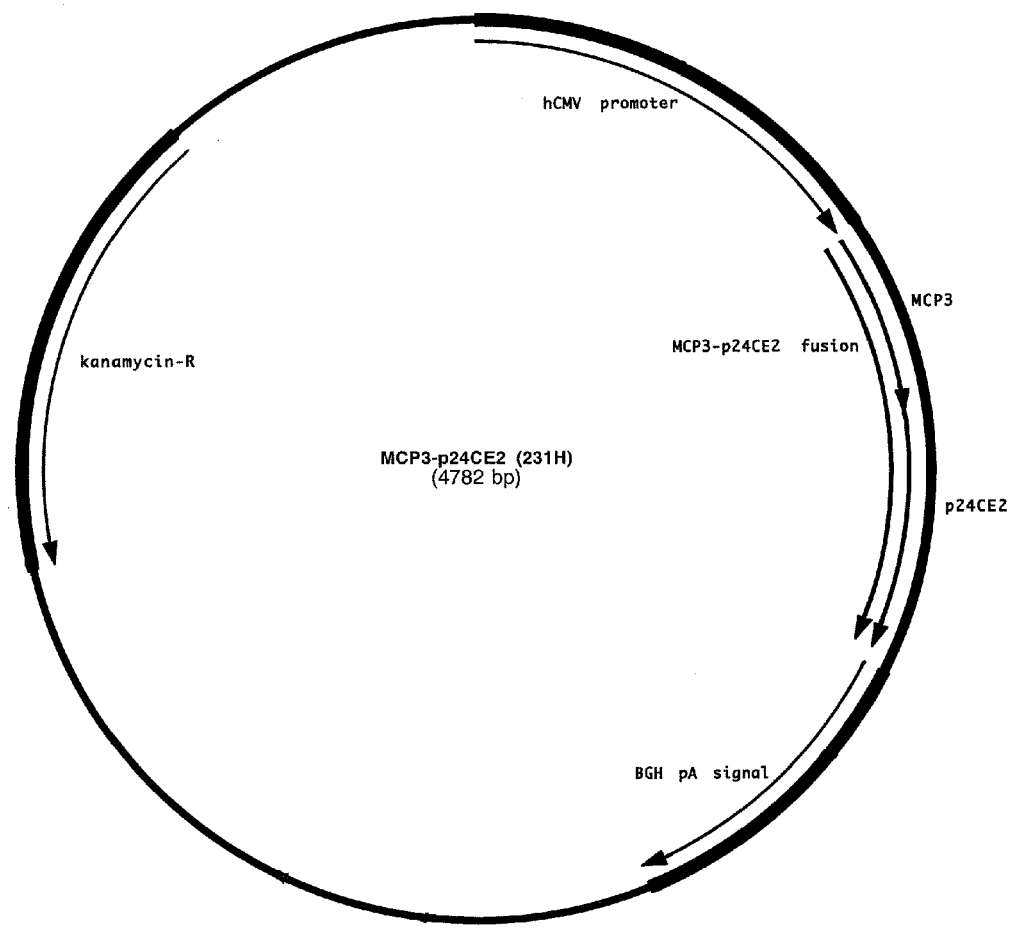
FIG. 18: Plasmid map (A) and sequence (B) of plasmid 231H that encodes MCP3-p24CE2.
Figure 19:
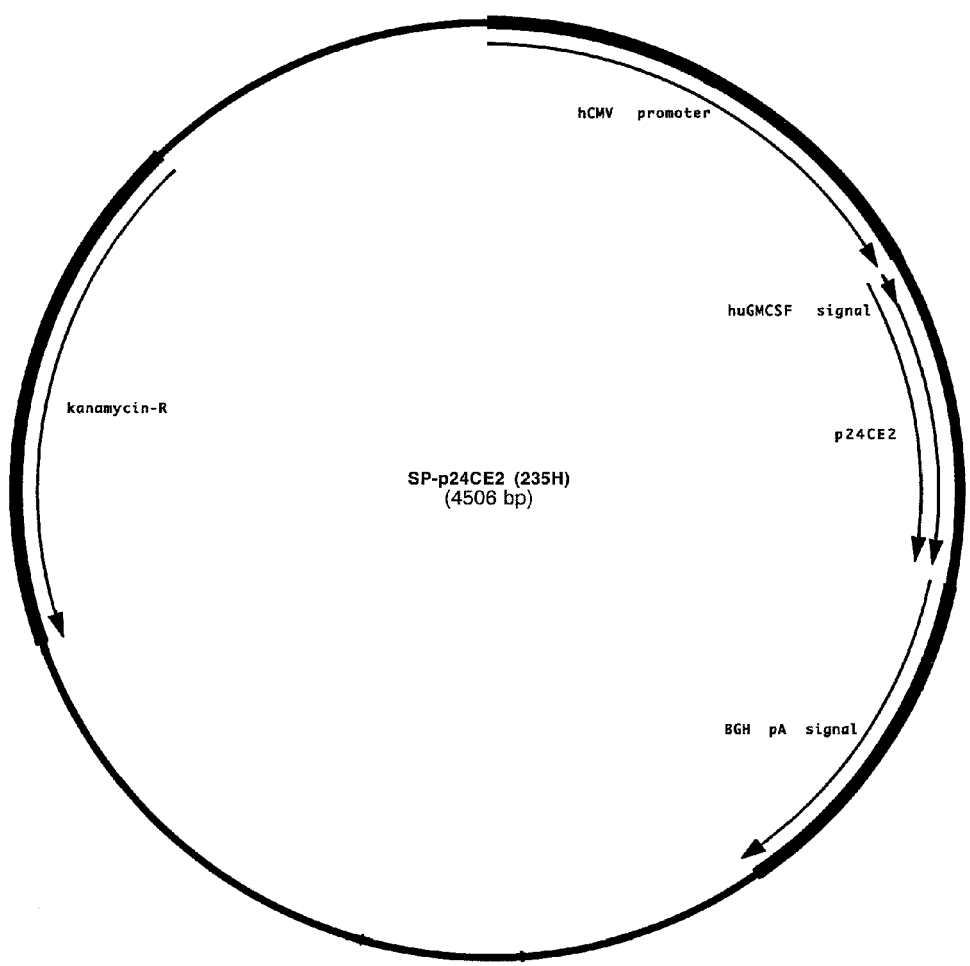
FIG. 19: Plasmid map (A) and sequence (B) of plasmid 235H that encodes SP-p24CE2.

We further assessed the ability of these antibodies to recognize the p24CE proteins as well as processed p24$^{gag}$ by Western immunoblots. The data from two representative macaques from each group are shown (group 1: L862 and M166, and group 2: P574 and R288) with similar data obtained from all animals from both vaccine groups. Plasma from macaques vaccinated with p24CE (Group 1) recognized naturally processed p24$^{gag}$ produced from a chide B molecular clone of HIV-1 (FIG. 12B, lane 1) as well as the p24CE1 (lane 2) and p24CE2 (lane 3) proteins. In contrast, vaccination with p55$^{gag}$ DNA (group 2) induced antibodies that strongly react with p24$^{gag}$ (lane 1), but failed to recognize p24CE proteins (FIG. 12B lanes 2 and 3). We conclude that only the p24CE DNA vaccination induces robust cellular and humoral responses to the conserved elements.

Lastly, we tested whether boosting with the heterologous DNA (EP3) affected the pre-existing humoral immune responses. ELISA assays showed similar increase in p24$^{gag}$ antibody levels in both groups (FIG. 12A). All Western immunoblot assays (FIG. 12B) were performed in parallel using the same plasma sample dilution and the same exposure time of the membrane to allow comparison of before and after the respective boosts. Following p55$^{gag}$ DNA boost of the p24CE DNA vaccinated animals (group 1), stronger reactivities to both p24$^{gag}$ (lane 4) as well as p24CE proteins (lanes 5 and 6) were found. These data demonstrate that p55$^{gag}$ DNA vaccination was able to substantially boost the CE-primed humoral immune responses despite its failure to induce de nova antibody responses able to recognize the CE protein. Vaccination of the p55$^{gag}$ DNA primed animals with p24CE DNA (group 2, bottom panels) showed induction of antibodies to p24CE proteins (lanes 5 and 6) and increased reactivity to p24$^{gag}$ (lane 4). Note, a significantly higher amount of plasma was used in order to detect p24CE proteins from the animals in group (dilution 1:500) compared to group 1 (dilution 1:2000). Thus, these data indicate that the heterologous p24CE DNA boost induced low level CE-specific responses, rather than inducing anamnestic responses (group 2). Together, these data show that prime immunization with p24CE DNA can alter the immunodominance of both cellular and humoral immune responses and that the immunodominance of epitopes outside of CE is not overcome by boosting with CE if the animal's vaccination involved priming with p55$^{gag}$. Therefore, priming with p24CE DNA followed by the heterologous p55$^{gag}$ DNA boost is a preferred approach to achieve broad and high cellular and humoral immune responses to the highly conserved elements of HIV-1 p24$^{gag}$ protein.

Discussion

We have described DNA vectors encoding collinearly 7 highly conserved elements of the HIV-1 Group M p24$^{gag}$ protein, and we have reported that vaccination of mice with these DNAs induced both cellular and humoral responses [57]. In the current report, we demonstrated that vaccination of rhesus macaques with these DNA vectors induced CE-specific cellular and humoral immune responses. Detailed analysis of cellular immune responses showed that p24CE DNA vaccination induced cytotoxic CD4$^+$ and CD8$^+$ T cells against CE and that the elicited T cell responses were polyfunctional. Therefore, our conserved element DNA vectors show desired features for an effective vaccine. Our vaccine regimen also shows a promising approach to overcoming a problem in the HIV vaccine field, where attempts to induce both antigen-specific CD4$^+$ and CD8$^+$ T cell responses and to broaden the vaccine-induced immunity to include subdominant epitopes have been less successful, even with a reported EP DNA/Ad boost immunization strategy [83].

Importantly, we found that the p55$^{gag}$ vaccine elicits no or only poor responses to CE. We also analyzed the responses from a previous report [4], where macaques were vaccinated with consensus or mosaic p55$^{gag}$ DNA as prime followed by recombinant Adenovirus boost. We found that 5 of the 12 animals that received the consensus molecule and 6 of 12 that received the mosaic molecules developed CE responses ranging from of 0-2 (consensus) and of 0-4 (mosaic) CE responses/animal, whereas several epitopes outside the CE were immunogenic in all the animals. In the study reported herein, we found that 5 of 11 macaques vaccinated with full-length COT-M or HXB2 p55$^{gag}$ DNA developed CE-specific responses (0-2 CE/animal), whereas epitopes outside the CE were immunogenic in all the macaques. The data of the two studies are thus in good agreement, although the methods of analysis were not identical [peptide mapping [4] versus analysis with CE-specific mixture of 15-mer and 10-mer peptides (this report)]. Irrespective of the nature of Gag vaccine (consensus, mosaic or wild type), we found responses to CE in only 42-50% of the animals, and the responses were to very few CE/animal, suggesting that immunodominant epitopes within Gag focus the CTL response away from these conserved targets. In this report, we experimentally tested this hypothesis and demonstrated that immunodominance of variable regions is indeed responsible for the poor immunogenicity of the CE.

Although vaccination with either p55$^{gag}$ or p37$^{gag}$ induced strong humoral responses, we found that these antibodies fail to cross-react with the CE protein, in contrast, our engineered p24CE DNA vaccine readily induced both antibodies and cell-mediated responses to several CE, bypassing the restriction associated with full-length Gag vaccination. Importantly, immunizing with a full-length Gag greatly boosted the pre-existing CE responses. Hence, exposure to virus might also have the effect of boosting CE responses in CE-vaccinated individuals.

In a recent paper, Stephenson et al, [17] compared responses of full-length molecules to their conserved elements (Gag, Pol, and Env) vaccine and concluded that the conserved element vaccine did not provide any benefit (breadth or magnitude). In contrast, we demonstrated a clear benefit from the CE vaccine, showing increased breadth and magnitude of responses. The difference between the studies may substantively by due to our more strict definition and selection of CE, which, in contrast to others, were selected in part by their association with virus control [34], further supporting their immunological relevance.

Previous analyses of HIV-1 infected persons with different HLA haplotypes demonstrated the presence of CE-specific T cells during the chronic phase of infection [20,34]. Higher avidity CTL responses in these regions were identified in HIV controllers and detailed analysis of the responses demonstrated that, for most epitopes analyzed, controllers were able to recognize more peptide variants [34]. This indicates that TCR promiscuity could be beneficial for the recognition of epitopes with mismatched amino acids resulting in better control of viral replication and prevention of escape mutants. These data also suggest that high avidity CE-specific responses are a potential correlate of HIV control. It is not clear why vaccination with full-length Gag generates poor CE responses (in mice or macaques), while these responses are detected in chronic HIV infection. It would be of interest to study different vaccination regimens and also to examine the time of development of CE responses during natural infection. The difference in elicited immune response is reminiscent of a previous report by Ferrari et al. [84], who showed that the immunodominant p17$^{gag}$ SL9 response identified in HLA-A*0201 infected persons could not be induced upon ALVAC-gag vaccination in these haplotype-selected volunteers, although this epitope has been implicated in the Sieve effect observed in the STEP HIV vaccine trial [85]. Both studies suggest that there may be differences between vaccine-induced and infection-induced cellular responses that should be taken into consideration for successful vaccine design; they also highlight the potential immunodominant decoy effect of a full-length immunogen design.

Impaired immunogenicity of the conserved elements in the context of the natural protein sequence could be due to the presence of variable regions, which may exert an immunodominant decoy effect preventing the recognition of the conserved epitopes. This possibility is supported by a recent study where a bias was found towards less-conserved regions in HIV-1 Ad5 gag/pol/nef vaccinated human volunteers [86]. Generation of responses mainly outside of the conserved elements by full-length Gag suggested an immunodominant decoy effect. In this context, the success of our p24CE DNA prince-p55$^{gag}$ DNA boost vaccine strategy is of great importance, because it showed strong boosting of pre-existing CE-specific cellular and humoral responses in macaques. Upon gag DNA boost, we report both a robust increase of the pre-existing CE-specific responses as well as development of de novo responses to regions outside the CE. These data imply that the immunodominance exerted by Gag epitopes outside of CE was lost in the context of pre-existing CE-specific responses.

The impaired immunogenicity of the conserved elements when expressed in the context of the complete Gag could in principle be related to suboptimal processing and presentation of the CE peptides, preventing efficient priming of adaptive immune responses. However, our p24CE prime-Gag boost study clearly demonstrates that processing of the full-length Gag protein produces a collection of CE-containing peptides that are recognized by T cells. We speculate that recognition of MHC-peptide complexes is less stringent for boosting memory T cell clones than for priming nave T cells. Similar to the observations on cellular immunity, full-length Gag boosted pre-existing B cell responses, while failing to prime the development of de novo antibodies able to recognize the CE protein. These findings support the concept that proper processing of CE-containing peptides from the native Gag protein takes place, and that these sets of CE containing peptides are able to potently augment pre-existing responses to different extents. Together, these findings point to a critical difference in T cell recognition of these peptides where a clear distinction between antigen-experienced and nave T cells is noted.

The question then arises whether a T cell vaccine can benefit from the responses elicited by selected T cell epitopes. A previous report [87] demonstrated the potency of T cell immunity in the absence of Env. In fact, a recent paper by Mudd et al. [88] showed that a T cell vaccine that induced Mamu-B*08-restricted CD8$^+$ T-cell responses targeting 3 different viral epitopes elicited responses able to control SIV$_{mac239}$ replication. Since our CE DNA vaccine was selected to highly restricted sequences and haplotype-independent, it is plausible that they too could induce such potent responses, which will be addressed in future studies.

The presented results contribute significantly to the development of improved vaccine candidates against HIV targeting the immune responses to essential highly conserved regions for the virus. We hypothesize that cellular immune responses targeting conserved regions of HIV and other highly variable pathogens, which do not allow rapid escape mutations without significant loss of viral fitness, are more likely to be protective [32-34]. Since there is evidence that vaccine-induced responses can change upon HIV infection resulting in virus escape in humans [89], a selection of strictly conserved elements is of great importance for the design of an effective vaccine. Such a selection should also avoid epitopes that may act as immunodominant decoys. Thus, a successful vaccine should be able to generate potent cross-clade specific humoral and cellular responses against conserved regions of the virus. Our results provide an effective strategy to overcome restrictions associated with immunodominance, while improving the magnitude and breadth of responses, especially those against conserved regions, minimizing the possibility of viral escape while increasing the recognition of naturally occurring divergent HIV strains. These results indicate that a vaccine candidate should be designed to extend this concept to the entire HIV proteome. Since the macaque model was in general shown to provide a similar response hierarchy to that obtained upon vaccination of humans comparing different vaccine platforms [90], our macaque study supports the evaluation of the novel CE vaccine strategies in humans.

Materials and Methods
DATA Vectors

The p24CE plasmids pSP-p24CE1 (plasmid 234H) and pSP-p24CE2 (plasmid 235H) have been described [57] and contain the human GM-CSF signal peptide at the N-terminus of the expression-optimized p24CE open reading frame. Briefly, the 7 CE were collinearly assembled in the order CE2-3-4-5-6-7-1 to avoid a strongly hydrophobic N-terminal CE1, and were connected via short linker sequences designed for efficient proteolytic cleavage [91,92]. The COT-M p55$^{gag}$ [93] DNA (plasmid 222H) expresses the full-length Gag from an RNA/codon optimized gene. The IL-12 DNA (plasmid AG157) produces the rhesus macaque IL-12 cytokine from an optimized expression vector [94,95]. The vaccine vector CMVkan [81] is comprised of a plasmid backbone optimized for growth in bacteria, the human cytomegalovirus (CMV) promoter without introns, the optimized p24CE or gag genes, the bovine growth hormone (BGH) polyadenylation site, and the kanamycin resistance gene. Endotoxin-free DNAs (Qiagen, Valencia, Calif.) were prepared according to the manufacturer's protocol.

Example 3

Additional Conserve Element Polypeptides

Alternative conserved elements were designed (FIG. 13). Briefly, CE1 was extended to provide a CE8. CE2 was extended to provide CE9. In this construct CE7 was removed. Accordingly, there are six conserve elements in the CE polypeptide. There were two variants of the conserve element polypeptide where one amino acid is changed in CE8 and CE9. Two versions were designed having different arrangements of the CEs. In the version termed "p24CEc" (p24CE1c and p24Ce2c), the order is CE8-9-2-3-4-6. In the version terms "p24CEd" (p24CE1d and p24CE2d), the order is CE9-3-4-5-6-8.

Example 4

Illustrative Data from 3 Different Vaccination Prime-Boost Schedules

Figure 20:
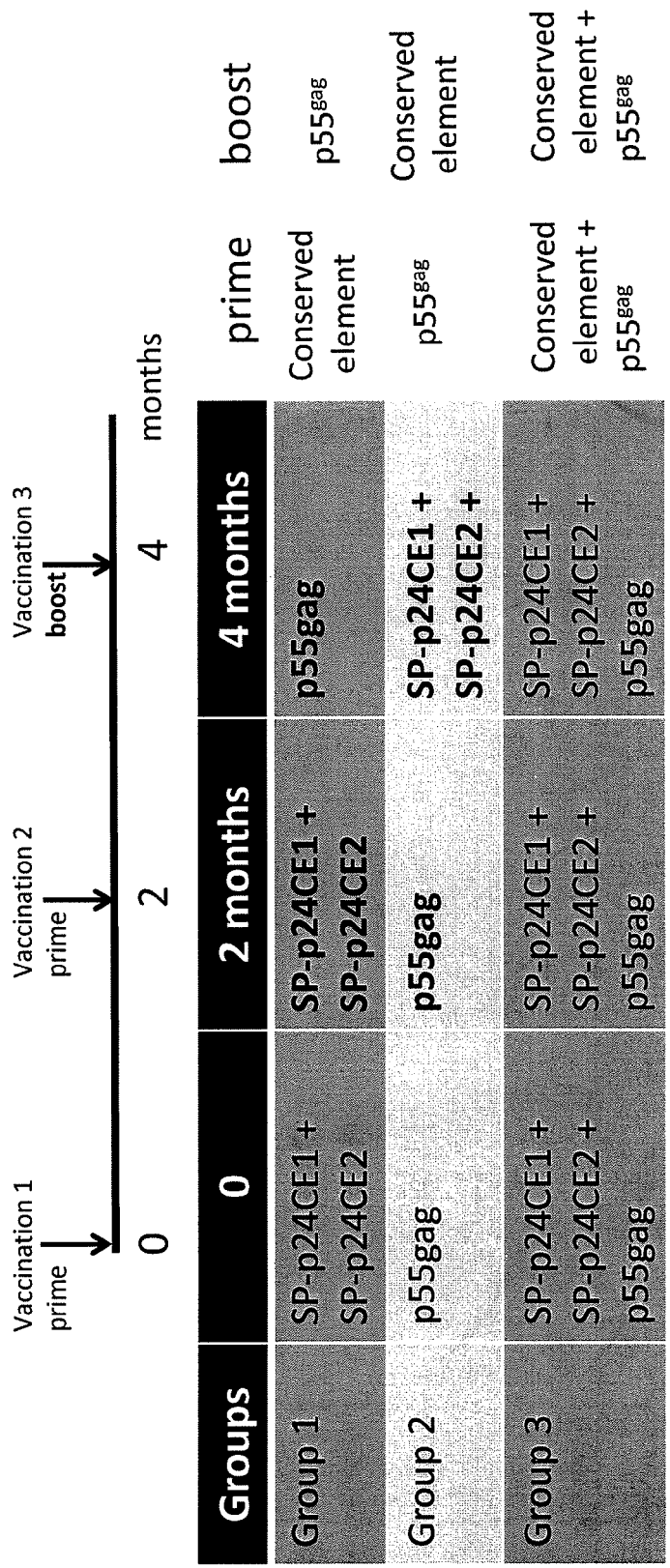
FIG. 20: Illustrative regimens for administering conserved element Gag vaccines and full-length p55gag vaccine.

We tested three different vaccination strategies in which the order of conserved element vaccines and full-length gag vaccine was varied. The three protocols are shown in FIG. 20:

1. p24CE prime followed by p55gag boost
2. p55gag prime followed by p24CE boost
3. combination of p24CE and p55gag in all vaccinations.

Figure 21:
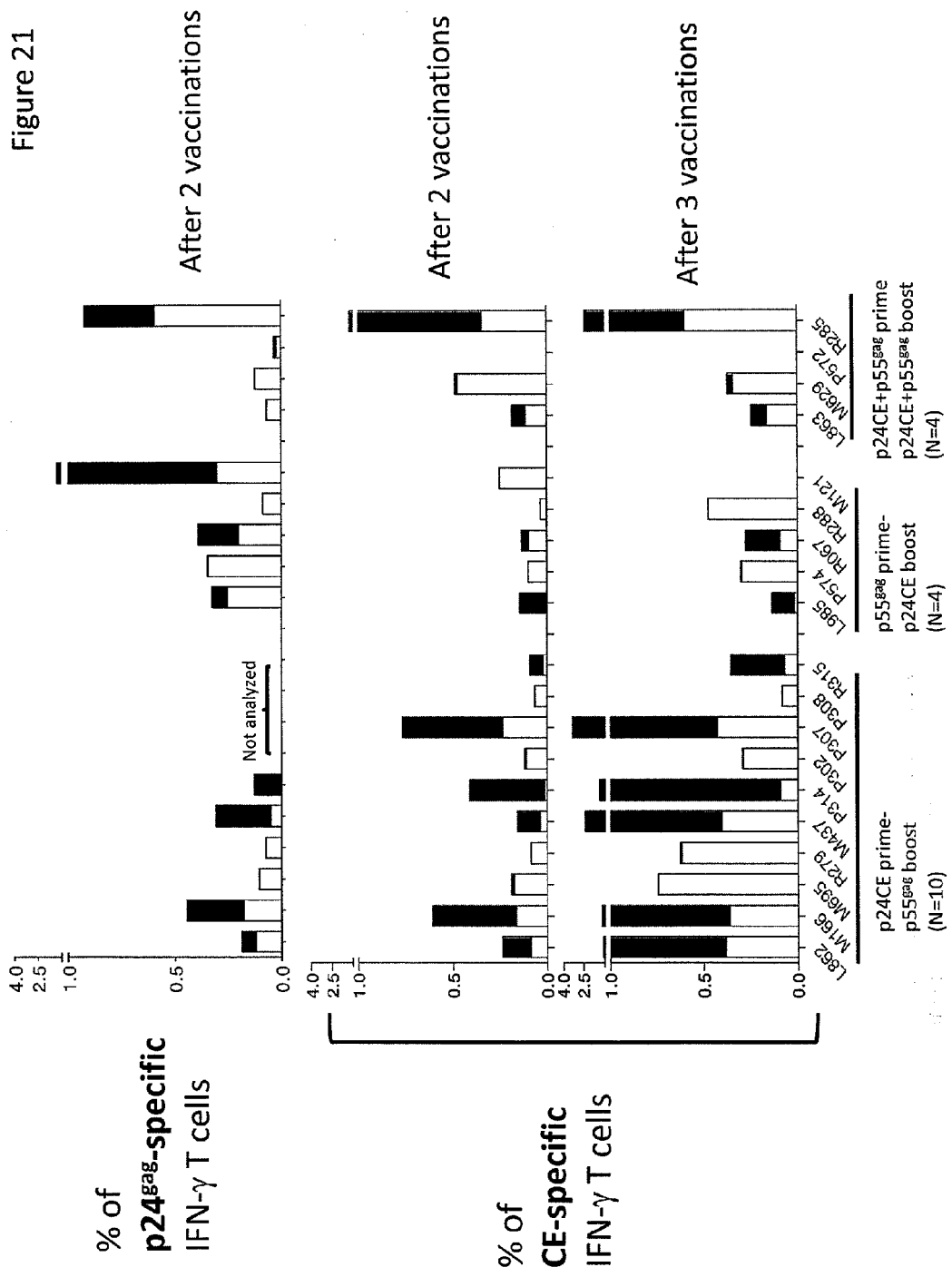
FIG. 21: Illustrative data showing cellular immune responses before and after the boost. Cellular immune responses were measured with peptides (15-mer overlapping by 11 amino acids) spanning the complete p24gag.

The animals received 1 mg of each DNA. For p24CE, SP-p24CE1 and SPp24CE2 were used. The DNA was administered via the intramuscular route followed by in vivo electroporation. FIG. 21 shows the cellular immune responses before and after the boost. Cellular immune responses were measured with peptides (15-mer overlapping by 11 amino acids) spanning the complete p24gag. This analysis showed responses in all the vaccinated animals.

The animals were also analyzed for CE-specific responses using a peptide pool (mixture of 10-me peptide overlapping by 9 amino acids and 15-mer overlapping by 11 amino acids) spanning the 7 CE. All the p24CE vaccinated animals showed positive responses. In contrayst, Only 5 of the 11 gag DNA vaccinated animals showed responses (data shown). Three of 4 animals with the combination vaccine (p24CE+p55$^{gag}$) showed positive responses. After boosting by p55gag DNA, the p24CE primed animals significantly increased CE-specific responses. p24CE DNA boost increased the responses of the gag vaccinated animals (no significant increase). A third vaccination of the animals vaccinated by the combination (p24CE+p55$^{gag}$) did not consistently further increase responses.

Figure 22:
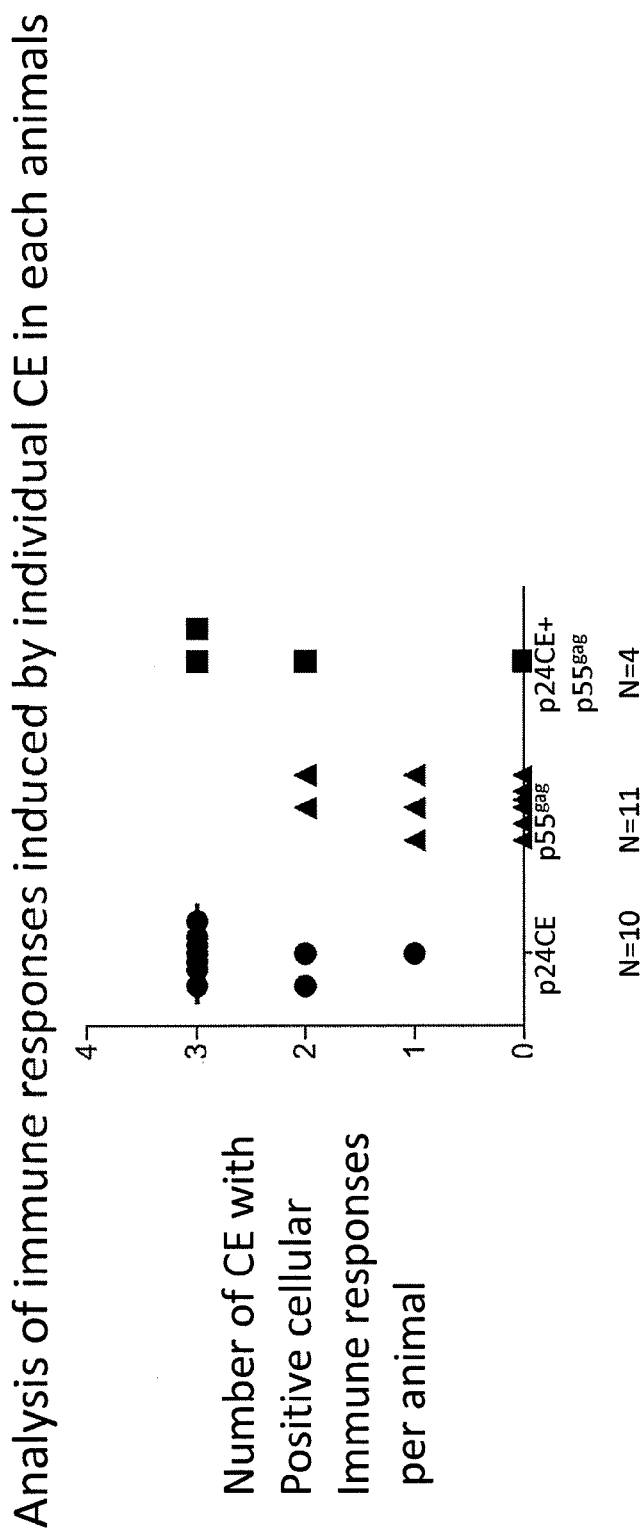
FIG. 22: Analysis of the responses to individual CE. The responses to each CE were mapped in all the animals using CE-specific peptides mixture of 10-mer peptide overlapping by 9 amino acids and 15-mer overlapping by 11 amino acids) for each CE. The number of CE that showed positive responses per animal are shown.

FIG. 22 shows the analysis of the responses to individual CE. The responses to each CE were mapped in all the animals using CE-specific peptides (mixture of 10-mer peptide overlapping by 9 amino acids and 15-mer peptides overlapping by 11 amino acids) for each CE. The number of CE that showed positive responses per animal are shown. The p24CE primed animals had 100% response rates with a range of 1-3 CE/animal and median of 3 CE per animal. The gag DNA primed animals have a response rate of 45% with a range of 0-2 CE/animal. The animals that received the combination vaccine are More similar to the CE primed animals.

Figure 23:
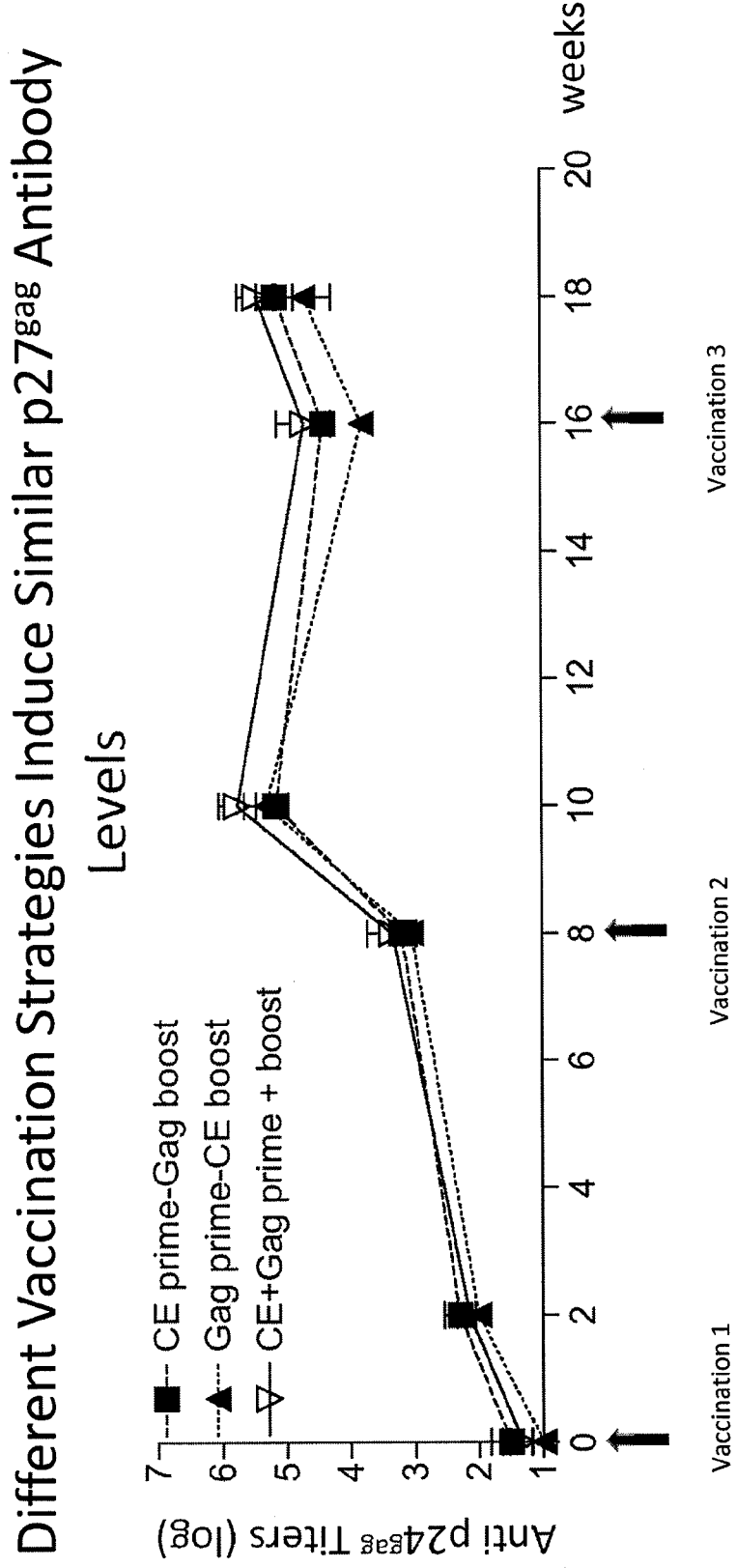
FIG. 23: Different vaccine strategies induced similar levels of p27gag antibody responses. Binding antibody titers were measured in the plasma by ELISA.

FIG. 23 shows that different vaccine strategies induced similar levels of p27gag antibody responses. Binding antibody titers were measured in the plasma of macaques by ELISA.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

All publications, accession numbers, patents, and patent applications cited in this specification are herein incorporated by reference as if each was specifically and individually indicated to be incorporated by reference.

REFERENCES

1. Nickle D C, Rolland M, Jensen M A, Pond S L, Deng W, et al. (2007) Coping with viral diversity in HIV vaccine design. PLoS Comput Biol 3: e75.
2. Nickle D C, Jojic Heckerman D, Jojic V, Kirovski D, et al. (2008) Comparison of immunogen designs that optimize peptide coverage: reply to Fischer et al. PLoS Comput Biol 4: e25.
3. Barouch D H, O'Brien K L, Simmons N L, King S L, Abbink P, et al. (20)0) Mosaic HIV-1 vaccines expand the breadth and depth of cellular immune responses in rhesus monkeys. Not Med 16: 319-323.
4. Santra S, Liao H X, Zhang R, Muldoon M, Watson S, et al. (2010) Mosaic vaccines elicit CD8+ T lymphocyte responses that confer enhanced immune coverage of diverse HIV strains in monkeys. Nat Med 16: 324-328.
5. Fischer W, Perkins S, Theiler J, Bhattacharya T, Yusim K, et al. (2007) Polyvalent vaccines for optimal coverage of potential T-cell epitopes in global HIV-1 variants. Nat Med 13: 100-106.
6. Fischer W, Liao H X, Haynes B F, Letvin N L, Korber B (2008) Coping with viral diversity in HIV vaccine design: a response to Nickle et al. PLoS Comput Biol. 4: e15; author reply e25,
7. Doric-Rose N A, Learn G H, Rodrigo A G. Nickle D C, Li F. et al. (2.005) Human immunodeficiency virus type 1 subtype B ancestral envelope protein is functional and elicits neutralizing antibodies in rabbits similar to those elicited by a circulating subtype B envelope. J Virol 79: 11214-11224.
8. Mullins J I, Nickle D C, Heath L, Rodrigo A G, Learn G H (2004) immunogen sequence: the fourth tier of AIDS vaccine design. Expert Rev Vaccines 3: S151-159.
9. Nickle D C, Jensen M A, Gottlieb G S, Shriner D, Learn G H, et al. (2003) Consensus and ancestral state HIV vaccines. Science 299: 1515-1518; author reply 1515-1518.
10. Dahirel V, Shekhar K, Pereyra F, Miura T, Artyomov M, et al. (2011) Coordinate linkage of HIV evolution reveals regions of immunological vulnerability. Proc Natl Acad Sci USA 108: 11530-11535.
11. Letourneau S, Im E J, Mashishi T, Brereton C, Bridgeman A, et al. (2007) Design and pre-clinical evaluation of a universal HIV-1 vaccine. PLoS One 2: e984.
12. Rosario M, Bridgeman A, Quakkelaar E D, Quigley M E, Hill B J, et al. (2010) Long peptides induce polyfunctional T cells against conserved regions of HIV-1 with superior breadth to single-gene vaccines in macaques. Eur J Immunol 40: 1973-1984.
13. De Groot A S, Rivera D S, McMurry J A, Buus S, Martin W (2008) Identification of immunogenic HLA-B7 "Achilles' heel" epitopes within highly conserved regions of HIV. Vaccine 26: 3059-3071.
14. Wilson C C, McKinney D, Anders M, MaWhinney S, Forster J, et al. (2003) Development of a DNA vaccine designed to induce cytotoxic T lymphocyte responses to multiple conserved epitopes in HIV-1. J Immunol 171: 5611-5623.
15. Kaufman D R, Li F, Cruz A N, Self S G, Barouch D H (2012) Focus and breadth of cellular tune responses elicited by a heterologous insert prime-boost vaccine regimen in rhesus monkeys. Vaccine 30: 506-509.
16. Almeida R R, Rosa D S, Ribeiro S P, Santana V C, Kallas E G, et al. (2012) Broad and cross-glade CD4+ T-cell responses elicited by a DNA vaccine encoding highly conserved and promiscuous HIV-1 M-group consensus peptides. PloS One 7: e45267.
17. Stephenson K E, SanMiguel A, Simmons N L, Smith K, Lewis M G, et al. (2012) Full-length HIV-1 immunogens induce greater magnitude and comparable breadth of T lymphocyte responses to conserved HIV-1 regions compared with conserved-region-only HIV-1 immunogens in rhesus monkeys. J Virol 86: 11434-11440.
18. Lichterfeld. M, Yu X G, Le Gall S, Altfeld M (2005) Immunodominance of HIV-1-specific CD8(+) T-cell responses in acute HIV-1 infection: at the crossroads of viral and host genetics. Trends Immunol 26: 166-171.
19. Friedrich T C, Valentine L E, Yant L J, Rakasz E G, Piaskowski S M, et al. (2007) Subdominant CD8+ T-cell responses are involved in durable control of AIDS virus replication. J Virol 81: 3465-3476.

20. Liu Y, McNevin J, Rolland M, Zhao H, Deng W, et al. (2009) Conserved HIV-1 epitopes continuously elicit subdominant cytotoxic T-lymphocyte responses. J infect Dis 200: 1825-1833,
21. Liu J, Ewald B A, Lynch D M, Nanda A, Sumida S M, et al. (2006) Modulation of DNA vaccine-elicited CD8+ T-lymphocyte, epitope immunodominance hierarchies. J Virol 80: 11991-11997.
22. Frahm. N, Kiepiela P, Adams S, Linde C H, Hewitt H S, et al. (2006) Control of human immunodeficiency virus replication by cytotoxic T lymphocytes targeting subdominant epitopes. Nat Immunol 7: 173-178.
23. Bockl K, Wild J, Bredl S, Kindsmuller K, Kostler J, et al. (2012) Altering an Artificial Gagpolnef Polyprotein and Mode of ENV Co-Administration Affects the Immunogenicity of a Clade C HIV DNA Vaccine. PLoS One 7: e34723.
24. Iversen A K, Stewart-Jones G, Learn G H, Christie N, Sylvester-Hviid C, et al. (2006) Conflicting selective forces affect T cell receptor contacts in an immunodominant human immunodeficiency virus epitope. Nat Immunol 7: 179-189.
25. Schneidewind A, Brumme Z L, Brumme C J, Power K A, Reyor L L, et al. (2009) Transmission and long-term stability of compensated CD8 escape mutations. J Virol 83: 3993-3997.
26. Altfeld M, Kalife E T, Qi Y, Streeck H, Lichterfeld M, et al. (2006) HLA Alleles S Associated with Delayed Progression to AIDS Contribute Strongly to the Initial CD8(+) T Cell Response against HIV-1, PLoS Med 3: e403,
27. Friedrich D, Jalbert E, Dinges W L, Sidney J, Sette A, et al. (2011) Vaccine-induced HIV-specific CD8+ T cells utilize preferential HLA alleles and target-specific regions of HIV-1. J Acquir Immune Defic Syndr 58: 248-252.
28. Maurer K, Harrer E G, Goldwich A, Eismann K, Bergmann 5, et al. (2008) Role of cytotoxic T-lymphocyte-mediated immune selection in a dominant human leukocyte antigen-B8-restricted cytotoxic T-lymphocyte epitope in Nef. J Acquir Immune Defic Synth 48: 133-141.
29. Toapanta F R, Craigo J K, Montelaro R C, Ross T M (2007) Reduction of anti-HIV-1 Gag immune responses during co-immunization: immune interference by the HIV-1 envelope. Current HIV research 5: 199-209.
30. Morozov V A, Morozov A V, Semaan M, Denner J (2012) Single mutations in the transmembrane envelope protein abrogate the immunosuppressive property of HIV-1. Retrovirology 9: 67,
31. Hovav A H, Santosuosso M, Bivas-Benita M, Plair A, Cheng A, et al. (2009) X4 human immunodeficiency type 1 gp120 down-modulates expression and immunogenicity of codelivered antigens. Journal of virology 83: 10941-10950.
32. Rolland M, Nickle D C, Mullins J I (2007) HIV-1 group M conserved elements vaccine. PLoS Pathog 3: e157.
33. Niu L, Termini J M, Kanagavelu S K, Gupta. S, Rolland M M, et al. (2011) Preclinical evaluation of HIV-1 therapeutic ex vivo dendritic cell vaccines expressing consensus Gag antigens and conserved Gag epitopes. Vaccine 29: 2110-2119.
34. Mothe B, Llano A, Ibarrondo J, Zamarreno J, Schiaulini M, et al. (2012) CTL responses of high functional avidity and broad variant cross-reactivity are associated with HIV control. PLoS One 7: e29717.
35. Herbeck J T, Nickle D C, Learn G H, Gottlieb G S, Curlin M E, et al, (2006) Human immunodeficiency virus type 1 env evolves toward ancestral states upon transmission to a new host. J Virol 80: 1637-1644.
36. Duda A, Lee-Turner L, Fox J, Robinson N, Dustan S, et al. (2009) HLA-associated clinical progression correlates with epitope reversion rates in early human immunodeficiency virus infection. J Virol 83: 1228-1239,
37. Kent S J, Fernandez C S, Dale C J, Davenport M P (2005) Reversion of immune escape HIV variants upon transmission: insights into effective viral immunity. Trends Microbiol 13: 243-246.
38. Li B, Gladden A D, Altfeld M, Kaldor J M, Cooper D A, et al. (2007) Rapid reversion of sequence polymorphisms dominates early human immunodeficiency virus type 1 evolution. J Virol 81: 193-201.
39. Martinez-Picado J, Prado J G, Fry E E, Pfafferott K, Leslie A, et al. (2006) Fitness cost of escape mutations in p24 Gag in association with control of human immunodeficiency virus type 1. J Virol 80: 3617-3623.
40. Peyerl F W, Bazick H S, Newberg M H, Barouch D H, Sodroski J, et al. (2004) Fitness costs limit viral escape from cytotoxic T lymphocytes at a structurally constrained epitope. J Virol 78: 13901-13910.
41. Liu Y, McNevin J, Zhao H, Tebit D M, Troyer R M, et al. (2007) Evolution of human immunodeficiency virus type 1 cytotoxic T-lymphocyte epitopes: fitness-balanced escape. J Virol 81: 12179-12188.
42. Troyer R M, Collins K R, Abraha A, Fraundorf E, Moore D M, et al. (2005) Changes in human immunodeficiency virus type 1 fitness and genetic diversity during disease progression. J Virol 79: 9006-9018,
43. Kiepiela P, Ngumbela K, Thohakgaie C, Ramduth D, Honeyborne I, et al. (2007) CD8+ T-cell responses to different HIV proteins have discordant associations with viral load. Nat Med 13: 46-53.
44. Honeyborne I, Prendergast A, Pereyra F, Leslie A, Crawford H, et al. (2007) Control of human immunodeficiency virus type 1 is associated with HLA-B*13 and targeting of multiple gag-specific CD8+ epitopes. J Virol 81: 3667-3672.
45. Schneidewind A, Brockman M A, Yang R, Adam R I, Li B, et al. (2007) Escape from the dominant HLA-B27-restricted cytotoxic T-lymphocyte response in Gag is associated with a dramatic reduction in human immunodeficiency virus type 1 replication. J Virol 81: 12382-12393.
46. Ngumbela K C, Day C L, Mncube Z, Nair K. Ramduth D, et al. (2008) Targeting of a CD8+ T cell env epitope presented by HLA-B*5802 is associated with markers of HIV disease progression and lack of selection pressure. AIDS Res Hum Retroviruses 24: 72-82.
47. Rolland M, Heckerman D, Deng W, Rousseau C M, Coovadia H, et al. (2008) Broad and Gag-biased HIV-1 epitope repertoires are associated with lower viral loads. PLoS One 3: e1424.
48. Masemola A, Mashishi T, Khoury G, Mohube P, Mokgotho P, et al. (2004) Hierarchical targeting of subtype C human immunodeficiency virus type 1 proteins by CD8+ T cells: correlation with viral load. J Virol 78: 3233-3243.
49. Mothe B, Ibarrondo J, Llano A, Brander C (2009) Virological, immune and host genetics markers in the control of HIV infection. Dis Markers 27: 105-120.
50. Zuniga R, Lucchetti A, Galvan P, Sanchez S, Sanchez C, et al. (2006) Relative dominance of Gag p24-specific cytotoxic T lymphocytes is associated with human immunodeficiency virus control. J Virol 80: 3122-3125.
51. Mothe B, Llano A, Ibarrondo J, Daniels M, Miranda C, et al. (2011) Definition of the viral targets of protective HIV-1-specific T cell responses. J Transl Med 9: 208.
52. Assarsson E, Sidney J, Oseoff C, Pasquetto V, Bui H H, et al. (2007) A quantitative analysis of the variables affecting 53. Altfeld M, Allen T M (2006) Hitting HIV where it hurts: an alternative approach to HIV vaccine design. Trends Immunol 27: 504-510.

54. Rosario M, Borthwick N, Stewart-Jones G B, Mbewe-Mvula A, Bridgeman A, et al. (2012) Prime-boost regimens with adjuvanted synthetic long peptides elicit T cells and antibodies to conserved regions of HIV-1 in macaques. AIDS 26: 275-284.

55. Ribeiro S P, Rosa. D S, Fonseca S G, Mairena. E C, Postol E, et al. (2010) A vaccine encoding conserved promiscuous HIV CD4 epitopes induces broad T cell responses in nice transgenic to multiple common HLA class II molecules. PloS One 5: e11072.

56. Rosa D S, Ribeiro S P, Almeida R R, Mairena E C, Postol E, et al. (2011) A DNA vaccine encoding multiple HIV CD4 epitopes elicits vigorous polyfunctional, long-lived CD4+ and CD8+ T cell responses. PloS One 6: e16921.

57. Kulkarni V, Rosati M, Valentin A, Ganneru B, Singh A K, et al. An HIV-1 p24gag derived conserved element DNA vaccine increased the breadth of immune response in mice. submitted.

58. Winstone N, Wilson A J, Morrow G, Boggiano C, Chiuchiolo M J, et al. (2011) Enhanced control of pathogenic SIV mac239 replication in macaques immunized with a plasmid IL12 and a DNA prime, viral vector boost vaccine regimen. J Virol 85: 9578-9587, 59. Aihara H, Miyazaki J (1998) Gene transfer into muscle by electroporation in vivo. Nat Biotechnol 16: 867-870.

60. Mathiesen I (1999) Electropermeabilization of skeletal muscle enhances gene transfer in vivo. Gene Ther 6: 508-514.

61. Prud'homme G J, Y, Khan A S, Draghia-Akli R (2006) Electroporation-enhanced nonviral gene transfer for the prevention or treatment of immunological, endocrine and neoplastic diseases. Curr Gene Ther 6: 243-273, 62. Rizzuto G, Cappelletti M, Maione D, Savino R, Lazzaro D, et al. (1999) Efficient and regulated erythropoietin production by naked DNA injection and muscle electroporation. Proc Natl Acad Sci USA 96: 6417-6422.

63. Wang Z, Troilo P J, Wang X, Griffiths T G, Pacchione S J, et al. (2004) Detection of integration of plasmid DNA into host genomic DNA following intramuscular injection and electroporation. Gene Ther 11: 711-721.

64. Widera G, Austin M, Rabussay D, Goldbeck C, Barnett S W, et al. (2000) increased DNA vaccine delivery and immunogenicity by electroporation in vivo. J Immunol 164: 4635-4640.

65. Often G, Schaefer M, Doe B, Liu H, Srivastava I, et al. (2004) Enhancement of DNA vaccine potency in rhesus macaques by electroporation. Vaccine 22: 2489-2493.

66. Often G R, Schaefer M, Doe B, Liu H, Megede J Z, et al. (2006) Potent immunogenicity of an HIV-1 gag-pol fusion DNA vaccine delivered by in vivo electroporation. Vaccine 24: 4503-4509.

67. Rosati M, Valentin A, Jalah R, Patel V, von Gegerfelt A, et al, (2008) Increased immune responses in rhesus macaques by DNA vaccination combined with electroporation. Vaccine 26:5223-5229.

68. Luckay A, Sidhu M K, Kjeken R, Megati S, Chong S Y, et al. (2007) Effect of plasmid DNA vaccine design and in vivo electroporation on the resulting vaccine-specific immune responses in rhesus macaques. J Virol 81: 5257-5269.

69. Hirao L A, Wu L, Khan A S, Hokey D A, Yan J, et al, (2008) Combined effects of IL-12 and electroporation enhances the potency of DNA vaccination in macaques. Vaccine 26: 3112-3120.

70. Rosati M, Bergamaschi C, Valentin A, Kulkarni V, Jalah R, et al. (2009) DNA vaccination in rhesus macaques induces potent immune responses and decreases acute and chronic viremia after SIVmac251 challenge. Proc Natl Acad Sci USA 06: 1:5831-15836.

71. Patel V, Valentin A, Kulkarni V, Rosati M, Bergamaschi C, et al. (2010) Long-lasting humoral and cellular immune responses and mucosal dissemination after intramuscular DNA immunization. Vaccine 28: 4827-4836.

72. Vasan S, Schlesinger S J, Chen Z, Hurley A, Lombardo A, et al. (2010) Phase 1 safety and immunogenicity evaluation of ADMVA, a multigenic, modified vaccinia Ankara-HIV-1 B'/C candidate vaccine. PLoS One 5: e8816.

73. Nasioulas G, Zolotukhin A S, Tabernero C, Solomin L, Cunningham C P, et al. (1994) Elements distinct from human immunodeficiency virus type 1 splice sites are responsible for the Rev dependence of env mRNA. J Virol 68: 2986-2993.

74. Schneider R, Campbell M, Nasioulas G, Felber B K, Pavlakis G N (1997) Inactivation of the human immunodeficiency virus type 1 inhibitory elements allows Rev-independent expression of Gag and Gag/protease and particle formation. J Virol 71: 4892-4903.

75. Schwartz S, Campbell M, Nasioulas G, Harrison J, Felber B K, et al, (1992) Mutational inactivation of an inhibitory sequence in human immunodeficiency virus type 1 results in Rev-independent gag expression. J Virol 66: 7176-7182.

76. Schwartz S, Felber B K, Pavlakis G N (1992) Distinct RNA sequences in the gag region of human immunodeficiency virus type 1 decrease RNA stability and inhibit expression in the absence of Rev protein. J Virol 66: 150-159.

77. Andre S, Seed B, Eberle J. Schraut W, Bultmann A, et al. (1998) Increased immune response elicited by DNA vaccination with a synthetic gp120 sequence with optimized codon usage. J Virol 72: 1497-1503.

78. Wagner R, Graf M, Bieler K, Wolf H, Grunwald T, et al. (2000) Rev-independent expression of synthetic gag-pol genes of human immunodeficiency virus type 1 and simian immunodeficiency virus: implications for the safety of lentiviral vectors. Hum Gene Ther 11: 2403-2413.

79. Graf M, Deml L, Wagner R (2004) Codon-optimized genes that enable increased heterologous expression in mammalian cells and elicit efficient immune responses in mice after vaccination of naked DNA. Methods Mol Med 94: 197-210.

80. Kulkarni V, Jalah R, Ganneru B, Bergamaschi C, Alicea C, et al. (2011) Comparison of immune responses generated by optimized DNA vaccination against SIV antigens in mice and macaques. Vaccine 29: 6742-6754.

81. Rosati M, von Gegerfelt A, Roth P, Alicea C, Valentin A, et al. (2005) DNA vaccines expressing different forms of simian immunodeficiency virus antigens decrease viremia upon SIVmac251 challenge. J Virol 79: 8480-8492.

82. Valentin A, Chikhlikar P, Patel V, Rosati M, Maciel M, et al. (2009) Comparison of DNA vaccines producing HIV-1 Gag and LAMP/Gag chimera in rhesus macaques reveals antigen-specific T-cell responses with distinct phenotypes. Vaccine 27: 4840-4849.

83. Vojnov L, Bean A T, Peterson E J, Chiuchiolo M J, Sacha J B, et al. (201)) DNA/Ad5 vaccination with SIV epitopes induced epitope-specific CD4 T cells, but few subdominant epitope-specific CD8 T cells. Vaccine 29: 7483-7490.

84. Ferrari G. Neal W, Ottinger J, Jones A M, Edwards B H, et al. (2004) Absence of immunodominant anti-Gag p17 (SL9) responses among Gag CTL-positive, HIV-uninfected vaccine recipients expressing the HLA-A*0201 allele. J Immunol 173: 2126-2133.
85. Rolland M, Tovanabutra S, deCamp A C, Frahm N, Gilbert P B, et al. (2011) Genetic impact of vaccination on breakthrough HIV-1 sequences from the STEP trial. Nat Med 17: 366-171.
86. Li F, Finnefrock A C, Dubey S A, Korber B T, Szinger J, et al. Mapping HIV-1 vaccine induced T-cell responses: bias towards less-conserved regions and potential impact on vaccine efficacy in the Step study. PLoS One 6: e20479.
87. Wilson N A, Keele B F, Reed J S, Piaskowski S M, MacNair C E, et al, (2009) Vaccine-induced cellular responses control simian immunodeficiency virus replication after heterologous challenge. J Virol 83: 6508-6521.
88. Mudd P A, Martins M A, Ericsen A J, Tully D C, Power K A, et al. (2012) Vaccine-induced CD8+ T cells control AIDS virus replication. Nature 491: 129-133.
89. Betts M R, Exley B, Price D A, Bansal A, Camacho Z T, et al. (2005) Characterization of functional and phenotypic changes in anti-Gag vaccine-induced T cell responses and their role in protection after HIV-1 infection, Proc Natl Acad Sci U.S.A. 102: 4512-4517.
90. Bett A J, Dubey S A, Mehrotra D V, Guan L, Long R, et al. (2010) Comparison of T cell immune responses induced by vectored HIV vaccines in non-human primates and humans. Vaccine 28: 7881-7889,
91. Le Gall S, Stamegna P, Walker B D (2007) Portable flanking sequences modulate CTL epitope processing. J Clin Invest 117: 3563-3575.
92. Zhang S C, Martin E, Shimada M, Godfrey S B, Fricke J, et al. (2012) Aminopeptidase Substrate Preference Affects HIV Epitope Presentation and Predicts Immune Escape Patterns in HIV-Infected Individuals, J Immunol 188: 5924-5934.
93. Rolland M, Jensen M A, Nickle D C, Van J, Learn G H, et al. (2007) Reconstruction and function of ancestral center-of-tree human immunodeficiency virus type 1 proteins. J Virol 81: 8507-8514.
94. Jalah R, Patel V, Kulkarni V, Rosati M, Alicea C, et al. (2012) IL-12 DNA as molecular vaccine adjuvant increases the cytotoxic T cell responses and breadth of humoral immune responses in SIV DNA vaccinated macaques. Hum Vaccin Immunother 8: 1620-1629.
95. Jalah R, Rosati M, Ganneru B, Pilkington G R, Valentin A, et al. (2013) The p40 Subunit of IL-12 Promotes Stabilization and Export of the p35 Subunit: Implications for Improved IL-12 Cytokine Production. J Biol Chem in press.
96. Ranke T, McMichael A (1999) Pre-clinical development of a multi-CTL epitope-based DNA prime MVA boost vaccine for AIDS. Immunol Lett 66: 177-181,
97. Pornillos O, Ganser-Pornillos B K, Kelly B N, Hua Y, Whitby F C, et al. (2009) X-ray structures of the hexameric building block of the HIV capsid. Cell 137: 1282-1292.
98. Chikhlikar P, de Arruda L B, Maciel M, Silvera P, Lewis M G, et al. (2006) DNA encoding an HIV-1 Gag/human lysosome-associated membrane protein-1 chimera elicits a broad cellular and Immoral immune response in Rhesus macaques. PLoS ONE 1: e135.
99. de Arruda L B, Chikhlikar P R, August J T, Marques E T (2004) DNA vaccine encoding human immunodeficiency virus-1 Gag, targeted to the major histocompatibility complex II compartment by lysosomal-associated membrane protein, elicits enhanced long-term memory response. Immunology 112: 126-133.
100. Marques E T, Jr., Chikhlikar P, de Arruda L B, Leao I C, Lu Y, et al. (2003) HIV-1 p55Gag encoded in the lysosome-associated membrane protein-1 as a DNA plasmid vaccine chimera is highly expressed, traffics to the major histocompatibility class II compartment, and elicits enhanced immune responses. J Biol Chem 278: 37926-37936.
101. Valentin A, Chikhlikar P, Patel V, Rosati M, Maciel M, et al. (2009) Comparison of DNA vaccines producing HIV-1 Gag and LAMP/Gag chimera in rhesus macaques reveals antigen-specific T-cell responses with distinct phenotypes. Vaccine 27: 4840-4849.
102. Qiu J T, Song R, Dettenhofer M, Tian C, August T, et al. (1999) Evaluation of novel human immunodeficiency virus type 1 Gag DNA vaccines for protein expression in mammalian cells and induction of immune responses. J Virol 73: 9145-9152.
103. von Gege felt A, Valentin A, Alicea C, Van Rompay K K, Marthas M L, et al. (2010) Emergence of simian immunodeficiency virus-specific cytotoxic CD4+ T cells and increased humoral responses correlate with control of rebounding viremia in CD8-depleted macaques infected with Rev-independent live-attenuated simian immunodeficiency virus. J Immunol 185: 3348-3358.
104. Lazard E, Kadie C, Stamegna P, Zhang S C, Gourdain P, et al. (2011) Variable HIV peptide stability in human cytosol is critical to epitope presentation and immune escape. J Clin Invest 121: 2480-2492.
105. Schwartz S, Felber B K, Pavlakis G N (1992) Mechanism of translation of monocistronic and multicistronic human immunodeficiency virus type 1 mRNAs. Mol Cell Biol 12: 207-219.
106. Rolland M, Jensen M A, Nickle D C, Yan J, Learn G H, et al. (2007) Reconstruction and function of ancestral center-of-tree human immunodeficiency virus type 1 proteins. J Virol 81: 8507-8514.

Table of Illustrative Conserved Element Sequences p24 Gag conserved elements for p24CE1 vaccine ("also referred to as Core1"):
conserved element 1 (CE1)

SEQ ID NO: 1

ISPRTLNAWVKV conserved element 2 (CE2)

SEQ ID NO: 2

VIPMFSALSEGATPQDLN conserved element 3 (CE3)

SEQ ID NO: 3

VGGHQAAMQMLKDTINEEAAEWDR conserved element 4 (CE4)

-continued

Table of Illustrative Conserved Element Sequences

SEQ ID NO: 4
PRGSDIAGTTSTLQEQIGW conserved element 5 (CE5)
SEQ ID NO: 5
KRWIILGLNKIVRMYSPTSI conserved element 6 (CE6)
SEQ ID NO: 6
YVDRFYKTLRAEQA conserved element 7 (CE7)
SEQ ID NO: 7
LEEMMTACQGVGGPGHK p24 Gag conserved elements for p24CE2 vaccine ("also referred to as Core2"):
conserved element 1 (CE1)
SEQ ID NO: 8
LSPRTLNAWVKV conserved element 2 (CE2)
SEQ ID NO: 9
VIPMFTALSEGATPQDLN conserved element 3 (CE3)
SEQ ID NO: 10
VGGHQAAMQMLKETINEEAAEWDR conserved element 4 (CE4)
SEQ ID NO: 11
PRGSDIAGTTSTLQEQIAW conserved element 5 (CE5)
SEQ ID NO: 12
KRWIILGLNKIVRMYSPVSI conserved element 6 (CE6)
SEQ ID NO: 13
YVDRFFKTLRAEQA conserved element 7 (CE7)
SEQ ID NO: 14
LEEMMTACQGVGGPSHK p24 Gag conserved elements for p24CE1 vaccine ("also referred to as Core1"):
SEQ ID NO: 15
VIPMFSALSEGATPQDLNAAVGGHQAAMQMLKDTINEEAAEWDRAAAEPRGSDIAGTTSTLQEQIGWAAAKRWIIL
GLNKIVRMYSPTSIAAKYVDRFYKTLRAEQAAGLEEMMTACQGVGGPGHKAAISPRTLNAWVKV p24 Gag conserved elements for p24CE2 vaccine ("also referred to as Core2"):
SEQ ID NO: 16
VIPMFTALSEGATPQDLNAAVGGHQAAMQMLKETINEEAAEWDRAAAEPRGSDIAGTTSTLQEQIAWAAAKRWIIL
GLNKIVRMYSPVSIAAKYVDRFFKTLRAEQAAGLEEMMTACQGVGGPSHKAALSPRTLNAWVKV Nucleic acid construct encoding Core1 plus Core2 (p24CE1 + p24CE2) (306H)
(genes underlined)
SEQ ID NO: 17
CCTGGCCATTGCATACGTTGTATCCATATCATAATATGTACATTTATATTGGCTCATGTCCAACATTACCGCCATG
TTGACATTGATTATTGACTAGTTATTAATAGTAATCAATTACGGGGTCATTAGTTCATAGCCCATATATGGAGTTC
CGCGTTACATAACTTACGGTAAATGGCCCGCCTGGCTGACCGCCCAACGACCCCCGCCCATTGACGTCAATAATGA
CGTATGTTCCCATAGTAACGCCAATAGGGACTTTCCATTGACGTCAATGGGTGGAGTATTTACGGTAAACTGCCCA
CTTGGCAGTACATCAAGTGTATCATATGCCAAGTACGCCCCCTATTGACGTCAATGATGGTAAATGGCCCGCCTGG
CATTATGCCCAGTACATGACCTTATGGGACTTTCCTACTTGGCAGTACATCTACGTATTAGTCATCGCTATTACCA
TGGTGATGCGGTTTTGGCAGTACATCAATGGGCGTGGATAGCGGTTTGACTCACGGGGATTTCCAAGTCTCCACCC
CATTGACGTCAATGGGAGTTTGTTTTGGCACCAAAATCAACGGGACTTTCCAAAATGTCGTAACAACTCCGCCCCA
TTGACGCAAATGGGCGGTAGGCGTGTACGGTGGGAGGTCTATATAAGCAGAGCTCGTTTAGTGAACCGTCAGATCG
CCTGGAGACGCCATCCACGCTGTTTTGACCTCCATAGAAGACACCGGGACCGATCCAGCCTCCGCGGGcgcgcgtc
gacaagaaATGTGGCTCCAGAGCCTGCTACTCCTGGGGACGGTGGCCTGCAGCATCTCGGTCATCCCGATGTTCTC
GGCGCTCAGCGAGGGAGCGACGCCGCAGGACCTGAACGCGGCCGTCGGAGGTCACCAGGCAGCGATGCAGATGCTG
AAGGACACGATCAACGAGGAGGCGGCCGAGTGGGACCGGGCGGCAGCCGAGCCACGCGGTTCCGACATCGCGGGCA
CCACCTCGACGCTCCAGGAGCAGATCGGGTGGGCCGCAGCTAAGCGCTGGATCATCCTCGGGCTGAACAAGATCGT
CCGGATGTACAGCCCGACGTCGATCGCTGCTAAGTACGTTGACCGGTTCTACAAGACCCTGAGGGCCGAGCAGGCG
GCCGGACTGGAGGAGATGATGACCGCGTGCCAGGGGGTCGGTGGACCAGGGCACAAGGCCGCGATCTCGCCGCGCA
CGCTGAACGCGTGGGTGAAGGTCTGATAAgaattcgctagcggcgcgccagatctgatatcggatctGCTGTGCCT
TCTAGTTGCCAGCCATCTGTTGTTTGCCCCTCCCCCGTGCCTTCCTTGACCCTGGAAGGTGCCACTCCCACTGTCC
TTTCCTAATAAAATGAGGAAATTGCATCGCATTGTCTGAGTAGGTGTCATTCTATTCTGGGGGGTGGGGTGGGGCA
GGACAGCAAGGGGGAGGATTGGGAAGACAATAGCAGGCATGCTGGGGATGCGGTGGGCTCTATGGGTACCCAGGTG -continued Table of Illustrative Conserved Element Sequences

```
CTGAAGAATTGACCCGGTTCCTCCTGGGCCAGAAAGAAGCAGGCACATCCCCTTCTCTGTGACACACCCTGTCCAC
GCCCCTGGTTCTTAGTTCCAGCCCCACTCATAGGACACTCATAGCTCAGGAGGGCTCCGCCTTCAATCCCACCCGC
TAAAGTACTTGGAGCGGTCTCTCCCTCCCTCATCAGCCCACCAAACCAAACCTAGCCTCCAAGAGTGGGAAGAAAT
TAAAGCAAGATAGGCTATTAAGTGCAGAGGGAGAGAAAATGCCTCCAACATGTGAGGAAGTAATGAGAGAAATCAT
AGAATTTCTTCCGCTTCCTCGCTCACTGACTCGCTGCGCTCGGTCGTTCGGCTGCGGCGAGCGGTATCAGCTCACT
CAAAGGCGGTAATACGGTTATCCACAGAATCAGGGGATAACGCAGGAAAGAACATGTGAGCAAAAGGCCAGCAAAA
GGCCAGGAACCGTAAAAAGGCCGCGTTGCTGGCGTTTTTCCATAGGCTCCGCCCCCCTGACGAGCATCACAAAAAT
CGACGCTCAAGTCAGAGGTGGCGAAACCCGACAGGACTATAAAGATACCAGGCGTTTCCCCCTGGAAGCTCCCTCG
TGCGCTCTCCTGTTCCGACCCTGCCGCTTACCGGATACCTGTCCGCCTTTCTCCCTTCGGGAAGCGTGGCGCTTTC
TCATAGCTCACGCTGTAGGTATCTCAGTTCGGTGTAGGTCGTTCGCTCCAAGCTGGGCTGTGTGCACGAACCCCCC
GTTCAGCCCGACCGCTGCGCCTTATCCGGTAACTATCGTCTTGAGTCCAACCCGGTAAGACACGACTTATCGCCAC
TGGCAGCAGCCACTGGTAACAGGATTAGCAGAGCGAGGTATGTAGGCGGTGCTACAGAGTTCTTGAAGTGGTGGCC
TAACTACGGCTACACTAGAAGAACAGTATTTGGTATCTGCGCTCTGCTGAAGCCAGTTACCTTCGGAAAAAGAGTT
GGTAGCTCTTGATCCGGCAAACAAACCACCGCTGGTAGCGGTGGTTTTTTGTTTGCAAGCAGCAGATTACGCGCA
GAAAAAAAGGATCTCAAGAAGATCCTTTGATCTTTTCTACGGGGTCTGACGCTCAGTGGAACGAAAACTCACGTTA
AGGGATTTTGGTCATGAGATTATCAAAAAGGATCTTCACCTAGATCCTTTTAAATTAAAAATGAAGTTTTAAATCA
ATCTAAAGTATATATGAGTAAACTTGGTCTGACAGTTACCAATGCTTAATCAGTGAGGCACCTATCTCAGCGATCT
GTCTATTTCGTTCATCCATAGTTGCCTGACTCGGGGGGGGGGGCGCTGAGGTCTGCCTCGTGAAGAAGGTGTTGC
TGACTCATACCAGGCCTGAATCGCCCCATCATCCAGCCAGAAAGTGAGGGAGCCACGGTTGATGAGAGCTTTGTTG
TAGGTGGACCAGTTGGTGATTTTGAACTTTTGCTTTGCCACGGAACGGTCTGCGTTGTCGGGAAGATGCGTGATCT
GATCCTTCAACTCAGCAAAAGTTCGATTTATTCAACAAAGCCGCCGTCCCGTCAAGTCAGCGTAATGCTCTGCCAG
TGTTACAACCAATTAACCAATTCTGATTAGAAAAACTCATCGAGCATCAAATGAAACTGCAATTTATTCATATCAG
GATTATCAATACCATATTTTTGAAAAAGCCGTTTCTGTAATGAAGGAGAAAACTCACCGAGGCAGTTCCATAGGAT
GGCAAGATCCTGGTATCGGTCTGCGATTCCGACTCGTCCAACATCAATACAACCTATTAATTTCCCCTCGTCAAAA
ATAAGGTTATCAAGTGAGAAATCACCCATGAGTGACGACTGAATCCGGTGAGAATGGCAAAAGCTTATGCATTTCTT
TCCAGACTTGTTCAACAGGCCAGCCATTACGCTCGTCATCAAAATCACTCGCATCAACCAAACCGTTATTCATTCG
TGATTGCGCCTGAGCGAGACGAAATACGCGATCGCTGTTAAAAGGACAATTACAAACAGGAATCGAATGCAACCGG
CGCAGGAACACTGCCAGCGCATCAACAATATTTTCACCTGAATCAGGATATTCTTCTAATACCTGGAATGCTGTTT
TCCCGGGGATCGCAGTGGTGAGTAACCATGCATCATCAGGAGTACGGATAAAATGCTTGATGGTCGGAAGAGGCAT
AAATTCCGTCAGCCAGTTTAGTCTGACCATCTCATCTGTAACATCATTGGCAACGCTACCTTTGCCATGTTTCAGA
AACAACTCTGGCGCATCGGGCTTCCCATACAATCGATAGATTGTCGCACCTGATTGCCCGACATTATCGCGAGCCC
ATTTATACCCATATAAATCAGCATCCATGTTGGAATTTAATCGCGGCCTCGAGCAAGACGTTTCCCGTTGAATATG
GCTCATAACACCCCTTGTATTACTGTTTATGTAAGCAGACAGTTTTATTGTTCATGATGATATATTTTTATCTTGT
GCAATGTAACATCAGAGATTTTGAGACACAACGTGGATCATCCAGACATGATAAGATACATTGATGAGTTTGGACA
AACCACAACTAGAATGCAGTGAAAAAAATGCTTTATTTGTGAAATTTGTGATGCTATTGCTTTATTTGTAACCATT
ATAAGCTGCAATAAACAAGTTAACAACAACAATTGCATTCATTTTTATGTTTCAGGTTCAGGGGGAGGTGTGGGAGG
TTTTTTAAAGCAAGTAAAACCTCTACAAATGTGGTATGGCTGATTATGATCgtcgaggatccggcgTTATCAGACC
TTCACCCAGGCGTTGAGGGTGCGAGGCGAGAGGGCCGCCTTGTGCGACGGTCCTCCGACTCCCTGGCAGGCTGTCA
TCATCTCCTCGAGACCCGCGGCCTGCTCTGCCCTCAGCGTCTTGAAGAAGCGGTCTACGTATTTGGCCGCGATGCT
GACTGGGCTGTACATCCTGACGATCTTGTTGAGGCCCAGGATGATCCAGCGCTTGGCTGCAGCCCAGGCGATCTGC
TCCTGGAGGGTGCTGGTCGTGCCTGCGATGTCGCTACCCCTTGGCTCAGCTGCTGCCCTGTCCCACTCGGCTGCCT
CCTCGTTGATGGTCTCCTTGAGCATCTGCATTGCCGCCTGGTGTCCACCGACCGCGGCGTTGAGGTCCTGCGGTGT
CGCACCCTCACTGAGTGCGGTGAACATGGGGATGACCGAGATCGAGCACGCCACGGTCCCGAGTAGCAGGAGCGAC
TGCAGCCACAT ttcttccgtttaaacgtcgacagatccaaac GCTCCTCCGACGTCCCCAGGCAGAATGGCGGTTC
CCTAAACGAGCATTGCTTATATAGACCTCCCATTAGGCACGCCTACCGCCCATTTACGTCAATGGAACGCCCATTT
GCGTCATTGCCCCTCCCCATTGACGTCAATGGGGATGTACTTGGCAGCCATCGCGGGCCATTTACCGCCATTGACG
TCAATGGGAGTACTGCCAATGTACCCTGGCGTACTTCCAATAGTAATGTACTTGCCAAGTTACTATTAATAGATAT
TGATGTACTGCCAAGTGGGCCATTTACCGTCATTGACGTCAATAGGGGGCGTGAGAACGGATATGAATGGGCAATG
AGCCATCCCATTGACGTCAATGGTGGGTGGTCCTATTGACGTCAATGGGCATTGAGCCAGGCGGCCATTTACCGT
AATTGACGTCAATGGGGAGGCGCCATATACGTCAATAGGACCGCCCATATGACGTCAATAGGTAAGACCATGAGG
CCCTTTCGTCTCGCGCGTTTCGGTGATGACGGTGAAAACCTCTGACACATGCAGCTCCCGGAGACGGTCACAGCTT
GTCTGTAAGCGGATGCCGGGAGCAGACAAGCCCGTCAGGGCGCGTCAGCGGGTGTTGGCGGGTGTCGGGGCTGGCT
TAACTATGCGGCATCAGAGCAGATTGTACTGAGAGTGCACCATATGCGGTGTGAAATACCGCACAGATGCGTAAGG
AGAAAATACCGCATCAGATTGGCTATTGGCATTATGCC
``` p24CE1 encoded by SEQ ID NO 17 (includes a GM-CSF signal peptide)
SEQ ID NO: 18
MWLQSLLLLGTVACSISVIPMFSALSEGATPQDLNAAVGGHQAAMQMLKDTINEEAAEWDRAAAEPRGSDIAGTTS
TLQEQIGWAAAKRWIILGLNKIVRMYSPTSIAAKYVDRFYKTLRAEQAAGLEEMMTACQGVGGPGHKAAISPRTLN
AWVKV p24CE2 encoded by SEQ ID NO 17 (includes a GM-CSF signal peptide)
SEQ ID NO: 19
MWLQSLLLLGTVACSISVIPMFTALSEGATPQDLNAAVGGHQAAMQMLKETINEEAAEWDRAAAEPRGSDIAGTTS
TLQEQIAWAAAKRWIILGLNKIVRMYSPVSIAAKYVDRFFKTLRAEQAAGLEEMMTACQGVGGPSHKAALSPRTLN
AWVKV LAMP-p24CE2 (202H) (gene underlined)
SEQ ID NO: 20
```
CCTGGCCATTGCATACGTTGTATCCATATCATAATATGTACATTTATATTGGCTCATGTCCAACATTACCGCCATG
TTGACATTGATTATTGACTAGTTATTAATAGTAATCAATTACGGGGTCATTAGTTCATAGCCCATATATGGAGTTC
CGCGTTACATAACTTACGGTAAATGGCCCGCCTGGCTGACCGCCCAACGACCCCCGCCCATTGACGTCAATAATGA
CGTATGTTCCCATAGTAACGCCAATAGGGACTTTCCATTGACGTCAATGGGTGGAGTATTTACGGTAAACTGCCCA
CTTGGCAGTACATCAAGTGTATCATATGCCAAGTACGCCCCCTATTGACGTCAATGATGGTAAATGGCCCGCCTGG
CATTATGCCCAGTACATGACCTTATGGGACTTTCCTACTTGGCAGTACATCTACGTATTAGTCATCGCTATTACCA
TGGTGATGCGGTTTTGGCAGTACATCAATGGGCGTGGATAGCGGTTTGACTCACGGGGATTTCCAAGTCTCCACCC
CATTGACGTCAATGGGAGTTTGTTTTGGCACCAAAATCAACGGGACTTTCCAAAATGTCGTAACAACTCCGCCCCA
```

Table of Illustrative Conserved Element Sequences

```
TTGACGCAAATGGGCGGTAGGCGTGTACGGTGGGAGGTCTATATAAGCAGAGCTCGTTTAGTGAACCGTCAGATCG
CCTGGAGACGCCATCCACGCTGTTTTGACCTCCATAGAAGACACCGGGACCGATCCAGCCTCCGcgggcgcgcgtc
gactagcATGGCGCCCCGCAGCGCCCGGCGACCCCTGCTGCTACTGCTGTTGCTGCTGCTCGGCCTCATGCAT
TGTGCGTCAGCAGCAATGTTTATGGTGAAAAATGGCAACGGGACCGCGTGCATAATGGCCAACTTCTCTGCTGCCT
TCTCAGTGAACTACGACACCAAGAGTGGCCCTAAGAACATGACCCTTGACCTGCCATCAGATGCCACAGTGGTGCT
CAACCGCAGCTCCTGTGGAAAAGAGAACACTTCTGACCCCAGTCTCGTGATTGCTTTTGGAAGAGGACATACACTC
ACTCTCAATTTCACGAGAAATGCAACACGTTACAGCGTTCAGCTCATGAGTTTTGTTTATAACTTGTCAGACACAC
CTTTTCCCCAATGCGAGCTCCAAAGAAATCAAGACTGTGGAATCTATAACTGACATCAGGGCAGATATAGATAAAA
AATACAGATGTGTTAGTGGCACCCAGGTCCACATGAACAACGTGACCGTAACGCTCCATGATGCCACCATCCAGGC
GTACCTTTCCAACAGCAGCTTCAGCAGGGGAGAGACACGCTGTGAACAAGACAGGCCTTCCCCAACCACAGCGCCC
CCTGCGCCACCCAGCCCCTCGCCCTCACCCGTGCCCAAGAGCCCCTCTGTGGACAAGTACACGTGAGCGGCACCA
ACGGGACCTGCCTGCTGGCCAGCATGGGGCTGCAGCTGAACCTCACCTATGAGAGGAAGGACAACACGACGGTGAC
AAGGCTTCTCAACATCAACCCCAACAAGACCTCGGCCAGCGGGAGCTGCGGCGCCCACCTGGTGACTCTGGAGCTG
CACAGCGAGGGCACCACCGTCCTGCTCTTCCAGTTCGGGATGAATGCAAGTTCTAGCCGGTTTTTCCTACAAGGAA
TCCAGTTGAATACAATTCTTCCTGACGCCAGAGACCCGTGCCTTTAAAGCTGCCAACGGCTCCCTGCGAGCGCTGC
AGGCCACAGTCGGCAATTCCTACAAGTGCAACGCGGAGGAGCACGTCCGTGCTCACGAAGGCGTTTTCAGTCAATAT
ATTCAAAGTGTGGGTCCAGGCTTTCAAGGTGGAAGGTGGCCAGTTTGGCTCTGTGGAGGAGTGTCTGCTGGACGAG
AACAGCCTCGAGGATATCGTCATCCCGATGTTCACGGCGCTCAGCGAGGGAGCGACGCCGCAGGACCTGAACGCGG
CCGTCGGAGGTCACCAGGCAGCGATGCAGATGCTGAAGGAGACGATCAACGAGGAGGCGGCCGAGTGGGACCGGGC
GGCAGCCGAGCCACGCGGTTCCGACATCGCGGGCACCACCTCGACGCTCCAGGAGCAGATCGCGTGGGCCGCAGCT
AAGCGCTGGATCATCCTCGGGCTGAACAAGATCGTCCGGATGTACAGCCCGGTCTCGATCGCTGCTAAGTACGTTG
ACCGGTTCTTCAAGACCCTGAGGGCCGAGCAGGCGGCCGGACTGGAGGAGATGATGACCGCGTGCCAGGGGGTCGG
TGGACCATCGCACAAGGCCGCGCTCTCGCCGCGCACGCTGAACGCGTGGGTGAAGGTCGGATCCGAATTCACGCTG
ATCCCCATCGCTGTGGGTGGTGCCCTGGCGGGCTGGTCCTCATCGTCCTCATCGCCTACCTCGTCGGCAGGAAGA
GGAGTCACGCAGGCTACCAGACTATCTAGggtacctctagGATCTGCTGTGCCTTCTAGTTGCCAGCCATCTGTTG
TTTGCCCCTCCCCCGTGCCTTCCTTGACCCTGGAAGGTGCCACTCCCACTGTCCTTTCCTAATAAAATGAGGAAAT
TGCATCGCATTGTCTGAGTAGGTGTCATTCTATTCTGGGGGGTGGGGTGGGGCAGGACAGCAAGGGGGAGGATTGG
GAAGACAATAGCAGGCATGCTGGGGATGCGGTGGGCTCTATGGGTACCCAGGTGCTGAAGAATTGACCCGGTTCCT
CCTGGGCCAGAAAGAAGCAGGCACATCCCCTTCTCTGTGACACACCCTGTCCACGCCCCTGGTTCTTAGTTCCAGC
CCCACTCATAGGACACTCATAGCTCAGGAGGGCTCCGCCTTCAATCCCACCCGCTAAAGTACTTGGAGCGGTCTCT
CCCTCCCTCATCAGCCCACCAAACCAAACCTAGCCTCCAAGAGTGGGAAGAAATTAAAGCAAGATAGGCTATTAAG
TGCAGAGGGAGAGAAAATGCCTCCAACATGTGAGGAAGTAATGAGAGAAATCATAGAATTCTTCCGCTTCCTCGC
TCACTGACTCGCTGCGCTCGGTCGTTCGGCTGCGGCGAGCGGTATCAGCTCACTCAAAGGCGGTAATACGGTTATC
CACAGAATCAGGGGATAACGCAGGAAAGAACATGTGAGCAAAAGGCCAGCAAAAGGCCAGGAACCGTAAAAAGGCC
GCGTTGCTGGCGTTTTTCCATAGGCTCCGCCCCCCTGACGAGCATCACAAAAATCGACGCTCAAGTCAGAGGTGGC
GAAACCCGACAGGACTATAAAGATACCAGGCGTTTCCCCCTGGAAGCTCCCTCGTGCGCTCTCCTGTTCCGACCCT
GCCGCTTACCGGATACCTGTCCGCCTTTCTCCCTTCGGGAAGCGTGGCGCTTTCTCAATGCTCACGCTGTAGGTAT
CTCAGTTCGGTGTAGGTCGTTCGCTCCAAGCTGGGCTGTGTGCACGAACCCCCCGTTCAGCCCGACCGCTGCGCCT
TATCCCGGTAACTATCGTCTTGAGTCCAACCCGGTAAGACACGACTTATCGCCACTGGCAGCAGCCACTGGTAACA
GGATTAGCAGAGCGAGGTATGTAGGCGGTGCTACAGAGTTCTTGAAGTGGTGGCCTAACTACGGCTACACTAGAAG
AACAGTATTTGGTATCTGCGCTCTGCTGAAGCCAGTTACCTTCGGAAAAAGAGTTGGTAGCTCTTGATCCGGCAAA
CAAACCACCGCTGGTAGCGGTGGTTTTTTTGTTTGCAAGCAGCAGATTACGCGCAGAAAAAAAGGATCTCAAGAAG
ATCCTTTGATCTTTTCTACGGGGTCTGACGCTCAGTGGAACGAAAACTCACGTTAAGGGATTTTGGTCATGAGATT
ATCAAAAAGGATCTTCACCTAGATCCTTTTAAATTAAAAATGAAGTTTTAAATCAATCTAAAGTATATATGAGTAA
ACTTGGTCTGACAGTTACCAATGCTTAATCAGTGAGGCACCTATCTCAGCGATCTGTCTATTTCGTTCATCCATAG
TTGCCTGACTCGGGGGGGGGGGGCGCTGAGGTCTGCCTCGTGAAGAAGGTGTTGCTGACTCATACCAGGCCTGAA
TCGCCCCATCATCCAGCCAGAAAGTGAGGGAGCCACGGTTGATGAGAGCTTTGTTGTAGGTGGACCAGTTGGTGAT
TTTGAACTTTTGCTTTGCCACGGAACGGTCTGCGTTGTCGGGAAGATGCGTGATCTGATCCTTCAACTCAGCAAAA
GTTCGATTTATTCAACAAAGCCGCCGTCCCGTCAAGTCAGCGTAATGCTCTGCCAGTGTTACAACCAATTAACCAA
TTCTGATTAGAAAAACTCATCGAGCATCAAATGAAACTGCAATTTATTCATATCAGGATTATCAATACCATATTTT
TGAAAAAGCCGTTTCTGTAATGAAGGAGAAAACTCACCGAGGCAGTTCCATAGGATGGCAAGATCCTGGTATCGGT
CTGCGATTCCGACTCGTCCAACATCAATACAACCTATTAATTTCCCCTCGTCAAAAATAAGGTTATCAAGTGAGAA
ATCACCATGAGTGACGACTGAATCCGGTGAGAATGGCAAAAGCTTATGCATTTCTTTCCAGACTTGTTCAACAGGC
CAGCCATTACGCTCGTCATCAAAATCACTCGCATCAACCAAACCGTTATTCATTCGTGATTGCGCCTGAGCGAGAC
GAAATACGCGATCGCTGTTAAAAGGACAATTACAAACAGGAATCGAATGCAACCGGCGCAGGAACACTGCCAGCGC
ATCAACAATATTTTCACCTGAATCAGGATATTCTTAATACCTGGAATGCTGTTTTCCCGGGGATCGCAGTGGTG
AGTAACCATGCATCATCAGGAGTACGGATAAAATGCTTGATGGTCGGAAGAGGCATAAATTCCGTCAGCCAGTTTA
GTCTGACCATCTCATCTGTAACATCATTGGCAACGCTACCTTTGCCATGTTTCAGAAACAACTCTGGCGCATCGGG
CTTCCCATACAATCGATAGATTGTCGCACCTGATTGCCCGACATTATCCGCCCATTATACCCATATAAATCA
GCATCCATGTTGGAATTTAATCGCGGCCTGGAGCAAGACGTTTCCCGTTGAATATGGCTCATAACACCCCTTGTAT
TACTGTTTATGTAAGCAGACAGTTTTATTGTTCATGATGATATATTTTTATCTTGTGCAATGTAACATCAGAGATT
TTGAGACACAACGTGGCTTTCCCCCCCCCCCCATTATTGAAGCATTTATCAGGGTTATTGTCTCATGAGCGGATAC
ATATTTGAATGTATTTAGAAAAATAAACAAATAGGGGTTCCGCGCACATTTCCCCGAAAAGTGCCACCTGACGTCT
AAGAAACCATTATTATCATGACATTAACCTATAAAAATAGGCGTATCACGAGGCCCTTTCGTCTCGCGCGTTTCGG
TGATGACGGTGAAAACCTCTGACACATGCAGCTCCCGGAGACGGTCACAGCTTGTCTGTAAGCGGATGCCGGGAGC
AGACAAGCCCGTCAGGGCGCGTCAGCGGGTGTTGGCGGGTGTCGGGGCTGGCTTAACTATGCGGCATCAGAGCAGA
TTGTACTGAGAGTGCACCATATGCGGTGTGAAATACCGCACAGATGCGTAAGGAGAAAATACCGCATCAGATTGGC
TATTGG
```

LAMP-p24CE2 fusion (p24CE2 underlined) encoded by SEQ ID NO: 20

SEQ ID NO: 21

MAPRSARRPLLLLLLLLLLGLMHCASAAMFMVKNGNGTACIMANFSAAFSVNYDTKSGPKNMTLDLPSDATVVLNR
SSCGKENTSDPSLVIAFGRGHTLTLNFTRNATRYSVQLMSFVYNLSDTHLFPNASSKEIKTVESITDIRADIDKKY
RCVSGTQVHMNNVTVTLHDATIQAYLSNSSFSRGETRCEQDRPSPTTAPPAPPSPSPSPVPKSPSVDKYNVSGTNG
TCLLASMGLQLNLTYERKDNTTVTRLLNINPNKTSASGSCGAHLVTLELHSEGTTVLLFQGGMNASSSRFFLQGIQ

Table of Illustrative Conserved Element Sequences

LNTILPDARDPAFKAANGSLRALQATVGNSYKCNAEEHVRVTKAFSVNIFKNWVQAFKVEGGQFGSVEECLLDENS
LEDI<u>VIPMFTALSEGATPQDLNAAVGGHQAAMQMLKETINEEAAEWDRAAAEPRGSDIAGTTSTLQEQIAWAAAKR
WIILGLNKIVRMYSPVSIAAKYVDRFFKTLRAEQAAGLEEMMTACQGVGGPSHKAALSPRTLNAWVKVGSEFTLIP
IAVGGALAGLVLIVLIAYLVGRKRSHAGYQTI</u>.

LAMP-p24CE1 (191H) (gene underlined)

SEQ ID NO: 22

CCTGGCCATTGCATACGTTGTATCCATATCATAATATGTACATTTATATTGGCTCATGTCCAACATTACCGCCATG
TTGACATTGATTATTGACTAGTTATTAATAGTAATCAATTACGGGGGTCATTAGTTCATAGCCCATATATGGAGTT
CCGCGTTACATAACTTACGGTAAATGGCCCGCCTGGCTGACCGCCCAACGACCCCCGCCCATTGACGTCAATAATG
ACGTATGTTCCCATAGTAACGCCAATAGGGACTTTCCATTGACGTCAATGGGTGGAGTATTTACGGTAAACTGCCC
ACTTGGCAGTACATCAAGTGTATCATATGCCAAGTACGCCCCCTATTGACGTCAATGATGGTAAATGGCCCGCCTG
GCATTATGCCCAGTACATGACCTTATGGGACTTTCCTACTTGGCAGTACATCTACGTATTAGTCATCGCTATTACC
ATGGTGATGCGGTTTTGGCAGTACATCAATGGGCGTGGATAGCGGTTTGACTCACGGGGATTTCCAAGTCTCCACC
CCATTGACGTCAATGGGAGTTTGTTTTGGCACCAAAATCAACGGGACTTTCCAAAATGTCGTAACAACTCCGCCCC
ATTGACGCAAATGGGCGGTAGGCGTGTACGGTGGGAGGTCTATATAAGCAGAGCTCGTTTAGTGAACCGTCAGATC
GCCTGGAGACGCCATCCACGCTGTTTTGACCTCCATAGAAGACACCGGGACCGATCCAGCCTCCGcgggcgcgcgt
cgactagcATGGCGCCCCGCAGCGCCCGGCGACCCCTGCTGCTGCTACTGCTGTTGCTGCTGCTCGGCCTCATGCA
TTGTGCGTCAGCAGCAATGTTTATGGTGAAAAATGGCAACGGGACCGCGTGCATAATGGCCAACTTCTCTGCTGCC
TTCTCAGTGAACTACGACACCAAGAGTGGCCCTAAGAACATGACCCTTGACCTGCCATCAGATGCCACAGTGGTGC
TCAACCGCAGCTCCTGTGGAAAAGAGAACACTTCTGACCCCAGTCTCGTGATTGCTTTTGGAAGAGGACATACACT
CACTCTCAATTTCACGAGAAATGCAACACGTTACAGCGTTCAGCTCATGAGTTTTGTTTATAACTTGTCAGACACA
CACCTTTTCCCCAATGCGAGCTCCAAAGAAATCAAGACTGTGGAATCTATAACTGACATCAGGGCAGATATAGATA
AAAAATACAGATGTGTTAGTGGCACCCAGGTCCACATGAACAACGTGACCGTAACGCTCCATGATGCCACCATCCA
GGCGTACCTTTCCAACAGCAGCTTCAGCAGGGGAGAGACACGCTGTGAACAAGACAGGCCTTCCCCAACCACAGCG
CCCCCTGCGCCACCCAGCCCCTCGCCCTCACCCGTGCCCAAGAGCCCTCTGTGGACAAGTACAACGTGAGCGGCA
CCAACGGGACCTGCCTGCTGGCCAGCATGGGGCTGCAGCTGAACCTCACCTATGAGAGGAAGGACAACACGACGGT
GACAAGGCTTCTCAACATCAACCCCAACAAGACCTCGGCCACGGAGCTGCGGCCCCACCTGGTGACTCTGGAG
CTGCACAGCGAGGGCACCACCGTCCTGCTCTTCCAGTTCGGGATGAATGCAAGTTCTAGCCGGTTTTTCCTACAAG
GAATCCAGTTGAATACAATTCTTCCTGACGCCAGAGACCCTGCCTTTAAAGCTGCCAACGGCTCCCTGCGAGCGCT
GCAGGCCACAGTCGGCAATTCCTACAAGTGCAACGCGGAGGAGCACGTCCGTGTCACGAAGGCGTTTTCAGTCAAT
ATATTCAAAGTGTGGTCCAGGCTTTCAAGGTGGAAGGTGGCCAGTTTGGCTCTGTGGAGGAGTGTCTGCTGGACG
AGAACAGCCTCGAGGATATCGTCATCCCGATGTTCTCGGCGCTCAGCGAGGGAGCGACGCCGCAGGACCTGAACGC
GGCCGTCGGAGGTCACCAGGCAGCGATGCAGATGCTGAAGGACACGATCAACGAGGAGGCGGCCGAGTGGGACCGG
GCGGCAGCCGAGCCACGCGGTTCCGACATCGCGGGCACCACCTCGACGCTCCAGGAGCAGATCGGGTGGGCCGCAG
CTAAGCGCTGGATCATCCTCGGGCTGAACAAGATCGTCCGGATGTACAGCCCGACGTCGATCGCTGCTAAGTACGT
TGACCGGTTCTACAAGACCCTGAGGGCCGAGCAGGCGGCCGGACTGGAGGAGGATGATGACCGCGTGCCAGGGGGTC
GGTGGACCAGGGCACAAGGCCGCGATCTCGCCGCGCACGCTGAACGCGTGGGTGAAGGTCGGATCCGAATTCACGC
TGATCCCCATCGCTGTGGGTGGTGCCCTGGCGGGGCTGGTCCTCATCGTCCTCATCGCCTACCTCGTCGGCAGGAA
GAGGAGTCACGCAGGCTACCAGACTATCTAGggtacctctagGATCTGCTGTGCCTTCTAGTTGCCAGCCATCTGT
TGTTTGCCCCTCCCCCGTGCCTTCCTTGACCCTGGAAGGTGCCACTCCCACTGTCCTTTCCTAATAAAATGAGGAA
ATTGCATCGCATTGTCTGAGTAGGTGTCATTCTATTCTGGGGGGTGGGGTGGGGCAGGACAGCAAGGGGGAGGATT
GGGAAGACAATAGCAGGCATGCTGGGGATGCGGTGGGCTCTATGGGTACCCAGGTGCTGAAGAATTGACCCGGTTC
CTCCTGGGCCAGAAAGAAGCAGGCACATCCCCTTCTCTGTGACACACCCTGTCCACGCCCCTGGTTCTTAGTTCCA
GCCCCACTCATAGGACACTCATAGCTCAGGAGGGCTCCGCCTTCAATCCCACCCGCTAAAGTACTTGGAGCGGTCT
CTCCCTCCCTCATCAGCCCACCAAACCAAACCTAGCCTCCAAGAGTGGGAAGAAATTAAAGCAAGATAGGCTATTA
AGTGCAGAGGGAGAGAAATGCCTCCAACATGTGAGGAAGTAATGAGAGAAATCATAGAATTTCTTCCGCTTCCTC
GCTCACTGACTCGCTGCGCTCGGTCGTTCGGCTGCGGCGAGCGGTATCAGCTCACTCAAAGGCGGTAATACGGTTA
TCCACAGAATCAGGGGATAACGCAGGAAAGAACATGTGAGCAAAAGGCCAGCAAAAGGCCAGGAACCGTAAAAAGG
CCGCGTTGCTGGCGTTTTTCCATAGGCTCCGCCCCCCTGACGAGCATCACAAAAATCGACGCTCAAGTCAGAGGTG
GCGAAACCCGACAGGACTATAAAGATACCAGGCGTTTCCCCCTGGAAGCTCCCTCGTGCGCTCTCCTGTTCCGACC
CTGCCGCTTACCGGATACCTGTCCGCCTTTCTCCCTTCGGGAAGCGTGGCGCTTTCTCAATGCTCACGCTGTAGGT
ATCTCAGTTCGGTGTAGGTCGTTCGCTCCAAGCTGGGCTGTGTGCACGAACCCCCCGTTCAGCCCGACCGCTGCGC
CTTATCCGGTAACTATCGTCTTGAGTCCAACCCGGTAAGACACGACTTATCGCCACTGGCAGCAGCCACTGGTAAC
AGGATTAGCAGAGCGAGGTATGTAGGCGGTGCTACAGAGTTCTTGAAGTGGTGGCCTAACTACGGCTACACTAGAA
GAACAGTATTTGGTATCTGCGCTCTGCTGAAGCCAGTTACCTTCGGAAAAAGAGTTGGTAGCTCTTGATCCGGCAA
ACAAACCACCGCTGGTAGCGGTGGTTTTTTTGTTTGCAAGCAGCAGATTACGCGCAGAAAAAAAGGATCTCAAGA
AGATCCTTTGATCTTTTCTACGGGGTCTGACGCTCAGTGGAACGAAAACTCACGTTAAGGGATTTTGGTCATGAG
ATTATCAAAAGGATCTTCACCTAGATCCTTTTAAATTAAAAATGAAGTTTTAAATCAATCTAAAGTATATATGAG
TAAACTTGGTCTGACAGTTACCAATGCTTAATCAGTGAGGCACCTATCTCAGCGATCTGTCTATTTCGTTCATCCA
TAGTTGCCTGACTCGGGGGGGGGGGGCGCTGAGGTCTGCCTCGTGAAGAAGGTGTTGCTGACTCATACCAGGCCT
GAATCGCCCCATCATCCAGCCAGAAAGTGAGGGAGCCACGGTTGATGAGAGCTTTGTTGTAGGTGGACCAGTTGGT
GATTTTGAACTTTTGCTTTGCCACGGAACGGTCTGCGTTGTCGGGAAGATGCGTGATCTGATCCTTCAACTCAGCA
AAAGTTCGATTTATTCAACAAAGCCGCCGTCCCGTCAAGTCAGCGTAATGCTCTGCCAGTGTTACAACCAATTAAC
CAATTCTGATTAGAAAAACTCATCGAGCATCAAATGAAACTGCAATTTATTCATATCAGGATTATCAATACCATAT
TTTTGAAAAAGCCGTTTCTGTAATGAAGGAGAAAACTCACCGAGGCAGTTCCATAGGATGGCAAGATCCTGGTATC
GGTCTGCGATTCCGACTCGTCCAACATCAATACAACCTATTAATTTCCCCTCGTCAAAAATAAGGTTATCAAGTGA
GAAATCACCATGAGTGACGACTGAATCCGGTGAGAATGGCAAAAGCTTATGCATTTCTTTCCAGACTTGTTCAACA
GGCCAGCCATTACGCTCGTCATCAAAATCACTCGCATCAACCAAACCGTTATTCATTCGTGATTGCGCCTGAGCG
AGACGAAATACGCGATCGCTGTTAAAAGGACAATTACAAACAGGAATCGAATGCAACCGGCGCAGGAACACTGCCA
GCGCATCAACAATATTTTCACCTGAATCAGGATATTCTTCTAATACCTGGAATGCTGTTTTCCCGGGGATCGCAG
TGGTGAGTAACCATGCATCATCAGGAGTACGGATAAAATGCTTGATGGTCGGAAGAGGCATAAATTCCGTCAGCCA
GTTTAGTCTGACCATCTCATCTGTAACATCATTGGCAACGCTACCTTTGCCATGTTTCAGAAACAACTCTGGCGCA
TCGGGCTTCCCATACAATCGATAGATTGTCGCACCTGATTGCCCGACATTATCGCGAGCCCATTTATACCCATATA
AATCAGCATCCATGTTGGAATTTAATCGCGGCCTGGAGCAAGACGTTTCCCGTTGAATATGGCTCATAACACCCCT
TGTATTACTGTTTATGTAAGCAGACAGTTTTATTGTTCATGATGATATATTTTTATCTTGTGCAATGTAACATCAG
AGATTTTGAGACACAACGTGGCTTTCCCCCCCCCCCCATTATTGAAGCATTTATCAGGGTTATTGTCTCATGAGCG

| Table of Illustrative Conserved Element Sequences |
|---|
| GATACATATTTGAATGTATTTAGAAAAATAAACAAATAGGGGTTCCGCGCACATTTCCCCGAAAAGTGCCACCTGA<br>CGTCTAAGAAACCATTATTATCATGACATTAACCTATAAAAATAGGCGTATCACGAGGCCCTTTCGTCTCGCGCGT<br>TTCGGTGATGACGGTGAAAACCTCTGACACATGCAGCTCCCGGAGACGGTCACAGCTTGTCTGTAAGCGGATGCCG<br>GGAGCAGACAAGCCCGTCAGGGCGCGTCAGCGGGTGTTGGCGGGTGTCGGGGCTGGCTTAACTATGCGGCATCAGA<br>GCAGATTGTACTGAGATGCACCATATGCGGTGTGAAATACCGCACAGATGCGTAAGGAGAAAATACCGCATCAGAT<br>TGGCTATTGG |

LAMP-p24CE1 (p24CE1 underlined)

SEQ ID NO: 23

MAPRSARRPLLLLLLLLLLLGLMHCASAAMFMVKNGNTACIMANFSAAFSVNYDTKSGPKNMTLDLPSDATVVLNRS
SCGKENTSDPSLVIAFGRGHTLTLNFTRNATRYSVQLMSFVYNLSDTHLFPNASSKEIKTVESITDIRADIDKKYR
CVSGTQVHMNNVTVTLHDATIQAYLSNSSFSRGETRCEQDRPSPTTAPPAPPSPSPSPVPKSPSVDKYNVSGTNGT
CLLASMGLQLNLTYERKDNTTVTRLLNINPNKTSASGSCGAHLVTLELHSEDTTVLLFQFGMNASSSRFFLQGIQL
NTILPDARDPAFKAANGSLRALQATVGNSYKCNAEEHVRVTKAFSVNIFKVWVQAFKVEGGQFGSVEECLLDENSL
EDI<u>VIPMFSALSEGATPQDLNAAVGGHQAAMQMLKDTINEEAAEWDRAAAERPGSDIAGTTSTLQEQIGQAAAKRW
IILGLNKIVRMYSPTSIAAKYVDRFYKTLRAEQAAGLEEMMTACQGVGGPGHKAAI SPRTLNAWVKVGS</u>EFTLIPI
AVGGALAGLVLIVLIAYLVGRKRSHAGYQTI.

SP-p24CE2 (235H) (gene underlined)

SEQ ID NO: 24

CCTGGCCATTGCATACGTTGTATCCATATCATAATATGTACATTTATATTGGCTCATGTCCAACATTACCGCCATG
TTGACATTGATTATTGACTAGTTATTAATAGTAATCAATTACGGGGTCATTAGTTCATAGCCCATATATGGAGTTC
CGCGTTACATAACTTACGGTAAATGGCCCGCCTGGCTGACCGCCCAACGACCCCCGCCCATTGACGTCAATAATGA
CGTATGTTCCATAGTAACGCCAATAGGGACTTTCCATTGACGTCAATGGGTGGAGTATTTACGGTAAACTGCCCA
CTTGGCAGTACATCAAGTGTATCATATGCCAAGTACGCCCCCTATTGACGTCAATGATGGTAAATGGCCCGCCTGG
CATTATGCCCAGTACATGACCTTATGGGACTTTCCTACTTGGCAGTACATCTACGTATTAGTCATCGCTATTACCA
TGGTGATGCGGTTTTGGCAGTACATCAATGGGCGTGGATAGCGGTTTGACTCACGGGGATTTCCAAGTCTCCACCC
CATTGACGTCAATGGGAGTTTGTTTTGGCACCAAAATCAACGGGACTTTCCAAATGTCGTAACAACTCCGCCCCA
TTGACGCAAATGGGCGGTAGGCGTGTACGGTGGGAGGTCTATATAAGCAGAGCTCGTTTAGTGAACCGTCAGATCG
CCTGGAGACGCCATCCACGCTGTTTTGACCTCCATAGAAGACACCGGGACCGATCCAGCCTCCGCGGGcgcgcgtc
gacaagaa<u>ATGTGGCTCCAGAGCCTGCTACTCCTGGGGACGGTGGCCTGCAGCATCTCGGTCATCCCGATGTTCAC
GGCGCTCAGCGAGGGAGCGACGCCGCAGGACCTGAACGCGGCCGTTCGGAGGTCACCAGGCAGCGATGCAGATGCTG
AAGGAGACGATCAACGAGGAGGCGGCCGAGTGGGACCGGGCGGCAGCCGAGCCACGCGGTTCCGACATCGCGGGCA
CCACCTCGACGCTCCAGGAGCAGATCGCGTGGGCCGCAGCTAAGCGCTGGATCATCCTCGGGCTGAACAAGATCGT
CCGGATGTACAGCCCGGTCTCGATCGCTGCTAAGTACGTTGACCGGTTCTTCAAGACCCTGAGGGCCGAGCAGGCG
GCCGGACTGGAGGAGATGATGACCGCGTGCCAGGGGGTCGGTGGACCATCGCACAAGGCGCGCTCTCGCCGCGCA
CGCTGAACGCGTGGGTGAAGGTCTGATAA</u>gaattcgcggatatcggttaacggatccAGATCTGCTGTGCCTTCTA
GTTGCCAGCCATCTGTTGTTTGCCCCTCCCCCGTGCCTTCCTTGACCCTGGAAGGTGCCACTCCCACTGTCCTTTC
CTAATAAAATGAGGAAATTGCATCGCATTGTCTGAGTAGGTGTCATTCTATTCTGGGGGGTGGGGTGGGCAGGAC
AGCAAGGGGGAGGATTGGGAAGACAATAGCAGGCATGCTGGGGATGCGGTGGGCTCTATGGGTACCCAGGTGCTGA
AGAATTGACCCGGTTCCTCCTGGGCCAGAAAGAAGCAGGCACATCCCTTCTCTGTGACACACCCTGTCCACGCCC
CTGGTTCTTAGTTCCAGCCCCACTCATAGGACACTCATAGCTCAGGAGGGCTCCGCCTTCAATCCCACCCGCTAAA
GTACTTGGAGCGGTCTCTCCCTCCCTCATCAGCCCACCAAACCAAACCTAGCCTCCAAGAGTGGGAAGAAATTAAA
GCAAGATAGGCTATTAAGTGCAGAGGGAGAGAAAATGCCTCCAACATGTGAGGAAGTAATGAGAGAAATCATAGAA
TTTCTTCCGCTTCCTCGCTCACTGACTCGCTGCGCTCGGTCGTTCGGCTGCGCGAGCGGTATCAGCTCACTCAAA
GGCGGTAATACGGTTATCCACAGAATCAGGGGATAACGCAGGAAAGAACATGTGAGCAAAAGGCCAGCAAAAGGCC
AGGAACCGTAAAAAGGCCGCGTTGCTGGCGTTTTTCCATAGGCTCCGCCCCCCTGACGAGCATCACAAAAATCGAC
GCTCAAGTCAGAGGTGGCGAAACCCGACAGGACTATAAAGATACCAGGCGTTTCCCCCTGGAAGCTCCCTCGTGCG
CTCTCCTGTTCCGACCCTGCCGCTTACCGGATACCTGTCCGCCTTTCTCCCTTCGGGAAGCGTGGCGCTTTCTCAT
AGCTCACGCTGTAGGTATCTCAGTTCGGTGTAGGTCGTTCGCTCCAAGCTGGGCTGTGTGCACGAACCCCCCGTTC
AGCCCGACCGCTGCGCCTTATCCGGTAACTATCGTCTTGAGTCCAACCCGGTAAGACACGACTTATCGCCACTGGC
AGCAGCCACTGGTAACAGGATTAGCAGAGCGAGGTATGTAGGCGGTGCTACAGAGTTCTTGAAGTGGTGGCCTAAC
TACGGCTACACTAGAAGAACAGTATTTGGTATCTGCGCTCTGCTGAAGCCAGTTACCTTCGGAAAAAGAGTTGGTA
GCTCTTGATCCGGCAAACAAACCACCGCTGGTAGCGGTGGTTTTTTTGTTTGCAAGCAGCAGATTACGCGCAGAAA
AAAAGGATCTCAAGAAGATCCTTTGATCTTTTCTACGGGGTCTGACGCTCAGTGGAACGAAAACTCACGTTAAGGG
ATTTTGGTCATGAGATTATCAAAAAGGATCTTCACCTAGATCCTTTTAAATTAAAAATGAAGTTTTAAATCAATCT
AAAGTATATATGAGTAAACTTGGTCTGACAGTTACCAATGCTTAATCAGTGAGGCACCTATCTCAGCGATCTGTCT
ATTTCGTTCATCCATAGTTGCCTGACTCGGGGGGGGGGGGCGCTGAGGTCTGCCTCGTGAAGAAGGTGTTGCTGAC
TCATACCAGGCCTGAATCGCCCCATCATCCAGCCAGAAAGTGAGGGAGCACGGTTGATGAGAGCTTTGTTGTAGG
TGGACCAGTTGGTGATTTTGAACTTTTGCTTTGCCACGGAACGGTCTGCGTTGTCGGGAAGATGCGTGATCTGATC
CTTCAACTCAGCAAAAGTTCGATTTATTCAACAAAGCCGCCGTCCCGTCAAGTCAGCGTAATGCTCTGCCAGTGTT
ACAACCAATTAACCAATTCTGATTAGAAAAACTCATCGAGCATCAAATGAAACTGCAATTTATTCATATCAGGATT
ATCAATACCATATTTTTGAAAAAGCCGTTTCTGTAATGAAGGAGAAAACTCACCGAGGCAGTTCCATAGGATGGCA
AGATCCTGGTATCGGTCTGCGATTCCGACTCGTCCAACATCAATACAACCTATTAATTTCCCCTCGTCAAAATAA
GGTTATCAAGTGAGAAATCACCATGAGTGACGACTGAATCCGGTGAGAATGGCAAAAGCTTATGCATTTCTTTCCA
GACTTGTTCAACAGGCCAGCCATTACGCTCGTCATCAAAATCACTCGCATCAACCAAACCGTTATTCATTCGTGAT
TGCGCCTGAGCGAGACGAAATACGCGATCGCTGTTAAAAGGACAATTACAAACAGGAATCGAATGCAACCGGCGCA
GGAACACTGCCAGCGCATCAACAATATTTTCACCTGAATCAGGATATTCTTCTAATACCTGGAATGCTGTTTTCCC
GGGGATCGCAGTGGTGAGTAACCATGCATCATCAGGAGTACGGATAAAATGCTTGATGGTCGGAAGAGGCATAAAT
TCCGTCAGCCAGTTTAGTCTGACCATCTCATCTGTAACATCATTGGCAACGCTACCTTTGCCATGTTTCAGAAACA
ACTCTGGCGCATCGGGCTTCCCATACAATCGATAGATTGTCGCACCTGATTGCCCGACATTATCGCGAGCCCATTT
ATACCCATATAAATCAGCATCCATGTTGGAATTTAATCGCGGCCTCGAGCAAGACGTTTCCCGTTGAATATGGCTC
ATAACACCCCTTGTATTACTGTTTATGTAAGCAGACAGTTTTATTGTTCATGATGATATATTTTTATCTTGTGCAA
TGTAACATCAGAGATTTTGAGACACAACGTGGCTTTCCCCCCCCCCCCATTATTGAAGCATTTATCAGGGTTATTG
TCTCATGAGCGGATACATATTTGAATGTATTTAGAAAAATAAACAAATAGGGGTTCCGCGCACATTTCCCCGAAAA
GTGCCACCTGACGTCTAAGAAACCATTATTATCATGACATTAACCTATAAAAATAGGCGTATCACGAGGCCCTTTCG
TCTCGCGCGTTTCGGTGATGACGGTGAAAACCTCTGACACATGCAGCTCCCGGAGACGGTCACAGCTTGTCTGTAA -continued Table of Illustrative Conserved Element Sequences GCGGATGCCGGGAGCAGACAAGCCCGTCAGGGCGCGTCAGCGGGTGTTGGCGGGTGTCGGGGCTGGCTTAACTATG
CGGCATCAGAGCAGATTGTACTGAGAGTGCACCATATGCGGTGTAAATACCGCACAGATGCGTAAGGAGAAAATAC
CGCATCAGATTGGCTATTGG SP-p24CE2 (p24CE1 underlined) encoded by SEQ ID NO: 24

SEQ ID NO: 25

MWLQSLLLLGTVACSIS<u>VIPMFTALSEGATPQDLNAAVGGHQAAMQMLKETINEEAAEWDRAAAEPRGSDIAGTTS
TLQEQIAWAAAKRWIILGLNKIVRMYSPVSIAAKYVDRFFKTLRAEQAAGLEEMMTACQGVGGPSHKAALSPRTLN
AWVKV</u>

MCP3-p24CE1 (230H) (gene underlined)

SEQ ID NO: 26

CCTGGCCATTGCATACGTTGTATCCATATCATAATATGTACATTTATATTGGCTCATGTCCAACATTACCGCCATG
TTGACATTGATTATTGACTAGTTATTAATAGTAATCAATTACGGGGTCATTAGTTCATAGCCCATATATGGAGTTC
CGCGTTACATAACTTACGGTAAATGGCCCGCCTGGCTGACCGCCCAACGACCCCGCCCATTGACGTCAATAATGA
CGTATGTTCCCATAGTAACGCCAATAGGGACTTTCCATTGACGTCAATGGGTGGAGTATTTACGGTAAACTGCCCA
CTTGGCAGTACATCAAGTGTATCATATGCCAAGTACGCCCCCTATTGACGTCAATGATGGTAAATGGCCCGCCTGG
CATTATGCCCAGTACATGACCTTATGGGACTTTCCTACTTGGCAGTACATCTACGTATTAGTCATCGCTATTACCA
TGGTGATGCGGTTTTGGCAGTACATCAATGGGCGTGGATAGCGGTTTGACTCACGGGGATTTCCAAGTCTCCACCC
CATTGACGTCAATGGGAGTTTGTTTTGGCACCAAAATCAACGGGACTTTCCAAAATGTCGTAACAACTCCGCCCCA
TTGACGCAAATGGGCGGTAGGCGTGTACGGTGGGAGGTCTATATAAGCAGAGCTCGTTTAGTGAACCGTCAGATCG
CCTGGAGACGCCATCCACGCTGTTTTGACCTCCATAGAAGACACCGGGACCGATCCAGCCTCCGCGGGcgcgcgtc
gacaagaa<u>ATGTGGAAGCCGATGCCCTCGCCAAGCAACATGAAGGCGTCCGCCGCGCTCCTGTCCTGCTCCTCAC
GGCCGCGGCTTTCAGCCCCCAGGGGCTCGCGCAGCCGGTCGGGATCAACACGAGCACGACCTGCTGCTACCGGTTC
ATCAACAAGAAGATCCCGAAGCAGCGTCTGGAGAGCTACCGCCGGACCACGTCGAGCCACTGCCCGCGGGAGGCGG
TCATCTTCAAGACGAAGCTGGACAAGGAGATCTGCGCCGACCCGACGCAGAAGTGGGTTCAGGACTTCATGAAGCA
CCTGGACAAGAAGACGCAGACGCCGAAGCTGGTCATCCCGATGTTCTCGGCGCTCAGCGAGGGAGCGACGCCGCAG
GACCTGAACGCGGCCGTCGGAGGTCACCAGGCAGCGATGCAGATGCTGAAGGACACGATCAACGAGGAGGCGGCCG
AGTGGGACCGGGCGGCAGCCGAGCCACGCGGTTCCGACATCGCGGGCACCACCTCGACGCTCCAGGAGCAGATCGG
GTGGGCCGCAGCTAAGCGCTGGATCATCCTCGGGCTGAACAAGATCGTCCGGATGTACAGCCCGACGTCGATCGCT
GCTAAGTACGTTGACCGGTTCTACAAGACCCTGAGGGCCGAGCAGGCGGCCGGACTGGAGGAGATGATGACCGCGT
GCCAGGGGGTCGGTGGACCAGGGCACAAGGCCGCGATCTCGCCGCACGCTGAACGCGTGGGTGAAGGTCTGATA</u>
Agaattcgcggatatcggttaacggatcaa<u>GATCTGCTGTGCCTTCTAGTTGCCAGCCATCTGTTGTTTGCCCCTC
CCCCGTGCCTTCCTTGACCCTGGAAGGTGCCACTCCCACTGTCCTTTCCTAATAAAATGAGGAAATTGCATCGCAT
TGTCTGAGTAGGTGTCATTCTATTCTGGGGGGTGGGGTGGGGCAGGACAGCAAGGGGGAGGATTGGGAAGACAATA
GCAGGCATGCTGGGGATGCGGTGGGCTCTATGGGTACCCAGGTGCTGAAGAATTGACCCGGTTCCTCCTGGGCCAG
AAAGAAGCAGGCACATCCCCTTCTCTGTGACACACCCTGTCCACGCCCCTGGTTCTTAGTTCCAGCCCCACTCATA
GGACACTCATAGCTCAGGAGGGCTCCGCCTTCAATCCCACCCGCTAAAGTACTTGGAGCGGTCTCTCCCTCCCTCA
TCAGCCCACCAAACCAAACCTAGCCTCCAAGAGTGGGAAGAAATTAAAGCAAGATAGGCTATTAAGTGCAGAGGGA
GAGAAAATGCCTCCAACATGTGAGGAAGTAATGAGAGAAATCATAGAATTTCTTCCGCTTCCTCGCTCACTGACTC
GCTGCGCTCGGTCGTTCGGCTGCGGCGAGCGGTATCAGCTCACTCAAAGGCGGTAATACGGTTATCCACAGAATCA
GGGGATAACGCAGGAAAGAACATGTGAGCAAAAGGCCAGCAAAAGGCCAGGAACCGTAAAAAGGCCGCGTTGCTGG
CGTTTTTCCATAGGCTCCGCCCCCTGACGAGCATCACAAAAATCGACGCTCAAGTCAGAGGTGGCGAAACCCGAC
AGGACTATAAAGATACCAGGCGTTTCCCCCTGGAAGCTCCCTCGTGCGCTCTCCTGTTCCGACCCTGCCGCTTACC
GGATACCTGTCCGCCTTTCTCCCTTCGGGAAGCGTGGCGCTTTCTCATAGCTCACGCTGTAGGTATCTCAGTTCGG
TGTAGGTCGTTCGCTCCAAGCTGGGCTGTGTGCACGAACCCCCCGTTCAGCCCGACCGCTGCGCCTTATCCGGTAA
CTATCGTCTTGAGTCCAACCCGGTAAGACACGACTTATCGCCACTGGCAGCAGCCACTGGTAACAGGATTAGCAGA
GCGAGGTATGTAGGCGGTGCTACAGAGTTCTTGAAGTGGTGGCCTAACTACGGCTACACTAGAAGAACAGTATTTG
GTATCTGCGCTCTGCTGAAGCCAGTTACCTTCGGAAAAAGAGTTGGTAGCTCTTGATCCGGCAAACAAACCACCGC
TGGTAGCGGTGGTTTTTTTGTTTGCAAGCAGCAGATTACGCGCAGAAAAAAAGGATCTCAAGAAGATCCTTTGATC
TTTTCTACGGGGTCTGACGCTCAGTGGAACGAAAACTCACGTTAAGGGATTTTGGTCATGAGATTATCAAAAAGGA
TCTTCACCTAGATCCTTTTAAATTAAAAATGAAGTTTTAAATCAATCTAAAGTATATATGAGTAAACTTGGTCTGA
CAGTTACCAATGCTTAATCAGTGAGGCACCTATCTCAGCGATCTGTCTATTTCGTTCATCCATAGTTGCCTGACTC
GGGGGGGGGGGCGCTGAGGTCTGCCTCGTGAAGAAGGTGTTGCTGACTCATACCAGGCCTGAATCGCCCCATCAT
CCAGCCAGAAAGTGAGGGAGCCACGGTTGATGAGAGCTTTGTTGTAGGTGGACCAGTTGGTGATTTTGAACTTTTG
CTTTGCCACGGAACGGTCTGCGTTGTCGGGAAGATGCGTGATCTGATCCTTCAACTCAGCAAAAGTTCGATTTATT
CAACAAAGCCGCCGTCCCGTCAAGTCAGCGTAATGCTCTGCCAGTGTTACAACCAATTAACCAATTCTGATTAGAA
AAACTCATCGAGCATCAAATGAAACTGCAATTTATTCATATCAGGATTATCAATACCATATTTTTGAAAAAGCCGT
TTCTGTAATGAAGGAGAAAACTCACCGAGGCAGTTCCATAGGATGGCAAGATCCTGGTATCGGTCTGCGATTCCGA
CTCGTCCAACATCAATACAACCTATTAATTTCCCCTCGTCAAAAATAAGGTTATCAAGTGAGAAATCACCATGAGT
GACGACTGAATCCGGTGAGAATGGCAAAAGCTTATGCATTTCTTTCCAGACTTGTTCAACAGGCCAGCCATTACGC
TCGTCATCAAAATCACTCGCATCAACCAAACCGTTATTCATTCGTGATTGCGCCTGAGCGAGACGAAATACGCGAT
CGCTGTTAAAAGGACAATTACAAACAGGAATCGAATGCAACCGGCGCAGGAACACTGCCAGCGCATCAACAATATT
TTCACCTGAATCAGGATATTCTTCTAATACCTGGAATGCTGTTTTCCCGGGGATCGCAGTGGTGAGTAACCATGCA
TCATCAGGAGTACGGATAAAATGCTTGATGGTCGGAAGAGGCATAAATTCCGTCAGCCAGTTTAGTCTGACCATCT
CATCTGTAACATCATTGGCAACGCTACCTTTGCCATGTTTCAGAAACAACTCTGGCGCATCGGGCTTCCCATACAA
TCGATAGATTGTCGCACCTGATTGCCCGACATTATCGCGAGCCCATTTATACCCATATAAATCAGCATCCATGTTG
GAATTTAATCGCGGCCTCGAGCAAGACGTTTCCCGTTGAATATGGCTCATAACACCCCTTGTATTACTGTTTATGT
AAGCAGACAGTTTTATTGTTCATGATGATATATTTTTATCTTGTGCAATGTAACATCAGAGATTTTGAGACACAAC
GTGGCTTTCCCCCCCCCCCATTATTGAAGCATTTATCAGGGTTATTGTCTCATGAGCGGATACATATTTGAATGT
ATTTAGAAAAATAAACAAATAGGGGTTCCGCGCACATTTCCCCGAAAAGTGCCACCTGACGTCTAAGAAACCATTA
TTATCATGACATTAACCTATAAAAATAGGCGTATCACGAGGCCCTTTCGTCTCGCGCGTTTCGGTGATGACGGTGA
AAACCTCTGACACATGCAGCTCCCGGAGACGGTCACAGCTTGTCTGTAAGCGGATGCCGGGAGCAGACAAGCCCGT
CAGGGCGCGTCAGCGGGTGTTGGCGGGTGTCGGGGCTGGCTTAACTATGCGGCATCAGAGCAGATTGTACTGAGAG
TGCACCATATGCGGTGTGAAATACCGCACAGATGCGTAAGGAGAAATACCGCATCAGATTGGCTATTGG -continued Table of Illustrative Conserved Element Sequences MCP3-p24CE1 (p24CE1 underlined) encoded by SEQ ID NO: 26

SEQ ID NO: 27

MWMPMPSPSNMKASAALLCLLLTAAAFSPQGLAQPVGINTSTTCCYRFINKKIPKQRLESYRRTTSSHCPREAVIF
KTKLDKEICADPTQKWVQDFMKHLDKKTQTPKL<u>VIPMFSALSEGATPQDLNAAVGGHQAAMQMLKDTINEEAAEWD
RAAAEPRGSDIAGTTSTLQEQIGWAAAKRWIILGLNKIVRMYSPTSIAAKYVDRFYKTLRAEQAAGLEEMMTACQG
VGGPGHKAAISPRTLNAWVKV</u>.

MCP3-p24CE2 (231H) (gene underlined)

SEQ ID NO: 28

CCTGGCCATTGCATACGTTGTATCCATATCATAATATGACATTTATATTGGCTCATGTCCAACATTACCGCCATGT
TGACATTGATTATTGACTAGTTATTAATAGTAATCAATTACGGGGTCATTAGTTCATAGCCCATATATGGAGTTCC
GCGTTACATAACTTACGGTAAATGGCCCGCCTGGCTGACCGCCCAACGACCCCCGCCCATTGACGTCAATAATGAC
GTATGTTCCCATAGTAACGCCAATAGGGACTTTCCATTGACGTCAATGGGTGGAGTATTTACGGTAAACTGCCCAC
TTGGCAGTACATCAAGTGTATCATATGCCAAGTACGCCCCCTATTGACGTCAATGATGGTAAATGGCCCGCCTGGC
ATTATGCCCAGTACATGACCTTATGGGACTTTCCTACTTGGCAGTACATCTACGTATTAGTCATCGCTATTACCAT
GGTGATGCGGTTTTGGCAGTACATCAATGGGCGTGGATAGCGGTTTGACTCACGGGGATTTCCAAGTCTCCACCCC
ATTGACGTCAATGGGAGTTTGTTTTGGCACCAAAATCAACGGGACTTTCCAAAATGTCGTAACAACTCCGCCCCAT
TGACGCAAATGGGCGGTAGGCGTGTACGGTGGGAGGTCTATATAAGCAGAGCTCGTTTAGTGAACCGTCAGATCGC
CTGGAGACGCCATCCACGCTGTTTTGACCTCCATAGAAGACACCGGGACCGATCCAGCCTCCGCGGGcgcgcgtcg
acaagaa<u>ATGTGGAAGCCGATGCCCTCGCCAAGCAACATGAAGGCGTCCGCCGCGCTCCTGTGCCTGCTCCTCACG
GCCGCGGCTTTCAGCCCCCAGGGGCTCGCGCAGCCGGTCGGGATCAACACGAGCACGACCTGCTGCTACCGGTTCA
TCAACAAGAAGATCCCGAAGCAGCGTCTGGAGAGCTACCGCCGGACCACGTCGAGCACTGCCCGCGGGAGGCGGT
CATCTTCAAGACGAAGCTGGACAAGGAGATCTGCGCCGACCCGACGCAGAAGTGGGTTCAGGACTTCATGAAGCAC
CTGGACAAGAAGACGCAGACGCCGAAGCTGGTCATCCCGATGTTCACGGCGCTCAGCGAGGGAGCGACGCCGCAGG
ACCTGAACGCGGCCGTCGGAGGTCACCAGGCAGCGATGCAGATGCTGAAGGAGACGATCAACGAGGAGGCGGCCGA
GTGGGACCGGGCGGCAGCCGAGCCACGCGGTTCCGACATCGCGGGCACCACCTCGACGCTCCAGGAGCAGATCGCG
TGGGCCGCAGCTAAGCGCTGGATCATCCTCGGGCTGAACAAGATCGTCCGGATGTACAGCCCGGTCTCGATCGCTG
CTAAGTACGTTGACCGGTTCTTCAAGACCCTGAGGGCCGAGCAGGCGGCCGGACTGGAGGAGATGATGACCGCGTG
CCAGGGGGTCGGTGGACCATCGCACAAGGCCGCGCTCTCGCCGCACGCTGAACGCGTGGGTGAAGGTCTGATAAg</u>a
attcgcggatatcggttaacggatccaGATCTGCTGTGCCTTCTAGTTGCCAGCCATCTGTTGTTTGCCCCTCCCC
CGTGCCTTCCTTGACCCTGGAAGGTGCCACTCCCACTGTCCTTTCCTAATAAAATGAGGAAATTGCATCGCATTGT
CTGAGTAGGTGTCATTCTATTCTGGGGGGTGGGGTGGGGCAGGACAGCAAGGGGGAGGATTGGGAAGACAATAGCA
GGCATGCTGGGGATGCGGTGGGCTCTATGGGTACCCAGGTGCTGAAGAATTGACCCGGTTCCTCCTGGGCCAGAAA
GAAGCAGGCACATCCCCTTCTCTGTGACACCCTGTCCACGCCCCTGGTTCTTAGTTCCAGCCCCACTCATAGGACA
CTCATAGCTCAGGAGGGCTCCGCCTTCAATCCCACCCGCTAAAGTACTTGGAGCGGTCTCTCCTCCCTCATCAGC
CCACCAAACCAAACCTAGCCTCCAAGAGTGGGAAGAAATTAAAGCAAGATAGGCTATTAAGTGCAGAGGGAGAGAA
AATGCCTCCAACATGTGAGGAAGTAATGAGAGAAATCATAGAATTTCTTCCGCTTCCTCGCTCACTGACTCGCTGC
GCTCGGTCGTTCGGCTGCGGCGAGCGGTATCAGCTCACTCAAAGGCGGTAATACGGTTATCCACAGAATCAGGGGA
TAACGCAGGAAAGAACATGTGAGCAAAAGGCCAGCAAAAGGCCAGGAACCGTAAAAAGGCCGCGTTGCTGGCGTTT
TTCCATAGGCTCCGCCCCCCTGACGAGCATCACAAAAATCGACGCTCAAGTCAGAGGTGGCGAAACCCGACAGGAC
TATAAAGATACCAGGCGTTTCCCCCTGGAAGCTCCCTCGTGCGCTCTCCTGTTCCGACCCTGCCGCTTACCGGATA
CCTGTCCGCCTTTCTCCCTTCGGGAAGCGTGGCGCTTTCTCATAGCTCACGCTGTAGGTATCTCAGTTCGGTGTAG
GTCGTTCGCTCCAAGCTGGGCTGTGTGCACGAACCCCCCGTTCAGCCCGACCGCTGCGCCTTATCCGGTAACTATC
GTCTTGAGTCCAACCCGGTAAGACACGACTTATCGCCACTGGCAGCAGCCACTGGTAACAGGATTAGCAGAGCGAG
GTATGTAGGCGGTGCTACAGAGTTCTTGAAGTGGTGGCCTAACTACGGCTACACTAGAAGAACAGTATTTGGTATC
TGCGCTCTGCTGAAGCCAGTTACCTTCGGAAAAAGAGTTGGTAGCTCTTGATCCGGCAAACAAACCACCGCTGGTA
GCGGTGGTTTTTTTGTTTGCAAGCAGCAGATTACGCGCAGAAAAAAAGGATCTCAAGAAGATCCTTTGATCTTTTC
TACGGGGTCTGACGCTCAGTGGAACGAAAACTCACGTTAAGGGATTTTGGTCATGAGATTATCAAAAAGGATCTTC
ACCTAGATCCTTTTAAATTAAAAATGAAGTTTTAAATCAATCTAAAGTATATATGAGTAAACTTGGTCTGACAGTT
ACCAATGCTTAATCAGTGAGGCACCTATCTCAGCGATCTGTCTATTTCGTTCATCCATAGTTGCCTGACTCGGGGG
GGGGGGGCGCTGAGGTCTGCCTCGTGAAGAAGGTGTTGCTGACTCATACCAGGCCTGAATCGCCCCATCATCCAGC
CAGAAAGTGAGGGAGCCACGGTTGATGAGAGCTTTGTTGTAGGTGGACCAGTTGGTGATTTTGAACTTTTGCTTTG
CCACGGAACGGTCTGCGTTGTCGGGAAGATGCGTGATCTGATCCTTCAACTCAGCAAAGTTCGATTTATTCAACA
AAGCCGCCGTCCCGTCAAGTCAGCGTAATGCTCTGCCAGTGTTACAACCAATTAACCAATTCTGATTAGAAAACT
CATCGAGCATCAAATGAAACTGCAATTTATTCATATCAGGATTATCAATACCATATTTTTGAAAAAGCCGTTTCTG
TAATGAAGGAGAAAACTCACCGAGGCAGTTCCATAGGATGGCAAGATCCTGGTATCGGTCTGCGATTCCGACTCGT
CCAACATCAATACAACCTATTAATTTCCCCTCGTCAAAAATAAGGTTATCAAGTGAGAAATCACCATGAGTGACGA
CTGAATCCGGTGAGAATGGCAAAAGCTTATGCATTTCTTTCCAGACTTGTTCAACAGGCCAGCCATTACGCTCGTC
ATCAAATCACTCGCATCAACCAAACCGTTATTCATTCGTGATTGCGCCTGAGCGAGACGAAATACGCGATCGCTG
TTAAAGGACAATTACAAACAGGAATCGAATGCAACCGGCGCAGGAACACTGCCAGCGCATCAACAATATTTTCAC
CTGAATCAGGATATTCTTCTAATACCTGGAATGCTGTTTTCCCGGGGATCGCAGTGGTGAGTAACCATGCATCATC
AGGAGTACGGATAAAATGCTTGATGGTCGGAAGAGGCATAAATTCCGTCAGCCAGTTTAGTCTGACCATCTCATCT
GTAACATCATTGGCAACGCTACCTTTGCCATGTTTCAGAAACAACTCTGGCGCATCGGGCTTCCCATACAATCGAT
AGATTGTCGCACCTGATTGCCCGACATTATCGCGAGCCCATTTATACCCATATAAATCAGCATCCATGTTGGAATT
TAATCGCGGCCTCGAGCAAGACGTTTCCCGTTGAATATGGCTCATAACACCCCTTGTATTACTGTTTATGTAAGCA
GACAGTTTTATTGTTCATGATGATATATTTTTATCTTGTGCAATGTAACATCAGAGATTTTGAGACAACACGTGGC
TTTCCCCCCCCCCCCATTATTGAAGCATTTATCAGGGTTATTGTCTCATGAGCGGATACATATTTGAATGTATTTA
GAAAAATAAACAAATAGGGGTTCCGCGCACATTTCCCCGAAAAGTGCCACCTGACGTCTAAGAAACCATTATTATC
ATGACATTAACCTATAAAAATAGGCGTATCACGAGGCCCTTTCGTCTCGCGCGTTTCGGTGATGACGGTGAAAACC
TCTGACACATGCAGCTCCCGGAGACGGTCACAGCTTGTCTGTAAGCGGATGCCGGGAGCAGACAAGCCCGTCAGGG
CGCGTCAGCGGGTGTTGGCGGGTGTCGGGGCTGGCTTAACTATGCGGCATCAGAGCAGATTGTACTGAGAGTGCAC
CATATGCGGTGTGAAATACCGCACAGATGCGTAAGGAGAAAATACCGCATCAGATTGGCTATTGG Table of Illustrative Conserved Element Sequences MCP3-p24CE2 (p24CE2 is underlined) encoded by SEQ ID NO: 28

SEQ ID NO: 29

MWKPMPSPSNMKASAALLCLLLTAAAFSPQGLAQPVGINTSTTCCYRFINKKIPKQRLESYRRTTSSHCPREAVIF
KTKLDKEICADPTQKWVQDFMKHLDKKTQTPKLVIPMFTALSEGATPQDLNAAVGGHQAAMQMLKETINEEAAEWD
RAAAEPRGSDIAGTTSTLQEQIAWAAAKRWIILGLNKIVRMYSPVSIAAKYVDRFFKTLRAEQAAGLEEMMTACQG
VGGPSHKAALSPRTLNAWVKV.

SP-p24CE1c-alternative conserved element nucleic acid construct

SEQ ID NO: 30

ATGTGGCTCCAGAGCCTGCTACTCCTGGGGACGGTGGCCTGCAGCATCTCGCAGGGGCAGATGGTCCACCAGGCGA
TCTCGCCGCGCACGCTGAACGCGTGGGTGAAGGTCCTGGCGAAGGAGGAGAAGGCGTTCAGCCCGGAGGTCATCCC
GATGTTCTCGGCGCTCAGCGAGGGAGCGACGCCGCAGGACCTGAACGCGGCCAAGGTCGGAGGTCACCAGGCAGCG
ATGCAGATGCTGAAGGAGACGATCAACGAGGAGGCGGCCGAGTGGGACCGGGCGGCAGCCGAGCCACGCGGTTCCG
ACATCGCGGGCACCACCTCGACGCTCCAGGAGCAGATCGGGTGGGCCGCAGCTAAGCGCTGGATCATCCTCGGGCT
GAACAAGATCGTCCGGATGTACAGCCCGACGTCGATCGCTGCTAAATACGTTGACCGGTTCTACAAGACCCTGAGG
GCCGAGCAGGCGGATTACAAGGACGATGACGACAAGCTGTGATAA

SP-p24CE1c (p24CE1c underlined) encoded by SEQ ID NO: 30. Includes GM-CSF
signal peptide, CE1 and CE2 replaced by CE8 and CE9, respectively, (relative
to p24 CE "Core1"); lacks CE7, arranged in the configuration of conserved
elements: CE 8-9-3-4-5-6

SEQ ID NO: 31

MWLQSLLLLGTVACSISQGQMVHQAISPRTLNAWVKKVLAKEEKAFSPEVIPMFSALSEGATPQDLNAAKVGGHQA
AMQMLKETINEEAAEWDRAAAEPRGSDIAGTTSTLQEQIGWAAAKRWILGLNKIVRMYSPTSIAAKYVDRFYKTLR
AEQADYKDDDDKL conderved element 8 (CE8)

SEQ ID NO: 32

QGQMVHQAISPRTLNAWVKV conserved element 9 (CE9)

SEQ ID NO: 33

EEKAFSPEVIPMFSALSEGATPQDLN

SP-p24CE2c-alternative

SEQ ID NO: 34

ATGTGGCTCCAGAGCCTGCTACTCCTGGGGACGGTGGCCTGCAGCATCTCGCAGGGGCAGATGGTCCACCAGGCGC
TGTCGCCGCGCACGCTGAACGCGTGGGTGAAGGTCCTGGCGAAGGAGGAGAAGGGGTTCAACCCGGAGGTCATCCC
GATGTTCACGGCGCTCAGCGAGGGAGCGACGCCGCAGGACCTGAACGCGGCCAAGGTCGGAGGTCACCAGGCAGCG
ATGCAGATGCTGAAGGACACGATCAACGAGGAGGCGGCCGAGTGGGACCGGGCGGCAGCCGAGCCACGCGGTTCCG
ACATCGCGGGCACCACCTCGACGCTCCAGGAGCAGATCGCGTGGGCCGCAGCTAAGCGCTGGATCATCCTCGGGCT
GAACAAGATCGTCCGGATGTACAGCCCGGTCTCGATCGCTGCTAAATACGTTGACCGGTTCTTCAAGACCCTGAGG
GCCGAGCAGGCGTGATAA

SP-p24CE2c (p24CE2c underlined)

SEQ ID NO: 35

MWLQSLLLLGTVACSISQGQMVHQALSPRTLNAWVKVLAKEEKGFNPEVIPMFTALSEGATPQDLNAAKVGGHQAA
MQMLKDTINEEAAEWDRAAAEPRGSDIAGTTSTLQEQIAWAAAKRWIILGLNKIVRMYSPVSIAAKYVDRFFKTLR
AEQA

SP-p24CE2d alternative nucleic acid conserved element nucleid acid
construct; in order CE9-3-4-5-6-8

SEQ ID NO: 36

ATGTGGCTCCAGAGCCTGCTACTCCTGGGGACGGTGGCCTGCAGCATCTCGGAGGAGAAGGGGTTCAACCCGGAGG
TCATCCCGATGTTCACGGCGCTCAGCGAGGGAGCGACGCCGCAGGACCTGAACGCGGCCAAGGTCGGAGGTCACCA
GGCAGCGATGCAGATGCTGAAGGACACGATCAACGAGGAGGCGGCCGAGTGGGACCGGGCGGCAGCCGAGCCACGC
GGTTCCGACATCGCGGGCACCACCTCGACGCTCCAGGAGCAGATCGCGTGGGCCGCAGCTAAGCGCTGGATCATCC
TCGGGCTGAACAAGATCGTCCGGATGTACAGCCCGGTCTCGATCGCTGCTAAATACGTTGACCGGTTCTTCAAGAC
CCTGAGGGCCGAGCAGGCGGCGCTGCAGGGGCAGATGGTCCACCAGGCGCTGTCGCCGCGCACGCTGAACGCGTGG
GTGAAGGTCTGATAA p24CE2d (protein underlined) encoded by SEQ ID NO: 36

SEQ ID NO: 37

MWLQSLLLGTVACSISEEKGFNPEVIPMFTALSEGATPQDLNAAKVGGHQAAMQMLKDTINEEAAEWDRAAAEPRG
SDIAGTTSTLQEQIAWAAAKRWIILGLNKIVRMYSPVSIAAKYVDRFFKTLRAEQAALQGQMVHQALSPRTLNAWV
KV

SP-24CE1d-conserved element nucleic acid construct; in order CE9-3-4-5-6-8

SEQ ID NO: 38

ATGTGGCTCCAGAGCCTGCTACTCCTGGGGACGGTGGCCTGCAGCATCTCGGAGGAGAAGGCGTTCAGCCCGGAGG
TCATCCCGATGTTCTCGGCGCTCAGCGAGGGAGCGACGCCGCAGGACCTGAACGCGGCCAAGGTCGGAGGTCACCA
GGCAGCGATGCAGATGCTGAAGGAGACGATCAACGAGGAGGCGGCCGAGTGGGACCGGGCGGCAGCCGAGCCACGC
GGTTCCGACATCGCGGGCACCACCTCGACGCTCCAGGAGCAGATCGGGTGGGCCGCAGCTAAGCGCTGGATCATCC
TCGGGCTGAACAAGATCGTCCGGATGTACAGCCCGACGTCGATCGCTGCTAAATACGTTGACCGGTTCTACAAGAC
CCTGAGGGCCGAGCAGGCGGCGCTGCAGGGGCAGATGGTCCACCAGGCGATCTCGCCGCGCACGCTGAACGCGTGG

Table of Illustrative Conserved Element Sequences

GTGAAGGTCTGATAA

SP-24CE1d encoded by SEQ ID NO: 38

SEQ ID NO: 39

MWLQSLLLGTVACSISEEKAFSPEVIPMFSALSEGATPQDLNAAKVGGHQAAMQMLKETINEEAAEWDRAAAEPRG
SDIAGTTSTLQEQIGWAAAKRWIILGLNKIVRMYSPTSIAAKYVDRFYKTLRAEQAALQGQMVHQAISPRTLNAWV
KV p24CE1d has 6 CE (is identical to p24CE1c except for the CE arrangement within the protein)

GM-CSF signal peptide
CE1 and C2 replaced by CE8 and CE9 respectively, lacks CE7 and has the CE arranged in the configuration
CE9-3-4-5-6-8 conserved element 8 (CE8-variant for CE2 constructs)

SEQ ID NO: 40

QGQMVHQALSPRTLNAWVKV conserved element 9 (CE9)

```
                1               5                  10                  15

Glu Glu Ala Ala Glu Trp Asp Arg
            20

<210> SEQ ID NO 4
<211> LENGTH: 19
<212> TYPE: PRT
<213> ORGANISM: Artificial Sequence
<220> FEATURE:
<223> OTHER INFORMATION: synthetic HIV-1 p24 gag conserved element 4
      (CE4) for p24CE1 (Core1) vaccine

<400> SEQUENCE: 4

Pro Arg Gly Ser Asp Ile Ala Gly Thr Thr Ser Thr Leu Gln Glu Gln
1               5                  10                  15

Ile Gly Trp

<210> SEQ ID NO 5
<211> LENGTH: 20
<212> TYPE: PRT
<213> ORGANISM: Artificial Sequence
<220> FEATURE:
<223> OTHER INFORMATION: synthetic HIV-1 p24 gag conserved element 5
      (CE5) for p24CE1 (Core1) vaccine

<400> SEQUENCE: 5

Lys Arg Trp Ile Ile Leu Gly Leu Asn Lys Ile Val Arg Met Tyr Ser
1               5                  10                  15

Pro Thr Ser Ile
            20

<210> SEQ ID NO 6
<211> LENGTH: 14
<212> TYPE: PRT
<213> ORGANISM: Artificial Sequence
<220> FEATURE:
<223> OTHER INFORMATION: synthetic HIV-1 p24 gag conserved element 6
      (CE6) for p24CE1 (Core1) vaccine

<400> SEQUENCE: 6

Tyr Val Asp Arg Phe Tyr Lys Thr Leu Arg Ala Glu Gln Ala
1               5                  10

<210> SEQ ID NO 7
<211> LENGTH: 17
<212> TYPE: PRT
<213> ORGANISM: Artificial Sequence
<220> FEATURE:
<223> OTHER INFORMATION: synthetic HIV-1 p24 gag conserved element 7
      (CE7) for p24CE1 (Core1) vaccine

<400> SEQUENCE: 7

Leu Glu Glu Met Met Thr Ala Cys Gln Gly Val Gly Gly Pro Gly His
1               5                  10                  15

Lys

<210> SEQ ID NO 8
<211> LENGTH: 12
<212> TYPE: PRT
<213> ORGANISM: Artificial Sequence
<220> FEATURE:
<223> OTHER INFORMATION: synthetic HIV-1 p24 gag conserved element 1
      (CE1) for p24CE2 (Core2) vaccine

<400> SEQUENCE: 8
```

```
Leu Ser Pro Arg Thr Leu Asn Ala Trp Val Lys Val
 1               5                  10
```

<210> SEQ ID NO 9
<211> LENGTH: 18
<212> TYPE: PRT
<213> ORGANISM: Artificial Sequence
<220> FEATURE:
<223> OTHER INFORMATION: synthetic HIV-1 p24 gag conserved element 2
      (CE2) for p24CE2 (Core2) vaccine

<400> SEQUENCE: 9

```
Val Ile Pro Met Phe Thr Ala Leu Ser Glu Gly Ala Thr Pro Gln Asp
 1               5                  10                  15

Leu Asn
```

<210> SEQ ID NO 10
<211> LENGTH: 24
<212> TYPE: PRT
<213> ORGANISM: Artificial Sequence
<220> FEATURE:
<223> OTHER INFORMATION: synthetic HIV-1 p24 gag conserved element 3
      (CE3) for p24CE2 (Core2) vaccine

<400> SEQUENCE: 10

```
Val Gly Gly His Gln Ala Ala Met Gln Met Leu Lys Glu Thr Ile Asn
 1               5                  10                  15

Glu Glu Ala Ala Glu Trp Asp Arg
                20
```

<210> SEQ ID NO 11
<211> LENGTH: 19
<212> TYPE: PRT
<213> ORGANISM: Artificial Sequence
<220> FEATURE:
<223> OTHER INFORMATION: synthetic HIV-1 p24 gag conserved element 4
      (CE4) for p24CE2 (Core2) vaccine

<400> SEQUENCE: 11

```
Pro Arg Gly Ser Asp Ile Ala Gly Thr Thr Ser Thr Leu Gln Glu Gln
 1               5                  10                  15

Ile Ala Trp
```

<210> SEQ ID NO 12
<211> LENGTH: 20
<212> TYPE: PRT
<213> ORGANISM: Artificial Sequence
<220> FEATURE:
<223> OTHER INFORMATION: synthetic HIV-1 p24 gag conserved element 5
      (CE5) for p24CE2 (Core2) vaccine

<400> SEQUENCE: 12

```
Lys Arg Trp Ile Ile Leu Gly Leu Asn Lys Ile Val Arg Met Tyr Ser
 1               5                  10                  15

Pro Val Ser Ile
                20
```

<210> SEQ ID NO 13
<211> LENGTH: 14
<212> TYPE: PRT
<213> ORGANISM: Artificial Sequence
<220> FEATURE:
<223> OTHER INFORMATION: synthetic HIV-1 p24 gag conserved element 6
      (CE6) for p24CE1 (Core1) vaccine

<400> SEQUENCE: 13

-continued

Tyr Val Asp Arg Phe Phe Lys Thr Leu Arg Ala Glu Gln Ala
1               5                   10

<210> SEQ ID NO 14
<211> LENGTH: 17
<212> TYPE: PRT
<213> ORGANISM: Artificial Sequence
<220> FEATURE:
<223> OTHER INFORMATION: synthetic HIV-1 p24 gag conserved element 7
      (CE7) for p24CE2 (Core2) vaccine

<400> SEQUENCE: 14

Leu Glu Glu Met Met Thr Ala Cys Gln Gly Val Gly Gly Pro Ser His
1               5                   10                  15

Lys

<210> SEQ ID NO 15
<211> LENGTH: 140
<212> TYPE: PRT
<213> ORGANISM: Artificial Sequence
<220> FEATURE:
<223> OTHER INFORMATION: synthetic HIV-1 p24 gag conserved elements 1-7
      (CE1-7) collinearly arranged for p24CE1 (Core1) vaccine with short
      linker sequences, first conserved element polypeptide,
      configuration p24CE1 CE2-3-4-5-6-7-1

<400> SEQUENCE: 15

Val Ile Pro Met Phe Ser Ala Leu Ser Glu Gly Ala Thr Pro Gln Asp
1               5                   10                  15

Leu Asn Ala Ala Val Gly Gly His Gln Ala Ala Met Gln Met Leu Lys
            20                  25                  30

Asp Thr Ile Asn Glu Glu Ala Ala Glu Trp Asp Arg Ala Ala Ala Glu
        35                  40                  45

Pro Arg Gly Ser Asp Ile Ala Gly Thr Thr Ser Thr Leu Gln Glu Gln
    50                  55                  60

Ile Gly Trp Ala Ala Ala Lys Arg Trp Ile Ile Leu Gly Leu Asn Lys
65                  70                  75                  80

Ile Val Arg Met Tyr Ser Pro Thr Ser Ile Ala Ala Lys Tyr Val Asp
                85                  90                  95

Arg Phe Tyr Lys Thr Leu Arg Ala Glu Gln Ala Ala Gly Leu Glu Glu
            100                 105                 110

Met Met Thr Ala Cys Gln Gly Val Gly Gly Pro Gly His Lys Ala Ala
        115                 120                 125

Ile Ser Pro Arg Thr Leu Asn Ala Trp Val Lys Val
    130                 135                 140

<210> SEQ ID NO 16
<211> LENGTH: 140
<212> TYPE: PRT
<213> ORGANISM: Artificial Sequence
<220> FEATURE:
<223> OTHER INFORMATION: synthetic HIV-1 p24 gag conserved elements 8-14
      (CE8-14) collinearly arranged for p24CE2 (Core2) vaccine with
      short linker sequences, second conserved element polypeptide,
      configuration p24CE2 CE9-10-11-12-13-14-8

<400> SEQUENCE: 16

Val Ile Pro Met Phe Thr Ala Leu Ser Glu Gly Ala Thr Pro Gln Asp
1               5                   10                  15

Leu Asn Ala Ala Val Gly Gly His Gln Ala Ala Met Gln Met Leu Lys
            20                  25                  30

Glu Thr Ile Asn Glu Glu Ala Ala Glu Trp Asp Arg Ala Ala Ala Glu
                 35                  40                  45

Pro Arg Gly Ser Asp Ile Ala Gly Thr Thr Ser Thr Leu Gln Glu Gln
 50                  55                  60

Ile Ala Trp Ala Ala Ala Lys Arg Trp Ile Ile Leu Gly Leu Asn Lys
 65                  70                  75                  80

Ile Val Arg Met Tyr Ser Pro Val Ser Ile Ala Ala Lys Tyr Val Asp
                 85                  90                  95

Arg Phe Phe Lys Thr Leu Arg Ala Glu Gln Ala Ala Gly Leu Glu Glu
                100                 105                 110

Met Met Thr Ala Cys Gln Gly Val Gly Gly Pro Ser His Lys Ala Ala
                115                 120                 125

Leu Ser Pro Arg Thr Leu Asn Ala Trp Val Lys Val
                130                 135                 140

<210> SEQ ID NO 17
<211> LENGTH: 5586
<212> TYPE: DNA
<213> ORGANISM: Artificial Sequence
<220> FEATURE:
<223> OTHER INFORMATION: synthetic HIV-1 p24 gag conserved element
      p24CE1+p24CE2 (Core1 plus Core2) vaccine
      construct, p24CE1 encoded by plasmid 306H

<400> SEQUENCE: 17

| | |
|---|---|
| cctggccatt gcatacgttg tatccatatc ataatatgta catttatatt ggctcatgtc | 60 |
| caacattacc gccatgttga cattgattat tgactagtta ttaatagtaa tcaattacgg | 120 |
| ggtcattagt tcatagccca tatatggagt tccgcgttac ataacttacg gtaaatggcc | 180 |
| cgcctggctg accgcccaac gacccccgcc cattgacgtc aataatgacg tatgttccca | 240 |
| tagtaacgcc aatagggact ttccattgac gtcaatgggt ggagtattta cggtaaactg | 300 |
| cccacttggc agtacatcaa gtgtatcata tgccaagtac gccccctatt gacgtcaatg | 360 |
| atggtaaatg gcccgcctgg cattatgccc agtacatgac cttatgggac tttcctactt | 420 |
| ggcagtacat ctacgtatta gtcatcgcta ttaccatggt gatgcggttt tggcagtaca | 480 |
| tcaatgggcg tggatagcgg tttgactcac ggggatttcc aagtctccac cccattgacg | 540 |
| tcaatgggag tttgttttgg caccaaaatc aacgggactt tccaaaatgt cgtaacaact | 600 |
| ccgccccatt gacgcaaatg ggcggtaggc gtgtacggtg gaggtctat ataagcagag | 660 |
| ctcgtttagt gaaccgtcag atcgcctgga gacgccatcc acgctgtttt gacctccata | 720 |
| gaagacaccg ggaccgatcc agcctccgcg ggcgcgcgtc gacaagaaat gtggctccag | 780 |
| agcctgctac tcctggggac ggtggcctgc agcatctcgg tcatcccgat gttctcggcg | 840 |
| ctcagcgagg gagcgacgcc gcaggacctg aacgcggccg tcggaggtca ccaggcagcg | 900 |
| atgcagatgc tgaaggacac gatcaacgag gaggcggccg agtgggaccg ggcggcagcc | 960 |
| gagccacgcg gttccgacat cgcgggcacc acctcgacgc tccaggagca gatcgggtgg | 1020 |
| gccgcagcta agcgctggat catcctcggg ctgaacaaga tcgtccggat gtacagcccg | 1080 |
| acgtcgatcg ctgctaagta cgttgaccgg ttctacaaga ccctgagggc cgagcaggcg | 1140 |
| gccggactga ggagatgat gaccgcgtgc caggggtcg gtggaccagg cacaaggcc | 1200 |
| gcgatctcgc cgcgcacgct gaacgcgtgg gtgaaggtct gataagaatt cgctagcggc | 1260 |
| gcgccagatc tgtatcgga tctgctgtgc cttctagttg ccagccatct gttgtttgcc | 1320 |
| cctcccccgt gccttccttg accctggaag gtgccactcc cactgtcctt tcctaataaa | 1380 |

```
atgaggaaat tgcatcgcat tgtctgagta ggtgtcattc tattctgggg ggtggggtgg   1440
ggcaggacag caaggggag gattgggaag acaatagcag gcatgctggg gatgcggtgg    1500
gctctatggg tacccaggtg ctgaagaatt gacccggttc ctcctgggcc agaaagaagc   1560
aggcacatcc ccttctctgt gacacaccct gtccacgccc ctggttctta gttccagccc   1620
cactcatagg acactcatag ctcaggaggg ctccgccttc aatcccaccc gctaaagtac   1680
ttggagcggt ctctccctcc ctcatcagcc caccaaacca aacctagcct caagagtgg    1740 gaagaaatta aagcaagata ggctattaag tgcagaggga gagaaaatgc ctccaacatg   1800
tgaggaagta atgagagaaa tcatagaatt cttccgcctt cctcgctcac tgactcgctg   1860
cgctcggtcg ttcggctgcg gcgagcggta tcagctcact caaaggcggt aatacggtta   1920
tccacagaat caggggataa cgcaggaaag aacatgtgag caaaaggcca gcaaaaggcc   1980
aggaaccgta aaaaggccgc gttgctggcg ttttccata ggctccgccc ccctgacgag    2040
catcacaaaa atcgacgctc aagtcagagg tggcgaaacc cgacaggact ataaagatac   2100
caggcgtttc ccctggaag ctccctcgtg cgctctcctg ttccgaccct gccgcttacc    2160
ggatacctgt ccgcctttct cccttcggga agcgtggcgc tttctcatag ctcacgctgt   2220
aggtatctca gttcggtgta ggtcgttcgc tccaagctgg gctgtgtgca cgaacccccc   2280
gttcagcccg accgctgcgc cttatccggt aactatcgtc ttgagtccaa cccggtaaga   2340
cacgacttat cgccactggc agcagccact ggtaacagga ttagcagagc gaggtatgta   2400
ggcggtgcta cagagttctt gaagtggtgg cctaactacg gctacactag aagaacagta   2460
tttggtatct gcgctctgct gaagccagtt accttcggaa aaagagttgg tagctcttga   2520
tccggcaaac aaaccaccgc tggtagcggt ggttttttg tttgcaagca gcagattacg    2580
cgcagaaaaa aaggatctca agaagatcct ttgatctttt ctacgggtc tgacgctcag    2640 tggaacgaaa actcacgtta agggattttg gtcatgagat tatcaaaaag gatcttcacc   2700
tagatccttt taaattaaaa atgaagtttt aaatcaatct aaagtatata tgagtaaact   2760
tggtctgaca gttaccaatg cttaatcagt gaggcaccta tctcagcgat ctgtctattt   2820
cgttcatcca tagttgcctg actcgggggg ggggggcgct gaggtctgcc tcgtgaagaa   2880
ggtgttgctg actcatacca ggcctgaatc gccccatcat ccagccagaa agtgagggag   2940
ccacggttga tgagagcttt gttgtaggtg gaccagttgg tgattttgaa cttttgcttt   3000
gccacggaac ggtctgcgtt gtcgggaaga tgcgtgatct gatccttcaa ctcagcaaaa   3060
gttcgattta ttcaacaaag ccgccgtccc gtcaagtcag cgtaatgctc tgccagtgtt   3120
acaaccaatt aaccaattct gattagaaaa actcatcgag catcaaatga aactgcaatt   3180
tattcatatc aggattatca ataccatatt tttgaaaaag ccgtttctgt aatgaaggag   3240
aaaactcacc gaggcagttc cataggatgg caagatcctg gtatcggtct gcgattccga   3300
ctcgtccaac atcaatacaa cctattaatt tcccctcgtc aaaaataagg ttatcaagtg   3360
agaaatcacc atgagtgacg actgaatccg gtgagaatgg caaaagctta tgcatttctt   3420
tccagacttg ttcaacaggc cagccattac gctcgtcatc aaaatcactc gcatcaacca   3480
aaccgttatt cattcgtgat tgcgcctgag cgagacgaaa tacgcgatcg ctgttaaaag   3540
gacaattaca aacaggaatc gaatgcaacc ggcgcaggaa cactgccagc gcatcaacaa   3600
tattttcacc tgaatcagga tattcttcta atacctggaa tgctgttttc ccggggatcg   3660
cagtggtgag taaccatgca tcatcaggag tacggataaa atgcttgatg gtcggaagag   3720 gcataaaattc cgtcagccag tttagtctga ccatctcatc tgtaacatca ttggcaacgc   3780
```

-continued

```
taccttttgcc atgtttcaga aacaactctg gcgcatcggg cttcccatac aatcgataga   3840
ttgtcgcacc tgattgcccg acattatcgc gagcccattt atacccatat aaatcagcat   3900
ccatgttgga atttaatcgc ggcctcgagc aagacgtttc ccgttgaata tggctcataa   3960
caccccttgt attactgttt atgtaagcag acagttttat tgttcatgat gatatatttt   4020
tatcttgtgc aatgtaacat cagagatttt gagacacaac gtggatcatc cagacatgat   4080
aagatacatt gatgagtttg acaaaccac aactagaatg cagtgaaaaa aatgctttat   4140
ttgtgaaatt tgtgatgcta ttgctttatt tgtaaccatt ataagctgca ataaacaagt   4200
taacaacaac aattgcattc attttatgtt tcaggttcag ggggaggtgt gggaggtttt   4260
ttaaagcaag taaaacctct acaaatgtgg tatggctgat tatgatcgtc gaggatccgg   4320
cgttatcaga ccttcaccca ggcgttgagg gtgcgaggcg agagggccgc cttgtgcgac   4380
ggtcctccga ctccctggca ggctgtcatc atctcctcga cccgcggc ctgctctgcc   4440 ctcagcgtct tgaagaagcg gtctacgtat tggccgcga tgctgactgg gctgtacatc   4500
ctgacgatct tgttgaggcc caggatgatc cagcgcttgg ctgcagccca ggcgatctgc   4560
tcctggaggg tgctggtcgt gcctgcgatg tcgctacccc ttggctcagc tgctgccctg   4620
tcccactcgg ctgcctcctc gttgatggtc tccttgagca tctgcattgc cgcctggtgt   4680
ccaccgaccg cggcgttgag gtcctgcggt gtcgcaccct cactgagtgc ggtgaacatg   4740
gggatgaccg agatcgagca cgccacggtc ccgagtagca ggagcgactg cagccacatt   4800
tcttccgttt aaacgtcgac agatccaaac gctcctccga cgtccccagg cagaatggcg   4860
gttccctaaa cgagcattgc ttatatagac ctcccattag gcacgcctac cgcccattta   4920
cgtcaatgga acgccatttt gcgtcattgc ccctccccat tgacgtcaat ggggatgtac   4980
ttggcagcca tcgcgggcca tttaccgcca ttgacgtcaa tgggagtact gccaatgtac   5040
cctggcgtac ttccaatagt aatgtacttg ccaagttact attaatagat attgatgtac   5100
tgccaagtgg gccattacc gtcattgacg tcaatagggg gcgtgagaac ggatatgaat   5160
gggcaatgag ccatcccatt gacgtcaatg gtgggtggtc ctattgacgt caatgggcat   5220
tgagccaggc gggccattta ccgtaattga cgtcaatggg ggaggcgcca tatacgtcaa   5280
taggaccgcc catatgacgt caataggtaa gaccatgagg ccctttcgtc tcgcgcgttt   5340
cggtgatgac ggtgaaaacc tctgacacat gcagctcccg gagacggtca cagcttgtct   5400
gtaagcggat gccggagca gacaagcccg tcagggcgcg tcagcgggtg ttggcgggtg   5460
tcggggctgg cttaactatg cggcatcaga gcagattgta ctgagagtgc accatatgcg   5520
gtgtgaaata ccgcacagat gcgtaaggag aaaataccgc atcagattgg ctattggcat   5580
tatgcc                                                              5586
```

```
<210> SEQ ID NO 18
<211> LENGTH: 157
<212> TYPE: PRT
<213> ORGANISM: Artificial Sequence
<220> FEATURE:
<223> OTHER INFORMATION: synthetic HIV-1 p24 gag conserved element
      p24CE1 (including GM-CSF signal peptide)

<400> SEQUENCE: 18

Met Trp Leu Gln Ser Leu Leu Leu Leu Gly Thr Val Ala Cys Ser Ile
1               5                   10                  15

Ser Val Ile Pro Met Phe Ser Ala Leu Ser Glu Gly Ala Thr Pro Gln
            20                  25                  30
```

Asp Leu Asn Ala Ala Val Gly Gly His Gln Ala Ala Met Gln Met Leu
         35                  40                  45

Lys Asp Thr Ile Asn Glu Glu Ala Ala Glu Trp Asp Arg Ala Ala Ala
 50                  55                  60

Glu Pro Arg Gly Ser Asp Ile Ala Gly Thr Thr Ser Thr Leu Gln Glu
 65                  70                  75                  80

Gln Ile Gly Trp Ala Ala Ala Lys Arg Trp Ile Ile Leu Gly Leu Asn
             85                  90                  95

Lys Ile Val Arg Met Tyr Ser Pro Thr Ser Ile Ala Ala Lys Tyr Val
                100                 105                 110

Asp Arg Phe Tyr Lys Thr Leu Arg Ala Glu Gln Ala Ala Gly Leu Glu
            115                 120                 125

Glu Met Met Thr Ala Cys Gln Gly Val Gly Pro Gly His Lys Ala
130                 135                 140

Ala Ile Ser Pro Arg Thr Leu Asn Ala Trp Val Lys Val
145                 150                 155

<210> SEQ ID NO 19
<211> LENGTH: 157
<212> TYPE: PRT
<213> ORGANISM: Artificial Sequence
<220> FEATURE:
<223> OTHER INFORMATION: synthetic HIV-1 p24 gag conserved element
      p24CE2 (including GM-CSF signal peptide)

<400> SEQUENCE:

-continued

```
caacattacc gccatgttga cattgattat tgactagtta ttaatagtaa tcaattacgg    120
ggtcattagt tcatagccca tatatggagt tccgcgttac ataacttacg gtaaatggcc    180
cgcctggctg accgcccaac gaccccgcc cattgacgtc aataatgacg tatgttccca     240
tagtaacgcc aatagggact ttccattgac gtcaatgggt ggagtattta cggtaaactg    300
cccacttggc agtacatcaa gtgtatcata tgccaagtac gccccctatt gacgtcaatg    360
atggtaaatg gcccgcctgg cattatgccc agtacatgac cttatgggac tttcctactt    420
ggcagtacat ctacgtatta gtcatcgcta ttaccatggt gatgcggttt tggcagtaca    480
tcaatgggcg tggatagcgg tttgactcac ggggatttcc aagtctccac cccattgacg    540
tcaatgggag tttgttttgg caccaaaatc aacgggactt tccaaaatgt cgtaacaact    600
ccgccccatt gacgcaaatg gcggtaggc gtgtacggtg ggaggtctat ataagcagag     660
ctcgtttagt gaaccgtcag atcgcctgga gacgccatcc acgctgtttt gacctccata    720
gaagacaccg ggaccgatcc agcctccgcg gcgcgcgtc gactagcatg gcgcccgca     780
gcgcccggcg accctgctg ctgctactgc tgttgctgct gctcggcctc atgcattgtg     840
cgtcagcagc aatgtttatg gtgaaaaatg gcaacgggac cgcgtgcata atggccaact    900
tctctgctgc cttctcagtg aactacgaca ccaagagtgg ccctaagaac atgacccttg    960
acctgccatc agatgccaca gtggtgctca accgcagctc ctgtggaaaa gagaacactt    1020
ctgaccccag tctcgtgatt gcttttggaa gaggacatac actcactctc aatttcacga    1080
gaaatgcaac acgttacagc gttcagctca tgagttttgt ttataacttg tcagacacac    1140
accttttccc caatgcgagc tccaaagaaa tcaagactgt ggaatctata actgacatca    1200
gggcagatat agataaaaaa tacagatgtg ttagtggcac ccaggtccac atgaacaacg    1260
tgaccgtaac gctccatgat gccaccatcc aggcgtacct ttccaacagc agcttcagca    1320
ggggagagac acgctgtgaa caagacaggc cttccccaac cacagcgccc cctgcgccac    1380
ccagcccctc gccctcaccc gtgcccaaga gcccctctgt ggacaagtac aacgtgagcg    1440
gcaccaacgg gacctgcctg ctggccagca tggggctgca gctgaacctc acctatgaga    1500
ggaaggacaa cacgacggtg acaaggcttc tcaacatcaa ccccaacaag acctcggcca    1560
gcggagctg cggcgcccac ctggtgactc tggagctgca cagcgagggc accaccgtcc    1620
tgctcttcca gttcgggatg aatgcaagtt ctagccggtt tttcctacaa ggaatccagt    1680
tgaatacaat tcttcctgac gccagagacc ctgcctttaa agctgccaac ggctccctgc    1740
gagcgctgca ggccacagtc ggcaattcct acaagtgcaa cgcggaggag cacgtccgtg    1800
tcacgaaggc gttttcagtc aatatattca agtgtgggt ccaggctttc aaggtggaag    1860
gtggccagtt tggctctgtg gaggagtgtc tgctggacga aacagcctc gaggatatcg     1920
tcatcccgat gttcacggcg ctcagcgagg gagcgacgcc gcaggacctg aacgcggccg    1980
tcggaggtca ccaggcagcg atgcagatgc tgaaggagac gatcaacgag gaggcggccg    2040
agtgggaccg ggcggcagcc gagccacgcg gttccgacat cgcgggcacc acctcgacgc    2100
tccaggagca gatcgcgtgg gccgcagcta agcgctggat catcctcggg ctgaacaaga    2160
tcgtccggat gtacagcccg gtctcgatcg ctgctaagta cgttgaccgg ttcttcaaga    2220
ccctgagggc cgagcaggcg gccggactgg aggagatgat gaccgcgtgc caggggtcg     2280
gtggaccatc gcacaaggcc gcgctctcgc gcgcacgct gaacgcgtgg gtgaaggtcg     2340
gatccgaatt cacgctgatc cccatcgctg tgggtggtgc cctggcgggg ctggtcctca    2400
```

```
tcgtcctcat cgcctacctc gtcggcagga agaggagtca cgcaggctac cagactatct    2460
agggtacctc taggatctgc tgtgccttct agttgccagc catctgttgt ttgcccctcc    2520
cccgtgcctt ccttgaccct ggaaggtgcc actcccactg tcctttccta ataaaatgag    2580
gaaattgcat cgcattgtct gagtaggtgt cattctattc tggggggtgg ggtggggcag    2640
gacagcaagg gggaggattg ggaagacaat agcaggcatg ctggggatgc ggtgggctct    2700
atgggtaccc aggtgctgaa gaattgaccc ggttcctcct gggccagaaa gaagcaggca    2760
catccccttc tctgtgacac accctgtcca cgcccctggt tcttagttcc agccccactc    2820
ataggacact catagctcag gagggctccg ccttcaatcc cacccgctaa agtacttgga    2880
gcggtctctc cctccctcat cagcccacca aaccaaacct agcctccaag agtgggaaga    2940
aattaaagca agataggcta ttaagtgcag agggagagaa aatgcctcca acatgtgagg    3000
aagtaatgag agaaatcata gaatttcttc cgcttcctcg ctcactgact cgctgcgctc    3060
ggtcgttcgg ctgcggcgag cggtatcagc tcactcaaag gcggtaatac ggttatccac    3120
agaatcaggg gataacgcag gaaagaacat gtgagcaaaa ggccagcaaa aggccaggaa    3180
ccgtaaaaag gccgcgttgc tggcgttttt ccataggctc cgcccccctg acgagcatca    3240
caaaaatcga cgctcaagtc agaggtggcg aaacccgaca ggactataaa gataccaggc    3300
gtttccccct ggaagctccc tcgtgcgctc tcctgttccg accctgccgc ttaccggata    3360
cctgtccgcc tttctccctt cgggaagcgt ggcgctttct caatgctcac gctgtaggta    3420
tctcagttcg gtgtaggtcg ttcgctccaa gctgggctgt gtgcacgaac cccccgttca    3480
gcccgaccgc tgcgccttat ccggtaacta tcgtcttgag tccaacccgg taagacacga    3540
cttatcgcca ctggcagcag ccactggtaa caggattagc agagcgaggt atgtaggcgg    3600
tgctacagag ttcttgaagt ggtggcctaa ctacggctac actagaagaa cagtatttgg    3660
tatctgcgct ctgctgaagc cagttacctt cggaaaaaga gttggtagct cttgatccgg    3720
caaacaaacc accgctggta gcggtggttt ttttgtttgc aagcagcaga ttacgcgcag    3780
aaaaaaagga tctcaagaag atcctttgat cttttctacg gggtctgacg ctcagtggaa    3840
cgaaaactca cgttaaggga ttttggtcat gagattatca aaaaggatct tcacctagat    3900
ccttttaaat taaaatgaag ttttaaatc aatctaaagt atatatgagt aaacttggtc    3960
tgacagttac caatgcttaa tcagtgaggc acctatctca gcgatctgtc tatttcgttc    4020
atccatagtt gcctgactcg ggggggggg ggcgctgagg tctgcctcgt gaagaaggtg    4080
ttgctgactc ataccaggcc tgaatcgccc catcatccag ccagaaagtg agggagccac    4140
ggttgatgag agctttgttg taggtggacc agttggtgat tttgaacttt tgctttgcca    4200
cggaacggtc tgcgttgtcg ggaagatgcg tgatctgatc cttcaactca gcaaagttc    4260
gatttattca acaaagccgc cgtcccgtca agtcagcgta atgctctgcc agtgttacaa    4320
ccaattaacc aattctgatt agaaaaactc atcgagcatc aaatgaaact gcaatttatt    4380
catatcagga ttatcaatac catattttg aaaagccgt ttctgtaatg aaggagaaaa    4440
ctcaccgagg cagttccata ggatggcaag atcctggtat cggtctgcga ttccgactcg    4500
tccaacatca atacaaccta ttaatttccc ctcgtcaaaa ataaggttat caagtgagaa    4560
atcaccatga gtgacgactg aatccggtga gaatggcaaa agcttatgca tttctttcca    4620
gacttgttca acaggccagc cattacgctc gtcatcaaaa tcactcgcat caaccaaacc    4680
gttattcatt cgtgattgcg cctgagcgag acgaaatacg cgatcgctgt taaaaggaca    4740
attacaaaca ggaatcgaat gcaaccggcg caggaacact gccagcgcat caacaatatt    4800
```

-continued

```
ttcacctgaa tcaggatatt cttctaatac ctggaatgct gttttcccgg ggatcgcagt    4860
ggtgagtaac catgcatcat caggagtacg gataaaatgc ttgatggtcg aagaggcat     4920 aaattccgtc agccagttta gtctgaccat ctcatctgta acatcattgg caacgctacc    4980
tttgccatgt tcagaaaaca actctggcgc atcgggcttc ccatacaatc gatagattgt    5040
cgcacctgat tgcccgacat tatcgcgagc ccatttatac ccatataaat cagcatccat    5100
gttggaattt aatcgcggcc tggagcaaga cgtttcccgt tgaatatggc tcataacacc    5160
ccttgtatta ctgtttatgt aagcagacag ttttattgtt catgatgata tatttttatc    5220
ttgtgcaatg taacatcaga gattttgaga cacaacgtgg ctttccccccc cccccccatta  5280 ttgaagcatt tatcagggtt attgtctcat gagcggatac atatttgaat gtatttagaa    5340
aaataaacaa ataggggttc gcgcacatt tccccgaaaa gtgccacctg acgtctaaga     5400
aaccattatt atcatgacat taacctataa aaataggcgt atcacgaggc cctttcgtct    5460
cgcgcgtttc ggtgatgacg gtgaaaacct ctgacacatg cagctcccgg agacggtcac    5520
agcttgtctg taagcggatg ccgggagcag acaagcccgt cagggcgcgt cagcgggtgt    5580
tggcgggtgt cggggctggc ttaactatgc ggcatcagag cagattgtac tgagagtgca    5640
ccatatgcgg tgtgaaatac cgcacagatg cgtaaggaga aaataccgca tcagattggc    5700
tattgg                                                               5706
```

<210> SEQ ID NO 21
<211> LENGTH: 564
<212> TYPE: PRT
<213> ORGANISM: Artificial Sequence
<220> FEATURE:
<223> OTHER INFORMATION: synthetic lysosomal associated membrane protein
      1 (LAMP-1) fusion protein with p24CE2 (Core2) vaccine construct,
      LAMP-p24CE2 encoded by plasmid 202H

<400> SEQUENCE: 21

```
Met Ala Pro Arg Ser Ala Arg Arg Pro Leu Leu Leu Leu Leu Leu Leu
 1               5                  10                  15

Leu Leu Leu Gly Leu Met His Cys Ala Ser Ala Ala Met Phe Met Val
            20                  25                  30

Lys Asn Gly Asn Gly Thr Ala Cys Ile Met Ala Asn Phe Ser Ala Ala
        35                  40                  45

Phe Ser Val Asn Tyr Asp Thr Lys Ser Gly Pro Lys Asn Met Thr Leu
    50                  55                  60

Asp Leu Pro Ser Asp Ala Thr Val Val Leu Asn Arg Ser Ser Cys Gly
65                  70                  75                  80

Lys Glu Asn Thr Ser Asp Pro Ser Leu Val Ile Ala Phe Gly Arg Gly
                85                  90                  95

His Thr Leu Thr Leu Asn Phe Thr Arg Asn Ala Thr Arg Tyr Ser Val
            100                 105                 110

Gln Leu Met Ser Phe Val Tyr Asn Leu Ser Asp Thr His Leu Phe Pro
        115                 120                 125

Asn Ala Ser Ser Lys Glu Ile Lys Thr Val Glu Ser Ile Thr Asp Ile
    130                 135                 140

Arg Ala Asp Ile Asp Lys Lys Tyr Arg Cys Val Ser Gly Thr Gln Val
145                 150                 155                 160

His Met Asn Asn Val Thr Val Thr Leu His Asp Ala Thr Ile Gln Ala
                165                 170                 175

Tyr Leu Ser Asn Ser Ser Phe Ser Arg Gly Glu Thr Arg Cys Glu Gln
```

```
                180               185               190
Asp Arg Pro Ser Pro Thr Thr Ala Pro Pro Ala Pro Pro Ser Pro Ser
            195               200               205
Pro Ser Pro Val Pro Lys Ser Pro Ser Val Asp Lys Tyr Asn Val Ser
210               215               220
Gly Thr Asn Gly Thr Cys Leu Leu Ala Ser Met Gly Leu Gln Leu Asn
225               230               235               240
Leu Thr Tyr Glu Arg Lys Asp Asn Thr Thr Val Thr Arg Leu Leu Asn
                245               250               255
Ile Asn Pro Asn Lys Thr Ser Ala Ser Gly Ser Cys Gly Ala His Leu
            260               265               270
Val Thr Leu Glu Leu His Ser Glu Gly Thr Thr Val Leu Leu Phe Gln
        275               280               285
Phe Gly Met Asn Ala Ser Ser Arg Phe Phe Leu Gln Gly Ile Gln
        290               295               300
Leu Asn Thr Ile Leu Pro Asp Ala Arg Asp Pro Ala Phe Lys Ala Ala
305               310               315               320
Asn Gly Ser Leu Arg Ala Leu Gln Ala Thr Val Gly Asn Ser Tyr Lys
                325               330               335
Cys Asn Ala Glu Glu His Val Arg Val Thr Lys Ala Phe Ser Val Asn
                340               345               350
Ile Phe Lys Val Trp Val Gln Ala Phe Lys Val Glu Gly Gly Gln Phe
                355               360               365
Gly Ser Val Glu Glu Cys Leu Leu Asp Glu Asn Ser Leu Glu Asp Ile
        370               375               380
Val Ile Pro Met Phe Thr Ala Leu Ser Glu Gly Ala Thr Pro Gln Asp
385               390               395               400
Leu Asn Ala Ala Val Gly Gly His Gln Ala Ala Met Gln Met Leu Lys
                405               410               415
Glu Thr Ile Asn Glu Glu Ala Ala Glu Trp Asp Arg Ala Ala Ala Glu
                420               425               430
Pro Arg Gly Ser Asp Ile Ala Gly Thr Thr Ser Thr Leu Gln Glu Gln
            435               440               445
Ile Ala Trp Ala Ala Ala Lys Arg Trp Ile Ile Leu Gly Leu Asn Lys
450               455               460
Ile Val Arg Met Tyr Ser Pro Val Ser Ile Ala Ala Lys Tyr Val Asp
465               470               475               480
Arg Phe Phe Lys Thr Leu Arg Ala Glu Gln Ala Ala Gly Leu Glu Glu
                485               490               495
Met Met Thr Ala Cys Gln Gly Val Gly Gly Pro Ser His Lys Ala Ala
                500               505               510
Leu Ser Pro Arg Thr Leu Asn Ala Trp Val Lys Val Gly Ser Glu Phe
            515               520               525
Thr Leu Ile Pro Ile Ala Val Gly Gly Ala Leu Ala Gly Leu Val Leu
            530               535               540
Ile Val Leu Ile Ala Tyr Leu Val Gly Arg Lys Arg Ser His Ala Gly
545               550               555               560
Tyr Gln Thr Ile

<210> SEQ ID NO 22
<211> LENGTH: 5706
<212> TYPE: DNA
<213> ORGANISM: Artificial Sequence
<220> FEATURE:
```

<223> OTHER INFORMATION: synthetic lysosomal associated membrane protein
1 (LAMP-1) fusion protein with p24CE1 (Core1) vaccine construct,
LAMP-p24CE1 encoded by plasmid 191H

<400> SEQUENCE: 22

| | | | | | |
|---|---|---|---|---|---|
| cctggccatt | gcatacgttg | tatccatatc | ataatatgta | catttatatt | ggctcatgtc | 60 |
| caacattacc | gccatgttga | cattgattat | tgactagtta | ttaatagtaa | tcaattacgg | 120 |
| ggtcattagt | tcatagccca | tatatggagt | tccgcgttac | ataacttacg | gtaaatggcc | 180 |
| cgcctggctg | accgcccaac | gacccccgcc | cattgacgtc | aataatgacg | tatgttccca | 240 |
| tagtaacgcc | aatagggact | ttccattgac | gtcaatgggt | ggagtattta | cggtaaactg | 300 |
| cccacttggc | agtacatcaa | gtgtatcata | tgccaagtac | gccccctatt | gacgtcaatg | 360 |
| atggtaaatg | gcccgcctgg | cattatgccc | agtacatgac | cttatgggac | tttcctactt | 420 |
| ggcagtacat | ctacgtatta | gtcatcgcta | ttaccatggt | gatgcggttt | tggcagtaca | 480 |
| tcaatgggcg | tggatagcgg | tttgactcac | ggggatttcc | aagtctccac | cccattgacg | 540 |
| tcaatgggag | tttgttttgg | caccaaaatc | aacgggactt | tccaaaatgt | cgtaacaact | 600 |
| ccgccccatt | gacgcaaatg | ggcggtaggc | gtgtacggtg | ggaggtctat | ataagcagag | 660 |
| ctcgtttagt | gaaccgtcag | atcgcctgga | gacgccatcc | acgctgtttt | gacctccata | 720 |
| gaagacaccg | ggaccgatcc | agcctccgcg | gccgcgcgtc | gactagcatg | cgccccgca | 780 |
| gcgcccggcg | acccctgctg | ctgctactgc | tgttgctgct | gctcggcctc | atgcattgtg | 840 |
| cgtcagcagc | aatgtttatg | gtgaaaaatg | caacgggac | cgcgtgcata | atggccaact | 900 |
| tctctgctgc | cttctcagtg | aactacgaca | ccaagagtgg | ccctaagaac | atgacccttg | 960 |
| acctgccatc | agatgccaca | gtggtgctca | accgcagctc | ctgtggaaaa | gagaacactt | 1020 |
| ctgaccccag | tctcgtgatt | gcttttggaa | gaggacatac | actcactctc | aatttcacga | 1080 |
| gaaatgcaac | acgttacagc | gttcagctca | tgagttttgt | ttataacttg | tcagacacac | 1140 |
| acctttccc | caatgcgagc | tccaaagaaa | tcaagactgt | ggaatctata | actgacatca | 1200 |
| gggcagatat | agataaaaaa | tacagatgtg | ttagtggcac | ccaggtccac | atgaacaacg | 1260 |
| tgaccgtaac | gctccatgat | gccaccatcc | aggcgtacct | ttccaacagc | agcttcagca | 1320 |
| ggggagagac | acgctgtgaa | caagacaggc | cttccccaac | cacagcgccc | cctgcgccac | 1380 |
| ccagcccctc | gccctcaccc | gtgcccaaga | gcccctctgt | ggacaagtac | aacgtgagcg | 1440 |
| gcaccaacgg | gacctgcctg | ctggccagca | tgggctgca | gctgaacctc | acctatgaga | 1500 |
| ggaaggacaa | cacgcggtg | acaaggcttc | tcaacatcaa | ccccaacaag | acctcggcca | 1560 |
| gcgggagctg | cggcgcccac | ctggtgactc | tggagctgca | cagcgagggc | accaccgtcc | 1620 |
| tgctcttcca | gttcgggatg | aatgcaagtt | ctagccggtt | tttcctacaa | ggaatccagt | 1680 |
| tgaatacaat | tcttcctgac | gccagagacc | ctgcctttaa | agctgccaac | ggctccctgc | 1740 |
| gagcgctgca | ggccacagtc | ggcaattcct | acaagtgcaa | cgcggaggag | cacgtccgtg | 1800 |
| tcacgaaggc | gttttcagtc | aatatattca | agtgtgggt | ccaggctttc | aaggtggaag | 1860 |
| gtggccagtt | tggctctgtg | gaggagtgtc | tgctggacga | aacagcctc | gaggatatcg | 1920 |
| tcatcccgat | gttctcggcg | ctcagcgagg | gagcgacgcc | gcaggacctg | aacgcggccg | 1980 |
| tcggaggtca | ccaggcagcg | atgcagatgc | tgaaggacac | gatcaacgag | gaggcggccg | 2040 |
| agtgggaccg | ggcggcagcc | gagccacgcg | gttccgacat | cgcgggcacc | acctcgacgc | 2100 |
| tccaggagca | gatcggtgg | gccgcagcta | agcgctggat | catcctcggg | ctgaacaaga | 2160 |
| tcgtccggat | gtacagcccg | acgtcgatcg | ctgctaagta | cgttgaccgg | ttctacaaga | 2220 |

```
ccctgagggc cgagcaggcg gccggactgg aggagatgat gaccgcgtgc caggggtcg      2280
gtggaccagg gcacaaggcc gcgatctcgc cgcgcacgct gaacgcgtgg gtgaaggtcg     2340
gatccgaatt cacgctgatc cccatcgctg tgggtggtgc cctggcgggg ctggtcctca     2400
tcgtcctcat cgcctacctc gtcggcagga agaggagtca cgcaggctac cagactatct     2460
agggtacctc taggatctgc tgtgccttct agttgccagc catctgttgt ttgcccctcc     2520
cccgtgcctt ccttgaccct ggaaggtgcc actcccactg tcctttccta ataaaatgag     2580
gaaattgcat cgcattgtct gagtaggtgt cattctattc tggggggtgg ggtggggcag     2640
gacagcaagg gggaggattg gaagacaat agcaggcatg ctggggatgc ggtgggctct      2700
atgggtaccc aggtgctgaa gaattgaccc ggttcctcct gggccagaaa gaagcaggca     2760
catccccttc tctgtgacac accctgtcca cgcccctggt tcttagttcc agccccactc     2820
ataggacact catagctcag gagggctccg ccttcaatcc cacccgctaa agtacttgga     2880
gcggtctctc cctccctcat cagcccacca aaccaaacct agcctccaag agtgggaaga     2940
aattaaagca agataggcta ttaagtgcag agggagagaa aatgcctcca acatgtgagg     3000
aagtaatgag agaaatcata gaatttcttc cgcttcctcg ctcactgact cgctgcgctc     3060
ggtcgttcgg ctgcggcgag cggtatcagc tcactcaaag gcggtaatac ggttatccac     3120
agaatcaggg gataacgcag gaaagaacat gtgagcaaaa ggccagcaaa aggccaggaa     3180
ccgtaaaaag gccgcgttgc tggcgttttt ccataggctc cgcccccctg acgagcatca     3240
caaaaatcga cgctcaagtc agaggtggcg aaacccgaca ggactataaa gataccaggc     3300
gtttccccct ggaagctccc tcgtgcgctc tcctgttccg accctgccgc ttaccggata     3360
cctgtccgcc tttctccctt cgggaagcgt ggcgctttct caatgctcac gctgtaggta     3420
tctcagttcg gtgtaggtcg ttcgctccaa gctgggctgt gtgcacgaac cccccgttca     3480
gcccgaccgc tgcgccttat ccggtaacta tcgtcttgag tccaacccgg taagacacga     3540
cttatcgcca ctggcagcag ccactggtaa caggattagc agagcgaggt atgtaggcgg     3600
tgctacagag ttcttgaagt ggtggcctaa ctacggctac actagaagaa cagtatttgg     3660
tatctgcgct ctgctgaagc cagttacctt cggaaaaaga gttggtagct cttgatccgg     3720
caaacaaacc accgctggta gcggtggttt ttttgtttgc aagcagcaga ttacgcgcag     3780
aaaaaaagga tctcaagaag atcctttgat cttttctacg gggtctgacg ctcagtggaa     3840
cgaaaactca cgttaaggga ttttggtcat gagattatca aaaaggatct tcacctagat     3900
ccttttaaat taaaaatgaa gttttaaatc aatctaaagt atatatgagt aaacttggtc     3960
tgacagttac caatgcttaa tcagtgaggc acctatctca gcgatctgtc tatttcgttc     4020
atccatagtt gcctgactcg ggggggggg ggcgctgagg tctgcctcgt gaagaaggtg      4080
ttgctgactc ataccaggcc tgaatcgccc catcatccag ccagaaagtg agggagccac     4140
ggttgatgag agctttgttg taggtggacc agttggtgat tttgaacttt tgctttgcca     4200
cggaacggtc tgcgttgtcg ggaagatgcg tgatctgatc cttcaactca gcaaaagttc     4260
gatttattca acaaagccgc cgtcccgtca agtcagcgta atgctctgcc agtgttacaa     4320
ccaattaacc aattctgatt agaaaaactc atcgagcatc aaatgaaact gcaatttatt     4380
catatcagga ttatcaatac catatttttg aaaagccgt ttctgtaatg aaggagaaaa      4440
ctcaccgagg cagttccata ggatggcaag atcctggtat cggtctgcga ttccgactcg     4500
tccaacatca atacaaccta ttaatttccc ctcgtcaaaa ataaggttat caagtgagaa     4560
```

-continued

```
atcaccatga gtgacgactg aatccggtga gaatggcaaa agcttatgca tttctttcca    4620
gacttgttca acaggccagc cattacgctc gtcatcaaaa tcactcgcat caaccaaacc    4680
gttattcatt cgtgattgcg cctgagcgag acgaaatacg cgatcgctgt taaaaggaca    4740
attacaaaca ggaatcgaat gcaaccggcg caggaacact gccagcgcat caacaatatt    4800
ttcacctgaa tcaggatatt cttctaatac ctggaatgct gttttcccgg ggatcgcagt    4860
ggtgagtaac catgcatcat caggagtacg gataaaatgc ttgatggtcg gaagaggcat    4920
aaattccgtc agccagttta gtctgaccat ctcatctgta acatcattgg caacgctacc    4980
tttgccatgt ttcagaaaca actctggcgc atcgggcttc ccatacaatc gatagattgt    5040
cgcacctgat tgcccgacat tatcgcgagc ccatttatac ccatataaat cagcatccat    5100
gttggaattt aatcgcggcc tggagcaaga cgtttcccgt tgaatatggc tcataacacc    5160
ccttgtatta ctgtttatgt aagcagacag ttttattgtt catgatgata tattttatc     5220 ttgtgcaatg taacatcaga gattttgaga cacaacgtgg ctttcccccc cccccatta     5280 ttgaagcatt tatcagggtt attgtctcat gagcggatac atatttgaat gtatttagaa    5340
aaataaacaa atagggttc cgcgcacatt tccccgaaaa gtgccacctg acgtctaaga     5400
aaccattatt atcatgacat aacctataa aaataggcgt atcacgaggc cctttcgtct     5460
cgcgcgtttc ggtgatgacg gtgaaaacct ctgacacatg cagctcccgg agacggtcac    5520
agcttgtctg taagcggatg ccgggagcag acaagcccgt cagggcgcgt cagcgggtgt    5580
tggcgggtgt cggggctggc ttaactatgc ggcatcagag cagattgtac tgagagtgca    5640
ccatatgcgg tgtgaaatac cgcacagatg cgtaaggaga aataccgca tcagattggc      5700 tattgg                                                              5706
```

<210> SEQ ID NO 23
<211> LENGTH: 564
<212> TYPE: PRT
<213> ORGANISM: Artificial Sequence
<220> FEATURE:
<223> OTHER INFORMATION: synthetic lysosomal associated membrane protein
     1 (LAMP-1) fusion protein with p24CE1 (Core1) vaccine construct,
     LAMP-p24CE1 encoded by plasmid 191H

<400> SEQUENCE: 23

```
Met Ala Pro Arg Ser Ala Arg Arg Pro Leu Leu Leu Leu Leu Leu Leu
 1               5                  10                  15

Leu Leu Leu Gly Leu Met His Cys Ala Ser Ala Ala Met Phe Met Val
            20                  25                  30

Lys Asn Gly Asn Gly Thr Ala Cys Ile Met Ala Asn Phe Ser Ala Ala
        35                  40                  45

Phe Ser Val Asn Tyr Asp Thr Lys Ser Gly Pro Lys Asn Met Thr Leu
    50                  55                  60

Asp Leu Pro Ser Asp Ala Thr Val Val Leu Asn Arg Ser Ser Cys Gly
65                  70                  75                  80

Lys Glu Asn Thr Ser Asp Pro Ser Leu Val Ile Ala Phe Gly Arg Gly
                85                  90                  95

His Thr Leu Thr Leu Asn Phe Thr Arg Asn Ala Thr Arg Tyr Ser Val
            100                 105                 110

Gln Leu Met Ser Phe Val Tyr Asn Leu Ser Asp Thr His Leu Phe Pro
        115                 120                 125

Asn Ala Ser Ser Lys Glu Ile Lys Thr Val Glu Ser Ile Thr Asp Ile
    130                 135                 140
```

```
Arg Ala Asp Ile Asp Lys Lys Tyr Arg Cys Val Ser Gly Thr Gln Val
145                 150                 155                 160

His Met Asn Asn Val Thr Val Thr Leu His Asp Ala Thr Ile Gln Ala
                165                 170                 175

Tyr Leu Ser Asn Ser Ser Phe Ser Arg Gly Glu Thr Arg Cys Glu Gln
            180                 185                 190

Asp Arg Pro Ser Pro Thr Thr Ala Pro Pro Ala Pro Pro Ser Pro Ser
        195                 200                 205

Pro Ser Pro Val Pro Lys Ser Pro Ser Val Asp Lys Tyr Asn Val Ser
    210                 215                 220

Gly Thr Asn Gly Thr Cys Leu Leu Ala Ser Met Gly Leu Gln Leu Asn
225                 230                 235                 240

Leu Thr Tyr Glu Arg Lys Asp Asn Thr Thr Val Thr Arg Leu Leu Asn
                245                 250                 255

Ile Asn Pro Asn Lys Thr Ser Ala Ser Gly Ser Cys Gly Ala His Leu
            260                 265                 270

Val Thr Leu Glu Leu His Ser Glu Gly Thr Thr Val Leu Leu Phe Gln
        275                 280                 285

Phe Gly Met Asn Ala Ser Ser Ser Arg Phe Phe Leu Gln Gly Ile Gln
    290                 295                 300

Leu Asn Thr Ile Leu Pro Asp Ala Arg Asp Pro Ala Phe Lys Ala Ala
305                 310                 315                 320

Asn Gly Ser Leu Arg Ala Leu Gln Ala Thr Val Gly Asn Ser Tyr Lys
                325                 330                 335

Cys Asn Ala Glu Glu His Val Arg Val Thr Lys Ala Phe Ser Val Asn
            340                 345                 350

Ile Phe Lys Val Trp Val Gln Ala Phe Lys Val Glu Gly Gly Gln Phe
        355                 360                 365

Gly Ser Val Glu Glu Cys Leu Leu Asp Glu Asn Ser Leu Glu Asp Ile
    370                 375                 380

Val Ile Pro Met Phe Ser Ala Leu Ser Glu Gly Ala Thr Pro Gln Asp
385                 390                 395                 400

Leu Asn Ala Ala Val Gly Gly His Gln Ala Ala Met Gln Met Leu Lys
                405                 410                 415

Asp Thr Ile Asn Glu Glu Ala Ala Glu Trp Asp Arg Ala Ala Ala Glu
            420                 425                 430

Pro Arg Gly Ser Asp Ile Ala Gly Thr Thr Ser Thr Leu Gln Glu Gln
        435                 440                 445

Ile Gly Trp Ala Ala Ala Lys Arg Trp Ile Ile Leu Gly Leu Asn Lys
    450                 455                 460

Ile Val Arg Met Tyr Ser Pro Thr Ser Ile Ala Ala Lys Tyr Val Asp
465                 470                 475                 480

Arg Phe Tyr Lys Thr Leu Arg Ala Glu Gln Ala Ala Gly Leu Glu Glu
                485                 490                 495

Met Met Thr Ala Cys Gln Gly Val Gly Gly Pro Gly His Lys Ala Ala
            500                 505                 510

Ile Ser Pro Arg Thr Leu Asn Ala Trp Val Lys Val Gly Ser Glu Phe
        515                 520                 525

Thr Leu Ile Pro Ile Ala Val Gly Gly Ala Leu Ala Gly Leu Val Leu
    530                 535                 540

Ile Val Leu Ile Ala Tyr Leu Val Gly Arg Lys Arg Ser His Ala Gly
545                 550                 555                 560

Tyr Gln Thr Ile
```

<210> SEQ ID NO 24
<211> LENGTH: 4506
<212> TYPE: DNA
<213> ORGANISM: Artificial Sequence
<220> FEATURE:
<223> OTHER INFORMATION: synthetic GM-CSF signal peptide (SP) fusion
protein with p24CE2 (Core2) vaccine construct,
SP-p24CE2 encoded by plasmid 235H

<400> SEQUENCE: 24
cctggccatt gcatacgttg tatccatatc ataatatgta catttatatt ggctcatgtc 60
caacattacc gccatgttga cattgattat tgactagtta ttaatagtaa tcaattacgg 120
ggtcattagt tcatagccca tatatggagt tccgcgttac ataacttacg gtaaatggcc 180
cgcctggctg accgcccaac gacccccgcc cattgacgtc aataatgacg tatgttccca 240
tagtaacgcc aatagggact ttccattgac gtcaatgggt ggagtattta cggtaaactg 300
cccacttggc agtacatcaa gtgtatcata tgccaagtac gccccctatt gacgtcaatg 360
atggtaaatg gcccgcctgg cattatgccc agtacatgac cttatgggac tttcctactt 420
ggcagtacat ctacgtatta gtcatcgcta ttaccatggt gatgcggttt tggcagtaca 480
tcaatgggcg tggatagcgg tttgactcac ggggatttcc aagtctccac cccattgacg 540
tcaatgggag tttgttttgg caccaaaatc aacgggactt tccaaaatgt cgtaacaact 600
ccgccccatt gacgcaaatg ggcggtaggc gtgtacggtg ggaggtctat ataagcagag 660
ctcgtttagt gaaccgtcag atcgcctgga gacgccatcc acgctgtttt gacctccata 720
gaagacaccg ggaccgatcc agcctccgcg ggcgcgcgtc gacaagaaat gtggctccag 780
agcctgctac tcctggggac ggtggcctgc agcatctcgg tcatcccgat gttcacggcg 840
ctcagcgagg gagcgacgcc gcaggacctg aacgcggccg tcggaggtca ccaggcagcg 900
atgcagatgc tgaaggagac gatcaacgag gaggcggccg agtgggaccg ggcggcagcc 960
gagccacgcg gttccgacat cgcgggcacc acctcgacgc tccaggagca gatcgcgtgg 1020
gccgcagcta agcgctggat catcctcggg ctgaacaaga tcgtccggat gtacagcccg 1080
gtctcgatcg ctgctaagta cgttgaccgg ttcttcaaga ccctgagggc cgagcaggcg 1140
gccggactgg aggagatgat gaccgcgtgc cagggggtcg gtggaccatc gcacaaggcc 1200
gcgctctcgc cgcgcacgct gaacgcgtgg gtgaaggtct gataagaatt cgcggatatc 1260
ggttaacgga tccagatctg ctgtgccttc tagttgccag ccatctgttg tttgcccctc 1320
ccccgtgcct tccttgaccc tggaaggtgc cactcccact gtcctttcct aataaaatga 1380
ggaaattgca tcgcattgtc tgagtaggtg tcattctatt ctggggggtg gggtggggca 1440
ggacagcaag ggggaggatt gggaagacaa tagcaggcat gctggggatg cggtgggctc 1500
tatgggtacc caggtgctga agaattgacc cggttcctcc tgggccagaa agaagcaggc 1560
acatcccctt ctctgtgaca caccctgtcc acgcccctgg ttcttagttc cagccccact 1620
cataggacac tcatagctca ggagggctcc gccttcaatc ccacccgcta aagtacttgg 1680
agcggtctct ccctccctca tcagcccacc aaaccaaacc tagcctccaa gagtgggaag 1740
aaattaaagc aagataggct attaagtgca gagggagaga aaatgcctcc aacatgtgag 1800
gaagtaatga gagaaatcat agaatttctt ccgcttcctc gctcactgac tcgctgcgct 1860
cggtcgttcg gctgcggcga gcggtatcag ctcactcaaa ggcggtaata cggttatcca 1920
cagaatcagg ggataacgca ggaaagaaca tgtgagcaaa aggccagcaa aaggccagga 1980

```
accgtaaaaa ggccgcgttg ctggcgtttt tccataggct ccgccccct dacgagcatc      2040 acaaaaatcg acgctcaagt cagaggtggc gaaacccgac aggactataa agataccagg      2100
cgtttccccc tggaagctcc ctcgtgcgct ctcctgttcc gaccctgccg cttaccggat      2160
acctgtccgc ctttctccct tcgggaagcg tggcgctttc tcatagctca cgctgtaggt      2220
atctcagttc ggtgtaggtc gttcgctcca agctgggctg tgtgcacgaa ccccccgttc      2280
agcccgaccg ctgcgcctta ccggtaact atcgtcttga gtccaacccg gtaagacacg       2340
acttatcgcc actggcagca gccactggta acaggattag cagagcgagg tatgtaggcg      2400
gtgctacaga gttcttgaag tggtggccta actacggcta cactagaaga acagtatttg      2460
gtatctgcgc tctgctgaag ccagttacct tcggaaaaag agttggtagc tcttgatccg      2520
gcaaacaaac caccgctggt agcggtggtt ttttgtttg caagcagcag attacgcgca       2580
gaaaaaaagg atctcaagaa gatcctttga tcttttctac ggggtctgac gctcagtgga      2640
acgaaaactc acgttaaggg attttggtca tgagattatc aaaaggatc ttcacctaga       2700 tcccttttaaa ttaaaaatga agtttttaaat caatctaaag tatatatgag taaacttggt   2760
ctgacagtta ccaatgctta atcagtgagg cacctatctc agcgatctgt ctatttcgtt     2820
catccatagt tgcctgactc gggggggggg ggcgctgagg tctgcctcgt gaagaaggtg     2880
ttgctgactc ataccaggcc tgaatcgccc catcatccag ccagaaagtg agggagccac     2940
ggttgatgag agctttgttg taggtggacc agttggtgat tttgaacttt tgctttgcca     3000
cggaacggtc tgcgttgtcg ggaagatgcg tgatctgatc cttcaactca gcaaaagttc    3060
gatttattca caaagccgc cgtcccgtca agtcagcgta atgctctgcc agtgttacaa     3120
ccaattaacc aattctgatt agaaaaactc atcgagcatc aaatgaaact gcaatttatt    3180
catatcagga ttatcaatac catattttg aaaaagccgt ttctgtaatg aaggagaaaa     3240
ctcaccgagg cagttccata ggatggcaag atcctggtat cggtctgcga ttccgactcg    3300
tccaacatca atacaaccta ttaatttccc ctcgtcaaaa ataaggttat caagtgagaa    3360
atcaccatga gtgacgactg aatccggtga gaatggcaaa agcttatgca tttctttcca    3420
gacttgttca acaggccagc cattacgctc gtcatcaaaa tcactcgcat caaccaaacc    3480
gttattcatt cgtgattgcg cctgagcgag acgaaatacg cgatcgctgt taaaaggaca    3540
attacaaaca ggaatcgaat gcaaccggcg caggaacact gccagcgcat caacaatatt    3600
ttcacctgaa tcaggatatt cttctaatac ctggaatgct gttttcccgg ggatcgcagt    3660
ggtgagtaac catgcatcat caggagtacg gataaaatgc ttgatggtcg gaagaggcat    3720
aaattccgtc agccagttta gtctgaccat ctcatctgta acatcattgg caacgctacc    3780
tttgccatgt ttcagaaaca actctggcgc atcgggcttc ccatacaatc gatagattgt    3840
cgcacctgat tgcccgacat tatcgcgagc ccatttatac ccatataaat cagcatccat    3900
gttggaattt aatcgcggcc tcgagcaaga cgtttcccgt tgaatatggc tcataacacc    3960
ccttgtatta ctgtttatgt aagcagacag ttttattgtt catgatgata tattttttatc   4020 ttgtgcaatg taacatcaga gattttgaga cacaacgtgg ctttccccc ccccccatta    4080 ttgaagcatt tatcagggtt attgtctcat gagcggatac atatttgaat gtatttagaa    4140
aaataaacaa atagggttc cgcgcacatt tccccgaaaa gtgccacctg acgtctaaga    4200
aaccattatt atcatgacat taacctataa aaataggcgt atcacgaggc cctttcgtct    4260
cgcgcgtttc ggtgatgacg gtgaaaacct ctgacacatg cagctcccgg agacggtcac    4320
agcttgtctg taagcggatg ccgggagcag acaagcccgt cagggcgcgt cagcgggtgt    4380
```

```
tggcgggtgt cggggctggc ttaactatgc ggcatcagag cagattgt

```
tcaatgggag tttgttttgg caccaaaatc aacgggactt tccaaaatgt cgtaacaact    600
ccgccccatt gacgcaaatg ggcggtaggc gtgtacggtg ggaggtctat ataagcagag    660
ctcgtttagt gaaccgtcag atcgcctgga gacgccatcc acgctgtttt gacctccata    720
gaagacaccg ggaccgatcc agcctccgcg ggcgcgcgtc gacaagaaat gtggaagccg    780
atgccctcgc caagcaacat gaaggcgtcc gccgcgctcc tgtgcctgct cctcacggcc    840
gcggctttca gccccagggg ctcgcgcagc cggtcgggga tcaacacgag cacgacctgc    900
tgctaccggt tcatcaacaa gaagatcccg aagcagcgtc tggagagcta ccgccggacc    960
acgtcgagcc actgcccgcg ggaggcggtc atcttcaaga cgaagctgga caaggagatc   1020
tgcgccgacc cgacgcagaa gtgggttcag gacttcatga agcacctgga caagaagacg   1080
cagacgccga agctggtcat cccgatgttc tcggcgctca gcgagggagc gacgccgcag   1140
gacctgaacg cggccgtcgg aggtcaccag gcagcgatgc agatgctgaa ggacacgatc   1200
aacgaggagg cggccgagtg ggaccgggcg gcagccgagc cacgcggttc cgacatcgcg   1260
ggcaccacct cgacgctcca ggagcagatc gggtgggccg cagctaagcg ctggatcatc   1320
ctcgggctga acaagatcgt ccggatgtac agcccgacgt cgatcgctgc taagtacgtt   1380
gaccggttct acaagaccct gagggccgag caggcggccg gactggagga gatgatgacc   1440
gcgtgccagg gggtcggtgg accagggcac aaggccgcga tctcgccgcg cacgctgaac   1500
gcgtgggtga aggtctgata agaattcgcg gatatcggtt aacggatcca gatctgctgt   1560
gccttctagt tgccagccat ctgttgtttg cccctccccc gtgccttcct tgaccctgga   1620
aggtgccact cccactgtcc tttcctaata aaatgaggaa attgcatcgc attgtctgag   1680
taggtgtcat tctattctgg ggggtggggt ggggcaggac agcaaggggg aggattggga   1740
agacaatagc aggcatgctg gggatgcggt gggctctatg ggtacccagg tgctgaagaa   1800
ttgacccggt tcctcctggg ccagaaagaa gcaggcacat ccccttctct gtgacacacc   1860
ctgtccacgc cctggttcct tagttccagc cccactcata ggacactcat agctcaggag   1920
ggctccgcct tcaatcccac ccgctaaagt acttggagcg gtctctccct ccctcatcag   1980
cccaccaaac caaacctagc ctccaagagt gggaagaaat taaagcaaga taggctatta   2040
agtgcagagg gagagaaaat gcctccaaca tgtgaggaag taatgagaga aatcatagaa   2100
tttcttccgc ttcctcgctc actgactcgc tgcgctcggt cgttcggctg cggcgagcgg   2160
tatcagctca ctcaaaggcg gtaatacggt tatccacaga atcaggggat aacgcaggaa   2220
agaacatgtg agcaaaaggc cagcaaaagg ccaggaaccg taaaaaggcc gcgttgctgg   2280
cgttttttcca taggctccgc cccctgacg agcatcacaa aaatcgacgc tcaagtcaga   2340
ggtggcgaaa cccgacagga ctataaagat accaggcgtt tccccctgga agctccctcg   2400
tgcgctctcc tgttccgacc ctgccgctta ccggatacct gtccgccttt ctcccttcgg   2460
gaagcgtggc gctttctcat agctcacgct gtaggtatct cagttcggtg taggtcgttc   2520
gctccaagct gggctgtgtg cacgaacccc ccgttcagcc cgaccgctgc gccttatccg   2580
gtaactatcg tcttgagtcc aacccggtaa gacacgactt atcgccactg gcagcagcca   2640
ctggtaacag gattagcaga gcgaggtatg taggcggtgc tacagagttc ttgaagtggt   2700
ggcctaacta cggctacact agaagaacag tatttggtat ctgcgctctg ctgaagccag   2760
ttaccttcgg aaaaagagtt ggtagctctt gatccggcaa acaaaccacc gctggtagcg   2820
gtggtttttt tgtttgcaag cagcagatta cgcgcagaaa aaaaggatct caagaagatc   2880
ctttgatctt ttctacgggg tctgacgctc agtggaacga aaactcacgt taagggattt   2940
```

```
tggtcatgag attatcaaaa aggatcttca cctagatcct tttaaattaa aaatgaagtt   3000
ttaaatcaat ctaaagtata tatgagtaaa cttggtctga cagttaccaa tgcttaatca   3060
gtgaggcacc tatctcagcg atctgtctat ttcgttcatc catagttgcc tgactcgggg   3120 gggggggcg ctgaggtctg cctcgtgaag aaggtgttgc tgactcatac caggcctgaa   3180
tcgccccatc atccagccag aaagtgaggg agccacggtt gatgagagct ttgttgtagg   3240
tggaccagtt ggtgattttg aacttttgct ttgccacgga acggtctgcg ttgtcgggaa   3300
gatgcgtgat ctgatccttc aactcagcaa aagttcgatt tattcaacaa agccgccgtc   3360
ccgtcaagtc agcgtaatgc tctgccagtg ttacaaccaa ttaaccaatt ctgattagaa   3420
aaactcatcg agcatcaaat gaaactgcaa tttattcata tcaggattat caataccata   3480
tttttgaaaa agccgtttct gtaatgaagg agaaaactca ccgaggcagt tccataggat   3540
ggcaagatcc tggtatcggt ctgcgattcc gactcgtcca acatcaatac aacctattaa   3600
tttcccctcg tcaaaaataa ggttatcaag tgagaaatca ccatgagtga cgactgaatc   3660
cggtgagaat ggcaaaagct tatgcatttc tttccagact tgttcaacag gccagccatt   3720
acgctcgtca tcaaaatcac tcgcatcaac caaaccgtta ttcattcgtg attgcgcctg   3780
agcgagacga aatacgcgat cgctgttaaa aggacaatta caaacaggaa tcgaatgcaa   3840
ccggcgcagg aacactgcca gcgcatcaac aatattttca cctgaatcag gatattcttc   3900
taatacctgg aatgctgttt tcccggggat cgcagtggtg agtaaccatg catcatcagg   3960
agtacggata aaatgcttga tggtcggaag aggcataaat tccgtcagcc agtttagtct   4020
gaccatctca tctgtaacat cattggcaac gctacctttg ccatgtttca gaaacaactc   4080
tggcgcatcg ggcttcccat acaatcgata gattgtcgca cctgattgcc cgacattatc   4140
gcgagcccat ttatacccat ataaatcagc atccatgttg gaatttaatc gcggcctcga   4200
gcaagacgtt tcccgttgaa tatggctcat aacacccctt gtattactgt ttatgtaagc   4260
agacagtttt attgttcatg atgatatatt tttatcttgt gcaatgtaac atcagagatt   4320
ttgagacaca acgtggcttt cccccccccc ccattattga agcatttatc agggttattg   4380
tctcatgagc ggatacatat ttgaatgtat ttagaaaaat aaacaaatag gggttccgcg   4440
cacatttccc cgaaaagtgc cacctgacgt ctaagaaacc attattatca tgacattaac   4500
ctataaaaat aggcgtatca cgaggccctt tcgtctcgcg cgtttcggtg atgacggtga   4560
aaacctctga cacatgcagc tcccggagac ggtcacagct tgtctgtaag cggatgccgg   4620
gagcagacaa gcccgtcagg gcgcgtcagc gggtgttggc gggtgtcggg gctggcttaa   4680
ctatgcggca tcagagcaga ttgtactgag agtgcaccat atgcggtgtg aaataccgca   4740
cagatgcgta aggagaaaat accgcatcag attggctatt gg                      4782
```

<210> SEQ ID NO 27
<211> LENGTH: 249
<212> TYPE: PRT
<213> ORGANISM: Artificial Sequence
<220> FEATURE:
<223> OTHER INFORMATION: synthetic monocyte chemoattractant protein 3 (MCP-3) fusion protein with p24CE1 (Core1) vaccine construct, MCP3-p24CE1 encoded by plasmid 230H

<400> SEQUENCE: 27

```
Met Trp Lys Pro Met Pro Ser Pro Ser Asn Met Lys Ala Ser Ala Ala
 1               5                  10                  15

Leu Leu Cys Leu Leu Leu Thr Ala Ala Ala Phe Ser Pro Gln Gly Leu
```

```
                20                  25                  30
Ala Gln Pro Val Gly Ile Asn Thr Ser Thr Thr Cys Cys Tyr Arg Phe
                35                  40                  45

Ile Asn Lys Lys Ile Pro Lys Gln Arg Leu Glu Ser Tyr Arg Arg Thr
            50                  55                  60

Thr Ser Ser His Cys Pro Arg Glu Ala Val Ile Phe Lys Thr Lys Leu
65                  70                  75                  80

Asp Lys Glu Ile Cys Ala Asp Pro Thr Gln Lys Trp Val Gln Asp Phe
                85                  90                  95

Met Lys His Leu Asp Lys Lys Thr Gln Thr Pro Lys Leu Val Ile Pro
            100                 105                 110

Met Phe Ser Ala Leu Ser Glu Gly Ala Thr Pro Gln Asp Leu Asn Ala
                115                 120                 125

Ala Val Gly Gly His Gln Ala Ala Met Gln Met Leu Lys Asp Thr Ile
            130                 135                 140

Asn Glu Glu Ala Ala Glu Trp Asp Arg Ala Ala Ala Glu Pro Arg Gly
145                 150                 155                 160

Ser Asp Ile Ala Gly Thr Thr Ser Thr Leu Gln Glu Gln Ile Gly Trp
                165                 170                 175

Ala Ala Ala Lys Arg Trp Ile Ile Leu Gly Leu Asn Lys Ile Val Arg
            180                 185                 190

Met Tyr Ser Pro Thr Ser Ile Ala Ala Lys Tyr Val Asp Arg Phe Tyr
                195                 200                 205

Lys Thr Leu Arg Ala Glu Gln Ala Ala Gly Leu Glu Glu Met Met Thr
            210                 215                 220

Ala Cys Gln Gly Val Gly Gly Pro Gly His Lys Ala Ala Ile Ser Pro
225                 230                 235                 240

Arg Thr Leu Asn Ala Trp Val Lys Val
                245

<210> SEQ ID NO 28
<211> LENGTH: 4782
<212> TYPE: DNA
<213> ORGANISM: Artificial Sequence
<220> FEATURE:
<223> OTHER INFORMATION: synthetic monocyte chemoattractant protein 3
      (MCP-3) fusion protein with p24CE2 (Core2) vaccine
      construct, MCP3-p24CE2 encoded by plasmid 231H

<400> SEQUENCE: 28
cctggccatt gcatacgttg tatccatatc ataatatgta catttatatt ggctcatgtc      60
caacattacc gccatgttga cattgattat tgactagtta ttaatagtaa tcaattacgg     120
ggtcattagt tcatagccca tatatggagt tccgcgttac ataacttacg gtaaatggcc     180
cgcctggctg accgcccaac gacccccgcc cattgacgtc aataatgacg tatgttccca     240
tagtaacgcc aatagggact ttccattgac gtcaatgggt ggagtattta cggtaaactg     300
cccacttggc agtacatcaa gtgtatcata tgccaagtac gccccctatt gacgtcaatg     360
atggtaaatg gcccgcctgg cattatgccc agtacatgac cttatgggac tttcctactt     420
ggcagtacat ctacgtatta gtcatcgcta ttaccatggt gatgcggttt tggcagtaca     480
tcaatgggcg tggatagcgg tttgactcac ggggatttcc aagtctccac cccattgacg     540
tcaatgggag tttgttttgg caccaaaatc aacgggactt tccaaaatgt cgtaacaact     600
ccgccccatt gacgcaaatg ggcggtaggc gtgtacggtg gaggtctat  ataagcagag     660 ctcgtttagt gaaccgtcag atcgcctgga gacgccatcc acgctgtttt gacctccata     720
```

```
gaagacaccg ggaccgatcc agcctccgcg ggcgcgcgtc gacaagaaat gtggaagccg    780
atgccctcgc caagcaacat gaaggcgtcc gccgcgctcc tgtgcctgct cctcacggcc    840
gcggctttca gccccagggg gctcgcgcag ccggtcggga tcaacacgag cacgacctgc    900
tgctaccggt tcatcaacaa gaagatcccg aagcagcgtc tggagagcta ccgccggacc    960
acgtcgagcc actgcccgcg ggaggcggtc atcttcaaga cgaagctgga caaggagatc   1020
tgcgccgacc cgacgcagaa gtgggttcag gacttcatga agcacctgga caagaagacg   1080
cagacgccga agctggtcat cccgatgttc acggcgctca gcgagggagc gacgccgcag   1140
gacctgaacg cggccgtcgg aggtcaccag gcagcgatgc agatgctgaa ggagacgatc   1200
aacgaggagg cggccgagtg ggaccgggcg gcagccgagc cacgcggttc cgacatcgcg   1260
ggcaccacct cgacgctcca ggagcagatc gcgtgggccg cagctaagcg ctggatcatc   1320
ctcgggctga caagatcgt ccggatgtac agcccggtct cgatcgctgc taagtacgtt    1380
gaccggttct tcaagaccct gagggccgag caggcggccg gactggagga gatgatgacc   1440
gcgtgccagg gggtcggtgg accatcgcac aaggccgcgc tctcgccgcg cacgctgaac   1500
gcgtgggtga aggtctgata agaattcgcg gatatcggtt aacggatcca gatctgctgt   1560
gccttctagt tgccagccat ctgttgtttg cccctccccc gtgccttcct tgaccctgga   1620
aggtgccact cccactgtcc tttcctaata aatgaggaa attgcatcgc attgtctgag    1680
taggtgtcat tctattctgg ggggtgggt ggggcaggac agcaagggg aggattggga     1740 agacaatagc aggcatgctg gggatgcggt gggctctatg ggtacccagg tgctgaagaa   1800
ttgacccggt tcctcctggg ccagaaagaa gcaggcacat ccccttctct gtgacacacc   1860
ctgtccacgc ccctggttct tagttccagc cccactcata ggacactcat agctcaggag   1920
ggctccgcct tcaatcccac ccgctaaagt acttggagcg gtctctccct ccctcatcag   1980
cccaccaaac caaacctagc ctccaagagt gggaagaaat taagcaaga taggctatta    2040 agtgcagagg gagagaaaat gcctccaaca tgtgaggaag taatgagaga aatcatagaa   2100
tttcttccgc ttcctcgctc actgactcgc tgcgctcggt cgttcggctg cggcgagcgg   2160
tatcagctca ctcaaaggcg gtaatacggt tatccacaga atcaggggat aacgcaggaa   2220
agaacatgtg agcaaaaggc cagcaaaagg ccaggaaccg taaaaaggcc gcgttgctgg   2280
cgtttttcca taggctccgc cccctgacg agcatcacaa aaatcgacgc tcaagtcaga    2340
ggtggcgaaa cccgacagga ctataaagat accaggcgtt ccccctggaa gctccctcg    2400 tgcgctctcc tgttccgacc ctgccgctta ccggatacct gtccgccttt ctcccttcgg   2460
gaagcgtggc gctttctcat agctcacgct gtaggtatct cagttcggtg taggtcgttc   2520
gctccaagct gggctgtgtg cacgaacccc cgttcagcc cgaccgctgc gccttatccg    2580
gtaactatcg tcttgagtcc aacccggtaa gacacgactt atcgccactg gcagcagcca   2640
ctggtaacag gattagcaga gcgaggtatg taggcggtgc tacagagttc ttgaagtggt   2700
ggcctaacta cggctacact agaagaacag tatttggtat ctgcgctctg ctgaagccag   2760
ttaccttcgg aaaaagagtt ggtagctctt gatccggcaa acaaaccacc gctggtagcg   2820
gtggtttttt tgtttgcaag cagcagatta cgcgcagaaa aaaaggatct caagaagatc   2880
ctttgatctt ttctacgggg tctgacgctc agtggaacga aaactcacgt taagggattt   2940
tggtcatgag attatcaaaa aggatcttca cctagatcct tttaaattaa aaatgaagtt   3000
ttaaatcaat ctaaagtata tatgagtaaa cttggtctga cagttaccaa tgcttaatca   3060
```

-continued

```
gtgaggcacc tatctcagcg atctgtctat ttcgttcatc catagttgcc tgactcgggg    3120
ggggggggcg ctgaggtctg cctcgtgaag aaggtgttgc tgactcatac caggcctgaa    3180
tcgccccatc atccagccag aaagtgaggg agccacggtt gatgagagct tgttgtagg     3240 tggaccagtt ggtgattttg aacttttgct ttgccacgga acggtctgcg ttgtcgggaa    3300
gatgcgtgat ctgatccttc aactcagcaa aagttcgatt tattcaacaa agccgccgtc    3360
ccgtcaagtc agcgtaatgc tctgccagtg ttacaaccaa ttaaccaatt ctgattagaa    3420
aaactcatcg agcatcaaat gaaactgcaa tttattcata tcaggattat caataccata    3480
tttttgaaaa agccgtttct gtaatgaagg agaaaactca ccgaggcagt tccataggat    3540
ggcaagatcc tggtatcggt ctgcgattcc gactcgtcca acatcaatac aacctattaa    3600
tttcccctcg tcaaaaataa ggttatcaag tgagaaatca ccatgagtga cgactgaatc    3660
cggtgagaat ggcaaaagct tatgcatttc tttccagact tgttcaacag gccagccatt    3720
acgctcgtca tcaaaatcac tcgcatcaac caaaccgtta ttcattcgtg attgcgcctg    3780
agcgagacga atacgcgat cgctgttaaa aggacaatta caaacaggaa tcgaatgcaa    3840
ccggcgcagg aacactgcca gcgcatcaac aatattttca cctgaatcag gatattcttc    3900
taatacctgg aatgctgttt ccccggggat cgcagtggtg agtaaccatg catcatcagg    3960
agtacggata aaatgcttga tggtcggaag aggcataaat tccgtcagcc agtttagtct    4020
gaccatctca tctgtaacat cattggcaac gctacctttg ccatgtttca gaaacaactc    4080
tggcgcatcg ggcttcccat acaatcgata gattgtcgca cctgattgcc cgacattatc    4140
gcgagcccat ttatacccat ataaatcagc atccatgttg gaatttaatc gcggcctcga    4200
gcaagacgtt tcccgttgaa tatggctcat aacacccctt gtattactgt ttatgtaagc    4260
agacagtttt attgttcatg atgatatatt tttatcttgt gcaatgtaac atcagagatt    4320
ttgagacaca acgtggcttt ccccccccc cattattga agcatttatc agggttattg     4380
tctcatgagc ggatacatat ttgaatgtat ttagaaaaat aaacaaatag gggttccgcg    4440
cacatttccc cgaaaagtgc cacctgacgt ctaagaaacc attattatca tgacattaac    4500
ctataaaaat aggcgtatca cgaggccctt tcgtctcgcg cgtttcggtg atgacggtga    4560
aaacctctga cacatgcagc tcccggagac ggtcacagct tgtctgtaag cggatgccgg    4620
gagcagacaa gcccgtcagg gcgcgtcagc gggtgttggc gggtgtcggg gctggcttaa    4680
ctatgcggca tcagagcaga ttgtactgag agtgcaccat atgcggtgtg aaataccgca    4740
cagatgcgta aggagaaaat accgcatcag attggctatt gg                      4782
```

<210> SEQ ID NO 29
<211> LENGTH: 249
<212> TYPE: PRT
<213> ORGANISM: Artificial Sequence
<220> FEATURE:
<223> OTHER INFORMATION: synthetic monocyte chemoattractant protein 3
      (MCP-3) fusion protein with p24CE2 (Core2) va Ile Asn Lys Lys Ile Pro Lys Gln Arg Leu Glu Ser Tyr Arg Arg Thr
 50                  55                  60

Thr Ser Ser His Cys Pro Arg Glu Ala Val Ile Phe Lys Thr Lys Leu
 65                  70                  75                  80

Asp Lys Glu Ile Cys Ala Asp Pro Thr Gln Lys Trp Val Gln Asp Phe
                 85                  90                  95

Met Lys His Leu Asp Lys Lys Thr Gln Thr Pro Lys Leu Val Ile Pro
             100                 105                 110

Met Phe Thr Ala Leu Ser Glu Gly Ala Thr Pro Gln Asp Leu Asn Ala
             115                 120                 125

Ala Val Gly Gly His Gln Ala Ala Met Gln Met Leu Lys Glu Thr Ile
         130                 135                 140

Asn Glu Glu Ala Ala Glu Trp Asp Arg Ala Ala Ala Glu Pro Arg Gly
145                 150                 155                 160

Ser Asp Ile Ala Gly Thr Thr Ser Thr Leu Gln Glu Gln Ile Ala Trp
                165                 170                 175

Ala Ala Ala Lys Arg Trp Ile Ile Leu Gly Leu Asn Lys Ile Val Arg
            180                 185                 190

Met Tyr Ser Pro Val Ser Ile Ala Ala Lys Tyr Val Asp Arg Phe Phe
        195                 200                 205

Lys Thr Leu Arg Ala Glu Gln Ala Ala Gly Leu Glu Glu Met Met Thr
    210                 215                 220

Ala Cys Gln Gly Val Gly Gly Pro Ser His Lys Ala Ala Leu Ser Pro
225                 230                 235                 240

Arg Thr Leu Asn Ala Trp Val Lys Val
                245

<210> SEQ ID NO 30
<211> LENGTH: 501
<212> TYPE: DNA
<213> ORGANISM: Artificial Sequence
<220> FEATURE:
<223> OTHER INFORMATION: synthetic GM-CSF signal peptide (SP) fusion
      protein with p24CE1c alternative conserved element vaccine
      construct, SP-p24CE1c configuration CE 8-9-3-4-5-6

<400> SEQUENCE: 30
atgtggctcc agagcctgct actcctgggg acggtggcct gcagcatctc gcaggggcag      60
atggtccacc aggcgatctc gccgcgcacg ctgaacgcgt gggtgaaggt cctggcgaag     120
gaggagaagg cgttcagccc ggaggtcatc ccgatgttct cggcgctcag cgagggagcg     180
acgccgcagg acctgaacgc ggccaaggtc ggaggtcacc aggcagcgat gcagatgctg     240
aaggagacga tcaacgagga ggcggccgag tgggaccggg cggcagccga gccacgcggt     300
tccgacatcg cgggcaccac ctcgacgctc caggagcaga tcgggtgggc cgcagctaag     360
cgctggatca tcctcgggct gaacaagatc gtccggatgt acagcccgac gtcgatcgct     420
gctaaatacg ttgaccggtt ctacaagacc ctgagggccg agcaggcgga ttacaaggac     480
gatgacgaca agctgtgata a                                               501

<210> SEQ ID NO 31
<211> LENGTH: 165
<212> TYPE: PRT
<213> ORGANISM: Artificial Sequence
<220> FEATURE:
<223> OTHER INFORMATION: synthetic GM-CSF signal peptide (SP) fusion
      protein with p24CE1c alternative conserved element vaccine
      construct, SP-p24CE1c configuration CE 8-9-3-4-5-6

<400> SEQUENCE: 31

Met Trp Leu Gln Ser Leu Leu Leu Gly Thr Val Ala Cys Ser Ile
1               5                   10                  15

Ser Gln Gly Gln Met Val His Gln Ala Ile Ser Pro Arg Thr Leu Asn
            20                  25                  30

Ala Trp Val Lys Val Leu Ala Lys Glu Glu Lys Ala Phe Ser Pro Glu
        35                  40                  45

Val Ile Pro Met Phe Ser Ala Leu Ser Glu Gly Ala Thr Pro Gln Asp
    50                  55                  60

Leu Asn Ala Ala Lys Val Gly His Gln Ala Ala Met Gln Met Leu
65                  70                  75                  80

Lys Glu Thr Ile Asn Glu Glu Ala Ala Glu Trp Asp Arg Ala Ala
                85                  90                  95

Glu Pro Arg Gly Ser Asp Ile Ala Gly Thr Thr Ser Thr Leu Gln Glu
            100                 105                 110

Gln Ile Gly Trp Ala Ala Ala Lys Arg Trp Ile Ile Leu Gly Leu Asn
        115                 120                 125

Lys Ile Val Arg Met Tyr Ser Pro Thr Ser Ile Ala Ala Lys Tyr Val
    130                 135                 140

Asp Arg Phe Tyr Lys Thr Leu Arg Ala Glu Gln Ala Asp Tyr Lys Asp
145                 150                 155                 160

Asp Asp Asp Lys Leu
                165

<210> SEQ ID NO 32
<211> LENGTH: 20
<212> TYPE: PRT
<213> ORGANISM: Artificial Sequence
<220> FEATURE:
<223> OTHER INFORMATION: synthetic HIV-1 p24 gag conserved element 8
      (CE8) for p24CE1c alternative conserved element vaccine

<400> SEQUENCE: 32

Gln Gly Gln Met Val His Gln Ala Ile Ser Pro Arg Thr Leu Asn Ala
1               5                   10                  15

Trp Val Lys Val
            20

<210> SEQ ID NO 33
<211> LENGTH: 26
<212> TYPE: PRT
<213> ORGANISM: Artificial Sequence
<220> FEATURE:
<223> OTHER INFORMATION: synthetic HIV-1 p24 gag conserved element 9
      (CE9) for p24CE1c alternative conserved element vaccine

<400> SEQUENCE: 33

Glu Glu Lys Ala Phe Ser Pro Glu Val Ile Pro Met Phe Ser Ala Leu
1               5                   10                  15

Ser Glu Gly Ala Thr Pro Gln Asp Leu Asn
            20                  25

<210> SEQ ID NO 34
<211> LENGTH: 474
<212> TYPE: DNA
<213> ORGANISM: Artificial Sequence
<220> FEATURE:
<223> OTHER INFORMATION: synthetic GM-CSF signal peptide (SP) fusion
      protein with p24CE2c alternative conserved element vaccine
      construct, SP-p24CE2c configuration CE 8-9-3-4-5-6

<400> SEQUENCE: 34

```
atgtggctcc agagcctgct actcctgggg acggtggcct gcagcatctc gcaggggcag    60
atggtccacc aggcgctgtc gccgcgcacg ctgaacgcgt gggtgaaggt cctggcgaag   120
gaggagaagg ggttcaaccc ggaggtcatc ccgatgttca cggcgctcag cgagggagcg   180
acgccgcagg acctgaacgc ggccaaggtc ggaggtcacc aggcagcgat gcagatgctg   240
aaggacacga tcaacgagga ggcggccgag tgggaccggg cggcagccga gccacgcggt   300
tccgacatcg cgggcaccac ctcgacgctc caggagcaga tcgcgtgggc cgcagctaag   360
cgctggatca tcctcgggct gaacaagatc gtccggatgt acagcccggt ctcgatcgct   420
gctaaatacg ttgaccggtt cttcaagacc ctgagggccg agcaggcgtg ataa         474
```

<210> SEQ ID NO 35
<211> LENGTH: 156
<212> TYPE: PRT
<213> ORGANISM: Artificial Sequence
<220> FEATURE:
<223> OTHER INFORMATION: synthetic GM-CSF signal peptide (SP) fusion
protein with p24CE2c alternative conserved element vaccine
construct, SP-p24CE2c configuration CE 8-9-3-4-5-6

<400> SEQUENCE: 35

```
Met Trp Leu Gln Ser Leu Leu Leu Gly Thr Val Ala Cys Ser Ile
1               5                   10                  15

Ser Gln Gly Gln

```
gcgggcacca cctcgacgct ccaggagcag atcgcgtggg ccgcagctaa gcgctggatc      300
atcctcgggc tgaacaagat cgtccggatg tacagcccgg tctcgatcgc tgctaaatac      360
gttgaccggt tcttcaagac cctgagggcc gagcaggcgg cgctgcaggg gcagatggtc      420
caccaggcgc tgtcgccgcg cacgctgaac gcgtgggtga aggtctgata a               471
```

<210> SEQ ID NO 37
<211> LENGTH: 155
<212> TYPE: PRT
<213> ORGANISM: Artificial Sequence
<220> FEATURE:
<223> OTHER INFORMATION: synthetic GM-CSF signal peptide (S
<210> SEQ ID NO 39
<211> LENGTH: 155
<212> TYPE: PRT
<213> ORGANISM: Artificial Sequence
<220> FEATURE:
<223> OTHER INFORMATION: synthetic GM-CSF signal peptide (SP) fusion
    protein with p24CE1d alternative conserved element vaccine
    construct, SP-p24CE2d configuration CE 9-3-4-5-6-8

<400> SEQUENCE: 39

```
Met Trp Leu Gln Ser Leu Leu Leu Gly Thr Val Ala Cys Ser Ile
 1               5                  10                  15

Ser Glu Glu Lys Ala Phe Ser Pro Glu Val Ile Pro Met Phe Ser Ala
                20                  25                  30

Leu Ser Glu Gly Ala Thr Pro Gln Asp Leu Asn Ala Ala Lys Val Gly
            35                  40                  45

Gly His Gln Ala Ala Met Gln Met Leu Lys Glu Thr Ile Asn Glu Glu
        50                  55                  60

Ala Ala Glu Trp Asp Arg Ala Ala Glu Pro Arg Gly Ser Asp Ile
65                  70                  75                  80

Ala Gly Thr Thr Ser Thr Leu Gln Glu Gln Ile Gly Trp Ala Ala
                85                  90                  95

Lys Arg Trp Ile Ile Leu Gly Leu Asn Lys Ile Val Arg Met Tyr Ser
                100                 105                 110

Pro Thr Ser Ile Ala Ala Lys Tyr Val Asp Arg Phe Tyr Lys Thr Leu
            115                 120                 125

Arg Ala Glu Gln Ala Ala Leu Gln Gly Gln Met Val His Gln Ala Ile
        130                 135                 140

Ser Pro Arg Thr Leu Asn Ala Trp Val Lys Val
145                 150                 155
```

<210> SEQ ID NO 40
<211> LENGTH: 20
<212> TYPE: PRT
<213> ORGANISM: Artificial Sequence
<220> FEATURE:
<223> OTHER INFORMATION: synthetic HIV-1 p24 gag conserved element 8
    (CE8) variant for CE2 constructs in conserved element vaccine

<400> SEQUENCE: 40

```
Gln Gly Gln Met Val His Gln Ala Leu Ser Pro Arg Thr Leu Asn Ala
 1

-continued

```
<212> TYPE: PRT
<213> ORGANISM: Artificial Sequence
<220> FEATURE:
<223> OTHER INFORMATION: synthetic short alanine linker

<400> SEQUENCE: 42

Ala Ala Ala Glu
 1

<210> SEQ ID NO 43
<211> LENGTH: 4
<212> TYPE: PRT
<213> ORGANISM: Artificial Sequence
<220> FEATURE:
<223> OTHER INFORMATION: synthetic short alanine linker

<400> SEQUENCE: 43

Ala Ala Ala Ala
 1

<210> SEQ ID NO 44
<211> LENGTH: 5
<212> TYPE: PRT
<213> ORGANISM: Artificial Sequence
<220> FEATURE:
<223> OTHER INFORMATION: synthetic short alanine linker

<400> SEQUENCE: 44

Ala Ala Ala Ala Leu
 1               5

<210> SEQ ID NO 45
<211> LENGTH: 9
<212> TYPE: PRT
<213> ORGANISM: Artificial Sequence
<220> FEATURE:
<223> OTHER INFORMATION: synthetic p55 gag T cell response
      immunodominant epitope

<400> SEQUENCE: 45

Ala Met Gln Met Leu Lys Glu Thr Ile
 1               5

<210> SEQ ID NO 46
<211> LENGTH: 139
<212> TYPE: PRT
<213> ORGANISM: Artificial Sequence
<220> FEATURE:
<223> OTHER INFORMATION: synthetic p24CE1c alternative conserved element
      vaccine construct, configuration CE 8-9-3-4-5-6

<400> SEQUENCE: 46

Gln Gly Gln Met Val His Gln Ala Ile Ser Pro Arg Thr Leu Asn Ala
 1               5                  10                  15

Trp Val Lys Val Leu Ala Lys Glu Glu Lys Ala Phe Ser Pro Glu Val
                20                  25                  30

Ile Pro Met Phe Ser Ala Leu Ser Glu Gly Ala Thr Pro Gln Asp Leu
            35                  40                  45

Asn Ala Ala Lys Val Gly Gly His Gln Ala Ala Met Gln Met Leu Lys
        50                  55                  60

Glu Thr Ile Asn Glu Glu Ala Ala Glu Trp Asp Arg Ala Ala Ala Glu
 65                 70                  75                  80

Pro Arg Gly Ser Asp Ile Ala Gly Thr Thr Ser Thr Leu Gln Glu Gln
                85                  90                  95
```

```
Ile Gly Trp Ala Ala Lys Arg Trp Ile Ile Leu Gly Leu Asn Lys
            100                 105                 110

Ile Val Arg Met Tyr Ser Pro Thr Ser Ile Ala Ala Lys Tyr Val Asp
        115                 120                 125

Arg Phe Tyr Lys Thr Leu Arg Ala Glu Gln Ala
        130                 135

<210> SEQ ID NO 47
<211> LENGTH: 139
<212> TYPE: PRT
<213> ORGANISM: Artificial Sequence
<220> FEATURE:
<223> OTHER INFORMATION: synthetic p24CE2c alternative conserved element
      vaccine construct, configuration CE 8-9-3-4-5-6

<400> SEQUENCE: 47

Gln Gly Gln Met Val His Gln Ala Leu Ser Pro Arg Thr Leu Asn Ala
1               5                   10                  15

Trp Val Lys Val Leu Ala Lys Glu Glu Lys Gly Phe Asn Pro Glu Val
            20                  25                  30

Ile Pro Met Phe Thr Ala Leu Ser Glu Gly Ala Thr Pro Gln Asp Leu
        35                  40                  45

Asn Ala Ala Lys Val Gly Gly His Gln Ala Ala Met Gln Met Leu Lys
50                  55                  60

Asp Thr Ile Asn Glu Glu Ala Glu Trp Asp Arg Ala Ala Ala Glu
65                  70                  75                  80

Pro Arg Gly Ser Asp Ile Ala Gly Thr Thr Ser Thr Leu Gln Glu Gln
                85                  90                  95

Ile Ala Trp Ala Ala Lys Arg Trp Ile Ile Leu Gly Leu Asn Lys
            100                 105                 110

Ile Val Arg Met Tyr Ser Pro Val Ser Ile Ala Ala Lys Tyr Val Asp
        115                 120                 125

Arg Phe Phe Lys Thr Leu Arg Ala Glu Gln Ala
        130                 135

<210> SEQ ID NO 48
<211> LENGTH: 138
<212> TYPE: PRT
<213> ORGANISM: Artificial Sequence
<220> FEATURE:
<223> OTHER INFORMATION: synthetic p24CE1d alternative conserved element
      vaccine construct, configuration CE 9-3-4-5-6-8

<400> SEQUENCE: 48

Glu Glu Lys Ala Phe Ser Pro Glu Val Ile Pro Met Phe Ser Ala Leu
1               5                   10                  15

Ser Glu Gly Ala Thr Pro Gln Asp Leu Asn Ala Ala Lys Val Gly Gly
            20                  25                  30

His Gln Ala Ala Met Gln Met Leu Lys Glu Thr Ile Asn Glu Glu Ala
        35                  40                  45

Ala Glu Trp Asp Arg Ala Ala Ala Glu Pro Arg Gly Ser Asp Ile Ala
50                  55                  60

Gly Thr Thr Ser Thr Leu Gln Glu Gln Ile Gly Trp Ala Ala Ala Lys
65                  70                  75                  80

Arg Trp Ile Ile Leu Gly Leu Asn Lys Ile Val Arg Met Tyr Ser Pro
                85                  90                  95

Thr Ser Ile Ala Ala Lys Tyr Val Asp Arg Phe Tyr Lys Thr Leu Arg
            100                 105                 110
```

```
Ala Glu Gln Ala Ala Leu Gln Gly Gln Met Val His Gln Ala Ile Ser
        115                 120                 125

Pro Arg Thr Leu Asn Ala Trp Val Lys Val
        130                 135

<210> SEQ ID NO 49
<211> LENGTH: 138
<212> TYPE: PRT
<213> ORGANISM: Artificial Sequence
<220> FEATURE:
<223> OTHER INFORMATION: synthetic p24CE2d alternative conserved element
      vaccine construct, configuration CE 9-3-4-5-6-8

<400> SEQUENCE: 49

Glu Glu Lys Gly Phe Asn Pro Glu Val Ile Pro Met Phe Thr Ala Leu
  1               5                  10                  15

Ser Glu Gly Ala Thr Pro Gln Asp Leu Asn Ala Ala Lys Val Gly Gly
             20                  25                  30

His Gln Ala Ala Met Gln Met Leu Lys Asp Thr Ile Asn Glu Glu Ala
         35                  40                  45

Ala Glu Trp Asp Arg Ala Ala Ala Glu Pro Arg Gly Ser Asp Ile Ala
     50                  55                  60

Gly Thr Thr Ser Thr Leu Gln Glu Gln Ile Ala Trp Ala Ala Ala Lys
 65                  70                  75                  80

Arg Trp Ile Ile Leu Gly Leu Asn Lys Ile Val Arg Met Tyr Ser Pro
                 85                  90                  95

Val Ser Ile Ala Ala Lys Tyr Val Asp Arg Phe Phe Lys Thr Leu Arg
            100                 105                 110

Ala Glu Gln Ala Ala Leu Gln Gly Gln Met Val His Gln Ala Leu Ser
        115                 120                 125

Pro Arg Thr Leu Asn Ala Trp Val Lys Val
        130                 135

<210> SEQ ID NO 50
<211> LENGTH: 231
<212> TYPE: PRT
<213> ORGANISM: Artificial Sequence
<220> FEATURE:
<223> OTHER INFORMATION: synthetic HXB2 p24 gag/clade B

<400> SEQUENCE: 50

Pro Ile Val Gln Asn Ile Gln Gly Gln Met Val His Gln Ala Ile Ser
  1               5                  10                  15

Pro Arg Thr Leu Asn Ala Trp Val Lys Val Val Glu Glu Lys Ala Phe
             20                  25                  30

Ser Pro Glu Val Ile Pro Met Phe Ser Ala Leu Ser Glu Gly Ala Thr
         35                  40                  45

Pro Gln Asp Leu Asn Thr Met Leu Asn Thr Val Gly Gly His Gln Ala
     50                  55                  60

Ala Met Gln Met Leu Lys Glu Thr Ile Asn Glu Glu Ala Ala Glu Trp
 65                  70                  75                  80

Asp Arg Val His Pro Val His Ala Gly Pro Ile Ala Pro Gly Gln Met
                 85                  90                  95

Arg Glu Pro Arg Gly Ser Asp Ile Ala Gly Thr Thr Ser Thr Leu Gln
            100                 105                 110

Glu Gln Ile Gly Trp Met Thr Asn Asn Pro Pro Ile Pro Val Gly Glu
        115                 120                 125

Ile Tyr Lys Arg Trp Ile Ile Leu Gly Leu Asn Lys Ile Val Arg Met
```

130                 135                 140
Tyr Ser Pro Thr Ser Ile Leu Asp Ile Arg Gln Gly Pro Lys Glu Pro
145                 150                 155                 160

Phe Arg Asp Tyr Val Asp Arg Phe Tyr Lys Thr Leu Arg Ala Glu Gln
                165                 170                 175

Ala Ser Gln Glu Val Lys Asn Trp Met Thr Glu Thr Leu Leu Val Gln
            180                 185                 190

Asn Ala Asn Pro Asp Cys Lys Thr Ile Leu Lys Ala Leu Gly Pro Ala
            195                 200                 205

Ala Thr Leu Glu Glu Met Met Thr Ala Cys Gln Gly Val Gly Gly Pro
            210                 215                 220

Gly His Lys Ala Arg Val Leu
225                 230

<210> SEQ ID NO 51
<211> LENGTH: 231
<212> TYPE: PRT
<213> ORGANISM: Artificial Sequence
<220> FEATURE:
<223> OTHER INFORMATION: synthetic clade B consensus sequence

<400> SEQUENCE: 51

Pro Ile Val Gln Asn Ala Gln Gly Gln Met Val His Gln Ser Leu Ser
1               5                   10                  15

Pro Arg Thr Leu Asn Ala Trp Val Lys Val Ile Glu Glu Lys Ala Phe
            20                  25                  30

Ser Pro Glu Val Ile Pro Met Phe Ser Ala Leu Ser Glu Gly Ala Thr
        35                  40                  45

Pro Gln Asp Leu Asn Met Met Leu Asn Ile Val Gly Gly His Gln Ala
    50                  55                  60

Ala Met Gln Met Leu Lys Asp Thr Ile Asn Glu Glu Ala Ala Glu Trp
65                  70                  75                  80

Asp Arg Leu His Pro Val His Ala Gly Pro Ile Pro Pro Gly Gln Met
                85                  90                  95

Arg Glu Pro Arg Gly Ser Asp Ile Ala Gly Thr Thr Ser Thr Pro Gln
            100                 105                 110

Glu Gln Ile Gly Trp Met Thr Ser Asn Pro Pro Ile Pro Val Gly Asp
        115                 120                 125

Ile Tyr Lys Arg Trp Ile Ile Leu Gly Leu Asn Lys Ile Val Arg Met
    130                 135                 140

Tyr Ser Pro Val Ser Ile Leu Asp Ile Lys Gln Gly Pro Lys Glu Pro
145                 150                 155                 160

Phe Arg Asp Tyr Val Asp Arg Phe Phe Lys Thr Leu Arg Ala Glu Gln
                165                 170                 175

Ala Thr Gln Asp Val Lys Asn Trp Met Thr Glu Thr Leu Leu Val Gln
            180                 185                 190

Asn Ala Asn Pro Asp Cys Lys Ser Ile Leu Arg Ala Leu Gly Ala Gly
            195                 200                 205

Ala Thr Leu Glu Glu Met Met Thr Ala Cys Gln Gly Val Gly Gly Pro
            210                 215                 220

Gly His Lys Ala Arg Val Leu
225                 230

<210> SEQ ID NO 52
<211> LENGTH: 231
<212> TYPE: PRT

-continued

<213> ORGANISM: Artificial Sequence
<220> FEATURE:
<223> OTHER INFORMATION: synthetic clade A consensus sequence

<400> SEQUENCE: 52

```
Pro Ile Val Gln Asn Leu Gln Gly Gln Met Val His Gln Ala Ile Ser
1               5                   10                  15

Pro Arg Thr Leu Asn Ala Trp Val Lys Val Val Glu Glu Lys Ala Phe
            20                  25                  30

Ser Pro Glu Val Ile Pro Met Phe Ser Ala Leu Ser Glu Gly Ala Thr
        35                  40                  45

Pro Gln Asp Leu Asn Thr Met Leu Asn Thr Val Gly Gly His Gln Ala
    50                  55                  60

Ala Met Gln Met Leu Lys Glu Thr Ile Asn Glu Glu Ala Ala Glu Trp
65                  70                  75                  80

Asp Arg Leu His Pro Val His Ala Gly Pro Ile Ala Pro Gly Gln Met
                85                  90                  95

Arg Glu Pro Arg Gly Ser Asp Ile Ala Gly Thr Thr Ser Thr Leu Gln
            100                 105                 110

Glu Gln Ile Gly Trp Met Thr Asn Asn Pro Pro Ile Pro Val Gly Glu
        115                 120                 125

Ile Tyr Lys Arg Trp Ile Ile Leu Gly Leu Asn Lys Ile Val Arg Met
    130                 135                 140

Tyr Ser Pro Thr Ser Ile Leu Asp Ile Arg Gln Gly Pro Lys Glu Pro
145                 150                 155                 160

Phe Arg Asp Tyr Val Asp Arg Phe Tyr Lys Thr Leu Arg Ala Glu Gln
                165                 170                 175

Ala Ser Gln Glu Val Lys Asn Trp Met Thr Glu Thr Leu Leu Val Gln
            180                 185                 190

Asn Ala Asn Pro Asp Cys Lys Thr Ile Leu Lys Ala Leu Gly Pro Ala
        195                 200                 205

Ala Thr Leu Glu Glu Met Met Thr Ala Cys Gln Gly Val Gly Gly Pro
    210                 215                 220

Gly His Lys Ala Arg Val Leu
225                 230
```

<210> SEQ ID NO 53
<211> LENGTH: 231
<212> TYPE: PRT
<213> ORGANISM: Artificial Sequence
<220> FEATURE:
<223> OTHER INFORMATION: synthetic clade C consensus sequence

<400> SEQUENCE: 53

```
Pro Ile Val Gln

```
Arg Glu Pro Arg Gly Ser Asp Ile Ala Gly Thr Thr Ser Thr Leu Gln
            100                 105                 110

Glu Gln Ile Ala Trp Met Thr Ser Asn Pro Val Pro Val Gly Asp
        115                 120                 125

Ile Tyr Lys Arg Trp Ile Ile Leu Gly Leu Asn Lys Ile Val Arg Met
    130                 135                 140

Tyr Ser Pro Val Ser Ile Leu Asp Ile Lys Gln Gly Pro Lys Glu Pro
145                 150                 155                 160

Phe Arg Asp Tyr Val Asp Arg Phe Phe Lys Thr Leu Arg Ala Glu Gln
                165                 170                 175

Ala Thr Gln Asp Val Lys Asn Trp Met Thr Asp Thr Leu Leu Val Gln
            180                 185                 190

Asn Ala Asn Pro Asp Cys Lys Thr Ile Leu Arg Ala Leu Gly Pro Gly
            195                 200                 205

Ala Ser Leu Glu Glu Met Met Thr Ala Cys Gln Gly Val Gly Gly Pro
210                 215                 220

Ser His Lys Ala Arg Val Leu
225                 230

<210> SEQ ID NO 54
<211> LENGTH: 231
<212> TYPE: PRT
<213> ORGANISM: Artificial Sequence
<220> FEATURE:
<223> OTHER INFORMATION: synthetic Group M consensus sequence

<400> SEQUENCE: 54

Pro Ile Val Gln As

Gly His Lys Ala Arg Val Leu
225                 230

<210> SEQ ID NO 55
<211> LENGTH: 231
<212> TYPE: PRT
<213> ORGANISM: Artificial Sequence
<220> FEATURE:
<223> OTHER INFORMATION: synthetic Group M Center-of-Tree (COT-M)
      sequence

<400> SEQUENCE: 55

Pro Ile Val Gln Asn Leu Gln Gly Gln Met Val His Gln Ala Ile Ser
1               5                   10                  15

Pro Arg Thr Leu Asn Ala Trp Val Lys Val Ile Glu Glu Lys Ala Phe
            20                  25                  30

Ser Pro Glu Val Ile Pro Met Phe Ser Ala Leu Ser Glu Gly Ala Thr
        35                  40                  45

Pro Gln Asp Leu Asn Thr Met Leu Asn Thr Val Gly Gly His Gln Ala
    50                  55                  60

Ala Met Gln Met Leu Lys Asp Thr Ile Asn Glu Glu Ala Ala Glu Trp
65                  70                  75                  80

Asp Arg Leu His Pro Val His Ala Gly Pro Ile Ala Pro Gly Gln Met
                85                  90                  95

Arg Glu Pro Arg Gly Ser Asp Ile Ala Gly Thr Thr Ser Thr Leu Gln
            100                 105                 110

Glu Gln Ile Gly Trp Met Thr Ser Asn Pro Pro Ile Pro Val Gly Glu
        115                 120                 125

Ile Tyr Lys Arg Trp Ile Ile Leu Gly Leu Asn Lys Ile Val Arg Met
    130                 135                 140

Tyr Ser Pro Val Ser Ile Leu Asp Ile Arg Gln Gly Pro Lys Glu Pro
145                 150                 155                 160

Phe Arg Asp Tyr Val Asp Arg Phe Phe Lys Thr Leu Arg Ala Glu Gln
                165                 170                 175

Ala Thr Gln Asp Val Lys Asn Trp Met Thr Asp Thr Leu Leu Val Gln
            180                 185                 190

Asn Ala Asn Pro Asp Cys Lys Thr Ile Leu Lys Ala Leu Gly Pro Gly
        195                 200                 205

Ala Thr Leu Glu Glu Met Met Thr Ala Cys Gln Gly Val Gly Gly Pro
    210                 215                 220

Gly His Lys Ala Arg Val Leu
225                 230

<210> SEQ ID NO 56
<211> LENGTH: 17
<212> TYPE: PRT
<213> ORGANISM: Artificial Sequence
<220> FEATURE:
<223> OTHER INFORMATION: synthetic plasmid 306H peptide

<400> SEQUENCE: 56

Met Trp Leu Gln Ser Leu Leu Leu Leu Gly Thr Val Ala Cys Ser Ile
1               5                   10                  15

Ser

<210> SEQ ID NO 57
<211> LENGTH: 140
<212> TYPE: PRT
<213> ORGANISM: Artificial Sequence

```
<220> FEATURE:
<223> OTHER INFORMATION: synthetic plasmid 306H peptide, p24CE1

<400> SEQUENCE: 57

Val Ile Pro Met Phe Ser Ala Leu Ser Glu Gly Ala Thr Pro Gln Asp
 1               5                  10                  15

Leu Asn Ala Ala Val Gly Gly His Gln Ala Ala Met Gln Met Leu Lys
            20                  25                  30

Asp Thr Ile Asn Glu Glu Ala Ala Glu Trp Asp Arg Ala Ala Ala Glu
        35                  40                  45

Pro Arg Gly Ser Asp Ile Ala Gly Thr Thr Ser Thr Leu Gln Glu Gln
    50                  55                  60

Ile Gly Trp Ala Ala Ala Lys Arg Trp Ile Ile Leu Gly Leu Asn Lys
65                  70                  75                  80

Ile Val Arg Met Tyr Ser Pro Thr Ser Ile Ala Ala Lys Tyr Val Asp
                85                  90                  95

Arg Phe Tyr Lys Thr Leu Arg Ala Glu Gln Ala Ala Gly Leu Glu Glu
            100                 105                 110

Met Met Thr Ala Cys Gln Gly Val Gly Gly Pro Gly His Lys Ala Ala
        115                 120                 125

Ile Ser Pro Arg Thr Leu Asn Ala Trp Val Lys Val
    130                 135                 140

<210> SEQ ID NO 58
<211> LENGTH: 271
<212> TYPE: PRT
<213> ORGANISM: Artificial Sequence
<220> FEATURE:
<223> OTHER INFORMATION: synthetic plasmid 306H, 202H, 191H, 230H, 231H
      and 235H peptide

<400> SEQUENCE: 58

Met Ser His Ile Gln Arg Glu Thr Ser Cys Ser Arg Pro Arg Leu Asn
 1               5                  10                  15

Ser Asn Met Asp Ala Asp Leu Tyr Gly Tyr Lys Trp Ala Arg Asp Asn
            20                  25                  30

Val Gly Gln Ser Gly Ala Thr Ile Tyr Arg Leu Tyr Gly Lys Pro Asp
        35                  40                  45

Ala Pro Glu Leu Phe Leu Lys His Gly Lys Gly Ser Val Ala Asn Asp
    50                  55                  60

Val Thr Asp Glu Met Val Arg Leu Asn Trp Leu Thr Glu Phe Met Pro
65                  70                  75                  80

Leu Pro Thr Ile Lys His Phe Ile Arg Thr Pro Asp Asp Ala Trp Leu
                85                  90                  95

Leu Thr Thr Ala Ile Pro Gly Lys Thr Ala Phe Gln Val Leu Glu Glu
            100                 105                 110

Tyr Pro Asp Ser Gly Glu Asn Ile Val Asp Ala Leu Ala Val Phe Leu
        115                 120                 125

Arg Arg Leu His Ser Ile Pro Val Cys Asn Cys Pro Phe Asn Ser Asp
    130                 135                 140

Arg Val Phe Arg Leu Ala Gln Ala Gln Ser Arg Met Asn Asn Gly Leu
145                 150                 155                 160

Val Asp Ala Ser Asp Phe Asp Asp Glu Arg Asn Gly Trp Pro Val Glu
                165                 170                 175

Gln Val Trp Lys Glu Met His Lys Leu Leu Pro Phe Ser Pro Asp Ser
            180                 185                 190
```

```
Val Val Thr His Gly Asp Phe Ser Leu Asp Asn Leu Ile Phe Asp Glu
            195                 200                 205

Gly Lys Leu Ile Gly Cys Ile Asp Val Gly Arg Val Gly Ile Ala Asp
    210                 215                 220

Arg Tyr Gln Asp Leu Ala Ile Leu Trp Asn Cys Leu Gly Glu Phe Ser
225                 230                 235                 240

Pro Ser Leu Gln Lys Arg Leu Phe Gln Lys Tyr Gly Ile Asp Asn Pro
                245                 250                 255

Asp Met Asn Lys Leu Gln Phe His Leu Met Leu Asp Glu Phe Phe
            260                 265                 270
```

<210> SEQ ID NO 59
<211> LENGTH: 140
<212> TYPE: PRT
<213> ORGANISM: Artificial Sequence
<220> FEATURE:
<223> OTHER INFORMATION: synthetic plasmid 202H peptide, p24CE2

<400> SEQUENCE: 59

```
Val Ile Pro Met Phe Thr Ala Leu Ser Glu Gly Ala Thr Pro Gln Asp
1               5                   10                  15

Leu Asn Ala Ala Val Gly Gly His Gln Ala Ala Met Gln Met Leu Lys
            20                  25                  30

Glu Thr Ile Asn Glu Glu Ala Ala Glu Trp Asp Arg Ala Ala Ala Glu
        35                  40                  45

Pro Arg Gly Ser Asp Ile Ala Gly Thr Thr Ser Thr Leu Gln Glu Gln
    50                  55                  60

Ile Ala Trp Ala Ala Lys Arg Trp Ile Ile Leu Gly Leu Asn Lys
65                  70                  75                  80

Ile Val Arg Met Tyr Ser Pro Val Ser Ile Ala Lys Tyr Val Asp
                85                  90                  95

Arg Phe Phe Lys Thr Leu Arg Ala Glu Gln Ala Ala Gly Leu Glu Glu
                100                 105                 110

Met Met Thr Ala Cys Gln Gly Val Gly Gly Pro Ser His Lys Ala Ala
            115                 120                 125

Leu Ser Pro Arg Thr Leu Asn Ala Trp Val Lys Val
        130                 135                 140
```

<210> SEQ ID NO 60
<211> LENGTH: 36
<212> TYPE: PRT
<213> ORGANISM: Artificial Sequence
<220> FEATURE:
<223> OTHER INFORMATION: synthetic plasmid 202H and 191H peptide

<400> SEQUENCE: 60

```
Thr Leu Ile Pro Ile Ala Val Gly Gly Ala Leu Ala Gly Leu Val Leu
1               5                   10                  15

Ile Val Leu Ile Ala Tyr Leu Val Gly Arg Lys Arg Ser His Ala Gly
            20                  25                  30

Tyr Gln Thr Ile
        35
```

<210> SEQ ID NO 61
<211> LENGTH: 380
<212> TYPE: PRT
<213> ORGANISM: Artificial Sequence
<220> FEATURE:
<223> OTHER INFORMATION: synthetic plasmid 191H peptide

<400> SEQUENCE: 61

```
Met Ala Pro Arg Ser Ala Arg Arg Pro Leu Leu Leu Leu Leu Leu Leu
  1               5                  10                  15

Leu Leu Leu Gly Leu Met His Cys Ala Ser Ala Met Phe Met Val
             20                  25                  30

Lys Asn Gly Asn Gly Thr Ala Cys Ile Met Ala Asn Phe Ser Ala Ala
             35                  40                  45

Phe Ser Val Asn Tyr Asp Thr Lys Ser Gly Pro Lys Asn Met Thr Leu
 50                  55                  60

Asp Leu Pro Ser Asp Ala Thr Val Val Leu Asn Arg Ser Ser Cys Gly
 65                  70                  75                  80

Lys Glu Asn Thr Ser Asp Pro Ser Leu Val Ile Ala Phe Gly Arg Gly
                 85                  90                  95

His Thr Leu Thr Leu Asn Phe Thr Arg Asn Ala Thr Arg Tyr Ser Val
             100                 105                 110

Gln Leu Met Ser Phe Val Tyr Asn Leu Ser Asp Thr His Leu Phe Pro
             115                 120                 125

Asn Ala Ser Ser Lys Glu Ile Lys Thr Val Glu Ser Ile Thr Asp Ile
130                 135                 140

Arg Ala Asp Ile Asp Lys Lys Tyr Arg Cys Val Ser Gly Thr Gln Val
145                 150                 155                 160

His Met Asn Asn Val Thr Val Thr Leu His Asp Ala Thr Ile Gln Ala
                 165                 170                 175

Tyr Leu Ser Asn Ser Ser Phe Ser Arg Gly Glu Thr Arg Cys Glu Gln
             180                 185                 190

Asp Arg Pro Ser Pro Thr Thr Ala Pro Pro Ala Pro Pro Ser Pro Ser
             195                 200                 205

Pro Ser Pro Val Pro Lys Ser Pro Ser Val Asp Lys Tyr Asn Val Ser
210                 215                 220

Gly Thr Asn Gly Thr Cys Leu Leu Ala Ser Met Gly Leu Gln Leu Asn
225                 230                 235                 240

Leu Thr Tyr Glu Arg Lys Asp Asn Thr Thr Val Thr Arg Leu Leu Asn
                 245                 250                 255

Ile Asn Pro Asn Lys Thr Ser Ala Ser Gly Ser Cys Gly Ala His Leu
             260                 265                 270

Val Thr Leu Glu Leu His Ser Glu Gly Thr Thr Val Leu Leu Phe Gln
             275                 280                 285

Phe Gly Met Asn Ala Ser Ser Ser Arg Phe Phe Leu Gln Gly Ile Gln
290                 295                 300

Leu Asn Thr Ile Leu Pro Asp Ala Arg Asp Pro Ala Phe Lys Ala Ala
305                 310                 315                 320

Asn Gly Ser Leu Arg Ala Leu Gln Ala Thr Val Gly Asn Ser Tyr Lys
                 325                 330                 335

Cys Asn Ala Glu Glu His Val Arg Val Thr Lys Ala Phe Ser Val Asn
             340                 345                 350

Ile Phe Lys Val Trp Val Gln Ala Phe Lys Val Glu Gly Gly Gln Phe
             355                 360                 365

Gly Ser Val Glu Glu Cys Leu Leu Asp Glu Asn Ser
370                 375                 380
```

<210> SEQ ID NO 62
<211> LENGTH: 109
<212> TYPE: PRT
<213> ORGANISM: Artificial Sequence -continued
<220> FEATURE:
<223> OTHER INFORMATION: synthetic plasmid 230H and 231H peptide

<400> SEQUENCE: 62

```
Met Trp Lys Pro Met Pro Ser Pro Ser Asn Met Lys Ala Ser Ala Ala
  1               5                  10                  15

Leu Leu Cys Leu Leu Leu Thr Ala Ala Ala Phe Ser Pro Gln Gly Leu
             20                  25                  30

Ala Gln Pro Val Gly Ile Asn Thr Ser Thr Thr Cys Cys Tyr Arg Phe
         35                  40                  45

Ile Asn Lys Lys Ile Pro Lys Gln Arg Leu Glu Ser Tyr Arg Arg Thr
         50                  55                  60

Thr Ser Ser His Cys Pro Arg Glu Ala Val Ile Phe Lys Thr Lys Leu
 65                  70                  75                  80

Asp Lys Glu Ile Cys Ala Asp Pro Thr Gln Lys Trp Val Gln Asp Phe
                 85                  90                  95

Met Lys His Leu Asp Lys Lys Thr Gln Thr Pro Lys Leu
            100                 105
```

What is claimed is:

1. A method of inducing an immune response in a subject, the method comprising:
   (a) administering a first Gag conserved element nucleic acid that encodes a first Gag conserved element polypeptide that comprises six conserved elements from Gag to the subject, wherein the conserved elements are from different regions of Gag, and further, wherein each conserved element is at least 12 amino acids in length, but less than 30 amino acids in length and the conserved elements are not contiguous;
   (b) administering a second Gag conserved element nucleic acid that encodes a second Gag conserved element polypeptide that comprises at least one variant of a conserved element polypeptide differs from the variant in the first polypeptide by 1, 2, or 3 amino acids; and
   (c) administering a nucleic acid encoding a full-length Gag protein;
      wherein the nucleic acid encoding the full-length Gag protein is administered after the first and the second Gag conserved element nucleic acids, and
   wherein the region of the nucleic acid encoding the full-length Gag protein encodes only the full-length Gag protein.

2. The method of claim 1, wherein the conserved elements are from HIV-1 p24$^{gag}$.

3. The method of claim 2, wherein the first conserved element polypeptide comprises at least one, two, three, four, five, or six conserved element that has an amino acid sequence set forth in SEQ ID NOS:1-7, 32, or 33.

4. The method of claim 2, wherein the first conserved element polypeptide comprises conserved elements that each have a sequence set forth in SEQ ID NOS:1-7; or the first conserved element polypeptide comprises conserved elements that each have a sequence set forth in SEQ ID NOS:3-6, 32, and 33.

5. The method of claim 1, wherein the first conserved element polypeptide comprises conserved elements that each have a sequence set forth in SEQ ID NOS:1-7 and the second conserved element polypeptide comprises conserved elements that each have a sequence set forth in SEQ ID NOS:8-14.

6. The method of claim 1, wherein the conserved element and variant conserved element each have a sequence set forth in FIG. 1 or in FIG. 13.

7. The method of claim 1, wherein the first Gag conserved element nucleic acid encodes a conserved element polypeptide comprising the sequence of SEQ ID NO:15 and the second Gag conserved element nucleic acid encodes a conserved element polypeptide comprising the sequence of SEQ ID NO:16.

8. The method of claim 1, wherein the first and second Gag conserved element nucleic acids are administered sequentially.

9. The method of claim 1, wherein the conserved element polypeptides encoded by the first and second nucleic acid Gag conserved element nucleic acids are each fused to a GM-CSF signal peptide.

10. The method of claim 1, wherein the first and second nucleic acid Gag conserved element nucleic acids are contained in the same vector.

11. The method of claim 1, wherein the first and second nucleic acid Gag conserved element nucleic acids are contained in different vectors.

12. The method of claim 1, wherein the nucleic acid constructs encoding the conserved element polypeptides and full-length Gag polypeptide are administered intramuscularly by in vivo electroporation.

13. A method of inducing an immune response to an HIV Gag protein, the method comprising:
   (a) administering:
      (i) a nucleic acid encoding a polypeptide comprising SEQ ID NO:15 and a nucleic acid encoding a polypeptide comprising SEQ ID NO: 16 to a subject; or
      (ii) a nucleic acid encoding a polypeptide comprising p24CE1c as shown in FIG. 13 and a nucleic acid encoding a polypeptide comprising p24CE2c as shown in FIG. 13 to the subject; or
      (iii) a nucleic acid encoding a polypeptide comprising p24CE1d as shown in FIG. 13 and a nucleic acid encoding a polypeptide comprising p24CE2d as shown in FIG. 13 to the subject; and (b) administering a nucleic acid encoding a p55 Gag protein;

wherein the region of the nucleic acid encoding the Gag protein encodes only the p55 Gag protein.

14. The method of claim 13, wherein the polypeptide of SEQ ID NO:15 and the polypeptide of SEQ ID NO:16; or the polypeptide of p24CE1c and p24CE2c; or the polypeptide of p24CE1d and p24CE2d are encoded by the same vector.

15. The method of claim 13, wherein the polypeptide of SEQ ID NO:15 and the polypeptide of SEQ ID NO:16; or the polypeptide of p24CE1c and p24CE2c; or the polypeptide of p24CE1d and p24CE2d are fused to a GM-CSF signal peptide.

16. The method of claim 13, wherein the nucleic acids are administered intramuscularly followed by in vivo electroporation.

17. The method of claim 13, wherein the nucleic acid encoding p55 gag is administered at least two weeks after step (a).

18. A method of inducing an immune response to an HIV gag protein, the method comprising:

(a) administering at least one nucleic acid encoding a conserved element polypeptide comprising a sequence set forth in SEQ ID NO: 18, SEQ ID NO: 19, SEQ ID NO:21, SE ID NO:23, SEQ ID NO:25, SEQ ID NO:27, SE ID NO:29, SEQ ID NO:31, SEQ ID NO:35, SEQ ID NO:37, or SEQ ID NO:39 to a patient; and (b) administering a nucleic acid encoding a full-length Gag protein to the patient;

wherein the region of the nucleic acid encoding the full-length Gag protein encodes only the full-length Gag protein.

19. The method of claim 18, wherein the nucleic acid encoding the full-length gag protein is administered at least 2 weeks after administering the nucleic acid encoding the conserved element polypeptide.

\* \* \* \* \*